US008846312B2

(12) United States Patent
Young

(10) Patent No.: US 8,846,312 B2
(45) Date of Patent: Sep. 30, 2014

(54) COMPOSITIONS AND METHODS FOR DETECTING CERTAIN FLAVIVIRUSES, INCLUDING MEMBERS OF THE JAPANESE ENCEPHALITIS VIRUS SEROGROUP

(71) Applicant: Roche Molecular Systems, Inc., Pleasanton, CA (US)

(72) Inventor: Karen K. Y. Young, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/864,102

(22) Filed: Apr. 16, 2013

(65) Prior Publication Data

US 2013/0316328 A1    Nov. 28, 2013

Related U.S. Application Data

(63) Continuation of application No. 12/340,224, filed on Dec. 19, 2008, now abandoned, which is a continuation of application No. 10/815,480, filed on Mar. 31, 2004, now Pat. No. 7,510,827.

(60) Provisional application No. 60/459,491, filed on Mar. 31, 2003, provisional application No. 60/552,454, filed on Mar. 12, 2004, provisional application No. 60/555,530, filed on Mar. 22, 2004.

(51) Int. Cl.
*C12Q 1/70* (2006.01)
*C07H 21/00* (2006.01)
*C12P 19/34* (2006.01)

(52) U.S. Cl.
CPC .................................. *C12Q 1/701* (2013.01)
USPC ............................................. 435/6; 435/91.2

(58) Field of Classification Search
None
See application file for complete search history.

(56) References Cited

U.S. PATENT DOCUMENTS

| 5,487,972 | A | 1/1996 | Gelfand et al. |
| 5,641,630 | A | 6/1997 | Snitman et al. |
| 6,001,611 | A | 12/1999 | Will |
| 6,040,166 | A | 3/2000 | Erlich et al. |
| 7,115,374 | B2 | 10/2006 | Linnen |
| 7,132,233 | B2 | 11/2006 | Shyamala |
| 2005/0164170 | A1 | 7/2005 | Despres et al. |

FOREIGN PATENT DOCUMENTS

| GB | 2279954 A | 1/1995 |
| WO | WO 93/06214 A1 | 4/1993 |
| WO | WO 93/22440 A1 | 11/1993 |
| WO | WO 02/081511 A1 | 10/2002 |

OTHER PUBLICATIONS

NCBI blast (http://blast.ncbi.nlm.nih.gov/Blast.cgi#341869847, downloaded Jan. 8, 2014).*
Tanaka ( Journal of Virological methods (1993) vol. 41, pp. 311-322).*
Pierre et al (Res. Virol (1994) vol. 145, pp. 93-104) (IDS Dec. 19, 2008).*
Warrilow (Journal of medical virology (2002) vol. 66, pp. 524-528, available electronically Feb. 22, 2002).*
1990, "Basic Study on Development of Rapid Diagnosis Method of Flavivirus Using PCR Assay", *Clinical Practice and Virus*, 18(3):322-325.
Batista et al.; 2001, *Virus Research*, 75:35-42.
Beasley et al.; 2002; EMBL AF458353; XP002300069 (2 pages).
Beasley et al.; 2002; EMBL AF458358; XP002300070 (2 pages).
Beasley, David W.C. et al.; "Mouse Neuroinvasive Phenotype of West Nile Virus Strains Varies Depending upon Virus Genotype"; 2002, Virology, vol. 296, pp. 17-23.
Beasley, David W.C. et al.; EMBL: 2002, AF458347; XP002288984, 1 page.
Beasley, David W.C. et al.; EMBL: 2002, AF458348; XP002288985, 1 page.
Beasley, David W.C. et al.; EMBL: 2002, AF458350; XP002288986, 1 page.
Briese et al; "Idenfication of a Kunjin/West Nile-like flavivirus in brains of patients with New York encephalitis"; *Lancet*; 354:1261-1262 (1999).
Brinton et al.; "The 3'-Nucleotides of Flaviviruses Genomic RNA Form a Conserved Secondary Structure"; *Virology*; 153:113-121 (1986).
Buck et al.; "Design Strategies and Performance of Custom DNA Sequencing Primers," 1999, *Biotechniques* 27(3):528-536.
Coia et al.; "Nucleotide and Comlete Amino Acid Sequences of Kunjin Virus: Definitive Gene Order and Characteristics of the Virus-specified Proteins"; J. Gen. Virol.; 69:1-21 (1988).
Fulop et al.; 1993, *Journal of Virological Methods*, 44:179-188.
Holtmeier et ah; "The TCR-δ repertoire in human intestine undergoes characteristic changes from fetal to adult development"; *J. Immunol.*; 112(4):5632-5641 (1997).
Hurrelbrink et al; "Characterization of infectious Murray Valley encephalitis virus derived from a stably cloned genome-lenth cDNA"; *J. Gen. Virol.*; 80:3115-3125 (1999).

(Continued)

*Primary Examiner* — Steven Pohnert
(74) *Attorney, Agent, or Firm* — Kilpatrick Townsend & Stockton LLP

(57) ABSTRACT

The present invention provides rapid and accurate methods, primers, probes and kits for identifying the presence of a certain flaviviruses in a sample. Flaviviruses that can be detected include members of the Japanese encephalitis virus serogroup, Dengue virus, St. Louis encephalitis virus, Montana myotis leukoencephalitis virus, Modoc virus, and Yellow Fever virus. The primers and probes of the invention can hybridize to regions in the 3' untranslated region of the viral genomes to be detected.

5 Claims, 22 Drawing Sheets

(56) References Cited

OTHER PUBLICATIONS

Igarashi et al.; "Detection of West Nile and Japanese Encephalitis viral genome sequences in cerebrospinal fluid from acute encephalitis cases in Karachi, Pakistan"; *Microbiol. Immunol.*; 38(10):827-830 (1994).

Lanciotti et al., "Complete Genome Sequences and Phylogenetic Analysis of West Nile Virus Strains Isolated From the United States, Europe and the Middle East," 2002, *Virology*, pp. 96-105.

Lanciotti, Robert S. et al.; "Nucleic Acid Sequence-Based Amplification Assays for Rapid Detection of West Nile and St. Louis Encephalitis Viruses"; 2001, *Journal of Clinical Microbiology*, vol. 39, No. 12, pp. 4506-4513.

Lanciotti, Robert S. et al.; "Rapid Detection of West Nile Virus from Human Clinical Specimens, Filed-Collected Mosquitoes, and Avian Samples by a TaqMan Reverse Transcriptase—PCR Assay"; 2000, *Journal of Clinical Microbiology*, vol. 38, No. 11, pp. 4066-4071.

Lee et al.; "Simultaneous Detection of Three Mosquito-Borne Encephalitis Viruses (Eastern Equine, La Crosse, and St. Louis) With a Single-Tube Multiplex Reverse Transcriptase Polymerase Chain Reaction Assay", Journal of the American Mosquito Control Association; 18(1):26-31 (2002).

Lo et al.; 2003, *Journal of Virology*, 77:10004-10014.

Mansy, Frederic et al.; "A PCR based DNA hybridization capture system for the detection of human cytomegalovirus. A comparative study with other identification methods"; 1999, *Journal of Virological Methods*, vol. 80, pp. 113-122.

Meiyu et al.; "Detection of Flaviviruses by Reverse Transcriptase-Polymerase Chain Reaction with the Universal Primer Set", *Microbiol. Immunol.*; 41(3):209-213 (1997).

Morris, Timothy et al.; "Rapid Reverse Transcription—PCR Detection of Hepatitis C Virus RNA in Serum by Using the TaqMan Fluorogenic Detection System"; 1996, *Journal of Clinical Microbiology*, vol. 34, No. 12, pp. 2933-2936.

Nam et al.; "High Level of Sequence Variation in the 3' Noncoding Region of Japanese Encephalitis Viruses Isolated in Korea"; *Virus Genes*; 24:21-27 (2002).

Nitsche, Andreas et al.; "Different Real-Time PCR Formats Compared for the Quantitative Detection of Human Cytomegalovirus DNA"; 1999, *Clinical Chemistry*, vol. 45, No. 11, pp. 1932-1937.

Olsthoorn et al.; "Sequence comparison and secondary structure analysis of the 3' noncoding region of flavivirus genomes reveals multiple pseudoknots", *RNA*; 7:1370-1377 (2001).

Pierre et al.; 1994, *Res. Virol.*, 145:93-104.

Poidinger et al.; "Molecular Characterization of the Japanese Encephalitis Serocomplex of the Flavivirus Genus", *Virology*; 218:417-421 (1996).

Porter et al.; "Detection of West Nile Virus by the polymerase chain reaction and analysis of nucleotide sequence variation"; *Am. J. Trop. Med. Hyg.*; 48(3):440-446 (1993).

Proutski, Vitali et al.; "Secondary structure of the 3' untranslated region of flaviviruses: similarities and differences"; 1997, *Nucleic Acids Research*, vol. 25, No. 6, pp. 1194-1202.

Rauscher et al.; 1997, *RNA*, 3:779-791.

Rigler et al.; "Fluorescence Cross-Correlation: A New Concept for Polymerase Chain Reaction," 1998, *Journal of Biotechnology*, 63:97-109.

Scaramozzino et al. (Journal of Clinical Microbiology 39: 1922-1927, 2001).

Sudiro et al.; "Rapid Diagnosis of Dengue Viremia by Reverse Transcriptase—Polymerase Chain Reaction Using 3'-Noncoding Region Universal Primers", *Am. J. Trop. Med. Hyg.*; 56(4):424-429 (1997).

Tanaka, Mariko; "Rapid identification of flavivirus using the polymerase chain reaction"; 1993, *Journal of Virological Methods*, vol. 41, pp. 311-322.

Vrati et al.; "Complete Nucleotide Sequence of an Indian Strain of Japanese Encephalitis Virus: Sequence Comparison with Other Strains and Phylogenetic Analysis", *Am. J. Trop. Med. Hyg.*; 61(4):677-680 (1999).

Warrilow et al.; 2002, *Journal of Medical Virology*, 66:524-528.

Wengler et al.; 1986, *Journal of General Virology*, 67:1183-1188.

Zhang et al.; "Amplification and cloning of the full-length genome of Japanese encephalitis virus by the novel long RT-PCR protocol in a cosmid vector"; *J. Virol. Meth.*; 96:171-182 (2001).

\* cited by examiner

```
Kern217    TGG.......C. .......T.T.......AACCC.GCTGGGT GCA.....C.... TT...A.....G...GTCC.TGGCACGTAG.CTGGAGAGG.C
CoaV608       .......C. .......T.T.......AATCC.GCTGGGT GCA.....C.... TT...A.....G...GTCC.TGGCACGTAG.CTGGAGAGG.C
TBH-28     TGG.......T. .......T.T.......AACCC.GCTGGGT GCA.....C.... TT...A.....G...GTCC.TGGCACGTAG.CCGGAGAGG.C
VR1265     TGG.......T. .......T.T.......AATCT.GCTGGGT GCA.....C.... TT...A.....G...GTCC.TGGCACGTAG.CTGGAG.GG.C
CoaV353       .......T. .......T.T.......AATCTAGCTGAGT GCA.....C.... TT...A.....G...GTCC.TGGCACGTAG.CTGGAGAGG.C
MVEV
VR77       ....................T.C......T.ATTCTCC.CGGTTG.A.....T.C.................AG.AGT...TGCCAACAATGGAGATG.A
AF161266   ....................T.C......T.ATTCTCC.CGGTTG.A.....T.C.................AG.AGT...TGCCAACAATGGAGATG.A
M35172     ....................T.C......T.ATTCTCC.CGGTTG.A.....T.C.................AG.AGT...TGCCAACAATGGAGATG.A
L48972     ....................T.C......T.ATTCTCC.CGGTTG.A.....T.C.................AG.AGT...T.CCAACAATGGAGATG.A
L48973     ....................T.C......T.ATTTTCC.CGGTTG.A.....T.C.................AG.AGT...TGCCAACAATGGAGATG.A
L48974     ....................T.C......T.ACTCTCT.CGGTTG.A.....T.C....C............AG.AG....TGCCAACAATGGAGATG.A
L48975     ....................T.C....A.T.ACTCTCT.CGGTTG.A.....T.C.................AG.AGT...TTCCAACAATGGAGATG.A
L48976     ....................T.C......T.ATTCTCC.CGGTTG.A.....T.C.........T.......AG.AGT...TGC.AACAATGGAGATG.A
Koutango virus
L48980     ....................C......T.T....G.A.. ....C....T.. ..............................G....T..TTC......
```

*Two potential binding sites for SEQ ID NOS.: 28 & 70 can be found in this region. These are denoted by single underline for SEQ ID NO.: 28, and shading for SEQ ID NO.: 70.

```
KY1129              5'-GTAAGCC CTCAGAACCGTCTCGGAA-3'

WNV
AF317203            ....... ..................
AF196835            ....... ..................
AF260967            ....... ..................
AF260968            ....... ..................
AF260969            ....... ..................
AF481864            ....... ..................
M12294              ....... ..................
AF206518            ....... ..................
AF317203            ....... ..................
AF202541            ....... ..................
AF404757            ....... ..................
AF404753            ....... ..................
AF404754            ....... ..................
AF404755            ....... ..................
AF404756            ....... ..................
AF017254            ....... ..................
L48977              ....... ..................
AF196536            ....... ..................
AF196537            ....... ..................
AF196538            ....... ..................
AF196540            ....... ..................
AF196541            ....... ..................
AF196542            ....... ..................
AF196543            ....... ..................
AF458343            ....... .C................
AF458344            ....... ..................
AF458347            ....... ..................
AF458348            ....... ..................
AF458350            ....... ..................
AF458352            ....... ........C.........
AF458353            ....... ..................
AF458355            ....... ..................
AF458358            ....... ..................
AF458360            ....... ..................
AF458361            ....... ..................
AF208017            ....... ..................
AF196539            ....... ..................
AF196535            ....... ..................
AF458359            ....... ..................
AF458357            ....... ..................
AF458354            ....... ..................
AF458349            ....... ..................
AF458345            ....... ..................
AF458346            .......T..........T......
AF533540            ....... ..................

JEV
AB051292            .A..... ..................
AF014160            .A..... ..................
AF014161            .A..... ..................
AF045551            .A..... ..................
AF069076            .A..... ..................
AF075723            .A..... ..................
AF080251            .A..... ....G.............
AF098735            .A..... ..................
AF098736            .A..... ..................
AF098737            .A..... ..................
AF217620            .A..... ..................
AF221499            .A..... ..................
AF221500            .A..... ..................
AF254452            .A..... ..................
AF254453            .A..... ..................
AF315119            .A..... ........T.........
AF416457            .A..... ..................
AF486638            .A..... ..................
U14163              .A..... ..................
U15763              .A..... ..................
```

FIG. 4A

```
KY1129         5'-GTAAGCC CTCAGAACCGTCTCGGAA-3'

JEV cont.
L48961         .A..... ..................
U47032         .A..... ..................
M18370         .A..... ..................
M55506         .A..... ..................
L78128         .A..... ..................
D90195         .A..... ..................
D90194         .A..... ..................
AF311748       .A..... ..................
AF092550       .A..... ..................
AF092552       .A..... ..................
AF092553       .A..... ..................
AF139531       .A..... ..................
AF148900       .A..... ..................
AF148902       .A..... ..................
AF218068       .A..... ..................
AF289816       .A..... ..................
AF318291       .A..... ..................
L48967         .A..... ..................
L48968         .A..C.. ..................
L54067         .A..... ..................
L54068         .A..... ..................
L54069         .A..... ..................
L54070         .A..... ..................
L54072         .A..... ..................
L54122         .A..... ..................
L54123         .A..... ..................
AF306514       .A..... ..................
AF306515       .A..... ..........T.......
AF306516       .A..... ..........T.......
AF306517       .A..... ....A.....T.......

MVEV
AF161266       .A.....T.C................
M35172         .A.....T.C................
L48972         .A.....T.C................
L48973         .A.....T.C................
L48974         .A.....T.C....C...........
L48975         .A.....T.C................
L48976         .A.....T.C.........C......

KUNJIN
AF458351       ....... ................G.
AF458356       ....... ..................
AF297840       ....... ...........C......
AF297841       ....... ..................
AF298942       ....... ..................
AF297843       ....... ..................
AF297844       ....... ..................
AF297845       ....... ..................
AF297846       ....... ...........C......
AF297847       ....... ...........C......
AF297848       ....... ..................
AF297849       ....... ..................
AF297850       ....... ...........C......
AF297851       ....... ...........C.....GT
AF297852       ....... ...........C......
AF297853       ....... ...........C......
AF297854       ....... ..................
AF297855       ....... ..................
AF297856       ....... ..................
AF297857       ....... ...G..............
AF297858       ....... ..................
AF297859       ....... ..................
L48978         ....... ..................
L49311         ....... ..................
D00246         ....... ..................
L48979         ....... ..................
L24512         ....... ..................

KOUTANGO
L48980         ....... ..................
```

FIG. 4B

```
KY1130              5'-TCCTAGTCTA TCCCAGGTGTCAA-3'

WNV
AF196835            .......... .............
AF260967            .......... .............
AF260968            .......... .............
AF260969            .......... .............
AF481864            .......... .............
M12294              C......... .............
AF206518            .......... .............
AF317203            .......... .............
AF202541            .......... .............
AF404757            .......... .............
AF404753            .......... .............
AF404754            .......... .............
AF404755            .......... .............
AF404756            .......... .............
AF017254            .......... ........A....

Kunjin
L24512              .......... .............

JEV
AB051292            ...C......T.............
AF014160            ...C......T.............
AF014161            ...C......T.............
AF045551            ...C.C....T.............
AF069076            ...C......T.............
AF075723            ...C......T.............
AF080251            ...C......T.............
AF098735            ...C......T.............
AF098736            ...C......T.............
AF098737            ...C......TCT...........
AF217620            ...C......T.............
AF221499            ...C......T.............
AF221500            ...C......T.............
AF254452            ...C......T.............
AF254453            ...C......T.............
AF315119            ...C......T.............
AF416457            ...C......T.............
AF486638            ...C...A..T.............
U14163              ...C......T.............
U15763              ...C......T.............
L48961              ...C......T.............
U47032              ..........T.............
M18370              ...C......T.............
M55506              ...C......T.............
L78128              ...C......T.............
D90195              ...C......T.............
D90194              ...C......T.............
AF311748            ...C......T.............
AF306514            ...C.C....T.............
AF306515            ...C......T.............
AF306516            ...C......T.............
AF306517            ...C.C....T.............
D00037              ...C......T.............
M14933              ...C......T.............

MVEV
AF161266            ........TT..............
M35172              ........TT..............
```

FIG. 4C

| | |
|---|---|
| KY1131 | 5'-GGACTAGAGGTTAGAGGAGACCCCGCGG-3' |

WNV
| | |
|---|---|
| AF196835 | ............................ |
| AF260967 | ............................ |
| AF260968 | ............................ |
| AF260969 | ............................ |
| AF481864 | ............................ |
| M12294 | ...........................T |
| AF206518 | ............................ |
| AF317203 | ............................ |
| AF202541 | ............................ |
| AF404757 | ............................ |
| AF404753 | ............................ |
| AF404754 | ............................ |
| AF404755 | ............................ |
| AF404756 | ............................ |
| AF017254 | ............................ |
| AF208017 | ........T..............A..T |

Kunjin
| | |
|---|---|
| L24512 | ...........................T |

JEV
| | |
|---|---|
| AB051292 | .........................T.. |
| AF014160 | .........................T.. |
| AF014161 | .........................T.. |
| AF045551 | .........................T.. |
| AF069076 | .........................T.. |
| AF075723 | .........................T.. |
| AF080251 | .........................T.. |
| AF098735 | .........................T.. |
| AF098736 | .........................T.. |
| AF098737 | .........................T.. |
| AF217620 | .........................T.. |
| AF221499 | .........................T.. |
| AF221500 | .........................T.. |
| AF254452 | .........................T.. |
| AF254453 | .........................T.. |
| AF315119 | .........................T.. |
| AF416457 | .........................T.. |
| AF486638 | .........................T.. |
| U14163 | .........................T.. |
| U15763 | .........................T.. |
| L48961 | .........................T.. |
| U47032 | .........................T.. |
| M18370 | .........................T.. |
| M55506 | .........................T.. |
| L78128 | .........................T.. |
| D90195 | .........................T.. |
| D90194 | .........................T.. |
| AF311748 | .........................T.. |
| AF306514 | .........................T.. |
| AF306515 | .........................T.. |
| AF306516 | .........................T.. |
| AF306517 | .........................T.. |

MVEV
| | |
|---|---|
| AF161266 | ........................A.TC |
| M35172 | ........................A.TC |

FIG. 4D

| KY1131 | 5'-GGACTAGAGGTTAGAGGAGACCCCGCGG-3' |
|---|---|
| DENGUE | |
| AF226685 | ........................C..C |
| AF311956 | ........................C..C |
| AF311957 | ........................C..C |
| AF311958 | ........................C..C |
| AY145121 | ........................C..C |
| AY145122 | ........................C..C |
| AF514878 | ........................C..C |
| AF514885 | ........................C..C |
| AF514889 | ........................C..C |
| AF489932 | ........................C.CA |
| AF226687 | ........................C..C |
| AX224213 | ........................C.C. |
| AX224215 | ........................C.C. |
| AX224217 | ........................C.C. |
| AX224219 | ........................C.C. |
| AX224225 | ........................C.C. |
| AX224227 | ........................C..C |
| AX224233 | ........................C..C |
| AB074760 | ........................C..C |
| AB074761 | ........................C..C |
| A75711 | ........................CG.C |
| AX224221 | ........................C.C. |
| AX224223 | ........................C.C. |
| U87412 | ........................C.C. |
| U61246 | ........................C.C. |
| U61247 | ........................C.C. |
| AF100465 | ........................C.CA |
| AF100466 | ........................C.CA |
| AX224209 | ........................C..C |
| AF180818 | ........................C..C |
| AF326573 | ........................C.CA |
| AF350498 | ........................C..C |
| AF359579 | ........................C.C. |
| AY037116 | ........................C.C. |
| AF309950 | ........................C.C. |
| AF309953 | ........................C.CA |
| AF309954 | ........................C.CA |
| AF309959 | ........................C.CA |
| AF309962 | ........................C.C. |
| AF309963 | ........................C.C. |
| AF309964 | ........................C.C. |
| AF309965 | ........................C.CA |
| AF289029 | ........................C.CA |
| AF208496 | ........................C.CA |
| AF310146 | ........................C..C |
| AF310149 | ........................C..C |
| AF310153 | ........................C.CA |
| AF226686 | ........................C..C |
| AF276619 | ........................C.C. |
| AF169678 | ........................C.C. |
| AF169679 | ........................C.C. |
| AF169680 | ........................C.C. |
| AF169681 | ........................C.C. |
| AF169682 | ........................C.C. |
| AF169683 | ........................C.C. |
| AF169684 | ........................C.C. |
| AF169685 | ........................C.C. |
| AF169686 | ........................C.C. |
| AF169687 | ........................C.C. |
| AF169688 | ........................C.C. |
| AF100145 | ........................C.CA |
| AF100467 | ........................T.CC |
| AF100468 | ........................T.CC |
| AF100149 | ........................T.CC |
| M20558 | ........................C.CA |
| M29095 | ........................C.CA |
| M19197 | ........................C.CA |
| M14931 | ........................C.CA |
| U87411 | ........................C.C. |
| U88536 | ........................C..C |

FIG. 5A

```
KY1131              5'-GGACTAGAGGTTAGAGGAGACCCCGCGG-3'

DENGUE (cont.)
U88537                      ........................C..C
AF038403                    ........................C.CA
AF326826                    ........................C.CA
AF326827                    ........................C.CA MONTANA MYOTIS LEUKOENCEPHALITIS VIRUS
NC_004119                   ........................TTCC

MODOC VIRUS
NC_003635                   ........................CG.C

YELLOW FEVER VIRUS
X03700                      ..T.....................TC.A.
U52393                      ..T.....................TC.A.
U52407                      ..T.....................TC.A.
AF052448                    ..T.....................TC.A.
```

```
BFS1750   TTGCCACCGATGGAGTGTCAGGTAAACGTTGCTGTCTGTAACCTGGCCCCAGGTGACTGGGTTATCAAAGCCAATCTGGCCGAGTGCAAAGCCC  90
1750-Std  ..........................................................................................
TD6-4G    ..........................................................................................
CoaV750   .........................C................................................................
L695121.05 ........................C................................................................
TNM771K   ..........................................................C...............................T..
MSI-7     ..........................................................C...............................T.G
Kern217   ..........................................................C...............................T.G
CoaV608   ..........................................................C.C.............................T.G
CoaV608   ..........................................................C.C.............................T.G
TBH-28    ..........................................................C.C.............................T.G
VR1265    ..........................................................C.C.............................T.G
CoaV353   ..............................A...........................................................A..T.

BFS1750   CTCATTCCGACTCGGGAGGGTCCCTAGCACGTAGGCTGGAGAGGACGCAAAAGTCAGACCCAGAGAAATGCCACCTGAAAGCATGCTAAAGGT 180
1750-Std  ..........................................................................................
TD6-4G    ..G.......................G................................................................
CoaV750   ..G........T.............G................................................................
L695121.05 .........................G........................................C.......................
TNM771K   .........................G.................................................................
MSI-7     .........................G..........................................C.....................
Kern217   .........................G..........................................C.....................
CoaV608   .........................G..........................................C.....................
TBH-28    .........................G..........................................C.....................
VR1265    .........................G......................C...................C.....................
CoaV353   .........................G..................................................................

BFS1750   GCTGTCTGTACATGCCCCAGGAGGACTGGGTTAACAAAGCTTAACAAGCCCCAAAACCATGCAGTGCCGTGACCATGCCTAAGG 270
1750-Std  ..........................................................................................
TD6-4G    ..........................................................................................
CoaV750   ..........................................................................................
L695121.05 ........................................................................A.................
TNM771K   ..........................................................................................
```

FIG. 7B

```
                 ACTAGAGGTTAGAGGAGACCCCGCTGCAACTTGGCAAGGCCCAAACCCGCTCGAAGCTGTAGAGACGGGGAAGGACTAGAGGTTAGAGG 360
BFS1750          ..........................................................................T.......
1750-Std         ....................................................................................
TD6-4G           ...................................C................................................
CoaV750          .................................................A..................................
L695121.05       ..............................................T.....................................
TNM771K          ..............................................T.....................................
MSI-7            ..............................................T............A........................
Kern217          ..............................................T............A........................
CoaV608          ..............................................T............A........................
TBH-28           ..............................................T.T...................................
V

COMPOSITIONS AND METHODS FOR DETECTING CERTAIN FLAVIVIRUSES, INCLUDING MEMBERS OF THE JAPANESE ENCEPHALITIS VIRUS SEROGROUP

CROSS-REFERENCE TO RELATED PATENT APPLICATIONS

The present application is a continuation of U.S. patent application Ser. No. 12/340,224, filed Dec. 19, 2008, which is a continuation of U.S. patent application Ser. No. 10/815,480, filed Mar. 31, 2004, now U.S. Pat. No. 7,510,827, issued Mar. 31, 2009, which claims benefit of priority to the following applications: U.S. Provisional Patent Application No. 60/459,491, filed Mar. 31, 2003; U.S. Provisional Patent Application No. 60/552,454, filed Mar. 12, 2004; and U.S. Provisional Patent Application No. 60/555,530 filed Mar. 22, 2004, each of which is incorporated by reference in their entirety for any purpose.

REFERENCE TO SUBMISSION OF A SEQUENCE LISTING AS A TEXT FILE

The Sequence Listing written in file 88883-873449-000232US.TXT, created on Apr. 16, 2013, 315,044 bytes, machine format IBM-PC, MS-Windows operating system, is hereby incorporated by reference.

BACKGROUND OF THE INVENTION

The family Flaviviridae and genus Flavivirus encompasses a number of viruses that are potentially lethal human pathogens. Such viruses include Dengue virus, Yellow Fever virus, Modoc virus, and viruses of the Japanese encephalitis virus serogroup. The Japanese encephalitis virus serogroup includes several closely related viruses, such as Japanese encephalitis virus (JEV), West Nile virus (WNV), St. Louis encephalitis virus, Murray Valley encephalitis virus, and Kunjin virus. Kunjin virus is often referred to as a variant of WNV because of the degree of sequence conservation between these two viruses. Characterized WNV strains have been divided into two groups, lineage I and lineage II, based on sequence analysis.

In 1999, the first case of human WNV infection in the U.S. was reported. Since then, annual epidemics have occurred. In August 2002, transmission of WNV via routes other than mosquito bites was confirmed when four organ recipients were infected by a single organ donor. The virus has since been found to be transmissible by transfusion of blood products (21 confirmed cases) and by breast milk.

Detection of active WNV infection is difficult, as symptoms are non-specific and virus-specific antibodies can usually be detected only after the viremic phase. Furthermore, WNV-specific IgM can persist for more than a year, making it difficult to differentiate between active infection and past exposure. More sensitive detection methods, such as direct detection of viral nucleic acids, are needed. Detection of viral nucleic acids presents a more sensitive method for the early detection of infection by WNV and other flaviviruses than serological methods currently in use.

Other flaviviruses, including members of the Japanese encephalitis virus serogroup, are also human pathogens. These pathogens include Japanese encephalitis serogroup members such as Japanese encephalitis virus, St. Louis encephalitis virus (SLEV), and Murray Valley encephalitis virus, and other flaviviruses such as Dengue virus, Yellow Fever virus, and Modoc virus. Transmission of members of the Japanese encephalitis virus serogroup other than WNV via blood products remains undocumented. However, such transmissions are possible, and increasingly likely to occur as these viruses become more widespread. Therefore, new, sensitive, and specific assays that are capable of detecting these flaviviruses that are human pathogens are highly desirable. Furthermore, a single assay that is capable of detecting several members of the Japanese encephalitis serogroup would also be very desirable.

BRIEF SUMMARY OF THE INVENTION

The present invention provides compositions, methods, and kits for detecting the presence of a nucleic acid of certain flaviviruses, including several members of the Japanese encephalitis virus serogroup. The compositions and methods of the present invention are based, in part, on the discovery of oligonucleotides that can be used e.g., as primers and probes to detect the presence of members of the Japanese encephalitis virus serogroup. For example, West Nile virus, Kunjin virus, Japanese encephalitis virus, St Louis encephalitis virus (SLEV) and Murray Valley encephalitis virus can be detected with the oligonucleotides of the invention. Further, the oligonucleotides of the invention can be used to detect flaviviruses outside the Japanese encephalitis virus serogroup, including, for example, Dengue virus, Montana myotis leukoencephalitis virus, Modoc virus, and Yellow Fever virus. The oligonucleotides of the invention can be used as primers and probes to detect these flaviviruses according to the methods described herein.

In certain aspects, the invention provides a method for detecting a nucleic acid of several members of the Japanese encephalitis virus serogroup. In the method, a detectably-labeled oligonucleotide of the invention, described in detail below, is used as a probe to detect a nucleic acid of several members of the Japanese encephalitis virus serogroup. The probe hybridizes to a nucleic acid of SEQ ID NO.: 16 or the complement thereof, which is a sequence of a conserved region in the 3' untranslated region of flaviviral nucleic acids that can be detected according to the present invention. In certain embodiments of the invention, a template-dependent nucleic acid polymerase with 5'-3' exonuclease activity fragments the probe, wherein fragmentation of the detectably-labeled probe indicates the presence of the nucleic acid of a member of the Japanese encephalitis serogroup.

In certain embodiments, the methods comprise amplifying the nucleic acid of a member of the Japanese encephalitis virus serogroup in the presence of a detectably-labeled oligonucleotide, wherein the detectably-labeled oligonucleotide comprises at least 20 consecutive nucleotides of SEQ ID NO.: 17, or the complement thereof. In other embodiments, the methods comprise amplifying the nucleic acid of a member of the Japanese encephalitis virus serogroup in the presence of a detectably-labeled oligonucleotide, wherein the detectably-labeled oligonucleotide comprises SEQ ID NO.: 18, or the complement thereof. SEQ ID NO.: 18 is an oligonucleotide sequence that hybridizes to a conserved region of currently known flaviviral nucleic acids that can be detected according to the present invention. In still other embodiments, the methods comprise amplifying the nucleic acid of a member of the Japanese encephalitis virus serogroup in the presence of a detectably-labeled nucleic acid probe, wherein the detectably-labeled probe comprises SEQ ID NO.: 28, or the complement thereof. SEQ ID NO.: 28 is a specific probe nucleic acid sequence that can be used to detect flaviviruses according to the present invention.

In certain embodiments, the probe comprises a detectable moiety. The detectable moiety can be any detectable moiety known to one of skill in the art without limitation. For example, the detectable moiety can be a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes. In a preferred embodiment, the fluorescent moiety is 6-carboxyfluorescein.

In certain embodiments, the probe comprises a quencher moiety. The quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl. In a preferred embodiment, the quencher moiety is Cy5™.

In certain aspects, a nucleic acid of a member of the Japanese encephalitis virus serogroup can be detected with an oligonucleotide of the invention. In certain embodiments, a first oligonucleotide that hybridizes to a nucleic acid of SEQ ID NO.: 1 can be used as a primer to amplify a nucleic acid of a member of the Japanese encephalitis virus serogroup. SEQ ID NO.: 1 is based on the discovery of sequences conserved among members of the Japanese encephalitis virus serogroup that can be detected according to the present invention. In certain embodiments, the first primer comprises at least 16 consecutive nucleotides of SEQ ID NO.: 2. In other embodiments, the first primer comprises SEQ ID NO.: 3. SEQ ID NO.: 3 is a primer sequence based on the discovery of a conserved region of all currently known sequences from Japanese encephalitis virus serogroup members that can be detected according to the present invention. In still other embodiments, the first primer comprises SEQ ID NO.: 8. SEQ ID NO.: 8 is a specific primer sequence that can be used to amplify Japanese encephalitis serogroup member nucleic acids according to the present invention.

In certain embodiments, a second oligonucleotide that hybridizes to a nucleic acid of SEQ ID NO.: 9 can be used as a primer to amplify a nucleic acid of a member of the Japanese encephalitis virus serogroup. SEQ ID NO.: 9 is a consensus sequence based on the discovery of sequences conserved among members of the Japanese encephalitis virus serogroup that can be detected according to the present invention. In certain embodiments, the second primer comprises at least 16 consecutive nucleotides of SEQ ID NO.: 10. SEQ ID NO.: 10 is the complement to SEQ ID NO.: 9. In other embodiments, the second primer comprises SEQ ID NO.: 11. SEQ ID NO.: 11 is a primer sequence based on the discovery of a conserved region of all currently known sequences from Japanese encephalitis virus serogroup members that can be detected according to the present invention. In yet other embodiments, the second primer comprises SEQ ID NO.: 15 or SEQ ID NO:74. SEQ ID NO.: 15 and SEQ ID NO:74 are specific primer sequences that can be used to amplify Japanese encephalitis serogroup member nucleic acids according to the present invention. In certain embodiments, the first and second primers can be used together in methods of detecting a nucleic acid of a member of the Japanese encephalitis serogroup.

In certain embodiments, the methods comprise amplifying the nucleic acid of a member of the Japanese encephalitis virus serogroup in the presence of a detectably-labeled nucleic acid probe which comprises a fluorescent moiety and a quencher moiety. In certain embodiments, fragmentation of the detectably-labeled probe by a template-dependent nucleic acid polymerase with 5'-3' nuclease activity separates the fluorescent moiety from the quencher moiety. In certain embodiments, the fragmentation of the probe and thus the presence of the nucleic acid of the a member of the Japanese encephalitis virus serogroup can be detected by monitoring emission of fluorescence.

In certain embodiments, a nucleic acid of a member of the Japanese encephalitis serogroup can be detected by hybridizing the nucleic acid to a primer or probe of the invention that is covalently linked to a solid support. In certain embodiments, the nucleic acid can be detected by hybridizing a detectably-labeled primer or probe to the nucleic acid. In other embodiments, the nucleic acid can be directly detected by incorporating detectable moieties into the nucleic acid.

In other embodiments, a nucleic acid of a member of the Japanese encephalitis serogroup can be detected using a nanoparticle with two or more primers or probes of the invention covalently linked thereto. In still other embodiments, a nucleic acid of a member of the Japanese encephalitis serogroup can be detected using a rolling circle amplification assay with primers and/or probes of the invention. In yet other embodiments, a nucleic acid of a member of the Japanese encephalitis serogroup can be detected using a Strand Displacement Amplification assay with two primers of the invention. In still other embodiments, a nucleic acid of a member of the Japanese encephalitis serogroup can be detected using a transcription-mediated amplification assay using primers and/or probes of the invention. In yet another embodiment, a nucleic acid of a member of the Japanese encephalitis serogroup can be detected using a nucleic acid sequence-based amplification (NASBA) assay, using the primers and/or probes of the invention. In yet another embodiment, a nucleic acid of a member of the Japanese encephalitis serogroup can be detected using diagnostic PCR with primers and/or probes of the invention.

In certain embodiments, the first and second primers and a probe of the invention can be used together in methods of detecting a member of the Japanese encephalitis serogroup. In certain embodiments, a nucleic acid of a member of the Japanese encephalitis serogroup can be detected using a probe of the invention that comprises a molecular beacon. In other embodiments, a nucleic acid of a member of the Japanese encephalitis serogroup can be detected using a nucleic acid sequenced-based amplification assay with primers and/or probes of the invention. In yet other embodiments, a nucleic acid of a member of the Japanese encephalitis serogroup can be detected by amplifying the nucleic acid with two primers of the invention, then detecting the nucleic acid with a detectably-labeled probe of the invention. In certain embodiments, a nucleic acid of a member of the Japanese encephalitis serogroup can be detected using a dot blot assay with primers and/or probes of the invention. In other embodiments, a nucleic acid of a member of the Japanese encephalitis serogroup can be detected using a reverse dot blot assay with primers and/or probes of the invention. In still other embodiments, a nucleic acid of a member of the Japanese encephalitis serogroup can be detected using a multivalent probe such as a dendrimer.

In addition to the foregoing methods, the present invention further provides nucleic acid primers and probes for detecting a nucleic acid of a member of the Japanese encephalitis serogroup. In certain aspects, the invention provides a nucleic acid primer for detecting a member of the Japanese encephalitis virus serogroup. In certain embodiments, the primer comprises a nucleic acid that hybridizes to a nucleic acid of SEQ ID NO.: 1. In certain embodiments, the nucleic acid primer comprises at least 16 consecutive nucleotides of SEQ ID NO.: 2. In other embodiments, the nucleic acid primer comprises SEQ ID NO.: 3. In still other embodiments, the nucleic acid primer comprises SEQ ID NO.: 8.

In certain embodiments, the nucleic acid primer comprises $N^6$-alkyl-deoxyadenosine at position 24 of SEQ ID NO.: 8. In a specific embodiment, the nucleic acid primer comprises $N^6$-methyl-deoxyadenosine at position 24 of SEQ ID NO.: 8. In certain embodiments, the nucleic acid primer comprises $N^6$-alkyl-deoxyadenosine at position 25 of SEQ ID NO.: 8. In a specific embodiment, the nucleic acid primer comprises $N^6$-tert-butyl-benzyl-deoxyadenosine at position 25 of SEQ ID NO.: 8. In certain embodiments, the nucleic acid primer comprises $N^6$-alkyl-deoxyadenosine at positions 24 and 25 of SEQ ID NO.: 8. In still another specific embodiment, the nucleic acid primer comprises $N^6$-methyl-deoxyadenosine at position 24 of SEQ ID NO.: 8 and $N^6$-tert-butyl-benzyl-deoxyadenosine at position 25 of SEQ ID NO.: 8.

In certain embodiments, the invention provides a nucleic acid primer for detecting a member of the Japanese encephalitis virus serogroup. In certain embodiments, the primer comprises a nucleic acid that hybridizes to a nucleic acid of SEQ ID NO.: 9. In other embodiments, the nucleic acid primer comprises at least 16 consecutive nucleotides of SEQ ID NO.: 10. In still other embodiments, the nucleic acid primer comprises SEQ ID NO.: 11. In yet other embodiments, the nucleic acid primer comprises SEQ ID NO.: 15 or SEQ ID NO:74. In certain embodiments, the nucleic acid primer comprises $N^6$-alkyl-deoxyadenosine at position 23 of SEQ ID NO.: 15 or at position 25 of SEQ ID NO:74. In a specific embodiment, the nucleic acid primer comprises $N^6$-tert-butyl-benzyl-deoxyadenosine at position 23 of SEQ ID NO.: 15 or at position 25 of SEQ ID NO:74.

In other aspects, the invention provides a nucleic acid probe for detecting a nucleic acid of a flavivirus. Flavivirus nucleic acids that can be detect with the probe include, for example, members of the Japanese encephalitis virus serogroup, Dengue virus, Yellow Fever virus, Montana myotis leukencephalitis virus, and Modoc virus. In certain embodiments, the probe comprises a nucleic acid that hybridizes to a nucleic acid of SEQ ID NO.: 16, or the complement thereof. In certain embodiments, the nucleic acid probe comprises at least 20 consecutive nucleotides of SEQ ID NO.: 17, or the complement thereof. In other embodiments, the nucleic acid probe comprises SEQ ID NO.: 18, or the complement thereof. In still other embodiments, the nucleic acid probe comprises SEQ ID NO.: 28, or the complement thereof.

In certain embodiments, the invention provides a nucleic acid probe comprising a fluorescent moiety and a quencher moiety. In certain embodiments, the fluorescent moiety is positioned relative to the quencher moiety such that a photon emitted by the fluorescent moiety is absorbed by the quencher moiety when the probe is intact. Fragmentation of the probe by an enzyme with 5' nuclease activity separates the fluorescent moiety from the quencher moiety such that a photon emitted by the fluorescent moiety can be detected.

In other aspects, the invention provides a kit for the detection of a nucleic acid of a member of the Japanese encephalitis virus serogroup. In certain embodiments, the kit comprises an oligonucleotide of the invention. In further embodiments, the kit comprises a combination of one or more of the primers and probes of the invention. For example, in one embodiment the kit comprises a first nucleic acid primer that hybridizes to a nucleic acid of SEQ ID NO.: 1; a second nucleic acid primer that hybridizes to a nucleic acid of SEQ ID NO.: 9; and a nucleic acid probe that hybridizes to a nucleic acid of SEQ ID NO.: 16, or the complement thereof.

In certain embodiments, the first nucleic acid primer of the kits of the invention comprises at least 16 consecutive nucleotides of SEQ ID NO.: 2. In other embodiments, the first nucleic acid primer comprises SEQ ID NO.: 3. In yet other embodiments, the first nucleic acid primer comprises SEQ ID NO.: 8. In certain embodiments, the first nucleic acid primer comprises $N^6$-alkyl-deoxyadenosine at position 24 of SEQ ID NO.: 8. In a specific embodiment, the first nucleic acid primer comprises $N^6$-methyl-deoxyadenosine at position 24 of SEQ ID NO.: 8. In certain embodiments, the first nucleic acid primer comprises $N^6$-alkyl-deoxyadenosine at position 25 of SEQ ID NO.: 8. In a specific embodiment, the first nucleic acid primer comprises $N^6$-tert-butyl-benzyl-deoxyadenosine at position 25 of SEQ ID NO.: 8. In certain embodiments, the first nucleic acid primer comprises $N^6$-alkyl-deoxyadenosine at positions 24 and 25 of SEQ ID NO.: 8. In still another specific embodiment, the first nucleic acid primer comprises $N^6$-methyl-deoxyadenosine at position 24 of SEQ ID NO.: 8 and $N^6$-tert-butyl-benzyl-deoxyadenosine at position 25 of SEQ ID NO.: 8.

In certain embodiments, the second nucleic acid primer of the kits of the invention comprises at least 16 consecutive nucleotides of SEQ ID NO.: 10. In other embodiments, the second nucleic acid primer comprises SEQ ID NO.: 11. In still other embodiments, the second nucleic acid primer comprises SEQ ID NO.: 15 or SEQ ID NO:74. In certain embodiments, the second nucleic acid primer comprises $N^6$-alkyl-deoxyadenosine at position 23 of SEQ ID NO.: 15 or at position 25 of SEQ ID NO:74. In a specific embodiment, the second nucleic acid primer comprises $N^6$-tert-butyl-benzyl-deoxyadenosine at position 23 of SEQ ID NO.: 15 or at position 25 of SEQ ID NO:74.

In certain embodiments, the nucleic acid probe of the kits of the invention comprises at least 20 consecutive nucleotides of SEQ ID NO.: 17, or the complement thereof. In other embodiments, the nucleic acid probe comprises SEQ ID NO.: 18, or the complement thereof. In still other embodiments, the nucleic acid probe comprises SEQ ID NO.: 28, or the complement thereof.

In certain embodiments, the kits of the invention comprise an oligonucleotide useful as a nucleic acid probe, wherein one or more detectable moieties is attached to the nucleic acid probe. In certain embodiments, the one or more detectable moieties is a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes. In a preferred embodiment, the fluorescent moiety is 6-carboxyfluorescein.

In certain embodiments, the kits of the invention comprise an oligonucleotide useful as a nucleic acid probe, wherein at least one quencher moiety is attached to the nucleic acid probe. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl. In a preferred embodiment, the quencher moiety is Cy5™. In other embodiments, the probe comprises at least one detectable moiety, e.g. a fluorescent moiety and at least one quencher moiety.

In certain embodiments, the kits of invention comprise a thermostable DNA polymerase. In certain embodiments, the thermostable DNA polymerase has reverse transcription activity. In certain embodiments, the kits of the invention additionally comprise instructions for detecting a nucleic acid of a member of the Japanese encephalitis virus serogroup according to the methods of the invention.

The present invention also provides isolated polynucleotides comprising SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

The present invention also provides vectors comprising a polynucleotide comprising SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

The present invention also provides oligonucleotides comprising a sequence of at least 10 contiguous nucleotides that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, SEQ ID NO:40 or a complement thereof. In some embodiments, the oligonucleotide hybridizes to SEQ ID NO: 68 or a complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67. In some embodiments, the oligonucleotide has fewer than 100 nucleotides.

The present invention also provides reaction mixtures comprising an oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, SEQ ID NO:40 or a complement thereof.

In some embodiments, the oligonucleotide hybridizes to SEQ ID NO: 68 or a complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67.

In some embodiments, the reaction mixtures comprise an oligonucleotide selected from the group consisting of SEQ ID NO:64 and SEQ ID NO:65; and an oligonucleotide selected from the group consisting of SEQ ID NO:66 and SEQ ID NO:67. In some embodiments, the oligonucleotide has fewer than 100 nucleotides. In some embodiments, the reaction mixtures further comprise a detectably-labeled oligonucleotide that hybridizes to SEQ ID NO:16 or a complement thereof.

In some embodiments, the reaction mixture comprises a DNA polymerase.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

The present invention also provides methods of detecting a St. Louis encephalitis virus. In some embodiments, the methods comprise amplifying a nucleic acid of St. Louis encephalitis virus with at least one oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, or SEQ ID NO:40 or a complement thereof, under conditions to allow for initiation of amplification of at least part of the nucleotide sequence from the oligonucleotide; and detecting the amplified nucleic acid, thereby detecting a St. Louis encephalitis virus.

In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67. In some embodiments, the oligonucleotide hybridizes to SEQ ID NO:68 or a complement of SEQ ID NO:69. In some embodiments, the oligonucleotide has fewer than 100 nucleotides.

In some embodiments, the nucleic acid of St. Louis encephalitis virus is amplified with a primer selected from the group consisting of SEQ ID NO:64 and SEQ ID NO:65; and a primer selected from the group consisting of SEQ ID NO:66 and SEQ ID NO:67.

In some embodiments, the detecting step comprises hybridizing a detectably-labeled oligonucleotide that hybridizes to SEQ ID NO:16 to the amplified nucleic acid of the nucleic acid of St. Louis encephalitis virus; and detecting hybridization of the probe to the amplified nucleic acid.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

In some embodiments, the quantity of amplified nucleic acid is determined during the amplifying step, thereby quantifying the virus in the sample.

In some embodiments, the amplifying step is performed in an amplification reaction mixture comprising a template-dependent nucleic acid polymerase with 5'-3' exonuclease activity under conditions that allow the template-dependent nucleic acid polymerase to fragment the detectably-labeled oligonucleotide; and the method further comprises detecting fragmentation of the detectably-labeled nucleic acid oligonucleotide.

The present invention also provides kits for detecting St. Louis encephalitis virus. In some embodiments, the kits comprise a oligonucleotide comprising a nucleotide sequence that hybridizes to SEQ ID NO:29 or a complement thereof, SEQ ID NO:30 or a complement thereof, SEQ ID NO:31 or a complement thereof, SEQ ID NO:32 or a complement thereof, SEQ ID NO:33 or a complement thereof, SEQ ID NO:34 or a complement thereof, SEQ ID NO:35 or a complement thereof, SEQ ID NO:36 or a complement thereof, SEQ ID NO:37 or a complement thereof, SEQ ID NO:38 or a complement thereof, SEQ ID NO:39 or a complement thereof, or SEQ ID NO:40 or a complement thereof.

In some embodiments, the oligonucleotide hybridizes to SEQ ID NO:68 or the complement of SEQ ID NO:69. In some embodiments, the oligonucleotide comprises a sequence selected from the group consisting of SEQ ID NO:64, SEQ ID NO:65, SEQ ID NO:66, and SEQ ID NO:67. In some embodiments, the oligonucleotide is selected from the group consisting of SEQ ID NO:64, SEQ ID NO:65, SEQ ID NO:66, and SEQ ID NO:67.

In some embodiments, the kits comprise an oligonucleotide selected from the group consisting of SEQ ID NO:64 and SEQ ID NO:65; and an oligonucleotide selected from the group consisting of SEQ ID NO:66 and SEQ ID NO:67. In some embodiments, the oligonucleotide has fewer than 100 nucleotides. In some embodiments, the kits further comprise a detectably-labeled oligonucleotide that hybridizes to SEQ ID NO:16 or a complement thereof.

The present invention also provides oligonucleotides comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

The present invention also provides reaction mixtures comprising an oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

In some embodiments, the reaction mixtures further comprise a detectably-labeled oligonucleotide that hybridizes to SEQ ID NO:25 or a complement thereof. In some embodiments, the reaction mixtures further comprise a detectably-labeled oligonucleotide comprising FGGTCTAGAIGGTTA-GAGGAGACCCTCCAG (SEQ ID NO:75), wherein F is CY5 and I is FAM. In some embodiments, the reaction mixtures further comprise a detectably-labeled oligonucleotide that hybridizes to SEQ ID NO:16 or a complement thereof.

In some embodiments, the reaction mixture comprises a DNA polymerase. In some embodiments, the reaction mixtures comprise at least one upstream primer and at least one downstream primer.

The present invention also provides methods of detecting a yellow fever virus. In some embodiments, the methods comprise amplifying a nucleic acid of yellow fever virus with at least one oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63 under conditions to allow for initiation of amplification of at least part of the nucleotide sequence from the oligonucleotide; and detecting the amplified nucleic acid, thereby detecting a yellow fever virus.

In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the detecting step comprises hybridizing a detectably-labeled oligonucleotide that hybridizes to SEQ ID NO:25, or a complement thereof, to the amplified nucleic acid of the nucleic acid of yellow fever virus; and detecting hybridization of the detectably-labeled oligonucleotide to the amplified nucleic acid.

In some embodiments, the detectably-labeled oligonucleotide comprises FGGTCTAGAIGGTTAGAGGAGAC-CCTCCAG (SEQ ID NO:75), wherein F is CY5 and I is FAM. In some embodiments, the detecting step comprises hybridizing a detectably-labeled oligonucleotide that hybridizes to SEQ ID NO:16, or a complement thereof, to the amplified nucleic acid of the nucleic acid of yellow fever virus; and detecting hybridization of the detectably-labeled oligonucleotide to the amplified nucleic acid.

In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

In some embodiments, the oligonucleotide has fewer than 100 nucleotides. In some embodiments, the quantity of amplified nucleic acid is determined during the amplifying step, thereby quantifying the virus in the sample.

In some embodiments, the amplifying step is performed in an amplification reaction mixture comprising a template-dependent nucleic acid polymerase with 5'-3' exonuclease activity under conditions that allow the template dependent nucleic acid polymerase to fragment the detectably-labeled oligonucleotide; and the method further comprises detecting fragmentation of the detectably-labeled oligonucleotide.

The present invention also provides kits for detecting yellow fever virus. The kit comprises an oligonucleotide comprising a sequence selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63. In some embodiments, the oligonucleotide is selected from the group consisting of SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63.

In some embodiments, the kits further comprise a detectably-labeled oligonucleotide that hybridizes to SEQ ID NO:16 or a complement thereof. In some embodiments, the kits further comprise a detectably-labeled oligonucleotide that hybridizes to SEQ ID NO:25 or a complement thereof. In some embodiments, the kits further comprise a detectably-labeled oligonucleotide comprising FGGTCTAGAIGGTTA-GAGGAGACCCTCCAG (SEQ ID NO:75), wherein F is CY5 and I is FAM.

In some embodiments, the reaction mixture comprises a DNA polymerase. In some embodiments, the reaction mixtures comprise at least one upstream primer and at least one downstream primer.

The present invention also provides oligonucleotides comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

The present invention also provides reaction mixtures comprising an oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the reaction mixtures further comprise a detectably-labeled oligonucleotide that hybridizes to SEQ ID NO:16 or a complement thereof. In some embodiments, the reaction mixture comprises a DNA polymerase. In some embodiments, the reaction mixtures comprise at least one upstream primer and at least one downstream primer.

The present invention also provides methods of detecting a Dengue fever virus. In some embodiments, the methods comprise amplifying a nucleic acid of Dengue fever virus with at least one oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55 under conditions to allow for initiation of amplification of at least part of the nucleotide sequence from the oligonucleotide; and detecting the amplified nucleic acid, thereby detecting a Dengue fever virus.

In some embodiments, the method further comprises hybridizing a detectably-labeled oligonucleotide that hybridizes to SEQ ID NO:16 to the amplified Dengue fever virus nucleic acid; and detecting hybridization of the oligonucleotide to the amplified nucleic acid. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the nucleic acid is amplified with at least one upstream primer and at least one downstream primer. In some embodiments, the detectably-labeled oligonucleotide comprises at least 20 consecutive nucleotides of SEQ ID NO.:17, or the complement thereof. In some embodiments, the detectably-labeled oligonucleotide comprises SEQ ID NO.:28, or the complement thereof. In some embodiments, the detectably-labeled oligonucleotide comprises a fluorescent moiety. In some embodiments, the detectably-labeled oligonucleotide further comprises a quencher moiety.

In some embodiments, the oligonucleotide has fewer than 100 nucleotides. In some embodiments, the quantity of amplified nucleic acid is determined during the amplifying step, thereby quantifying the virus in the sample. In some embodiments, the amplifying step is performed in an amplification reaction mixture comprising a template-dependent nucleic acid polymerase with 5'-3' exonuclease activity under conditions that allow the template dependent nucleic acid polymerase to fragment the detectably-labeled oligonucleotide; and the method further comprises detecting fragmentation of the detectably-labeled nucleic acid oligonucleotide.

The present invention also provides kits for detecting Dengue virus. In some embodiments, the kit comprises an oligonucleotide comprising a sequence selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. In some embodiments, the oligonucleotide is selected from the group consisting of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

In some embodiments, the kits further comprise a detectably-labeled oligonucleotide that hybridizes to SEQ ID NO:16 or a complement thereof. In some embodiments, the reaction mixture comprises a DNA polymerase.

In some embodiments, quantification step is performed using either an internal or an external control nucleic acid. See U.S. Pat. Nos. 5,476,774 and 5,219,727, which are incorporated by reference in their entirety.

BRIEF DESCRIPTION OF THE DRAWINGS

FIGS. 1A-1E present a region of conserved sequence, identified as SEQ ID NO.: 1, in the 3' untranslated region of the genomes of the flaviviruses that can be detected using the compositions and methods of the present invention and that can be bound by a primer of the invention. SEQ ID NO.: 2 represents the complement of SEQ ID NO.: 1. The conserved region in the 3' untranslated region of the genomes of the flaviviruses=SEQ ID NOS:71 and 81-241, respectively.

FIGS. 2A-2B present a region of conserved sequence, identified as SEQ ID NO.: 9, in the 3' untranslated region of the genomes of the flaviviruses that can be detected using the compositions and methods of the present invention and that can be bound by a primer of the invention. SEQ ID NO.: 10 represents the complement of SEQ ID NO.: 9. The conserved region in the 3' untranslated region of the genomes of the flaviviruses=SEQ ID NOS:72 and 242-315, respectively.

FIGS. 3A-3F present a region of conserved sequence, identified as SEQ ID NO.: 16, in the 3' untranslated region of the genomes of the flaviviruses that can be detected using the compositions and methods of the present invention and that can be bound by a probe of the invention. SEQ ID NO.: 17 represents the complement of SEQ ID NO.: 16. The conserved region in the 3' untranslated region of the genomes of the flaviviruses=SEQ ID NO:73 and 316-605, respectively.

FIGS. 4A-4D present an alignment of the nucleic acid sequences of the oligonucleotides of the invention with nucleic acid sequences of Japanese encephalitis virus serogroup members (SEQ ID NOS:7, 606-670, 7, 671-736, 15, 737-788, 16 and 789-839, respectively).

FIGS. 5A-5B present an alignment of the nucleic acid sequences of the oligonucleotides of the invention with nucleic acid sequences of detectable flaviviruses that are not members of the Japanese encephalitis virus serogroup (SEQ ID NOS:16, 840-909, 16 and 910-919, respectively).

FIGS. 7A-7B present the sequence of the 3' untranslated region of the genomes of a number of SLEV isolates that can be detected using the compositions and methods of the present invention and that can be bound by a primer of the invention. Sequences for the following isolates are depicted: BFS1750 (SEQ ID NO:29), 1750-Std (SEQ ID NO:30), TD6-4G (SEQ ID NO:31), CoaV750 (SEQ ID NO:32), L695121.05 (SEQ ID NO:33), TNM771K (SEQ ID NO:34), MSI-7 (SEQ ID NO:35), Kern217 (SEQ ID NO:36), CoaV608 (SEQ ID NO:37), TBH-28 (SEQ ID NO:38), VR1265 (SEQ ID NO:39), and CoaV353 (SEQ ID NO:40).

DETAILED DESCRIPTION OF THE INVENTION

1. Abbreviations

Figure 6:
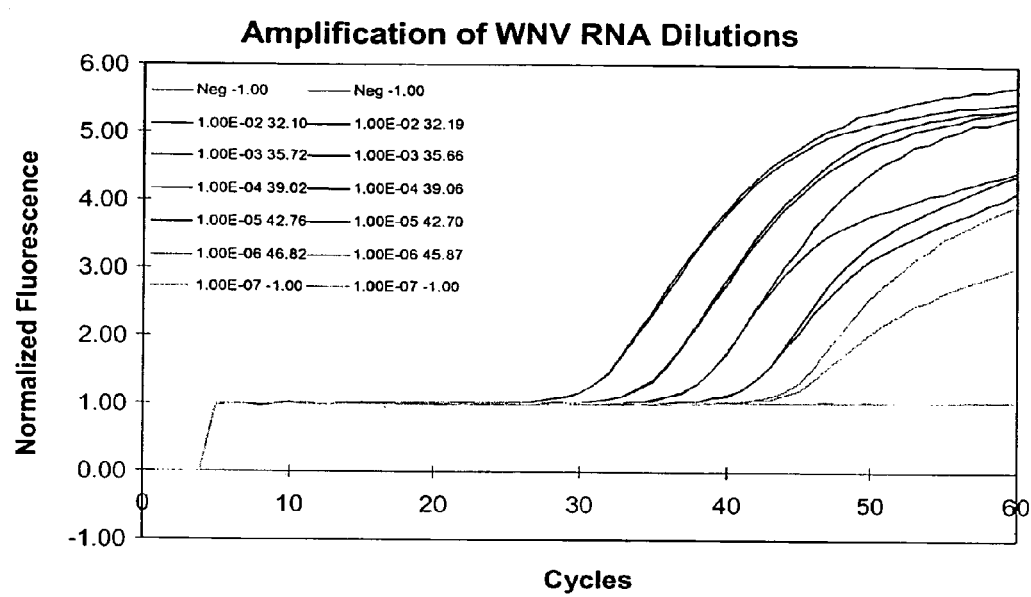
FIG. 6 presents a plot of normalized fluorescence versus number of amplification cycles showing detection of serially diluted extracted WNV RNA using the oligonucleotides of the invention.

The abbreviations used throughout the specification to refer to nucleic acids comprising specific nucleotide sequences are the conventional one-letter abbreviations. Thus, when included in a nucleic acid, the naturally occurring encoding nucleotides are abbreviated as follows: adenine (A), guanine (G), cytosine (C), thymine (T) and uracil (U). Also, unless otherwise specified, nucleic acid sequences that are represented as a series of one-letter abbreviations are presented in the 5'->3' direction.

2. Definitions

An "amplification reaction" refers to any reaction (e.g., chemical, enzymatic, or other type of reaction) that results in increased copies of a template nucleic acid sequence or increased signal indicating the presence of the template. Amplification reactions include, e.g., the polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) branched DNA signal amplification (bDNA) (Iqbal et al., *Mol. Cell. Probes* 13(4): 315-320 (1999)) and Q-Beta Replicase (Lizardi et al., *Bio/Technology* 6:1197 (1988)).

As used herein, a "sample" refers to any substance containing or presumed to contain nucleic acid. The sample can be of natural or synthetic origin and can be obtained by any means known to those of skill in the art. The sample can be a sample of tissue or fluid isolated from an individual or individuals, including, but not limited to, for example, skin, plasma, serum, whole blood, spinal fluid, semen, seminal fluid, lymph fluid, synovial fluid, urine, tears, blood cells, organs, tumors, bronchio-alveolar lavage, and also to samples of in vitro cell culture constituents (including but not limited to conditioned medium resulting from the growth of cells in cell culture medium, recombinant cells and cell components). A nucleic acid can be obtained from a biological sample by any procedure known in the art.

As used herein, the terms "nucleic acid," "polynucleotide" and "oligonucleotide" refer to primers, probes, oligomer fragments to be detected, oligomer controls and unlabeled blocking oligomers and is generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611, 5,955,589, 5,844,106, 5,789,562, 5,750,343, 5,728,525, and 5,679,785, each of which is incorporated herein by reference in its entirety.

Furthermore, a nucleic acid, polynucleotide or oligonucleotide can comprise one or more modified sugar moieties including, but not limited to, arabinose, 2-fluoroarabinose, xylulose, and a hexose.

It is not intended that the present invention be limited by the source of a nucleic acid, polynucleotide or oligonucleotide. A nucleic acid, polynucleotide or oligonucleotide can be from a human or non-human mammal, or any other organism, or derived from any recombinant source, synthesized in vitro or by chemical synthesis. A nucleic acid, nucleotide, polynucleotide or oligonucleotide may be DNA, RNA, cDNA, DNA-RNA, locked nucleic acid (LNA), peptide nucleic acid (PNA), a hybrid or any mixture of the same, and may exist in a double-stranded, single-stranded or partially double-stranded form. A nucleic acid may also be a derivative nucleic acid as described in U.S. Pat. No. 5,696,248, which is hereby incorporated by reference in its entirety. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

There is no intended distinction in length between the terms nucleic acid, polynucleotide and oligonucleotide, and these terms will be used interchangeably. These terms include double- and single-stranded DNA, as well as double- and single-stranded RNA. Oligonucleotides of the invention may be used as primers and/or probes. Thus oligonucleotides referred to herein as "primers" may act as probes and oligonucleotides referred to as "probes" may act as primer in some embodiments.

The term "residue" as used herein refers to a nucleotide or base within a nucleic acid as defined above. A residue can be any nucleotide known to one of skill in the art without limitation, including all of the biologically occurring nucleotides and non-biologically occurring nucleotides described above.

The term "primer" refers to an oligonucleotide which is capable of acting as a point of initiation of polynucleotide synthesis along a template nucleic acid strand when placed under conditions that permit synthesis of a primer extension product that is complementary to the template strand. The primer can be obtained from a recombinant source, as in a purified restriction fragment, or produced synthetically. Primer extension conditions typically include the presence of four different deoxyribonucleoside triphosphates and an agent with polymerization activity such as DNA polymerase or reverse transcriptase, in a suitable buffer (a "buffer" can include substituents which are cofactors, or which affect pH, ionic strength, etc.), and at a suitable temperature. The primer is preferably single-stranded for maximum efficiency in amplification. Primers of the invention may be, e.g., between 5 to 500 nucleotides, and in some embodiments will have at least 10, 20, 30, 25, 30, 40, 50, 75, or 100 nucleotides and/or have fewer than 500, 300, 200, 100, 90, 80, 70, 60, 50, 40, 30, 25, or 20 nucleotides.

The term "hybridize" refers to binding of a single-stranded nucleic acid or a locally single-stranded region of a double-stranded nucleic acid to another single-stranded nucleic acid or a locally single-stranded region of a double-stranded nucleic acid having a complementary sequence. As one of skill in the art is aware, it is not necessary for two nucleic acid strands to be entirely complementary to hybridize to each other. Depending on the hybridization conditions, a nucleic acid can hybridize to its complement even if there are few, some, or many mismatches, deletions, or additions in one or both strands. In certain embodiments, the primers and probes of the invention can hybridize to an at least partially complementary nucleic acid selectively, as defined below. In certain embodiments, the primers and probes of the invention can hybridize to an at least partially complementary sequence under stringent conditions, as defined below.

The terms "stringent" or "stringent conditions", as used herein, denote hybridization conditions of low ionic strength and high temperature, as is well known in the art; see for example Maniatis et al., 1989, Molecular Cloning: A Laboratory Manual, 2d Edition; Current Protocols in Molecular Biology, 1988, ed. Ausubel et al., J. Wiley & Sons publ., New York, and Tijssen, 1993, Techniques in Biochemistry and Molecular Biology—Hybridization with Nucleic Acid Probes, "Overview of principles of hybridization and the strategy of nucleic acid assays," each of which is hereby incorporated by reference. Generally, stringent conditions are selected to be about 5-30° C. lower than the thermal melting point (Tm) for the specified sequence at a defined ionic strength and pH. Alternatively, stringent conditions are selected to be about 5-15° C. lower than the thermal melting point (Tm) for the specified sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). Stringent conditions may also be modified with the addition of hybridization destabilizing agents such as formamide.

The terms "selective" or "selective conditions", as used herein, denote hybridization conditions for the primers and/or probes of the invention that permit amplification, detection and/or quantification of a detectable flavivirus nucleic acid in a sample that may contain additional nucleic acids not derived from the detectable flavivirus, or derived from unrelated regions of the flaviviral genome. Detectable flaviviruses are described below.

The "complement" of a nucleic acid sequence, as used herein, refers to an oligonucleotide which, when aligned with the nucleic acid sequence such that the 5' end of one sequence is paired with the 3' end of the other, is in anti-parallel association. The complement of a nucleic acid sequence need not exactly match every nucleotide of the sequence; stable duplexes may contain mismatched base pairs or unmatched bases. Those skilled in the art of nucleic acid technology can determine duplex stability by empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the potential base pairs are disassociated.

As used herein, the term "probe" refers to an oligonucleotide which can form a duplex structure with a region of a nucleic acid, due to complementarity of at least one sequence in the probe with a sequence in the region. The probe, preferably, does not contain a sequence complementary to sequence(s) of a primer. As discussed below, the probe can be labeled or unlabeled. The 3' terminus of the probe can be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3' hydroxyl or by using a nucleotide that lacks a 3' hydroxyl such as a dideoxynucleotide.

The term "detectable moiety" as used herein refers to any atom or molecule which can be used to provide a detectable (optionally quantifiable) signal, and which can be attached to a nucleic acid or protein. Detectable moieties may provide signals detectable by fluorescence, radioactivity, colorimetry, gravimetry, X-ray diffraction or absorption, magnetism, enzymatic activity, and the like. Convenient detectable moieties for the present invention include those that facilitate detection of the size of an oligonucleotide fragment.

The term "fluorescent moiety" as used herein refers to a chemical moiety that can emit light under conditions appropriate for the particular moiety. Typically, a particular fluorescent moiety can emit light of a particular wavelength following absorbance of light of shorter wavelength. The wavelength of the light emitted by a particular fluorescent moiety is characteristic of that moiety. Thus, a particular fluorescent moiety can be detected by detecting light of an appropriate wavelength following excitation of the fluorescent moiety with light of shorter wavelength. Examples of fluorescent moieties that can be used in the methods and compositions of the present invention include, but are not limited to, fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

The term "quencher moiety" as used herein refers to a chemical moiety that can absorb energy emitted by a fluorescent moiety when the quencher moiety is sufficiently close to the fluorescent moiety, for example, when both the quencher and fluorescent moiety are linked to a common polynucleotide. This phenomenon is generally known in the art as fluorescent resonance energy transfer ("FRET"). A quencher moiety can re-emit the energy absorbed from a fluorescent moiety in a signal characteristic for that quencher moiety, and thus a quencher can also be a "fluorescent moiety." Alternatively, a quencher moiety may dissipate the energy absorbed from a fluorescent moiety as heat.

As defined herein, "5' to 3' nuclease activity" or "5' nuclease activity" refers to that activity of an enzyme whereby nucleotides are removed from the 5' end of an oligonucleotide in a sequential manner. The 5' nuclease activity can be a 5' to 3' exonuclease activity or a 5' to 3' endonuclease activity. For example, many template-specific nucleic acid polymerases exhibit a 5' to 3' exonuclease activity that is traditionally associated with some DNA polymerases, (i.e., E. coli DNA polymerase I has this activity whereas the Klenow fragment of E. coli DNA polymerase I does not). The 5' to 3' exonuclease activity can also cleave a substrate nucleic acid more than one phosphodiester bond (nucleotide) from the 5' end of the substrate. Although not intending to be bound by any particular theory of operation, it is believed that this aspect of 5' to 3' exonuclease activity associated with DNA polymerases, which leads to release of cleaved oligonucleotide fragments from probes, can depend upon the particular nucleotide composition of the probe. For instance, the number of matches or mismatches between nucleotides of the oligonucleotide and template nucleic acid, particularly at the 5' end of the oligonucleotide, can influence this activity, as described, for example, by Holland et al., 1991, Proc. Natl. Acad. Sci. USA 88:7276-80, which is incorporated herein by reference in its entirety.

The term "control 5' nuclease reaction" as used herein refers to a 5' nuclease reaction performed as described below on a known amount, e.g., copy number, of a nucleic acid of a detectable flavivirus. The amount of fluorescence emitted by such a reaction can be compared to a reaction performed on a sample with an unknown quantity of a nucleic acid of a Japanese encephalitis virus serogroup to assess the amount of such nucleic acid present in the sample.

The term "adjacent" as used herein refers to the positioning of the primer with respect to the probe on the same or the complementary strand of the template nucleic acid. The primer and probe may be separated by more than about 150 nucleotides, more than about 125 nucleotides, more than about 100 nucleotides, more than about 80 nucleotides, more than about 60 nucleotides, more than about 50 nucleotides, more than about 40 nucleotides, more than about 30 nucleotides, more than about 20 nucleotides, by about 1 to about 20 nucleotides, by about 1 to about 10 nucleotides, or may directly abut one another. If it is desired to detect a flavivirus nucleic acid with a polymerization-independent process, the probe is preferably separated from the probe by about 1 to about 10 nucleotides. In the polymerization-dependent process, for example, a PCR amplification and detection methods as taught herein, the probe may hybridize to the detectable nucleic acid anywhere within the sequence to be amplified that is downstream of a primer, thus allowing primer extension to position the polymerase so that the probe is fragmented.

The term "thermostable nucleic acid polymerase" refers to an enzyme which is relatively stable to heat when compared, for example, to nucleotide polymerases from *E. coli* and which catalyzes the polymerization of nucleoside triphosphates. Generally, such enzymes are obtained from organisms considered by those in the art to be thermophilic organisms. Generally, the enzyme will initiate synthesis at the 3' end of a primer annealed to the primer binding sequence, and will continue synthesis of a new strand toward the 5' end of the template. If the polymerase possesses a 5' to 3' nuclease activity, it can hydrolyze intervening probes annealed to the template to release both labeled and unlabeled probe fragments, until polymerization terminates or all probe fragments dissociate from the nucleic acid to be detected. A representative thermostable enzyme isolated from *Thermus aquaticus* (Taq) is described in U.S. Pat. No. 4,889,818 and a method for using it in conventional PCR is described in Saiki et al., 1988, *Science* 239:487-91. Another representative thermostable enzyme includes *Thermus* species Z05 DNA polymerase. See, e.g., U.S. Pat. No. 5,674,738."

Taq DNA polymerase has a DNA synthesis-dependent, strand replacement 5'-3' exonuclease activity (see Gelfand, "Taq DNA Polymerase" in PCR Technology Principles and Applications for DNA Amplification, Erlich, Ed., Stockton Press, N.Y. (1989), Chapter 2). Thus, Taq DNA polymerase does not degrade the probe when it is unbound to template DNA.

The term "5' nuclease reaction" of a nucleic acid primer or probe refers to the degradation of a probe hybridized to the nucleic acid when the primer is extended by a nucleic acid polymerase having 5' to 3' nuclease activity, as defined above and described in detail below. Such reactions are based on those described in U.S. Pat. Nos. 6,214,979, 5,804,375, 5,487,972 and 5,210,015, each of which is hereby incorporated by reference in its entirety.

To determine "percent complementarity" or "percent identity" of two nucleic acid sequences, the sequences are aligned for optimal comparison purposes (e.g., gaps can be introduced in the sequence of a first nucleic acid sequence for optimal alignment with a second nucleic acid sequence). The nucleotides at corresponding nucleotide positions are then compared. When a position in the first sequence is occupied by a complementary nucleotide as the corresponding position in the second sequence, then the molecules are complementary at that position. Likewise, when a position in the first sequence is occupied by the same nucleotide as the corresponding position in the second sequence, then the molecules are identical at that position. The percent complementarity (or percent identity) between the two sequences is a function of the number of complementary positions (or identical positions) shared by the sequences divided by the total number of positions compared (i.e., % complementarity=number of complementary overlapping positions/total number of positions of the shorter nucleotide×100%; and % identity=number of identical overlapping positions/total number of positions of the shorter nucleotide×100%).

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST program of Altschul et al., 1990, J. Mol. Biol. 215:403.

The practice of the present invention will employ, unless otherwise indicated, conventional techniques of molecular biology, microbiology and recombinant DNA techniques, which are within the skill of the art. Such techniques are explained fully in the literature. See, e.g., Sambrook et al., 2001, Molecular Cloning: A Laboratory Manual, Third Edition, Cold Spring Harbor Laboratory Press, Cold Spring Harbor, N.Y.; Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.).

3. Nucleic Acid Primers and Probes for Detecting a Nucleic Acid of a Member of the Japanese Encephalitis Serogroup and Certain Other Flaviviruses The present invention provides oligonucleotides useful as primers and probes to detect the presence of a nucleic acid of a member of the Japanese encephalitis virus serogroup and certain other members of the genus Flavivirus, and methods of their use. These primers and probes are described in detail below. It is noted that while the primers discussed herein may be designated as particularly useful for amplifying a particular virus type (e.g., West Nile virus, SLEV, Dengue virus, yellow fever virus, etc.), the primers an be useful for amplifying other viruses as well.

The oligonucleotides useful in the methods of the invention may be designed to comprise nucleotide sequences, or complements thereof, that are conserved between different strains of Flaviviruses or that are conserved between two or more members of the Japanese encephalitis virus serogroup or other members of the genus Flavivirus. Oligonucleotides that comprise sequences conserved between different strains or members of a serogroup or genus may be useful, for example, as primers or probes that may be employed to detect the different strains or members, thereby reducing the number of primers or probes necessary to detect the different strains or members. Conserved sequences may include, for example, at least 5, 6, 7, 8, 9, 10, 11, 12, 13, 14, 15, 16, 17, 18, 19, 20, 21, 22, 23, 24, 25, 30, 40, 50, or more contiguous nucleotides that are completely (i.e., 100%) or substantially identical between the two or more strains or two or more members of the Japanese encephalitis virus serogroup or other members of the genus Flavivirus. Substantially identical sequences include those that are, e.g., 80%, 85%, 90%, 91%, 92%, 93%, 94%, 95%, 96%, 97%, 98%, or 99% identical between the two or more strains across the above-listed contiguous nucleotides.

3.1. Nucleic Acid Primers

Primers Based On SEQ ID NO:1

In one aspect, the invention provides nucleic acid primers that can be used in methods of detecting members of the Japanese encephalitis virus serogroup. In certain embodiments, a first nucleic acid primer that can be used to detect a member of the Japanese encephalitis virus serogroup comprises a nucleic acid that hybridizes to a nucleic acid of SEQ ID NO.: 1 or a complement thereof. SEQ ID NO.: 1, as presented in FIGS. 1A-E, represent a region of conserved sequence in the 3' untranslated region of the genomes of the flaviviruses that can be detected using the compositions and methods of the present invention. SEQ ID NO.: 2 represents the complement to SEQ ID NO.: 1.

In such embodiments of the invention, the first nucleic acid primer has a nucleotide composition, i.e., chemical structure, that allows it to hybridize under the defined conditions to a nucleic acid of SEQ ID NO.: 1. In some cases, each nucleotide of a primer that hybridizes to a nucleic acid will form base-pair complements with a nucleotide of the nucleic acid. For example, a primer containing a standard nucleotide that hybridizes to a C residue in the nucleic acid of SEQ ID NO.: 1 should have a G residue in the corresponding position. Thus, hybridization to the nucleic acid of SEQ ID NO.: 1 defines the nucleotide sequence and therefore the exact chemical structure of the primer. In addition, the first nucleic acid primer can also comprise non-standard nucleotides according to the definitions of oligonucleotide and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the primers of the invention. Exemplary embodiments are described in detail below.

In certain embodiments, the first nucleic acid primer that hybridizes to a nucleic acid of SEQ ID NO.: 1 can be as short as about 6 nucleotides. In other embodiments, the first nucleic acid primer can be as long as about 80 nucleotides. In certain embodiments, the first nucleic acid primer comprises about 10, about 12, about 14, about 15, about 16, about 17, about 18, about 19, about 20, about 21, about 22, about 23, about 24, about 25, about 26, about 27, about 28, about 29, about 30, about 35, or about 40 nucleotides. In some embodiments, the first nucleic acid primer will comprise fewer than 100, 80, 70, 60, 50, 40, 30, 25, 21 or 20 nucleotides.

The length and composition of the primer can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303, each of which is hereby incorporated by reference in its entirety. As another example, primers with G/C-rich sequences may anneal to target sequences at higher temperatures that a primer of similar length with A/T-rich sequences. Thus, in certain embodiments, the first nucleic acid primer comprises modified, non-standard, or derivatized bases, as defined above.

In certain embodiments, the first nucleic acid primer comprises at least about 16 consecutive nucleotides of SEQ ID NO.: 2. SEQ ID NO.: 2 is the complement to SEQ ID NO.: 1, as shown in FIGS. 1A-1E. In other embodiments, the first nucleic acid primer comprises at least about 18 consecutive nucleotides of SEQ ID NO.: 2. In still other embodiments, the first nucleic acid primer comprises at least about 20 consecutive nucleotides of SEQ ID NO.: 2. In yet other embodiments, the first nucleic acid primer comprises at least about 22 consecutive nucleotides of SEQ ID NO.: 2. In still other embodiments, the first nucleic acid primer comprises at least about 24 consecutive nucleotides of SEQ ID NO.: 2.

In certain embodiments, the invention provides nucleic acid primers that can be used to detect a member of the Japanese encephalitis virus serogroup. These primers can be structurally defined by reference to their nucleic acid sequences, as presented in Table 1.

TABLE 1

| | |
|---|---|
| SEQ ID NO.: 3<br>Japanese encephalitis virus serogroup Primer 1 | GN$^2$AAN$^5$CCN$^8$N$^9$N$^{10}$CN$^{12}$NDAN$^{15}$CN$^{17}$N$^{18}$N$^{19}$N$^{20}$TCGGN$^{25}$N$^{26}$<br>Wherein N$^2$ is T or A; N$^5$ is G or C; N$^8$ is T or absent; N at position 9 is C or G; N$^{10}$ is T or C; N$^{12}$ is A or G; N$^{13}$ is G or A; N$^{15}$ is A or C; N$^{17}$ is C or T; N$^{18}$ is G or C; N$^{19}$ is T or C; N$^{20}$ is C or T; N$^{25}$ is A or G; and N$^{26}$ is A or T. |
| SEQ ID NO.: 4<br>West Nile virus Primer 1 | GTAAGCCN$^8$CN$^{10}$CAGAACCGN$^{19}$N$^{20}$TCGGAA<br>Wherein N$^8$ is absent or T; N$^{10}$ is T or C; N$^{19}$ is T or C; and N$^{20}$ is C or T. |
| SEQ ID NO.: 5<br>Japanese encephalitis virus Primer 1 | GAAAN$^5$CCN$^8$CTCN$^{12}$N$^{13}$AAC N$^{17}$GTN$^{20}$TCGGAA<br>Wherein N$^5$ is G or C; N$^8$ is absent; N$^{12}$ is A or G; N$^{13}$ is G or A; N$^{17}$ is C or T; and N$^{20}$ is C or T. |
| SEQ ID NO.: 6<br>Murray Valley encephalitis virus Primer 1 | GAAAGCCTCCCAGAN$^{15}$CCGTN$^{20}$TCGGAA<br>Wherein N$^{15}$ is A or C; and N$^{20}$ is C or T. |
| SEQ ID NO.: 7<br>Koutango virus Primer 1 | GTAAGCCCTCAGAACCGTCTCGGAA |
| SEQ ID NO.: 8<br>Example Primer 1 | GTAAGCCCTCAGAACCGTCTCGGAA |
| SEQ ID NO.: 11<br>Japanese encephalitis virus serogroup Primer 2 | N$^1$CCN$^4$AN$^6$TN$^8$TN$^{10}$N$^{11}$N$^{12}$N$^{13}$NCCAGGTN$^{20}$TCAA<br>Wherein N$^1$ is T or C; N$^4$ is C or T; N$^6$ is G or C; N$^8$ is C or A; N$^{10}$ is A or T; N$^{11}$ is absent or T; N$^{12}$ is T or C; N$^{13}$ is C or T; and N$^{20}$ is G or A. |
| SEQ ID NO.: 12<br>West Nile virus Primer 2 | N$^1$CCTAGTCTATCCCAGGTN$^{20}$TCAA<br>Wherein N$^1$ is T or C and N$^{20}$ is G or A. |
| SEQ ID NO.: 13<br>Japanese encephalitis virus Primer 2 | CCCN$^4$AN$^6$TN$^8$TATN$^{12}$N$^{13}$CCAGGTGTCAA<br>Wherein N$^4$ is C or T; N$^6$ is G or C; N$^8$ is C or A; N$^{12}$ is T or C; and N$^{13}$ is C or T. |
| SEQ ID NO.: 14<br>Murray Valley encephalitis virus Primer 2 | TCCTAGTCTTTTCCCAGGTGTCAA |
| SEQ ID NO.: 15<br>Example Primer 2 | TCCTAGTCTATCCCAGGTGTCAA |
| SEQ ID NO.: 74<br>Example Primer 2 | TCTCCTAGTCTATCCCAGGTGTCAA |

In certain embodiments, the first nucleic acid primer comprises any of SEQ ID NOS.: 3-8. In certain embodiments of the invention, in order to improve primer specificity, the primers can comprise one or more alkylated nucleotides at or near its 3' end. For instance, in certain embodiments, first nucleic acid primer comprises SEQ ID NO.: 8, wherein the residue at position 23 is N$^6$-alkyl-deoxyadenosine. In a specific embodiment, the first nucleic acid primer comprises SEQ ID NO.: 8, wherein the residue at position 23 is N$^6$-methyl-deoxyadenosine. In certain embodiments, the first nucleic acid comprises SEQ ID NO.: 8, wherein the residue at position 24 is N$^6$-alkyl-deoxyadenosine. In a specific embodiment, the first nucleic acid comprises SEQ ID NO.: 8, wherein the residue at position 24 is N$^6$-tert-butyl-benzyl-deoxyadenosine. In certain embodiments, the first nucleic acid primer comprises SEQ ID NO.: 8, wherein the residue at position 23 is N$^6$-alkyl-deoxyadenosine and the residue at position 24 is N$^6$-alkyl-deoxyadenosine. In yet another specific embodiment, the first nucleic acid primer comprises SEQ ID NO.: 8, wherein the residue at position 23 is N$^6$-methyl-deoxyadenosine and the residue at position 24 is N$^6$-tert-butyl-benzyl-deoxyadenosine. U.S. Pat. No. 6,001,611, incorporated by reference above, describes N$^6$-alkyl-deoxyadenosine as well as the identity of the alkyl moieties that can be used with such non-standard nucleotides. For example, in certain embodiments, the alkyl moiety comprises $C_1$ to about $C_{10}$ branched or unbranched alkyl. In other embodiments, the alkyl moiety comprises $C_1$ to about $C_{20}$ branched or unbranched alkyl.

In another aspect, the invention provides a second nucleic acid primer for detecting a member of the Japanese encephalitis virus serogroup comprising a nucleic acid that hybridizes to a nucleic acid of SEQ ID NO.: 9 a complement thereof. SEQ ID NO.: 9, as presented in FIGS. 2A-2B, represent a region of conserved sequence in the 3' untranslated region of the genomes of the flaviviruses that can be detected using the compositions and methods of the present invention. FIGS. 2A-2B also show that SEQ ID NO.: 10 represents the complement to SEQ ID NO.: 9.

In such embodiments of the invention, the second nucleic acid primer has a nucleotide composition, i.e., chemical structure, that allows it to hybridize to a nucleic acid of SEQ ID NO.: 9. For example, a primer containing a standard nucleotide that hybridizes to a C residue in the nucleic acid of SEQ ID NO.: 9 should have a G residue in the corresponding position. Thus, hybridization to the nucleic acid of SEQ ID NO.: 9 defines the nucleotide sequence and therefore the exact chemical structure of the primer. In addition, the second nucleic acid primer can also comprise non-standard nucleotides according to the definitions of oligonucleotides and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the primers of the invention. Exemplary embodiments are described in detail below.

In certain embodiments, the second nucleic acid primer that hybridizes to a nucleic acid of SEQ ID NO.: 9 can be as short as about 6 nucleotides. In other embodiments, the second nucleic acid primer can be as long as about 80 nucleotides. In certain embodiments, the second nucleic acid primer comprises about 10, about 12, about 14, about 15, about 16, about 17, about 18, about 19, about 20, about 21, about 22, about 23, about 24, about 25, about 26, about 27, about 28, about 29, about 30, about 35, or about 40 nucleotides.

The length and composition of the second primer can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303, each of which is hereby incorporated by reference in its entirety. As another example, primers with G/C-rich sequences may anneal to target sequences at higher temperatures that a primer of similar length with A/T-rich sequences. Thus, in certain embodiments, the second nucleic acid primer comprises modified, non-standard, or derivatized bases as defined above.

In certain embodiments, the second nucleic acid primer comprises at least 16 consecutive nucleotides of SEQ ID NO.: 10. SEQ ID NO.: 10 represents the complement of SEQ ID NO.: 9, as shown in FIGS. 2A-2B. In other embodiments, the second nucleic acid primer comprises at least about 18 consecutive nucleotides of SEQ ID NO.: 10. In still other embodiments, the second nucleic acid primer comprises at least about 20 consecutive nucleotides of SEQ ID NO.: 10. In yet other embodiments, the second nucleic acid primer comprises at least about 22 consecutive nucleotides of SEQ ID NO.: 10. In still other embodiments, the second nucleic acid primer comprises at least about 24 consecutive nucleotides of SEQ ID NO.: 10.

In certain embodiments, the second nucleic acid primer comprises SEQ ID NO.: 11. In other embodiments, the second nucleic acid primer comprises SEQ ID NO.: 12. In yet other embodiments, the second nucleic acid primer comprises SEQ ID NO.: 13. In still other embodiments, the second nucleic acid primer comprises SEQ ID NO.: 14. In yet other embodiments, the second nucleic acid primer comprises SEQ ID NO.: 15 or SEQ ID NO:74. In certain embodiments, the second nucleic acid primer comprises non-standard or derivatized nucleotides. In other embodiments, the second nucleic acid primer can comprise one or more alkylated nucleotides at or near the 3' end. In certain embodiments, the second nucleic acid primer comprises SEQ ID NO.: 15 or SEQ ID NO:74, wherein the residue at position 23 of SEQ ID NO:15 or position 25 of SEQ ID NO:74 is $N^6$-alkyl-deoxyadenosine. In certain embodiments, the alkyl moiety comprises $C_1$ to about $C_{10}$ branched or unbranched alkyl. In other embodiments, the alkyl moiety comprises $C_1$ to about $C_{20}$ branched or unbranched alkyl. In a specific embodiment, the second nucleic acid primer comprises SEQ ID NO.: 15 or SEQ ID NO:74, wherein the residue at position 23 of SEQ ID NO:15 or position 25 of SEQ ID NO:74 is $N^6$-tert-butyl-benzyl-deoxyadenosine.

The nucleic acid primers of the invention may additionally comprise nucleic acid sequences that are not complementary and/or do not hybridize to a member of the Japanese encephalitis virus serogroup. These additional sequences can be selected by one of skill in the art to, for example, assist in the detection of the member of the Japanese encephalitis virus serogroup. Methods of detecting a nucleic acid, including a nucleic acid of a member of the Japanese encephalitis virus serogroup are extensively described in Sections 4.2 and 4.3, below. These methods describe both the additional nucleic acid sequences that can be present in the nucleic acid primers of the invention as well as methods of using these additional sequences to detect a member of the Japanese encephalitis virus serogroup.

The nucleic acid primers may be prepared by any suitable method known to one of skill in the art without limitation. Methods for preparing oligonucleotides of defined sequence are well-known to the art, and include, for example, cloning and restriction of appropriate sequences and direct chemical synthesis. Chemical synthesis methods may include, for example, the phosphotriester method described by Narang et al., 1979, Methods in Enzymology 68:90, the phosphodiester method disclosed by Brown et al., 1979, Methods in Enzymology 68:109, the diethylphosphoramidate method disclosed in Beaucage et al., 1981, Tetrahedron Letters 22:1859, and the solid support method disclosed in U.S. Pat. No. 4,458,066. In addition, modifications to the above-described methods of synthesis may be used to desirably impact enzyme behavior with respect to the synthesized oligonucleotides. For example, incorporation of modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

Dengue Virus Primers

Additional primers of the invention hybridize to the Dengue virus 3' UTR. Exemplary primers useful for amplifying and/or detecting Dengue viruses nucleic acids include those depicted in Table 2.

TABLE 2

| Sequence | Comments | SEQ ID NO: |
|---|---|---|
| GAGCCCCGTCCAAGGACGTAAAAAGAA | *Dengue virus* consensus upstream primer. | 41 |

TABLE 2 -continued

| Sequence | Comments | SEQ ID NO: |
|---|---|---|
| GAGCCCCGTCCAAGGACGTAAAA AGAJ | Dengue virus consensus upstream primer. | 42 |
| GAGCCCCGTCCAAGGACGTAAAA AGEJ | Dengue virus consensus upstream primer. | 43 |
| GAGCCCCGTCCAAGGACGTAAAAT GAA | Dengue virus type I upstream primer. | 44 |
| GAGCCCCGTCCAAGGACGTAAAAT GAJ | Dengue virus type I upstream primer. | 45 |
| GAGCCCCGTCCAAGGACGTAAAAT GEJ | Dengue virus type I upstream primer. | 46 |
| GAGCCCCGTCCAAGGACGTTAAAA GAA | Dengue virus types II & III upstream primer. | 47 |
| GAGCCCCGTCCAAGGACGTTAAAA GAJ | Dengue virus types II & III upstream primer. | 48 |
| GAGCCCCGTCCAAGGACGTTAAAA GEJ | Dengue virus types II & III upstream primer. | 49 |
| ATTGAAGTCAGGCCACTTGTGCCA | Dengue virus type IV upstream primer. | 50 |
| ATTGAAGTCAGGCCACTTGTGCCJ | Dengue virus type IV upstream primer. | 51 |
| ATTGAAGTCAGGCCACTTGTGCUJ | Dengue virus type IV upstream primer. | 52 |
| GATCTCTGGTCTTTCCCAGCGTCA A | Dengue virus downstream primer. | 53 |
| GATCTCTGGTCTTTCCCAGCGTCA J | Dengue virus downstream primer. | 54 |
| GATCTCTGGTCTTTCCCAGCGTCE J | Dengue virus downstream primer. | 55 |

Definition of primer suffixes:
J = t-butyl-benzyl-dA,
E = methyl-dA;
U= ethyl-dC In some embodiments, one "upstream" primers and a "downstream" primer are used in combination to amplify a Dengue virus nucleic acid. In some embodiments more than one upstream primer is used in combination with at least one downstream primer to detect one or more Dengue virus nucleic acids. The use of multiple upstream primers in a single amplification reaction allows for the amplification and/or detection of different Dengue virus nucleic acid variants. For example, in some embodiments, a first upstream primer (selected from SEQ ID NO:41, SEQ ID NO:42 and SEQ ID NO:43) and a second upstream primer (selected from SEQ ID NO:50, SEQ ID NO:51, and SEQ ID NO:52) are used in combination with a Dengue virus downstream primer (e.g., selected from a primer comprising SEQ ID NO:53, SEQ ID NO:54, and SEQ ID NO:55). These embodiments are useful, e.g., to detect any the Dengue virus types 1, 2, 3, or 4.

Yellow Fever Virus Primers

Additional primers of the invention hybridize to the yellow fever virus 3' UTR. Exemplary primers useful for amplifying and/or detecting Dengue virus nucleic acids include those depicted in Table 3.

TABLE 3

| Sequence | Comments | SEQ ID NO: |
|---|---|---|
| AACCGGGATAAAAACTACGGGTG GAGAA | Yellow fever virus upstream primer. | 56 |
| AACCGGGATAAAAACTACGGGTG GAGAJ | Yellow fever virus upstream primer. | 57 |
| AACCGGGATAAAAACTACGGGTG GAGEJ | Yellow fever virus upstream primer. | 58 |
| ATAAAAACTACGGGTGGAGAACCG GA | Yellow fever virus upstream primer. | 59 |
| ATAAAAACTACGGGTGGAGAACCG GJ | Yellow fever virus upstream primer. | 60 |
| ACTCCGGTCTTTCCCTGGCGTCAA | Yellow fever virus downstream primer. | 61 |
| ACTCCGGTCTTTCCCTGGCGTCAJ | Yellow fever virus downstream primer. | 62 |

TABLE 3 -continued

| Sequence | Comments | SEQ ID NO: |
|---|---|---|
| ACTCCGGTCTTTCCCTGGCGTCEJ | Yellow fever virus downstream primer. | 63 |

In some embodiments, one "upstream" primers and a "downstream" primer are used in combination to amplify a yellow fever virus nucleic acid. In some embodiments more than one upstream primer is used in combination with at least one downstream primer to detect one or more yellow fever virus nucleic acids. Multiple upstream primers may be used in a single amplification reaction. For example, in some embodiments, a first upstream primer (e.g., selected from SEQ ID NO:56, SEQ ID NO:57 and SEQ ID NO:58) and a second upstream primer (e.g., selected from SEQ ID NO:59, SEQ ID NO:60, and SEQ ID NO:61) are used in combination with a yellow fever virus downstream primer (e.g., selected from a primer comprising SEQ ID NO:62 and SEQ ID NO:63).

Primers Based on the Sequences of FIGS. 7A-7B

Additional primers of the invention hybridize to any of the sequences depicted in FIGS. 7A-7B (e.g., SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40), or a complement thereof, under conditions to allow for priming of an amplification reaction. In some cases, these primers are useful for amplifying and/or detecting nucleic acids from SLEV.

Like the primers that hybridize to SEQ ID NO:1 described above, primers that hybridize to any of the sequences depicted in FIGS. 7A-7B can also comprise non-standard nucleotides according to the definitions of oligonucleotide and primers recited above.

The length and composition of the primers that hybridize to any of the sequences depicted in FIGS. 7A-7B can be chosen to give sufficient thermodynamic stability to ensure hybridization of the primer to the flaviviral nucleic acid under the appropriate reaction conditions, which depend on the detection method to be performed. For example, primers with modified, non-standard, or derivatized nucleotides may be longer or shorter than those with conventional nucleotides while having similar thermodynamic hybridization properties. Thus, in certain embodiments, the second nucleic acid primer comprises modified, non-standard, or derivatized bases as defined above. Primers that hybridize to any of the sequences depicted in FIGS. 7A-7B can comprise at least, e.g., 4, 5, 6, 7, 8, 9, 10, 11, 12, 13, 14, 15, 16, 17, 18, 19, 20, 21, 22, 23, 24, 25, 30, 40, 50 or more contiguous nucleotides of any of the sequences depicted in FIGS. 7A-7B or a complement thereof.

Those of skill in the art will appreciate that primer pairs can be designed using SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 to amplify desired sequences from the 3' UTR region of SLEV. In some embodiments, a first primer of the invention hybridizes to TTGACACCTGGAAAGACAGGAGA (SEQ ID NO: 68 and a second primer hybridizes to the complement of CAAAGCCCCTCATTCCGACTCGGG (SEQ ID NO: 69) under conditions to allow for priming of an amplification reaction.

Exemplary primers for detecting and/or amplifying SLEV include those depicted in Table 4.

TABLE 4

| Sequence | Comments | SEQ ID NO: |
|---|---|---|
| CAAAGCCCCTCATTC CGACTCGGGA | St. Louis encephalitis virus upstream primer. | 64 |
| CAAAGCCCCTCATTC CGACTCGGGJ | St. Louis encephalitis virus upstream primer. | 65 |
| TCTCCTGTCTTTCCA GGTGTCAA | St. Louis encephalitis virus downstream primer. | 66 |
| TCTCCTGTCTTTCCA GGTGTCAJ | St. Louis encephalitis virus downstream primer. | 67 |

3.2. Nucleic Acid Probes

In another aspect, the invention provides a probe for the detection of a nucleic acid of certain flaviviruses. Flaviviral nucleic acids that can be detected with the probes of the invention are described in Sections 3.3 and 3.4, below. The probe can be any nucleic acid probe that can be used to identify the presence of a nucleic acid of a detectable flavivirus known to one of skill in the art without limitation. Typically, the probe comprises a nucleotide sequence that hybridizes to a region in a nucleic acid of a flavivirus to be detected.

The probe nucleotide sequence can be of any length sufficient to specifically bind a nucleic acid of a flavivirus to be detected. In certain embodiments, the probe comprises at least about 6 nucleotides. In certain embodiments, the probe comprises fewer than about 140 nucleotides. In certain embodiments, the probe can be about 18 to about 25, about 25 to about 35, or about 35 to about 45 nucleotides in length. The length and composition of the probe can be chosen to give sufficient thermodynamic stability to ensure hybridization of the probe to the flaviviral nucleic acid under the appropriate reaction conditions, which depend on the detection method to be performed. For example, probes with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303, each of which is hereby incorporated by reference in its entirety. As another example, probes with G/C-rich sequences may anneal to target sequences at higher temperatures that a probe of similar length with A/T-rich sequences.

Typically, the portion of the probe nucleotide sequence that hybridizes to the detectable nucleic acid is identical or complementary to the region of the detectable nucleic acid to which the probe hybridizes. However, this portion of the probe can have less than 100% sequence identity or complementarity to the region of the detectable viral nucleic acid to which the probe hybridizes. In certain embodiments of the invention, nucleotide sequence of the portion of the probe that hybridizes to the detectable viral nucleic acid can have about 99%, about 98%, about 97%, about 96%, about 95%, about 90%, about 85% or about 80% complementarity or identity to the region of the detectable viral nucleic acid to which the probe hybridizes.

In certain embodiments, the invention provides a probe for detecting a member of the Japanese encephalitis virus serogroup comprising a nucleic acid that hybridizes to a nucleic acid of SEQ ID NO.: 16. SEQ ID NO.: 16, as presented in FIGS. 3A-3F, represent a region of conserved sequence in the 3' untranslated region of the genomes of the flaviviruses that can be detected using the compositions and methods of the present invention. FIGS. 3A-3F also show that SEQ ID NO.: 17 represents the complement to SEQ ID NO.: 16.

In such embodiments of the invention, the probe has a nucleotide composition, i.e., chemical structure, that allows it to hybridize under the defined conditions to a nucleic acid of SEQ ID NO.: 16. For example, a probe containing a standard nucleotide that hybridizes to a C residue in the nucleic acid of SEQ ID NO.: 16 must have a G residue in the corresponding position. Thus, hybridization to the nucleic acid of SEQ ID NO.: 16 defines the nucleotide sequence and therefore the exact chemical structure of the probe. In addition, the probe can also comprise non-standard nucleotides according to the definitions of oligonucleotide and primers recited above. Certain of such non-standard nucleotides can also bind to other standard or non-standard nucleotides to form a base-pair. For example, the nonstandard nucleotide inosine can pair with uracil, cytosine, and adenine. Given the known correlation between hybridization and chemical structure, one of skill in the art can easily recognize the standard features of the probes of the invention. Exemplary embodiments are described in detail below.

In certain embodiments, the probes that can hybridize to SEQ ID NO.: 16 comprise about 10, about 12, about 14, about 15, about 16, about 17, about 18, about 19, about 20, about 21, about 22, about 23, about 24, about 25, about 26, about 27, about 28, about 29, about 30, about 32, about 34, about 36, about 38, about 40, about 42, about 44, about 46, about 48, about 50, about 55, about 60, about 65, about 70, about 75, or about 80 nucleotides. In certain embodiments, the probe comprises modified, non-standard, or derivatized bases, as defined above.

In certain embodiments, the probe comprises at least about 20 consecutive nucleotides of SEQ ID NO.: 17. In other embodiments, the probe comprises at least about 22 consecutive nucleotides of SEQ ID NO.: 17. In still other embodiments, the probe comprises at least about 24 consecutive nucleotides of SEQ ID NO.: 17. In yet other embodiments, the probe comprises at least about 26 consecutive nucleotides of SEQ ID NO.: 17. In still other embodiments, the probe comprises at least about 28 consecutive nucleotides of SEQ ID NO.: 17. In yet other embodiments, the probe comprises at least about 30 consecutive nucleotides of SEQ ID NO.: 17. In still other embodiments, the probe comprises at least about 32 consecutive nucleotides of SEQ ID NO.: 17. In yet other embodiments, the probe comprises at least about 34 consecutive nucleotides of SEQ ID NO.: 17. In still other embodiments, the probe comprises at least about 36 consecutive nucleotides of SEQ ID NO.: 17. In yet other embodiments, the probe comprises at least about 38 consecutive nucleotides of SEQ ID NO.: 17. In still other embodiments, the probe comprises at least about 40 consecutive nucleotides of SEQ ID NO.: 17.

In certain embodiments, the invention provides particular nucleic acid probes that can be used to detect a member of the Japanese encephalitis virus serogroup, as well as certain other flaviviruses. These probes can be structurally defined by reference to their nucleic acid sequences, as presented in Table 5.

TABLE 5

| | |
|---|---|
| SEQ ID NO.: 18<br>Probe for Detecting<br>*Flaviviruses* | GGN$^3$CTAGN$^8$GGTTAGAGGAGACCCN$^{24}$N$^{25}$N$^{26}$N$^{27}$N$^{28}$<br>Wherein N$^3$ is A or T; N$^8$ is A or T; N$^{24}$ is C or T; N$^{25}$ is G, C, T, A, or absent; N$^{26}$ is C, T, G, or absent; N$^{27}$ is G, C, A, T, or absent; and N$^{28}$ is G, C, A, T, or absent. |
| SEQ ID NO.: 19<br>Probe for Detecting<br>*Japanese Encephalitis<br>Virus* Serogroup<br>Members | GGACTAGN$^8$GGTTAGAGGAGACCCN$^{25}$N$^{26}$N$^{27}$N$^{28}$<br>Wherein N$^8$ is A or T; N$^{25}$ is G or A; N$^{26}$ is C or T; N$^{27}$ is G or T; and N$^{28}$ is G or T. |
| SEQ ID NO.: 20<br>Probe for Detecting<br>*West Nile Virus* | GGACTAGN$^8$GGTTAGAGGAGACCCCN$^{25}$CGN$^{28}$<br>Wherein N$^8$ is A or T; N$^{25}$ is G or A; and N$^{28}$ is G or T. |
| SEQ ID NO.: 21<br>Probe for Detecting<br>*Japanese Encephalitis<br>Virus* | GGACTAGAGGTTAGAGGAGACCCCGN$^{26}$GG<br>Wherein N$^{26}$ is C or T. |
| SEQ ID NO.: 22<br>Probe for Detecting<br>*Murray Valley<br>Encephalitis Virus* | GGACTAGAGGTTAGAGGAGACCCCACTC |
| SEQ ID NO.:23<br>Probe for Detecting<br>*Kunjin Virus* | AATAN$^5$GTGGATTACATGAN$^{19}$TTCAN$^{24}$TGAAG<br>Wherein N$^5$ is T or C; N$^{19}$ is G or C; and N$^{24}$ is T or C. |
| SEQ ID NO.: 24<br>Probe for Detecting<br>*Dengue Virus* | GGACTAGAGGTTAGAGGAGACCCCN$^{25}$N$^{26}$N$^{27}$N$^{28}$<br>Wherein N$^{25}$ is C or T; N$^{26}$ is C or G; N$^{27}$ is C or G; and N$^{28}$ is G, C or A. |
| SEQ ID NO.: 25<br>Probe for Detecting<br>*Yellow Fever Virus* | GGTCTAGAGGTTAGAGGAGACCCTCCAG |
| SEQ ID NO.: 26<br>Probe for Detecting<br>*Montana Myotis<br>Leukencephalitis Virus* | GGACTAGAGGTTAGAGGAGACCCCTTCC |

TABLE 5 -continued

| SEQ ID NO.: 27<br>Probe for Detecting<br>*Modoc Virus* | GGACTAGAGGTTAGAGGAGACCCCCGGC |
|---|---|
| SEQ ID NO.: 28<br>Example Probe 1 | GGACTAGAGGTTAGAGGAGACCCCGCGG |
| SEQ ID NO.: 70<br>*Flavivirus* anti-sense probe | GGGTCTCCTCTAACCTCTAGTCCTTCCCCC |

In certain embodiments of the invention, the probe comprises any of SEQ ID NOS.: 18-28 or 70, or complements thereof.

The nucleic acid probes of the invention can additionally comprise other nucleic acid sequences that are not derived from and/or do not hybridize to a nucleic acid of a member of the Japanese encephalitis virus serogroup or another flavivirus that can be detected with the disclosed probes. These additional nucleic acid sequences can be selected by one of skill in the art to provide desired functionality to the probes. For example, the nucleic acid probes can comprise additional sequences that allow improved methods of detection. Examples of probes that can comprise additional nucleic acid sequences or can otherwise be adapted for use in the probes, methods, and kits of the invention can be found in U.S. Pat. Nos. 6,323,337, 6,248,526, 6,150,097, 6,117,635, 6,090,552, 5,866,336, and 5,723,591, each of which is hereby incorporated by reference in its entirety. Further, methods of detecting a nucleic acid, including a nucleic acid of a member of the Japanese encephalitis virus serogroup or other detectable flaviviruses are extensively described in Sections 4.2 and 4.3, below. Certain of these methods also use additional nucleic acid sequences that can be present in the nucleic acid primers of the invention; such additional nucleic acid sequences and methods of using these additional sequences to detect a member of the Japanese encephalitis virus serogroup are described below.

The nucleic acid probes of the invention can be prepared by any method known to one of skill in the art without limitation. In particular, the methods used to prepare the nucleic acid primers of the invention described above may also be used to prepare the nucleic acid probes of the invention.

In addition to the probe nucleotide sequence, the probe can comprise additional nucleotide sequences or other moieties that do not inhibit the methods of the instant invention. In convenient embodiments of the invention, the probe can comprise additional nucleotide sequences or other moieties that facilitate the methods of the instant invention. For instance, the probe can be blocked at its 3' terminus to prevent undesired nucleic acid polymerization priming by the probe. Also, moieties may be present within the probe that stabilize or destabilize hybridization of the probe or probe fragments with the nucleotide sequence. The probes of the invention can also comprise modified, non-standard, or derivatized nucleotides as defined above.

In certain embodiments of the invention, the probe can comprise a detectable moiety. The detectable moiety can be any detectable moiety known by one of skill in the art without limitation. Further, the detectable moiety can be detectable by any means known to one of skill in the art without limitation. For example, the detectable moiety can be detectable by spectroscopic, photochemical, biochemical, immunochemical, or chemical means.

A variety of detectable moieties that can be used to detect the probes of the invention, as well as methods for their linkage to the probe, are known to the art and include, but are not limited to, enzymes (e.g., alkaline phosphatase and horseradish peroxidase) and enzyme substrates, radioactive moieties, fluorescent moieties, chromophores, chemiluminescent labels, electrochemiluminescent labels, such as Origin™ (Igen, Rockville, Md.), ligands having specific binding partners, or any other labels that may interact with each other to enhance, alter, or diminish a signal. Of course, should a 5' nuclease reaction be performed using a thermostable DNA polymerase at elevated temperatures, the detectable moiety should not be degraded or otherwise rendered undetectable by such elevated temperatures.

In certain embodiments, the detectable moiety can be a fluorescent moiety. The fluorescent moiety can be any fluorescent moiety known to one of skill in the art without limitation. In general, fluorescent moieties with wide Stokes shifts are preferred, allowing the use of fluorometers with filters rather than monochromometers and increasing the efficiency of detection. In certain embodiments, the fluorescent moiety can be selected from the group consisting of fluorescein-family dyes (Integrated DNA Technologies, Inc., Coralville, Iowa), polyhalofluorescein-family dyes, hexachlorofluorescein-family dyes, coumarin-family dyes (Molecular Probes, Inc., Eugene, Or), rhodamine-family dyes (Integrated DNA Technologies, Inc.), cyanine-family dyes, oxazine-family dyes, thiazine-family dyes, squaraine-family dyes, chelated lanthanide-family dyes, and BODIPY®-family dyes (Molecular Probes, Inc.). In a preferred embodiment, the fluorescent moiety is 6-carboxyfluorescein (FAM™)(Integrated DNA Technologies, Inc.). Other examples of fluorescent moieties that can be used in the probes, methods, and kits of the invention can be found in U.S. Pat. Nos. 6,406,297, 6,221,604, 5,994,063, 5,808,044, 5,880,287, 5,556,959, and 5,135,717, each of which is hereby incorporated by reference in its entirety.

In other embodiments, the detectable moiety can be a detectable moiety other than a fluorescent moiety. Among radioactive moieties, $^{32}$P-labeled compounds are preferred. Any method known to one of skill in the art without limitation may be used to introduce $^{32}$P into a probe. For example, a probe may be labeled with $^{32}$P by 5' labeling with a kinase or by random insertion by nick translation. Detectable moieties that are enzymes can typically be detected by their activity. For example, alkaline phosphatase can be detected by measuring fluorescence produced by action of the enzyme on appropriate substrate compounds. Where a member of specific binding partners are used as detectable moieties, the presence of the probe can be detected by detecting the specific binding of a molecule to the member of the specific binding partner. For example, an antigen can be linked to the probe, and a monoclonal antibody specific for that antigen can be used to detect the presence of the antigen and therefore the probe. Other specific binding partners that can be used as detectable moieties include biotin and avidin or streptavidin, IgG and protein A, and numerous other receptor-ligand couples well-known to the art. Still other examples of detectable moieties that are not fluorescent moieties can be found in U.S. Pat. Nos. 5,525,465, 5,464,746, 5,424,414, and 4,948,882, each of which is hereby incorporated by reference in its entirety.

The above description of detectable moieties is not meant to categorize the various labels into distinct classes, as the same label may serve in several different modes. For example, $^{125}$I may serve as a radioactive moiety or as an electron-dense reagent. Horseradish peroxidase may serve as enzyme or as antigen for a monoclonal antibody. Further, one may combine various detectable moieties for desired effect. For example, one might label a probe with biotin, and detect its presence with avidin labeled with $^{125}$I, or with an anti-biotin monoclonal antibody labeled with horseradish peroxidase. Other permutations and possibilities will be readily apparent to those of ordinary skill in the art, and are considered as equivalents within the scope of the instant invention.

The method of linking or conjugating the detectable moiety to the probe depends, of course, on the type of detectable moiety or moieties used and the position of the detectable moiety on the probe.

The detectable moiety may be attached to the probe directly or indirectly by a variety of techniques. Depending on the precise type of detectable moiety used, the detectable moiety can be located at the 5' or 3' end of the probe, located internally in the probe's nucleotide sequence, or attached to spacer arms of various sizes and compositions to facilitate signal interactions. Using commercially available phosphoramidite reagents, one can produce oligonucleotides containing functional groups (e.g., thiols or primary amines) at either terminus via an appropriately protected phosphoramidite, and can attach a detectable moiety thereto using protocols described in, for example, PCR Protocols: A Guide to Methods and Applications, ed. by Innis et al., Academic Press, Inc., 1990.

Methods for introducing oligonucleotide functionalizing reagents to introduce one or more sulfhydryl, amino or hydroxyl moieties into the oligonucleotide probe sequence, typically at the 5' terminus are described in U.S. Pat. No. 4,914,210. A 5' phosphate group can be introduced as a radio-isotope by using polynucleotide kinase and [gamma-$^{32}$P]ATP to provide a reporter group. Biotin can be added to the 5' end by reacting an aminothymidine residue or alkylamino linker, introduced during synthesis, with an N-hydroxysuccinimide ester of biotin. Other methods of attaching a detectable moiety, including a fluorescent moiety, to the probe can be found in U.S. Pat. No. 5,118,802, which is hereby incorporated by reference in its entirety.

It is also possible to attach a detectable moiety at the 3' terminus of the probe by employing, for example, polynucleotide terminal transferase to add a desired moiety, such as, for example, cordycepin $^{35}$S-dATP, and biotinylated dUTP.

Oligonucleotide derivatives are also detectable moieties that can be used in the probes, methods and kits of the present invention. For example, etheno-dA and etheno-A are known fluorescent adenine nucleotides which can be incorporated into an oligonucleotide probe. Similarly, etheno-dC is another analog that could be used in probe synthesis. The probes containing such nucleotide derivatives can be degraded to release mononucleotides that are much more strongly fluorescent than the intact probe by, for example, a polymerase's 5' to 3' nuclease activity.

In certain embodiments of the invention, a probe can be labeled with more than one detectable moiety. In certain of such embodiments, each detectable moiety can be individually attached to different bases of the probe. In other embodiments, more than one detectable moiety can be attached to the same base of the probe.

In certain embodiments, the detectable moiety can be attached to the 5' end of the probe. In other embodiments, the detectable moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 5' end of the probe. In certain embodiments, the detectable moiety can be attached to the 3' end of the probe. In other embodiments, the detectable moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 3' end of the probe. The detectable moiety can be attached to any portion of a residue of the probe. For example, the detectable moiety can be attached to a sugar, phosphate, or base moiety of a nucleotide in the probe. In other embodiments, the detectable moiety can be attached between two residues of the probe.

In certain embodiments of the invention, the probe can comprise a fluorescent moiety and a quencher moiety. In such embodiments, the fluorescent moiety can be any fluorescent moiety known to one of skill in the art, as described above. Further, the quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes (including the quenchers described in WO 01/86001), Iowa Black™, or Dabcyl (Integrated DNA Technologies, Inc.). Other examples of specific quencher moieties include, for example, but not by way of limitation, TAMRA (N,N,N',N'-tetramethyl-6-carboxyrhodamine) (Molecular Probes, Inc.), DABCYL (4-(4'-dimethylaminophenylazo)benzoic acid), Iowa Black™ (Integrated DNA Technologies, Inc.), Cy3™ (Integrated DNA Technologies, Inc.) or Cy5™ (Integrated DNA Technologies, Inc.). In a preferred embodiment, the quencher moiety is Cy5™. Other examples of quencher moieties that can be used in the probes, methods, and kits of the invention can be found in U.S. Pat. Nos. 6,399,392, 6,348,596, 6,080,068, and 5,707,813, each of which is hereby incorporated by reference in its entirety.

In certain embodiments, the quencher moiety can be attached to the 5' end of the probe. In other embodiments, the quencher moiety can be attached to the probe at a residue that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 5' end of the probe. In certain embodiments, the quencher moiety can be attached to the 3' end of the probe. In other embodiments, the quencher moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, or about 40 residues from the 3' end of the probe. In some embodiments, the quencher moiety is attached to the 5' end of the probe and the fluorescent moiety is attached to a residue that is within about 10 residues of the 5' end of the probe. The quencher moiety can be attached to any portion of a residue of the probe. For example, the quencher moiety can be attached to a sugar, phosphate, or base moiety of a nucleotide in the probe. In other embodiments, the quencher moiety can be attached between two residues of the probe.

While not intending to be bound to any particular theory or mechanism of action, it is believed that when the probe is intact, a photon emitted by the fluorescent moiety can be absorbed and thus quenched by the quencher moiety. The quencher moiety then either releases the energy of the photon as a photon of different wavelength or as heat. Thus, the quencher moiety can also be a fluorescent moiety. As described above, this phenomenon is termed fluorescence resonance energy transfer ("FRET"). Cleaving the probe between the fluorescent moiety and quencher results in a reduction in quenching of the fluorescent moiety's emitted fluorescence by the quencher moiety.

Generally, transfer of energy between the fluorescent moiety and the quencher moiety depends on the distance between the fluorescent moiety and the quencher moiety and the critical transfer distance of the particular fluorescent moiety-quencher moiety pair. The critical transfer distance is both characteristic and constant for a given fluorescent moiety paired with a given quencher moiety. Further, the spatial relationship of the fluorescent moiety in reference to the quencher moiety can be more sensitively determined when the critical transfer distance of the fluorescent moiety-quencher moiety pair is close to the distance between the fluorescent moiety and the quencher moiety. Accordingly, the skilled practitioner can select the fluorescent moiety and the quencher moiety to have a critical transfer distance that is close to the distance separating the fluorescent moiety from the quencher moiety on the probe. Critical transfer distances of particular fluorescent moiety-quencher moiety pairs are well known in the art and can be found, for example, in an article by Wu and Brand, 1994, Anal. Biochem. 218:1-13, which is hereby incorporated by reference in its entirety.

Other criteria for section of particular fluorescent moiety-quencher moiety pairs include, for example, the quantum yield of fluorescent emission by the fluorescent moiety; the wavelength of fluorescence emitted by the fluorescent moiety; the extinction coefficient of the quencher moiety; the wavelength of fluorescence, if any, emitted by the quencher moiety; and the quantum yield of fluorescent emission, if any, by the quencher moiety. In addition, if the quencher moiety is also a fluorescent moiety, the quencher moiety and the fluorescent moiety can preferably be selected so that fluorescence emitted by one can easily be distinguished from fluorescence emitted by the other. Further guidance on the selection of particular fluorescent moiety-quencher moiety pairs may be found in a review article by Klostermeier and Millar, 2002, Biopolymers 61:159-179, which is hereby incorporated by reference in its entirety.

Exemplary combinations of fluorescent moieties and quencher moieties that can be used in this aspect of the invention include, but are not limited to the fluorescent moiety rhodamine 590 and the quencher moiety crystal violet. A preferred combination of fluorescent and quencher moieties is the fluorescent moiety 6-carboxyfluorescein and the quencher moiety Cy5™. Other examples of fluorescent moiety-quencher moiety pairs that can be used in the probes, methods, and kits of the invention can be found in U.S. Pat. No. 6,245,514, which is hereby incorporated by reference in its entirety.

Examples of molecules that can be used as both fluorescent or quencher moieties in FRET include fluorescein, 6-carboxyfluorescein, 2'7'-dimethoxy-4'5'-dichloro-6-carboxyfluorescein, rhodamine, 6-carboxyrhodamine, 6-carboxy-X-rhodamine, and 5-(2'-aminoethyl)aminonaphthalene-1-sulfonic acid (EDANS). Whether a fluorescent moiety is a donor or an acceptor is defined by its excitation and emission spectra, and the fluorescent moiety with which it is paired. For example, FAM™ is most efficiently excited by light with a wavelength of 488 nm, and emits light with a spectrum of 500 to 650 nm, and an emission maximum of 525 nm. Accordingly, FAM™ is a suitable fluorescent moiety for use with, for example, with TAMRA as quencher moiety, which has at its excitation maximum 514 nm.

In some embodiments, the following probe variants are used:

```
FGGACTAGAIGGTTAGAGGAGACCCCGCGGP;            (SEQ ID NO: 76, which is a variant of SEQ ID NO: 28)

FGGAEUAGAIGGUUAGAGGAGAEEEEGEGGP;            (SEQ ID NO: 77, which is a variant of SEQ ID NO: 28)

FGGGTCTCCITCTAACCTCTAGTCCTTCCCCCP;          (SEQ ID NO: 78, which is a variant of SEQ ID NO: 70)

FGGGUEUEEIUEUAACCTCTAGTCCTTCCCCCP;          (SEQ ID NO: 79, which is a variant of SEQ ID NO: 70)
and FGGTCTAGAIGGTTAGAGGAGACCCTCCAGP.            (SEQ ID NO: 80, which is a variant of SEQ ID NO: 25)
In all of the above probes, F = CY5; I = FAM; P = PO4; U = propynyl dU; E = 5-methyl-
dC).
```

3.3. Nucleic Acids of Detectable Members of the Japanese Encephalitis Virus Serogroup The primers, probes, methods, and kits of the invention are useful for the detection of certain members of the genus Flavivirus. In particular, the primers, probes, methods, and kits are useful for detecting members of the Japanese encephalitis virus serogroup. For example, the members of the Japanese encephalitis virus serogroup that can be detected according to the present invention include, but are not limited to, Japanese encephalitis virus, West Nile virus, Murray Valley encephalitis virus, SLEV, and Kunjin virus. In several instances, the complete sequence of at least one strain of some of these viruses has been determined. These sequences may be found by reference to the GenBank accession numbers presented in FIGS. 4A-4D, which present an alignment of nucleic acid sequences of Japanese encephalitis virus serogroup members with the oligonucleotides of the invention. The nucleic acid sequences of each flaviviral genome identified by accession number in FIGS. 4A-4D are hereby incorporated by reference in its entirety.

The complete nucleic acid sequences of the genomes of other members of the Japanese encephalitis virus serogroup, e.g., Cacipacore virus, St. Louis encephalitis virus, Usutu virus, and Youende virus, have not yet been determined. Nonetheless, it is believed that the primers and probes of the present invention hybridize to sequences that have a high degree of conservation with all members of the Japanese encephalitis virus serogroup. Further, one of skill in the art can easily recognize that the primers and probes can hybridize to a nucleic acid from one of the as yet unsequenced members following determination of the nucleic acid sequences of these viral genomes.

In certain embodiments, a nucleic acid of a member of the Japanese encephalitis virus serogroup can be detected. In other embodiments, a nucleic acid of Japanese encephalitis virus can be detected. In yet other embodiments, a nucleic acid of West Nile virus can be detected. In still other embodiments, a nucleic acid of Kunjin virus can be detected. In yet other embodiments, a nucleic acid of Murray Valley encephalitis virus can be detected. In yet other embodiments, a nucleic acid of SLEV can be detected. In still other embodiments, a nucleic acid of Japanese encephalitis virus, West Nile virus, SLEV or Murray Valley encephalitis virus can be detected.

The nucleic acid to be detected can be any nucleic acid from a detectable flavivirus as described herein. Typically, the nucleic acid will be a single-stranded RNA, as the flaviviruses to be detected have plus-strand single stranded RNA genomes. However, the nucleic acid to be detected can also be DNA corresponding in sequence to an RNA genome of a flavivirus that can be detected. Such DNA can be prepared, for example, by reverse-transcribing the viral RNA as described in Section 4.1, below.

The presence of a nucleic acid of a detectable flavivirus can be detected in a sample from any source known to one of skill in the art without limitation. For example, the viral nucleic acid can be detected in a biological sample, as defined above. The viral nucleic acid can be detected in a sample from any natural source, including a vertebrate animal, such as a fish, amphibian, reptile, bird, or mammal, and an invertebrate animal, such as insects, crustaceans, arachnids, etc. In addition, the sample to be tested can be from a non-living source, such as a water or soil sample or a swipe sample, such as is derived from testing a surface.

It certain embodiments of the invention, the nucleic acid to be detected can be amplified according to methods known to those of skill in the art. The amplification can be performed prior to detection according to the methods described herein or the amplification can be performed concurrently with detection as described herein. Methods of amplifying a nucleic acid are described below and in, for example, Saiki et al., 1988, Science 239:487-91, the contents of which are hereby incorporated by reference in their entirety.

3.4. Nucleic Acids of Other Detectable Flaviviruses

The probes, methods and kits of the invention can also be used to detect a nucleic acid from other flaviviruses, including, but not limited to, Dengue virus, Montana myotis leukoencephalitis virus, Modoc virus, and Yellow Fever virus. As with members of the Japanese encephalitis virus serogroup, the nucleic acid sequences of at least one strain of some of these viruses has been determined. These sequences may be found by reference to the accession numbers presented in FIGS. 5A-5B, which present an alignment of nucleic acid sequences of these detectable flaviviruses with SEQ ID NO:16. The nucleic acid sequences of each flaviviral genome identified by GenBank accession number in FIGS. 5A-5B are hereby incorporated by reference in its entirety.

As discussed herein, primers SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55 are useful for amplifying and/or detecting Dengue virus and primers SEQ ID NO: 56, SEQ ID NO: 57, SEQ ID NO: 58, SEQ ID NO: 59, SEQ ID NO: 60, SEQ ID NO: 61, SEQ ID NO: 62, and SEQ ID NO:63 are useful for amplifying and/or detecting yellow fever virus.

3.5. Multiplex Amplification Reactions To Detect Different Virus Variants or Different Viruses The primers and probes of the invention can be combined in reactions to detect more than one viral nucleic acid. For example, in some cases, multiple upstream and/or multiple downstream primers are combined in one reaction mixture for use in detecting different viral variants (e.g., that would not be detected, or would only be poorly detected by a single primer or primer pair). In some embodiments, multiple upstream and/or multiple downstream primers are combined in one reaction mixture to detect more than one virus. In such embodiments, primers specific for each virus to be detected are included in the reaction mixture, thereby allowing for amplification of each viral nucleic acid present in a sample. For example, any combination of primers for amplification of West Nile Virus, SLEV, Dengue virus and yellow fever virus can be included depending on what virus is desired to be detected. Detection of multiple viruses using a single reaction is useful, for example, when screening the blood supply or in other cases where contamination with any virus is all that needs to be detected.

Probes of the invention can be used in the reactions described above. Depending on what result is desired, a single probe capable of detecting any possible viral nucleic acid product can be used. Alternatively, a different probe that specifically hybridizes to each possible viral nucleic acid product can be used. In such cases, it can be useful to employ a different detectable label with each probe, thereby allowing for differentiation of viral nucleic acid products.

In some embodiments, multiplex PCR can be used to detect multiple viral nucleic acids using the components described above. Multiplex PCR allows for amplification and/or detection of multiple polynucleotide fragments in the same reaction. See, e.g., PCR Primer, A Laboratory Manual (Dieffenbach, ed. 1995) Cold Spring Harbor Press, pages 157-171.

In some embodiments, primers for the detection of both West Nile virus and SLEV are used. In some embodiments, primers for the detection of West Nile virus, SLEV, and Dengue virus are used. In some embodiments, primers for the detection of West Nile virus, SLEV, and yellow fever virus are used. In some embodiments, primers for the detection of West Nile virus, SLEV, yellow fever and Dengue virus are used. In some cases, the multiplex reactions further comprise at least one probe as described herein.

4. Methods for Detecting and/or Quantifying a Nucleic Acid of a Member of the Japanese Encephalitis Serogroup and Certain Other Flaviviruses In Certain Aspects, the Present Invention Provides Methods for Using nucleic acid primers and probes to detect a nucleic acid of certain flaviviruses. In other aspects, the present invention provides methods for using nucleic acid primers and probes to quantify a nucleic acid of certain flaviviruses in a sample. Any method for using nucleic acid primers and probes to detect a nucleic acid known to one of skill in the art without limitation can be used to detect a nucleic acid of a detectable flavivirus, as described above. In certain embodiments, the methods provide using a primer and a probe to detect a nucleic acid of a member of the Japanese encephalitis virus serogroup. In other embodiments, the methods provide using two primers and a probe to detect a nucleic acid of a member of the Japanese encephalitis virus serogroup. In still other embodiments, the methods provide using a probe to detect certain flaviviruses, as described below.

4.1. 5' Nuclease Reaction-Based Assays for Detecting and/or Quantifying a Nucleic Acid of a Member of the Japanese Encephalitis Serogroup In certain aspects of the invention, the methods comprise detecting a nucleic acid of a member of the Japanese encephalitis virus serogroup with a primer and a probe. These methods generally comprise contacting a primer hybridized to a nucleic acid of a member of the Japanese encephalitis virus serogroup with an enzyme with 5' nuclease activity. The enzyme with 5' nuclease activity then fragments a probe hybridized to the nucleic acid of the member of the Japanese encephalitis virus serogroup in a 5' nuclease reaction. The probe can be labeled with a detectable moiety that enables detection of fragmentation of the probe. Such methods are based on those described in U.S. Pat. Nos. 6,214,979, 5,804,375, 5,487,972 and 5,210,015, each of which is hereby incorporated by reference in its entirety.

In a 5' nuclease reaction, the nucleic acid, primer and probe can be contacted with any enzyme known by one of skill in the art to have 5' to 3' nuclease activity without limitation. The conditions are preferably chosen to permit the polymerase to cleave the probe and release a plurality of fragments of the probe from the nucleic acid. Preferred enzymes with 5' nuclease activity include template-dependent nucleic acid polymerases. Known native and recombinant forms of such polymerases include, for example, *E. coli* DNA polymerase I (Fermentas, Inc., Hanover, Md.), *Bacillus stearothermophilus* DNA polymerase, and *Thermococcus littoralis* DNA polymerase.

In preferred embodiments, the enzymes with 5' nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*. For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, and *Thermus* species sps17 (spsl7), as described in U.S. Pat. Nos. 5,405,774, 5,352,600, 5,079,352, 4,889,818, 5,466,591, 5,618,711, 5,674,738, and 5,795,762, each of which is incorporated herein by reference in its entirety. *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International patent application Ser. No. PCT/US91/07035 with Publication No. WO 92/06200, which is incorporated herein by reference in its entirety. The sequence of *Thermatoga neapolitana* may be found in International Patent Publication No. WO 97/09451, which is incorporated herein by reference in its entirety.

A 5' nuclease reaction comprises contacting the nucleic acid to be detected with a primer, a probe, and an enzyme having 5' to 3' nuclease activity, under conditions in which the primer and the probe hybridize to the nucleic acid. Components of a 5' nuclease reaction can contact the nucleic acid to be detected in any order, e.g., the primer can contact the nucleic acid to be detected first, followed by the probe and enzyme with 5' nuclease activity, or alternatively the enzyme with 5' nuclease activity can contact the nucleic acid to be detected first, followed by the probe and primer. In certain embodiments, more than one primer or probe may be added to a 5' nuclease reaction. In certain preferred embodiments, a pair of primers can contact the nucleic acid in a 5' nuclease reaction. The primer can be any primer capable of priming a DNA synthesis reaction. Where only one primer is used, the primer should hybridize to the nucleic acid upstream of the probe, i.e., the 3' end of the primer should point toward the 5' end of the probe. The 3' end of the primer can hybridize adjacent to the 5' end of the probe, or the 3' end of the primer can hybridize further upstream of the 5' end of the probe. Where more than one primer is used, at least one primer should hybridize to the nucleic acid to be detected upstream of the probe, as described above.

Certain embodiments of the 5' nuclease reactions of the present invention are based on several 5' nuclease reactions that are known to those of skill in the art. Examples of such reactions are described in detail, for instance, in U.S. Pat. No. 5,210,015, the content of which is hereby incorporated by reference in its entirety.

Briefly, in a 5' nuclease reaction, a target nucleic acid is contacted with a primer and a probe under conditions in which the primer and probe hybridize to a strand of the nucleic acid. The nucleic acid, primer and probe are also contacted with an enzyme, for example a nucleic acid polymerase, having 5' to 3' nuclease activity. Nucleic acid polymerases possessing 5' to 3' nuclease activity can cleave the probe hybridized to the nucleic acid downstream of the primer. The 3' end of the primer provides a substrate for extension of a new nucleic acid as based upon the template nucleic acid by the nucleic acid polymerase. As the polymerase extends the new nucleic acid, it encounters the 5' end of the probe and begins to cleave fragments from the probe.

The primer and probe can be designed such that they hybridize to the target nucleic acid in close proximity to each other such that binding of the nucleic acid polymerase to the 3' end of the primer puts it in contact with the 5' end of the probe. In this process, nucleic acid extension is not required to bring the nucleic acid polymerase into position to accomplish the cleavage. The term "polymerization-independent cleavage" refers to this process.

Alternatively, if the primer and probe anneal to more distantly spaced regions of the nucleic acid, nucleic acid extension must occur before the nucleic acid polymerase encounters the 5' end of the probe. As the polymerization continues, the polymerase progressively cleaves fragments from the 5' end of the probe. This cleaving continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. In the absence of primer extension, the strand of the nucleic acid is substantially single-stranded. Provided the primer and probe are adjacently bound to the nucleic acid, sequential rounds of oligonucleotide annealing and cleavage of fragments can occur. Thus, sufficient amounts of the probe can be fragmented to yield a detectable signal, thereby permitting detection in the absence of polymerization.

In either process, a sample is provided which contains the nucleic acid. If the nucleic acid is double-stranded, it should first be denatured, e.g., the strands of the nucleic acid separated from each other. Any suitable denaturing method, including physical, chemical, or enzymatic means, known to one of skill in the art without limitation can be used to separate the nucleic acid strands. A preferred physical means for strand separation is heating the nucleic acid until it is completely (>99%) denatured. Typical heat denaturation involves temperatures ranging from about 80° C. to about 105° C., for about 10 seconds to about 10 minutes. As an alternative to denaturation, the nucleic acid may exist in a single-stranded form in the sample, such as, for example, single stranded RNA or DNA viruses.

It should be noted that the viruses that can be detected with the primers, probes, methods, and kits of the invention are single stranded plus-strand RNA viruses. Accordingly, denaturation of the native viral genome is not required to detect an unamplified viral genome. However, if the native viral genome is reverse-transcribed into DNA according to certain embodiments of the invention, described below, denaturation of the amplified viral nucleic acids is necessary prior to detection with the primers and probes of the invention.

If the nucleic acid to be detected is RNA, the RNA can either be used as an RNA template for a 5' nuclease reaction as described above, or the RNA can be used as a template for reverse-transcription into cDNA, or both simultaneously. In certain embodiments, the RNA can be detected without reverse-transcription into cDNA using the methods of the invention. Polymerization-independent cleavage methods as described above are particularly well-suited for such embodiments. In other embodiments, the RNA can be first reverse-transcribed into cDNA in the absence of a probe, and then the cDNA product can be detected according to the methods of the invention. In still other embodiments, the RNA can be reverse-transcribed in the presence of a probe, simultaneously producing cDNA that can subsequently be amplified and/or detected and detecting the presence of the RNA by assessing fragmentation of the probe as described herein.

Where the RNA is reverse-transcribed in the absence of a probe, the RNA can be reverse transcribed into cDNA by any method known to one of skill in the art. The products of such reverse transcription can then be detected like any detectable nucleic acid according to the methods described herein.

Where the RNA is reverse-transcribed in the presence of a probe, the RNA can be reverse-transcribed by a DNA polymerase with 5'-3' nuclease activity that can use RNA as a template for DNA strand synthesis. As with all known DNA polymerase synthesis activities, such synthesis requires the presence of a primer, such as those described herein. The DNA polymerase that can use RNA is a template is preferably thermostable, so that multiple cycles of denaturation and DNA synthesis can occur without destroying the polymerase. Further, the DNA polymerase used for reverse transcription can preferably also synthesize DNA using a DNA template. Such polymerases are described in, for example, U.S. Pat. Nos. 6,468,775 (*Carboxydothermus hydrogenformans* DNA polymerase), 5,968,799 (*Thermosipho africanus* DNA polymerase), 5,736,373 (*Bacillus pallidus* DNA polymerase), 5,674,738 (*Thermus* species Z05 DNA polymerase), and 5,407,800 (*Thermus aquaticus* and *Thermus thermophilus* DNA polymerases), each of which is incorporated herein by reference in its entirety. In addition, methods and compositions for reverse transcribing an RNA using a thermostable DNA polymerase with reverse transcription activity are described in U.S. Pat. Nos. 5,693,517, 5,561,058, 5,405,774, 5,352,600, 5,310,652, and 5,079,352, each of which is incorporated herein by reference in its entirety.

Whether RNA or DNA, the denatured nucleic acid strand is then contacted with a primer and a probe under hybridization conditions, which enable the primer and probe to bind to the nucleic acid strand. In certain embodiments, two primers can be used to amplify the nucleic acid. In such embodiments, the two primers can be selected so that their relative positions along the nucleic acid are such that an extension product synthesized from one primer, after the extension produce is separated from its template (complement), can serve as a template for the extension of the other primer to yield an amplified product of defined length. The length of the product depends on the length of the sequence between the two primers and the length of the two primers themselves.

Because the complementary strands are typically longer than either the probe or primer, the strands have more points of contact and thus a greater chance of finding and binding each other over any given period of time. A high molar excess of probe and primer helps shift the equilibrium toward primer and probe annealing rather than template reannealing.

The primer should be sufficiently long to prime the synthesis of extension products in the presence of the agent for polymerization. The exact length and composition of the primer can depend on many factors, including temperature of the annealing reaction, source and composition of the primer, proximity of the probe annealing site to the primer annealing site, and ratio of primer:probe concentration. For example, depending on the complexity of the sequence, an oligonucleotide primer typically contains about 15-30 nucleotides, although it may contain fewer or more nucleotides. The primers must be sufficiently complementary to selectively anneal to their respective strands and form stable duplexes.

Each primer can be selected to be "substantially" complementary to a strand of the nucleic acid. The primers need not reflect the exact sequence of the template, but must be sufficiently complementary to selectively hybridize to their respective strands under the appropriate reaction conditions. Non complementary bases or longer sequences can be interspersed into the primer or located at the ends of the primer, provided the primer retains sufficient complementarity with its template strand to form a stable duplex therewith. The non-complementary nucleotide sequences of the primers may include restriction enzyme sites. Any non-complementary nucleotide sequences are preferably not at the 3' end of the primer.

The probe preferably hybridizes to the nucleic acid to be detected before the polymerase binds the nucleic acid and primer and begins to extend the new nucleic acid strand from the primer based upon the template of the detectable nucleic acid. It is possible for the polymerase to bind the primer and nucleic acid to be detected before the probe contacts the detectable nucleic acid; however, this arrangement can result in decreased probe fragmentation unless multiple cycles of primer extension are performed, as in a preferred PCR based 5' nuclease reaction as described below. Accordingly, it is preferable that the probe hybridize to the nucleic acid to be detected before primer extension by the polymerase begins.

A variety of techniques known to one of skill in the art can be employed to enhance the likelihood that the probe will hybridize to the detectable nucleic acid before primer extension polymerization reaches this duplex region, or before the polymerase attaches to the upstream oligonucleotide in the polymerization-independent process. For example, short primer molecules generally require cooler temperature to form sufficiently stable hybrid complexes with the nucleic acid. Therefore, the probe can be designed to be longer than the primer so that the probe anneals preferentially to the nucleic acid at higher temperatures relative to primer annealing.

One can also use primers and probes having differential thermal stability based upon their nucleotide composition. For example, the probe can be chosen to have greater G/C content and, consequently, greater thermal stability than the primer. Alternatively or additionally, one or more modified, non-standard or derivatized DNA bases may be incorporated into primers or probes to result in either greater or lesser thermal stability in comparison to primers or probes having only conventional DNA bases. Examples of such modified, non-standard or derivatized bases may be found in U.S. Pat. Nos. 6,320,005, 6,174,998, 6,001,611, and 5,990,303, each of which is hereby incorporated by reference in its entirety.

Further, the temperature of the reaction can also be varied to take advantage of the differential thermal stability of the probe and primer. For example, following denaturation at high temperatures as described above, the reaction can be incubated at an intermediate temperature which permits probe but not primer binding, followed by a further temperature reduction to permit primer annealing and subsequent extension.

A high molar excess of probe to primer concentration can also be used to preferentially favor binding of the probe before the primer. Such probe concentrations are typically in the range of about 2 to 20 times higher than the respective primer concentration, which is generally $0.5-5\times10^{-7}$ M.

Template-dependent extension of the oligonucleotide primer(s) is catalyzed by a DNA polymerase in the presence of adequate amounts of the four deoxyribonucleoside triphosphates (dATP, dGTP, dCTP, and dTTP) or analogs, e.g., dUTP, as discussed above, in a reaction medium which is comprised of the appropriate salts, metal cations, and pH buffering system. Suitable polymerizing agents are enzymes known to catalyze primer and template-dependent DNA synthesis and possess the 5' to 3' nuclease activity. Such enzymes include, for example, *Escherichia coli* DNA polymerase I, *Thermus thermophilus* DNA polymerase, *Bacillus stearothermophilus* DNA polymerase, *Thermococcus littoralis* DNA polymerase, *Thermus aquaticus* DNA polymerase, *Thermatoga maritima* DNA polymerase and *Thermatoga neapolitana* DNA polymerase and Z05 DNA polymerase. Further, the reaction conditions for performing DNA synthesis using these DNA polymerases are well known in the art. To be useful in the methods of the present invention, the polymerizing agent should possess 5' nuclease activity that can efficiently cleave the oligonucleotide and release labeled fragments so that a detectable signal is directly or indirectly generated.

The products of the synthesis are duplex molecules consisting of the template strands and the primer extension strands. Byproducts of this synthesis are probe fragments which can consist of a mixture of mono-, di- and oligonucleotide fragments. In preferred embodiments, repeated cycles of denaturation, probe and primer annealing, and primer extension and cleavage of the probe can be performed, resulting in exponential accumulation of the amplified region defined by the primers and exponential generation of labeled fragments. Such repeated thermal cycling is generally known in the art as the polymerase chain reaction (PCR). Sufficient cycles can be performed to achieve fragment a sufficient amount of the probe to distinguish positive reactions, i.e., the nucleic acid to be detected is present, from negative reactions, i.e., the nucleic acid to be detected is not present. Generally, positive reactions will exhibit a signal that is several orders of magnitude greater than a negative reaction.

In certain preferred embodiments, the PCR reaction is carried out as an automated process which utilizes a thermostable enzyme. In this process the reaction mixture is cycled through a denaturing step, a probe and primer annealing step, and a synthesis step, whereby cleavage and displacement occur simultaneously with primer dependent template extension. A thermal cycler, such as the ABI 3700 (Applied Biosystems, Inc., Foster City, Calif.), which is specifically designed for use with a thermostable enzyme, may be employed. In certain of such embodiments of the invention, the nucleic acids to be detected can be amplified in the absence of a detectably-labeled probe, followed by detection of the amplification product in a separate reaction. Alternatively, the nucleic acids to be detected can be amplified in the presence of the probe, allowing amplification and detection in a single reaction.

Temperature stable polymerases are preferred in this automated process because the preferred way of denaturing the double stranded extension products is by exposing them to a high temperature (about 95° C.) during the PCR cycle. For example, U.S. Pat. No. 4,889,818 discloses a representative thermostable enzyme isolated from *Thermus aquaticus*. Additional representative temperature stable polymerases include, e.g., polymerases extracted from the thermostable bacteria *Thermus flavus, Thermus Tuber, Thermus thermophilus, Bacillus stearothermophilus* (which has a somewhat lower temperature optimum than the others listed), *Thermus lacteus, Thermus rubens, Thermotoga maritima, Thermococcus littoralis, Methanothermus fervidus,* and *Pyrococcus furiosus* (Stratagene, La Jolla, Calif.). As described above, certain of these thermostable polymerases can synthesize DNA from an RNA template. Where an RNA molecule is to be detected according to the methods of the invention, a DNA polymerase that can synthesize DNA from an RNA template, i.e., with reverse transcription activity, should be used.

In other aspects, the methods of the present invention can also be used to quantify an amount of a nucleic acid of a member of the Japanese encephalitis virus serogroup in a sample. In such methods, a 5' nuclease reaction as described above is performed, and the amount of fluorescence produced is quantified. The amount of fluorescence can be quantified by any method known to one of skill in the art without limitation. In certain embodiments, the amount of fluorescence emitted can be quantified with a fluorometer. This amount of fluorescence can be compared to the amount of fluorescence emitted by a control reaction. The control reaction is preferably performed with the same reagents and at the same time as the reaction performed with the sample with a known amount of nucleic acid of a member of the Japanese encephalitis virus serogroup. Alternatively, the amount of fluorescence emitted by the fluorescent moiety can be compared to a standard curve plotting fluorescence against viral nucleic acid concentration. A representative standard curve is presented in FIG. 6. Further guidance in quantifying an amount of a nucleic acid of a member of the Japanese encephalitis virus serogroup can be found in published U.S. Patent Application Publication No. 2002/0058262 and European Patent Nos. 1 138 780, 1 138 783, and 1 138 784.

4.2. Other Methods for Detecting a Nucleic Acid of a Member of the Japanese Encephalitis Serogroup that Use One or More Primers and a Probe In addition to the 5' nuclease reactions described above, the invention further provides other methods can be used to be used to detect a nucleic acid of a member of the Japanese encephalitis virus serogroup, as described below.

In certain embodiments, any method known by one of skill in the art that uses two nucleic acid primers and a nucleic acid probe to detect a nucleic acid can be used to detect a nucleic acid of a member of the Japanese encephalitis virus serogroup. The nucleic acid primers and probes described Sections 3.1 and 3.2 can be used in any such method known to one of skill in the art, without limitation. Exemplary amplification reactions that can be used to detect the viral nucleic acids include, e.g., polymerase chain reaction (PCR) and ligase chain reaction (LCR) (see U.S. Pat. Nos. 4,683,195 and 4,683,202; PCR Protocols: *A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313): 91-2 (1991), rolling circle amplification (RCA) (Lisby, *Mol. Biotechnol.* 12(1):75-99 (1999)); Hatch et al., *Genet. Anal.* 15(2):35-40 (1999)) branched DNA signal amplification (bDNA) (see, e.g., Iqbal et al., *Mol. Cell. Probes* 13(4):315-320 (1999)) and Q-Beta Replicase (Lizardi et al., *Bio/Technology* 6:1197 (1988)).

One example of such methods is amplifying a nucleic acid of a member of the Japanese encephalitis serogroup and detecting the presence of the nucleic acid with a probe that is a molecular beacon. Such probes contain a target recognition sequence that can hybridize to a flanked by complementary sequences that can form a hairpin. The molecular beacon has a fluorescent moiety and a quencher moiety on opposite ends of the probe. Hybridization of the molecular beacon to the nucleic acid of a member of the Japanese encephalitis serogroup separates the fluorescent moiety from the quencher moiety allowing detection of the fluorescent moiety, and thus revealing the presence of the nucleic acid of a member of the Japanese encephalitis serogroup. Any probe of the invention may be used in such methods with the addition of several residues on the 5' and 3' ends of the probe that one of skill in the art recognizes as capable of forming a hairpin structure. Further guidance in selection and use of molecular beacons may be found in an article by Tyagi and Kramer, 1996, *Nat. Biotechnol.* 14:303-308, which is hereby incorporated by reference in its entirety.

In still another example, two primers and a probe of the invention may be used to detect a nucleic acid of a member of the Japanese encephalitis serogroup using nucleic acid sequence-based amplification. Nucleic acid sequence-based amplification (NASBA) is a robust amplification technology that can be used to detect a nucleic acid of a member of the Japanese encephalitis serogroup. In NASBA methods, three enzymes are used, including reverse transcriptase, T7 RNA polymerase, and RNase H. The final amplification product is single-stranded RNA with a polarity opposite that of the nucleic acid to be detected. The amplified RNA product can be detected through the use of a target-specific capture probe bound to magnetic particles in conjunction with a ruthenium-labeled detector probe and an instrument (NucliSens Reader; bioMérieux) capable of measuring electrochemiluminescence (ECL). Alternatively, RNA amplified by NASBA can specifically be detected in real time by including molecular beacon probes in the amplification reaction, as described above. Further guidance on use of the primers and probes of the invention may be found in articles by Compton, 1991, Nature 350:91-92 and Kievits et al., 1991, J. Virol. Methods 35:273-86, each of which is hereby incorporated by reference in its entirety.

Other examples of such methods include the 5' nuclease reactions described extensively above. Another example of such methods include amplification of a nucleic acid of a member of the Japanese encephalitis serogroup with two primers of the invention, followed by detection of the amplified nucleic acid with a probe of the invention. Still other examples of such methods that may be used or adapted by one of skill in the art to detect a nucleic acid of a member of the Japanese encephalitis virus serogroup may be found in U.S. Pat. Nos. 6,403,339, 6,329,152, 5,952,202, and 5,387,510, each of which is hereby incorporated by reference in its entirety.

In other embodiments, any method known by one of skill in the art that uses a nucleic acid primer and a nucleic acid probe to detect a nucleic acid can be used to detect a nucleic acid of a member of the Japanese encephalitis virus serogroup. The nucleic acid primers and probes described Sections 3.1 and 3.2 can be used in any such method known to one of skill in the art, without limitation. In certain of these methods, one of skill in the art will recognize that a primer of the invention may also be used as a probe, and a probe of the invention used as a primer.

For example, a nucleic acid of a member of the Japanese encephalitis virus serogroup can be hybridized to a primer of the invention that is bound to a solid support. A detectably-labeled probe of the invention can then be hybridized to the nucleic acid to be detected, thereby indicating the presence of the nucleic acid. Alternatively, the probe can be bound to the solid support and used to capture the nucleic acid, and then the primer can be detectably labeled and hybridized to the nucleic acid, thereby indicating the presence of the nucleic acid.

Another example of methods that use a nucleic acid primer and a probe to detect a nucleic acid of a member of the Japanese encephalitis virus serogroup involves the use of nanoparticles. In such methods, two oligonucleotides, such as a primer or probe of the invention, that can hybridize to different regions of a nucleic acid to be detected are covalently linked to a nanoparticle. The nanoparticles are contacted with a nucleic acid of a member of the Japanese encephalitis virus serogroup under hybridization conditions. If the nucleic acid is present, the nucleic acid will bind to the oligonucleotides attached to the nanoparticles, producing a large molecular weight complex that can be detected. The complex can be detected by any method known to one of skill in the art without limitation. In certain embodiments, the complex is detected by precipitation of the complex. Further guidance on methods of using nanoparticles in connection with the primers and probes of the invention may be found in Taton et al., 2000, Science 289(5485):1757-60 and U.S. Pat. Nos. 6,506,564, 6,495,324, 6,417,340, 6,399,303, and 6,361,944.

In yet another example, rolling circle amplification ("RCA") can be used as part of a method for detecting a nucleic acid of a member of the Japanese encephalitis virus serogroup. In certain embodiments of RCA methods, a DNA circle is amplified by polymerase extension of a complementary primer. Any of the primers or probes of the invention can be used in such methods. Methods of circularizing DNA are well known in the art, and include, for example, ligating the ends of a DNA molecule together under conditions which favor intramolecular ligation. The single-stranded product concatamer product can then be detected by any method of detecting a nucleic acid known to one of skill in the art without limitation. For example, the concatamer product can be detected using a detectably-labeled probe of the invention. Other examples of methods of detecting a nucleic acid of known sequence are extensively described herein. In other embodiments of RCA, a second primer can be used that is complementary to the concatamer product. This primer allows exponential amplification of the sequences present in the circular DNA template. The products of the amplification can still be detected, for example, by using a detectably-labeled probe of the invention. Further guidance on using the primers and probes of the invention in RCA methods for detecting a nucleic acid of a member of the Japanese encephalitis virus serogroup may be found in U.S. Pat. Nos. 6,344,329, 6,350,580, 6,221,603, 6,210,884, 5,648,245, and 5,714,320 and international patent publication no. WO95/35390, each of which is hereby incorporated by reference in its entirety.

Still another example of such methods is the polymerization-independent 5' nuclease reaction described above. Still other examples of methods of using a primer and a probe that can be used or adapted by one of skill in the art to detect a member of the Japanese encephalitis virus serogroup are described in U.S. Pat. Nos. 6,316,200, 6,268,128, 6,180,338, 5,716,784, and 5,573,906, each of which is hereby incorporated by reference in its entirety.

In certain embodiments, any assay known by one of skill in the art that uses two nucleic acid primers that can amplify a nucleic acid to detect the nucleic acid can be used to detect a nucleic acid of a member of the Japanese encephalitis virus serogroup. The nucleic acid primers described in Section 3.1 can be used in any such method known to one of skill in the art, without limitation. In addition, one of skill in the art will recognize that a probe of the invention may also be used as a primer in certain of these methods.

In one example of such methods, a nucleic acid of a member of the Japanese encephalitis virus serogroup can be detected by amplifying the nucleic acid with at least one primer that comprises a hairpin structure containing a fluorescent moiety and a quencher moiety at the 5' end of the molecule. Incorporation of the primer into the amplification product can then separate the fluorescent moiety from the quencher moiety, allowing detection of the fluorescent moiety. Detection of the fluorescent moiety reveals the presence of the nucleic acid of a member of the Japanese encephalitis virus serogroup. One of skill in the art will easily recognize the use of the primers or probes of the invention in such methods by incorporating additional residues in the primer or probe to form the necessary hairpin structure. Further guidance in design and selection of such primers and probes may be found in Nazerenko et al., 1997, Nucleic Acids Res. 25:2516-2521 and in Thelwell et al., 2000, Nucleic Acids Res. 28:3752-3761, each of which is hereby incorporated by reference in its entirety.

In another example of such methods, a nucleic acid of a member of the Japanese encephalitis virus serogroup can be detected using Strand Displacement Amplification ("SDA"). In such methods, amplified Japanese encephalitis virus serogroup nucleic acids are detected by incorporation of a single-stranded primer that comprises a fluorescent moiety, a quencher moiety, and an engineered restriction site separating the two moieties. One of skill in the art can easily recognize how to modify any of the primers or probes of the invention for use in SDA.

In a first amplification reaction used in SDA, the primer is used to amplify the nucleic acid of a member of the Japanese encephalitis serogroup in the presence of, for example, thio-dCTP, thereby incorporating the primer into the amplification product. Then, a restriction endonuclease can be used to nick the restriction site in the primer. The restriction endonuclease cannot cut both strands of the amplification product because of the incorporation of thio-dCTP in the amplification product. Finally, the 3' end of the primer created by the nick can be used to prime a new polymerization reaction, thereby displacing the portion of the strand 3' to the nick from the template strand. Displacement of the strand separates the fluorescent moiety from the quencher moiety, thereby preventing quenching of fluorescence emitted by the fluorescent moiety. The nucleic acid of a member of the Japanese encephalitis serogroup can thereby be detected and/or quantified by measuring the presence and/or amount of fluorescence. Further guidance on selection and modification of primers and probes for use in SDA may be found in Little et al., 1999, Clin. Chem. 45-777-784 and U.S. Pat. Nos. 6,528,254 and 6,528,632, each of which is hereby incorporated by reference in its entirety.

In another example, a nucleic acid of a member of the Japanese encephalitis serogroup may be detecting using transcription-mediated amplification ("TMA"). TMA is an RNA transcription amplification system that uses RNA polymerase and reverse transcriptase to amplify the nucleic acids to be detected. In the method, a primer of the invention with a promoter for RNA polymerase is used to prime reverse transcription of an RNA of a member of the Japanese encephalitis virus serogroup. The RNAse activity of reverse transcriptase then degrades the RNA template, releasing the cDNA strand. Second strand synthesis is primed with a second primer of the invention and catalyzed by reverse transcriptase. RNA polymerase then recognizes the promoter synthesized in the second strand and catalyzes multiple cycles of RNA transcription from the second strand. The RNA product can then be detected or can serve as template for another round of amplification.

The RNA product of TMA can then be detected by any method known to one of skill in the art. In certain embodiments, the RNA product can be detected with a probe of the invention. In other embodiments, the RNA product can be detected with a probe of the invention that has been labeled with an acridine-ester label (Gen-Probe, Inc., San Diego, Calif.). Such labels can be chemically removed from unhybridized probe while labels on hybridized probes remain undisturbed. Thus, in such embodiments, presence of a nucleic acid of a member of the Japanese encephalitis virus serogroup can be detected by detecting the presence of the acridine-ester label. Further guidance in using the primers and probes of the invention in TMA-based methods may be found in Arnold et al., 1989, Clin. Chem. 35:1588-1594, Miller et al., 1994, J. Clin. Microbiol. 32-393-397, and U.S. Pat. Nos. 6,335,166 and 6,294,338, each of which is hereby incorporated by reference in its entirety.

In yet another example, a nucleic acid of a member of the Japanese encephalitis virus serogroup can be detected using diagnostic PCR. In such methods, the presence of a nucleic acid to be detected is indicated by the successful template-dependent amplification of a PCR product. Generally, the identity of the PCR product can be determined from the size of the PCR product; successful amplification of the nucleic acid to be detected will generally result in a PCR product of known size. Methods for determining the size of a nucleic acid, such as a PCR product, are well-known to the art and include, for example, gel and capillary electrophoresis, among others.

Other methods of detecting successful amplification of a PCR product thereby revealing the presence of a member of the Japanese encephalitis serogroup include using non-specific DNA binding dyes. For example, SYBR® Green (Molecular Probes, Inc., Eugene, Oreg.) can be included in the amplification reaction, which allows the detection and quantification of any double-stranded DNA generated during PCR. Examples of such methods may be found in U.S. Pat. Nos. 6,323,337 and 5,863,753, each of which is incorporated by reference in its entirety.

Finally, other methods that can be used or adapted by one of skill in the art to use the primers and probes of the invention to detect a member of the Japanese encephalitis virus serogroup are described in U.S. Pat. Nos. 6,528,632, 6,475,729, 6,361,944, 6,329,152, 6,270,967, 6,258,546, 6,063,603, 6,057,099, 6,040,166, 5,914,230, 5,843,650, 5,747,255, 5,747,251, 5,731,146, 5,712,386, 5,635,347, 5,554,517, 5,409,818, 5,384,242, 4,965,188, 4,868,104, 4,800,159, and 4,683,195, each of which is hereby incorporated by reference in its entirety.

In other embodiments, any assay known by one of skill in the art that uses a single nucleic acid primer or probe that can hybridize to a nucleic acid to detect the nucleic acid can be used to detect a nucleic acid of a member of the Japanese encephalitis virus serogroup. The nucleic acid primers and probes described in Section 3.1 and 3.2 can be used in any such method known to one of skill in the art, without limitation. In addition, one of skill in the art will recognize that a primer of the invention may also be used as a probe, and a probe of the invention used as a primer in certain of the described methods.

For example, a nucleic acid of a member of the Japanese encephalitis virus serogroup can be detected using a primer to initiate a primer extension reaction. Successful extension of the primer by a nucleic acid polymerase indicates the presence of the nucleic acid of a member of the Japanese encephalitis virus serogroup. A primer extension product that indicates the presence of a member of the Japanese encephalitis virus serogroup can be detected by any method known to one of skill in the art. For example, the primer extension reaction can incorporate $^{32}P$-labeled or fluorescently-labeled nucleotides.

Other examples of single primer or probe detection methods that describe methods that can be used as described or adapted by one of skill in the art to detect a member of the Japanese encephalitis virus serogroup can be found in U.S. Pat. Nos. 6,440,707, 6,379,888, 6,368,803, 6,365,724, 6,361,944, 6,352,827, 6,326,145, 6,312,906, 6,268,128, 6,261,784, 6,177,249, 6,140,055, 6,130,047, 6,124,090, 6,121,001, 6,110,677, 6,054,279, 6,022,686, 5,981,176, 5,958,700, 5,945,283, 5,935,791, 5,919,630, 5,888,739, 5,888,723, 5,882,867, 5,876,924, 5,866,336, 5,856,092, 5,853,990, 5,846,726, 5,814,447, 5,808,036, 5,800,989, 5,795,718, 5,792,614, 5,710,028, 5,683,875, 5,683,872, 5,679,510, 5,641,633, 5,597,696, 5,595,890, 5,571,673, 5,547,861, 5,525,462, 5,514,546, 5,491,063, 5,437,977, 5,294,534, 5,118,605, 5,102,784, 4,994,373, 4,851,331, 4,767,700, and 4,683,194, each of which is hereby incorporated by reference in its entirety.

Certain of the above-referenced U.S. Patents disclose methods that can use either one or two primers, or either one or two primers and a probe. The above description is not meant to categorize such methods. Methods of detecting a nucleic acid using, for example, two primers provided in a U.S. patent that is described as providing a method for detecting a nucleic acid using a single primer are also incorporated by reference and can be used with the primers, probes, and kits of the invention.

4.3. Methods for Detecting a Nucleic Acid of a Member of the Japanese Encephalitis Serogroup and Certain Other Flaviviruses Using a Probe In addition to the assays for detecting a nucleic acid of a member of the Japanese encephalitis virus serogroup described above, the invention further provides methods for detecting a nucleic acid of a member of the Japanese encephalitis virus serogroup and certain other flaviviruses. The flaviviruses that can be detected according to these methods are described in Section 3.4, above.

In certain embodiments, any method known to one of skill in the art that uses a nucleic acid probe to detect a nucleic acid can be used to detect a nucleic acid of a member of the Japanese encephalitis virus serogroup and certain other flaviviruses. Nucleic acid probes that can be used to detect nucleic acids of members of the Japanese encephalitis virus serogroup and certain other flaviviruses are described in Section 3.2, above.

In certain embodiments, the probes of the invention can be used to determine if viral sequences of nucleic acids of members of the Japanese encephalitis virus serogroup and certain other flaviviruses are present in a sample by determining if the probes bind to the viral sequences present in the sample. For example, the detection can be accomplished using a dot blot format. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with a single probe, the dot blot format is quite useful. Many samples can be immobilized at discrete locations on a single membrane and hybridized simultaneously by immersing the membrane in a solution of probe.

An alternate method that is quite useful when large numbers of different probes are to be used is a "reverse" dot blot format, in which the amplified sequence contains a label, and the probe is bound to the solid support. This format would be useful if the assay methods of the present invention were used as one of a battery of methods to be performed simultaneously on a sample. In this format, the unlabeled probes are bound to the membrane and exposed to the labeled sample under appropriately stringent hybridization conditions. Unhybridized labeled sample is then removed by washing under suitably stringent conditions, and the filter is then monitored for the presence of bound sequences.

Both the forward and reverse dot blot assays can be carried out conveniently in a microtiter plate; see U.S. patent application Ser. No. 695,072, filed May 3, 1991, which is a CIP of U.S. patent application Ser. No. 414,542, filed Sep. 29, 1989, now abandoned, each of which is incorporated herein by reference in its entirety. The probes can be attached to bovine serum albumen (BSA), for example, which adheres to the microliter plate, thereby immobilizing the probe.

Another example of a method of using a probe of the invention to detect a nucleic acid of members of the Japanese encephalitis virus serogroup and certain other flaviviruses is described in U.S. Pat. No. 6,383,756, which provides a method for detecting a nucleic acid bound to a membrane, and which is hereby incorporated by reference in its entirety.

In another example, a nucleic acid of a member of the Japanese encephalitis virus serogroup can be detected using branched-DNA-based methods. In such methods, a dendrimer monomer is constructed of two DNA strands that share a region of sequence complementarity located in the central portion of each strand. When the two strands anneal to form the monomer the resulting structure has a central double-stranded center bordered by four single-stranded ends. A dendrimer can be assembled from monomers by hybridization of the single stranded ends of the monomers to each other, while still leaving many single-stranded ends free. These free single-stranded ends can have the sequences of any of the primers or probes of the invention. A dendrimer can be detectably-labeled with any detectable moiety known to one of skill in the art without limitation, as described above in connection with the probes of the invention.

Dendrimers can then be used as a probe, in, for example, the "dot blot" assays described below. In addition, a dendrimer can be used as a probe in any method known to one of skill in the art in which the probe is directly detected. A probe is directly detected when the presence of the probe can be determined without any subsequent reaction or modification, such as a dot blot or Southern hybridization. Further guidance on the selection and use of dendrimers as probes to detect a nucleic acid of a member of the Japanese encephalitis serogroup or other detectable flaviviruses may be found in U.S. Pat. No. 6,261,779 and in Nilsen et al., 1997, J. Theoretical Biology 187:273-284, Capaldi et al., 2000, Nucleic. Acids Res., 28(7):21e, Wang et al., 1998, J. Am. Chem. Soc. 120: 8281-8282, and Wang et al., 1998, Electroanalysis 10(8):553-556, each of which is hereby incorporated by reference in its entirety.

One of skill in the art will recognize that the probes of the invention can be used in combination with any primer that selectively hybridizes to a virus that can be detected with the probes of the invention. Accordingly, it is intended that methods of detecting a detectable flavivirus with a probe of the invention in combination with any primers that selectively hybridize to a detectable flavivirus fall within the scope of the present invention.

Any method that uses a single primer or probe that can be used to detect a nucleic acid of a member of the Japanese encephalitis virus serogroup described in Section 4.2, above, can be used with a probe of the invention to detect other flaviviruses described in Section 3.4, above.

5. Kits

In another aspect, the present invention provides kits that can be used to detect a nucleic acid of a Japanese encephalitis virus serogroup member and/or certain other flaviviruses. The members of the Japanese encephalitis virus serogroup that can be detected with the kits of the invention are described in Section 3.3, above, while the nucleic acids of other flaviviruses that can be detected with the kits of the invention are described in Section 3.4, above.

In certain embodiments, the kit comprises a probe of the invention. In some embodiments, the kit comprises a primer of the invention. In some embodiments, the kit comprises a combination of one or more of the primers and probes of the invention.

For example, in one embodiment the kit comprises a first nucleic acid primer that hybridizes to a nucleic acid of SEQ ID NO.: 1 and a second nucleic acid primer that hybridizes to a nucleic acid of SEQ ID NO.: 9. In other embodiments, the kits comprise a primer (e.g., at least one upstream and/or one downstream primer) comprising a polynucleotide that hybridizes to SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 or a complement thereof. Exemplary primers may be selected from, e.g., SEQ ID NO:64, SEQ ID NO:65, SEQ ID NO:66, and SEQ ID NO:67.

In some embodiments, the kits comprise at least one upstream and/or one downstream primer selected from SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:48, SEQ ID NO:49, SEQ ID NO:50, SEQ ID NO:51, SEQ ID NO:52, SEQ ID NO:53, SEQ ID NO:54, or SEQ ID NO:55.

In other embodiments, the kits comprise at least one upstream and/or one downstream primer selected from SEQ ID NO: 56, SEQ ID NO: 57, SEQ ID NO: 58, SEQ ID NO: 59, SEQ ID NO: 60, SEQ ID NO: 61, SEQ ID NO: 62, or SEQ ID NO:63.

In some of the above-described embodiments, the kits also comprise a nucleic acid probe that hybridizes to a nucleic acid of SEQ ID NO.: 16, or the complement thereof, as described herein.

In certain embodiments, the kits comprise two nucleic acid primers and a nucleic acid probe for detecting a nucleic acid of a member of the Japanese encephalitis virus serogroup. The nucleic acid primers that can be a component of the kits of the invention are extensively described in Section 3.1, above, while the nucleic acid probes that can be a component of the kits of the invention are described in Section 3.2, above. The probes can optionally be labeled as described above. In certain embodiments, the kits comprise a thermostable DNA polymerase. In certain embodiments, the thermostable DNA polymerase has reverse transcription activity. In certain embodiments, the kits comprise instructions for detecting a nucleic acid of a detectable flavivirus according to the methods of the invention. In other embodiments, the kits comprise instructions for detecting a member of the Japanese encephalitis virus serogroup. In other embodiments, the kits comprise one or more containers to hold the components of the kit.

In certain embodiments, the kits can contain a composition comprising a primer of the invention. The kits can also contain a composition comprising a probe of the invention. The kits can further contain a composition comprising a thermostable DNA polymerase. In some embodiments, the thermostable DNA polymerase is selected from the group of *Carboxydothermus hydrogenformans* DNA polymerase, *Thermosipho africanus* DNA polymerase, *Bacillus pallidus* DNA polymerase, *Thermus* species Z05 DNA polymerase, *Thermus aquaticus* DNA polymerase, *Thermus thermophilus* DNA polymerase, *Thermatoga maritima* DNA polymerase, *Thermatoga neapolitana* DNA polymerase and *Thermus* sps17 DNA polymerase The compositions comprising a primer or probe of the invention or a thermostable DNA polymerase can further comprise additional reagents. For example, the compositions can comprise suitable preservatives prevent degradation of the composition, suitable buffers to modulate the pH of the composition, suitable diluents to alter the viscosity of the compositions, and the like.

The kits can additionally comprise other reagents for carrying out a 5' nuclease reactions, as described above. In addition, the kits can comprise reagents to facilitate the detection of a fragmented probe that indicates the presence of a nucleic acid of a Japanese encephalitis virus serogroup member. Kits that can be used to detect a nucleic acid of defined sequence are described in U.S. Pat. Nos. 6,514,736, 6,197,563, 6,040166, and 5,641,864, each of which is incorporated herein by reference in its entirety. One of skill in the art can easily use the primers and probes of the invention to modify the disclosures of these U.S. patents to design additional kits that are also within the scope of the present invention.

EXAMPLES

Example 1

Amplification and Detection of West Nile Virus RNA

A lysate of virus-infected cell culture supernatant was received from Dr. R. Lanciotti of the Centers for Disease Control and Prevention. Nucleic acids were purified from the lysate using reagents from the QIAamp Viral RNA Mini Kit (Qiagen Inc., Valencia, Calif.) according to the manufacturer's instructions. Serial 10-fold dilutions ($10^{-2}$-$10^{-7}$) of the purified nucleic acids were made. Fifty microliters of each dilution were amplified in 5' nuclease reaction assays using TaqMan® reagents and methods by RT-PCR in 100 µl reactions containing 1 µM primers (each of SEQ ID NO:8 and SEQ ID NO:15), 55 mM Tricine (pH 7.7), 450 µM dNTPs (each of dATP, dCTP, dGTP, and dUTP), 2.7 mM manganese acetate, 135 mM potassium acetate, 7% (v/v) DMSO, 6% (V/V) glycerol, 5 units uracil-N-glycosylase, 40 units ZO5 DNA polymerase, and 0.15 µM probe (SEQ ID NO:28, labeled with FAM and CY5). Reverse transcription/PCR was performed in a COBAS TaqMan™ Instrument (Roche Diagnostics, Pleasanton, Calif.) using the following thermalcycling parameters: 4 minutes at 50° C. →30 minutes at 59° C.→2 cycles of 15 seconds at 95° C., 50 seconds at 58° C.→60 cycles of 15 seconds at 91° C., 50 seconds at 58° C.→2 minutes at 40° C. An example of the amplification results is shown in FIG. 6.

Various embodiments of the invention have been described. The descriptions and examples are intended to be illustrative of the invention rather than limiting. Indeed, it will be apparent to those of skill in the art that modifications may be made to the various embodiments of the invention described without departing from the spirit of the invention or scope of the appended claims set forth below.

Each reference cited herein is hereby incorporated by reference in its entirety.

SEQUENCE LISTING

```
<160> NUMBER OF SEQ ID NOS: 919

<210> SEQ ID NO 1
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genomes of flaviviruses

<400> SEQUENCE: 1
gtaagccctc agaaccgtct cggaa                                          25

<210> SEQ ID NO 2
<211> LENGTH: 25
<212> TYPE: DNA
<213> ORGANISM: Artificial Sequence
<220> FEATURE:
<223> OTHER INFORMATION: synthetic complement to SEQ ID NO:1

<400> SEQUENCE: 2
ttccgagacg gttctgaggg cttac                                          25

<210> SEQ ID NO 3
<211> LENGTH: 26
<212> TYPE: DNA
<213> ORGANISM: Artificial Sequence
<220> FEATURE:
<223> OTHER INFORMATION: synthetic Japanese encephalitis virus serogroup
      Primer 1
<220> FEATURE:
<221> NAME/KEY: modified_base
<222> LOCATION: (8)...(8)
<223> OTHER INFORMATION: n = t or absent

<400> SEQUENCE: 3
gwaasccnsy crramcysyy tcggrw                                         26

<210> SEQ ID NO 4
<211> LENGTH: 26
<212> TYPE: DNA
<213> ORGANISM: Artificial Sequence
<220> FEATURE:
<223> OTHER INFORMATION: synthetic West Nile virus Primer 1
<220> FEATURE:
<221> NAME/KEY: modified_base
<222> LOCATION: (8)...(8)
<223> OTHER INFORMATION: n = t or absent

<400> SEQUENCE: 4
gtaagccncy cagaaccgyy tcggaa                                         26

<210> SEQ ID NO 5
<211> LENGTH: 25
<212> TYPE: DNA
```

<210> SEQ ID NO 5
<211> LENGTH: 25
<212> TYPE: DNA
<213> ORGANISM: Artificial Sequence
<220> FEATURE:
<223> OTHER INFORMATION: synthetic Japanese encephalitis virus Primer 1

<400> SEQUENCE: 5
gaaasccctc rraacygtyt cggaa        25

<210> SEQ ID NO 6
<211> LENGTH: 26
<212> TYPE: DNA
<213> ORGANISM: Artificial Sequence
<220> FEATURE:
<223> OTHER INFORMATION: synthetic Murray Valley encephalitis virus
      Primer 1

<400> SEQUENCE: 6
gaaagcctcc cagamccgty tcggaa        26

<210> SEQ ID NO 7
<211> LENGTH: 25
<212> TYPE: DNA
<213> ORGANISM: Artificial Sequence
<220> FEATURE:
<223> OTHER INFORMATION: synthetic Koutango virus Primer 1, region of
      conserved sequence in 3' untranslated region of the genome
      of Japanese encephalitis virus serogroup, KY1129

<400> SEQUENCE: 7
gtaagccctc agaaccgtct cggaa        25

<210> SEQ ID NO 8
<211> LENGTH: 25
<212> TYPE: DNA
<213> ORGANISM: Artificial Sequence
<220> FEATURE:
<223> OTHER INFORMATION: synthetic Example Primer 1, Japanese
      encephalitis virus serogroup amplification primer

<400> SEQUENCE: 8
gtaagccctc agaaccgtct cggaa        25

<210> SEQ ID NO 9
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genomes of flaviviruses, consensus
      sequence

<400> SEQUENCE: 9
tctcctagtc tatcccaggt gtcaa        25

<210> SEQ ID NO 10
<211> LENGTH: 25
<212> TYPE: DNA
<213> ORGANISM: Artificial Sequence
<220> FEATURE:
<223> OTHER INFORMATION: synthetic complement to SEQ ID NO:9

<400> SEQUENCE: 10
agaggatcag atagggtcca cagtt        25

<210> SEQ ID NO 11
<211> LENGTH: 24
<212> TYPE: DNA
<213> ORGANISM: Artificial Sequence

```
<220> FEATURE:
<223> OTHER INFORMATION: synthetic Japanese encephalitis virus serogroup
      Primer 2
<220> FEATURE:
<221> NAME/KEY: modified_base
<222> LOCATION: (11)...(11)
<223> OTHER INFORMATION: n = t or absent

<400> SEQUENCE: 11
yccyastmtw nyyccaggtr tcaa                                              24

<210> SEQ ID NO 12
<211> LENGTH: 23
<212> TYPE: DNA
<213> ORGANISM: Artificial Sequence
<220> FEATURE:
<223> OTHER INFORMATION: synthetic West Nile virus Primer 2

<400> SEQUENCE: 12
ycctagtcta tcccaggtrt caa                                               23

<210> SEQ ID NO 13
<211> LENGTH: 24
<212> TYPE: DNA
<213> ORGANISM: Artificial Sequence
<220> FEATURE:
<223> OTHER INFORMATION: synthetic Japanese encephalitis virus Primer 2

<400> SEQUENCE: 13
cccyastmta tyyccaggtg tcaa                                              24

<210> SEQ ID NO 14
<211> LENGTH: 24
<212> TYPE: DNA
<213> ORGANISM: Artificial Sequence
<220> FEATURE:
<223> OTHER INFORMATION: synthetic Murray Valley encephalitis virus
      Primer 2

<400> SEQUENCE: 14
tcctagtctt ttcccaggtg tcaa                                              24

<210> SEQ ID NO 15
<211> LENGTH: 23
<212> TYPE: DNA
<213> ORGANISM: Artificial Sequence
<220> FEATURE:
<223> OTHER INFORMATION: synthetic Example Primer 2, Japanese
      encephalitis virus serogroup amplification primer, region of
      conserved sequence in 3' untranslated region of the genome of
      Japanese encephalitis virus serogroup, KY1129

<400> SEQUENCE: 15
tcctagtcta tcccaggtgt caa                                               23

<210> SEQ ID NO 16
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of flaviviruses, KY1129

<400> SEQUENCE: 16
ggactagagg ttagaggaga ccccgcgg                                          28

<210> SEQ ID NO 17
```

```
<211> LENGTH: 28
<212> TYPE: DNA
<213> ORGANISM: Artificial Sequence
<220> FEATURE:
<223> OTHER INFORMATION: synthetic complement to SEQ ID NO:16

<400> SEQUENCE: 17
ccgcggggtc tcctctaacc tctagtcc                                          28

<210> SEQ ID NO 18
<211> LENGTH: 28
<212> TYPE: DNA
<213> ORGANISM: Artificial Sequence
<220> FEATURE:
<223> OTHER INFORMATION: synthetic probe for detecting flaviviruses,
      oligonucleotide that hybridizes to conserved region of flaviviral
      nucleic acid
<220> FEATURE:
<221> NAME/KEY: modified_base
<222> LOCATION: (25)...(25)
<223> OTHER INFORMATION: n = g, c, t, a or absent
<220> FEATURE:
<221> NAME/KEY: modified_base
<222> LOCATION: (26)...(26)
<223> OTHER INFORMATION: n = c, t, g or absent
<220> FEATURE:
<221> NAME/KEY: modified_base
<222> LOCATION: (27)...(28)
<223> OTHER INFORMATION: n = g, c, a, t or absent

<400> SEQUENCE: 18
ggwctagwgg ttagaggaga cccynnnn                                          28

<210> SEQ ID NO 19
<211> LENGTH: 28
<212> TYPE: DNA
<213> ORGANISM: Artificial Sequence
<220> FEATURE:
<223> OTHER INFORMATION: synthetic probe for detecting Japanese
      encephalitis virus serogroup members

<400> SEQUENCE: 19
ggactagwgg ttagaggaga ccccrykk                                          28

<210> SEQ ID NO 20
<211> LENGTH: 28
<212> TYPE: DNA
<213> ORGANISM: Artificial Sequence
<220> FEATURE:
<223> OTHER INFORMATION: synthetic probe for detecting West Nile virus

<400> SEQUENCE: 20
ggactagwgg ttagaggaga ccccrcgk                                          28

<210> SEQ ID NO 21
<211> LENGTH: 28
<212> TYPE: DNA
<213> ORGANISM: Artificial Sequence
<220> FEATURE:
<223> OTHER INFORMATION: synthetic probe for detecting Japanese
      encephalitis virus

<400> SEQUENCE: 21
ggactagagg ttagaggaga ccccgygg                                          28

<210> SEQ ID NO 22
<211> LENGTH: 28
<212> TYPE: DNA
<213> ORGANISM: Artificial Sequence
```

<220> FEATURE:
<223> OTHER INFORMATION: synthetic probe for detecting Murray Valley encephalitis virus

<400> SEQUENCE: 22
ggactagagg ttagaggaga ccccactc 28

<210> SEQ ID NO 23
<211> LENGTH: 29
<212> TYPE: DNA
<213> ORGANISM: Artificial Sequence
<220> FEATURE:
<223> OTHER INFORMATION: synthetic probe for detecting Kunjin virus

<400> SEQUENCE: 23
aataygtgga ttacatgast tcaytgaag 29

<210> SEQ ID NO 24
<211> LENGTH: 28
<212> TYPE: DNA
<213> ORGANISM: Artificial Sequence
<220> FEATURE:
<223> OTHER INFORMATION: synthetic probe for detecting Dengue virus

<400> SEQUENCE: 24
ggactagagg ttagaggaga ccccyssv 28

<210> SEQ ID NO 25
<211> LENGTH: 28
<212> TYPE: DNA
<213> ORGANISM: Artificial Sequence
<220> FEATURE:
<223> OTHER INFORMATION: synthetic probe for detecting yellow fever virus

<400> SEQUENCE: 25
ggtctagagg ttagaggaga ccctccag 28

<210> SEQ ID NO 26
<211> LENGTH: 28
<212> TYPE: DNA
<213> ORGANISM: Artificial Sequence
<220> FEATURE:
<223> OTHER INFORMATION: synthetic probe for detecting Montana myotis leukencephalitis virus

<400> SEQUENCE: 26
ggactagagg ttagaggaga ccccttcc 28

<210> SEQ ID NO 27
<211> LENGTH: 28
<212> TYPE: DNA
<213> ORGANISM: Artificial Sequence
<220> FEATURE:
<223> OTHER INFORMATION: synthetic probe for detecting Modoc virus

<400> SEQUENCE: 27
ggactagagg ttgagggaga cccccggc 28

<210> SEQ ID NO 28
<211> LENGTH: 28
<212> TYPE: DNA
<213> ORGANISM: Artificial Sequence
<220> FEATURE:
<223> OTHER INFORMATION: synthetic Example Probe 1, Japanese encephalitis virus serogroup amplification primer

<400> SEQUENCE: 28
ggactagagg ttagaggaga ccccgcgg                                              28

<210> SEQ ID NO 29
<211> LENGTH: 418
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate BFS1750

<400> SEQUENCE: 29
ttgccaccgg atgtcaggta aacggtgctg tctgtaacct ggccccaggt gactgggtta          60
tcaaagccaa tctggccgag tgcaaagccc ctcattccga ctcgggaggg tccctagcac         120
gtaggctgga gaggacgcaa aagtcagacc agaaatgcca cctgaaagca tgctaaaggt         180
gctgtctgta catgccccag gaggactggg ttaacaaagc ttaacagccc cagcggccca         240
aaccatggag tgcgtgacca tggcgtaagg actagaggtt agaggagacc ccgctgcaac         300
ttggcaaggc ccaaacccgc tcgaagctgt agagacgggg aaggactag aggttagagg          360 agacccctg ccgttaacgc aaacaacagc atattgacac ctggaaagac aggagatc           418

<210> SEQ ID NO 30
<211> LENGTH: 342
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate 1750-Std

<400> SEQUENCE: 30
ttgccaccgg atgtcaggta aacggtgctg tctgtaacct ggccccaggt gactgggtta          60
tcaaagccaa tctggccgag tgcaaagccc ctcattccga ctcgggaggg tccctagcac         120
gtaggctgga gaggacgcaa aagtcagacc agaaatgcca cctgaaagca tgctaaaggt         180
gctgtctgta catgccccag gaggactggg ttaacaaagc ttaacagccc cagcggccca         240
aaccatggag tgcgtgacca tggcgtaagg actagaggtt agaggagacc ccgcgcaact         300
tggcaaggcc caaacccgct cgaagctgta gagacggggg aa                            342

<210> SEQ ID NO 31
<211> LENGTH: 418
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate TD6-4G

<400> SEQUENCE: 31
ttgccaccgg atgtcaggta aacggtgctg cctgtaacct ggccccaggt gactgggtta          60
tcaaagccaa tctggccgag tgcaaagccc ctcattccga ctcgggaggg tccctggcac         120
gtaggctgga gaggacgcaa aagtcagacc agaaatgcca cctgaaagca tgctaaaggt         180
gctgtctgta catgccccag gaggactggg ttaacaaagc ttaacagccc cagcggccca         240
aaccatggag tgcgtgacca tggcgtaagg actagaggtt agaggagacc ccgctgcaac         300
tcggcaaggc ccaaacccgc tcgaagctgt agagatgggg aaggactag aggttagagg          360 agacccctg ccgttaacgc aaacaacagc atattgacac ctggaaagac aggagatc           418

<210> SEQ ID NO 32

```
<211> LENGTH: 342
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate CoaV750

<400> SEQUENCE: 32
ttgccaccgg atgtcaggta acggtgctg cctgtaacct ggccccaggt gactgggtta      60
ccaaagccaa tctggctgag tgcaaagccc ctcgttccga ttcgggaggg tccctggcac    120
gtaggctgga gaggacgcaa aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgcgcaact    300
tggcaaggcc aaaacccgct cgaagctgta gagatggggg aa                      342

<210> SEQ ID NO 33
<211> LENGTH: 418
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate L695121.05

<400> SEQUENCE: 33
ttgccaccgg atgtcaggta acggtgctg tctgtaacct ggccccaggt gactgggtta      60
tcaaagccaa tccggctggg tgcaaagccc ctcattccga ctcgggaggg tccctggcat    120
gtaggctgga gaggacgcac aagtcagacc agaaatgcca cctgaaagca tgctaaaggt    180
gctgtctgta catgccccag gaggactggg ttaacaaagc ttaacagccc cagcggccca    240
aaccatggag tgcgtgacca tggcgtaagg actagaggtt agaggagacc ccgctgtaac    300
ttggcaaggc ccaaacccgc tcgaagctgt agagacgggg aaggactag aggttagagg    360 agaccccttg ccgttaacgc aaacaacagc atattgacac ctggaaagac aggagatc     418

<210> SEQ ID NO 34
<211> LENGTH: 418
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate TNM771K
<220> FEATURE:
<221> NAME/KEY: modified_base
<222> LOCATION: (384)...(384)
<223> OTHER INFORMATION: n = g, a, c or t

<400> SEQUENCE: 34
ttgccaccgg atgtcaggta acggtgctg tctgtaacct ggccccaggt gactgggtca      60
tcaaagccaa tctggctggg tgcaaagccc ctcattccga ctcgggaggg tccctggcac    120
gtaggctgga gaggacgcac aagtcagacc agaaatgcca cctgaaagca tgctaaaggt    180
gctgtctgta catgccccag gaggactggg ttaacaaagc ttaacagccc cagcggccca    240
aaccatggag agcgtgacca tggcgtaagg actagaggtt agaggagacc ccgctgtaac    300
ttggcaaggc ccaaacccgc tcgaagctgt agagacgggg aaggactag aggttagagg    360 agaccccttg ccgttaacgc aaanaacagc atattgacac ctggaaagac aggagatc     418

<210> SEQ ID NO 35
<211> LENGTH: 418
<212> TYPE: DNA
```

<213> ORGANISM: St. Louis encephalitis virus
<220> FEATURE:
<223> OTHER INFORMATION: 3' untranslated region of the genome of St.
      Louis encephalitis virus (SLEV) isolate MSI-7

<400> SEQUENCE: 35

```
ttgccaccgg atgtcaggta aacggtgctg tctgtaacct ggccccaggc gactgggtta      60
tcaaagccaa tccggctggg tgcaaagccc ctcattccga ctcgggaggg tccctggcac     120
gtaggctgga gaggacgcac aagtcagacc agaaatgcca cctgaaagca tgctaaaggt     180
gctgtctgta catgccccag gaggactggg ttaacaaagc ttaacagccc cagcggccca     240
aaccatggag tgcgtgacca tggcgtaagg actagaggtt agaggagacc ccgctgtaac     300
ttggcaaggc ccaaacccgc tcaaagctgt agagacgggg aaggactag aggttagagg      360
agaccccttg ccgttaacgc aaacaacagc atattgacac ctggaaagac aggagatc      418
```

<210> SEQ ID NO 36
<211> LENGTH: 405
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate Kern217

<400> SEQUENCE: 36

```
ccggatgtca ggtaaacggt gctgtctgta acctggcccc aggtcactgg gttatcaaag      60
ccaacccggc tgggtgcaaa gcccctcatt ccgactcggg agggtccctg cacgtaggc     120
tggagaggac gcacaagtca gaccagaaat gccacctgaa agcatgctaa aggtgctgtc     180
tgtacatgcc ccaggaggac tgggttaaca agcttaaca gccccagcgg cccaaaccat     240
ggagtgcgtg accatggcgt aaggactaga ggttagagga ccccgctg taacttggca     300
aggcccaaac ccgctcaaag ctgtagagac ggggaaagga ctagaggtta gaggagaccc     360
cttgccgtta acgcaaacaa cagcatattg acacctggaa agaca              405
```

<210> SEQ ID NO 37
<211> LENGTH: 375
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate CoAV608

<400> SEQUENCE: 37

```
cccaggcgac tgggttatca aagccaatcc ggctgggtgc aaagcccctc attccgactc      60
ggagggtcc ctggcacgta ggctggagag gacgcacaag tcagaccaga aatgccacct     120
gaaagcatgc taaaggtgct gtctgtacat gccccaggag gactgggtta acaaagctta     180
acagccccag cggcccaaac catggagtgc gtgaccatgg cgtaaggact agaggttaga     240
ggagaccccg ctgtaacttg gcaaggccca aacccgctca aagctgtaga gacggggaa      300
ggactagagg ttagaggaga ccccttgccg ttaacgcaaa caacagcata ttgacacctg     360
gaaagacagg agatc                                                      375
```

<210> SEQ ID NO 38
<211> LENGTH: 411
<212> TYPE: DNA
<213> ORGANISM: St. Louis encephalitis virus
<220> FEATURE:
<223> OTHER INFORMATION: 3' untranslated region of the genome of St.
      Louis encephalitis virus (SLEV) isolate TBH-28

<400> SEQUENCE: 38

```
ttgccaccgg atgtcaggta aacggtgctg tctgtaacct ggccccaggt gactgggtta      60
tcaaagccaa cccggctggg tgcaaagccc ctcattccga ctcgggaggg tccctggcac     120
gtaggccgga gaggacgcac aagtcagacc agaaatgcca cctgaaagca tgctaaaggt     180
gctgtctgta catgccccag gaggactggg ttaacaaagc ttaacagccc cagcggccca     240
aaccatggag tgcgtgacca tggcgtaagg actagaggtt agaggagacc ccgctgtaat     300
ttggcaaggc ccaaacccgc tcgaagctgt agagacgggg aaggactag  aggttagagg     360
agacccctg ccgttaacgc aaacaacagc atattgacac ctggaaagac a              411
```

<210> SEQ ID NO 39
<211> LENGTH: 402
<212> TYPE: DNA
<213> ORGANISM: St. Louis encephalitis virus
<220> FEATURE:
<223> OTHER INFORMATION: 3' untranslated region of the genome of St.
    Louis encephalitis virus (SLEV) isolate VR1265

<400> SEQUENCE: 39

```
ccggaagtca ggtaaacggt gctgtctgta acctggcccc aggtgactgg ttatcaaag      60
ccaatctggc tgggtgcaaa gcccctcatt ccgactcggg agggtccctg cacgtaggc     120
tggagcggac gcacaagtca gaccagaaat gccacctgaa agcatgctaa aggtgctgtc     180
tgtacatgcc ccaggaggac tgggttaaca agcttaaca gccccagcgg cccaaaccat     240
ggagtgcgtg accatggcgt aaggactaga ggttagagga ccccgctg taacttggca     300
aggcccaaac ccgctcgaag ctgtagagac ggggaagga ctagaggtta gaggagaccc     360
cttgccgtca acgcaaacaa cagcatattg acacctggaa ag                      402
```

<210> SEQ ID NO 40
<211> LENGTH: 374
<212> TYPE: DNA
<213> ORGANISM: St. Louis encephalitis virus
<220> FEATURE:
<223> OTHER INFORMATION: 3' untranslated region of the genome of St.
    Louis encephalitis virus (SLEV) isolate CoaV353

<400> SEQUENCE: 40

```
cccaggtgac tgggttatca aagccaatct agctgagtgc aaagcccctc attccgactc      60
gggagggtcc ctggcacgta ggctggagag gacgcaaaag tcagaccaga aatgccacct     120
gaaagcatgc taaaggtgct gtctgtacat gccccaggag gactgggtta acaaagctta     180
acagccccag cggcccaaac catggagtgc gtgaccatgg cgtaaggact agaggttaga     240
ggagaccccg ctgcaacttg gcaaggccca aaccgctcg aagctgtaga cggggga       300
ggactagagg ttagaggaga ccccttgccg ttaacgcaaa caacagcata ttgacacctg     360
gaaagacagg agat                                                     374
```

<210> SEQ ID NO 41
<211> LENGTH: 27
<212> TYPE: DNA
<213> ORGANISM: Artificial Sequence
<220> FEATURE:
<223> OTHER INFORMATION: synthetic Dengue virus consensus upstream
    primer

<400> SEQUENCE: 41

```
gagccccgtc caaggacgta aaaagaa                                         27
```

<210> SEQ ID NO 42
<211> LENGTH: 27
<212> TYPE: DNA
<213> ORGANISM: Artificial Sequence
<220> FEATURE:
<223> OTHER INFORMATION: synthetic Dengue virus consensus upstream
      primer
<220> FEATURE:
<221> NAME/KEY: modified_base
<222> LOCATION: (27)...(27)
<223> OTHER INFORMATION: n = t-butyl-benzyl-dA

<400> SEQUENCE: 42
gagccccgtc caaggacgta aaaagan                                          27

<210> SEQ ID NO 43
<211> LENGTH: 27
<212> TYPE: DNA
<213> ORGANISM: Artificial Sequence
<220> FEATURE:
<223> OTHER INFORMATION: synthetic Dengue virus consensus upstream
      primer
<220> FEATURE:
<221> NAME/KEY: modified_base
<222> LOCATION: (26)...(26)
<223> OTHER INFORMATION: n = methyl-dA
<220> FEATURE:
<221> NAME/KEY: modified_base
<222> LOCATION: (27)...(27)
<223> OTHER INFORMATION: n = t-butyl-benzyl-dA

<400> SEQUENCE: 43
gagccccgtc caaggacgta aaaagnn                                          27

<210> SEQ ID NO 44
<211> LENGTH: 27
<212> TYPE: DNA
<213> ORGANISM: Artificial Sequence
<220> FEATURE:
<223> OTHER INFORMATION: synthetic Dengue virus type I upstream primer

<400> SEQUENCE: 44
gagccccgtc caaggacgta aaatgaa 27

<210> SEQ ID NO 45
<211> LENGTH: 27
<212> TYPE: DNA
<213> ORGANISM: Artificial Sequence
<220> FEATURE:
<223> OTHER INFORMATION: synthetic Dengue virus type I upstream primer
<220> FEATURE:
<221> NAME/KEY: modified_base
<222> LOCATION: (27)...(27)
<223> OTHER INFORMATION: n = t-butyl-benzyl-dA

<400> SEQUENCE: 45
gagccccgtc caaggacgta aaatgan 27

<210> SEQ ID NO 46
<211> LENGTH: 27
<212> TYPE: DNA
<213> ORGANISM: Artificial Sequence
<220> FEATURE:
<223> OTHER INFORMATION: synthetic Dengue virus type I upstream primer
<220> FEATURE:
<221> NAME/KEY: modified_base
<222> LOCATION: (26)...(26)
<223> OTHER INFORMATION: n = methyl-dA
<220> FEATURE:

```
<221> NAME/KEY: modified_base
<222> LOCATION: (27)...(27)
<223> OTHER INFORMATION: n = t-butyl-benzyl-dA

<400> SEQUENCE: 46
gagccccgtc caaggacgta aaatgnn                                          27

<210> SEQ ID NO 47
<211> LENGTH: 27
<212> TYPE: DNA
<213> ORGANISM: Artificial Sequence
<220> FEATURE:
<223> OTHER INFORMATION: synthetic Dengue virus types II and III
      upstream primer

<400> SEQUENCE: 47
gagccccgtc caaggacgtt aaagaa                                           27

<210> SEQ ID NO 48
<211> LENGTH: 27
<212> TYPE: DNA
<213> ORGANISM: Artificial Sequence
<220> FEATURE:
<223> OTHER INFORMATION: synthetic Dengue virus types II and III
      upstream primer
<220> FEATURE:
<221> NAME/KEY: misc_feature
<222> LOCATION: (27)...(27)
<223> OTHER INFORMATION: n = t-butyl-benzyl-dA

<400> SEQUENCE: 48
gagccccgtc caaggacgtt aaagan                                           27

<210> SEQ ID NO 49
<211> LENGTH: 27
<212> TYPE: DNA
<213> ORGANISM: Artificial Sequence
<220> FEATURE:
<223> OTHER INFORMATION: synthetic Dengue virus types II and III
      upstream primer
<220> FEATURE:
<221> NAME/KEY: modified_base
<222> LOCATION: (26)...(26)
<223> OTHER INFORMATION: n = methyl-dA
<220> FEATURE:
<221> NAME/KEY: modified_base
<222> LOCATION: (27)...(27)
<223> OTHER INFORMATION: n = t-butyl-benzyl-dA

<400> SEQUENCE: 49
gagccccgtc caaggacgtt aaagnn                                           27

<210> SEQ ID NO 50
<211> LENGTH: 24
<212> TYPE: DNA
<213> ORGANISM: Artificial Sequence
<220> FEATURE:
<223> OTHER INFORMATION: synthetic Dengue virus type IV upstream primer

<400> SEQUENCE: 50
attgaagtca ggccacttgt gcca                                             24

<210> SEQ ID NO 51
<211> LENGTH: 24
<212> TYPE: DNA
<213> ORGANISM: Artificial Sequence
<220> FEATURE:
<223> OTHER INFORMATION: synthetic Dengue virus type IV upstream primer
<220> FEATURE:
```

<221> NAME/KEY: modified_base
<222> LOCATION: (24)...(24)
<223> OTHER INFORMATION: n = t-butyl-benzyl-dA

<400> SEQUENCE: 51
attgaagtca ggccacttgt gccn 24

<210> SEQ ID NO 52
<211> LENGTH: 24
<212> TYPE: DNA
<213> ORGANISM: Artificial Sequence
<220> FEATURE:
<223> OTHER INFORMATION: synthetic Dengue virus type IV upstream primer
<220> FEATURE:
<221> NAME/KEY: modified_base
<222> LOCATION: (23)...(23)
<223> OTHER INFORMATION: n = ethyl-dC
<220> FEATURE:
<221> NAME/KEY: modified_base
<222> LOCATION: (24)...(24)
<223> OTHER INFORMATION: n = t-butyl-benzyl-dA

<400> SEQUENCE: 52
attgaagtca ggccacttgt gcnn 24

<210> SEQ ID NO 53
<211> LENGTH: 25
<212> TYPE: DNA
<213> ORGANISM: Artificial Sequence
<220> FEATURE:
<223> OTHER INFORMATION: synthetic Dengue virus downstream primer

<400> SEQUENCE: 53
gatctctggt ctttcccagc gtcaa 25

<210> SEQ ID NO 54
<211> LENGTH: 25
<212> TYPE: DNA
<213> ORGANISM: Artificial Sequence
<220> FEATURE:
<223> OTHER INFORMATION: synthetic Dengue virus downstream primer
<220> FEATURE:
<221> NAME/KEY: modified_base
<222> LOCATION: (25)...(25)
<223> OTHER INFORMATION: n = t-butyl-benzyl-dA

<400> SEQUENCE: 54
gatctctggt ctttcccagc gtcan 25

<210> SEQ ID NO 55
<211> LENGTH: 25
<212> TYPE: DNA
<213> ORGANISM: Artificial Sequence
<220> FEATURE:
<223> OTHER INFORMATION: synthetic Dengue virus downstream primer
<220> FEATURE:
<221> NAME/KEY: modified_base
<222> LOCATION: (24)...(24)
<223> OTHER INFORMATION: n = methyl-dA
<220> FEATURE:
<221> NAME/KEY: modified_base
<222> LOCATION: (25)...(25)
<223> OTHER INFORMATION: n = t-butyl-benzyl-dA

<400> SEQUENCE: 55
gatctctggt ctttcccagc gtcnn 25

<210> SEQ ID NO 56
<211> LENGTH: 28

```
<212> TYPE: DNA
<213> ORGANISM: Artificial Sequence
<220> FEATURE:
<223> OTHER INFORMATION: synthetic yellow fever virus upstream primer

<400> SEQUENCE: 56
aaccgggata aaaactacgg gtggagaa                                          28

<210> SEQ ID NO 57
<211> LENGTH: 28
<212> TYPE: DNA
<213> ORGANISM: Artificial Sequence
<220> FEATURE:
<223> OTHER INFORMATION: synthetic yellow fever virus upstream primer
<220> FEATURE:
<221> NAME/KEY: modified_base
<222> LOCATION: (28)...(28)
<223> OTHER INFORMATION: n = t-butyl-benzyl-dA

<400> SEQUENCE: 57
aaccgggata aaaactacgg gtggagan                                          28

<210> SEQ ID NO 58
<211> LENGTH: 28
<212> TYPE: DNA
<213> ORGANISM: Artificial Sequence
<220> FEATURE:
<223> OTHER INFORMATION: synthetic yellow fever virus upstream primer
<220> FEATURE:
<221> NAME/KEY: modified_base
<222> LOCATION: (27)...(27)
<223> OTHER INFORMATION: n = methyl-dA
<220> FEATURE:
<221> NAME/KEY: modified_base
<222> LOCATION: (28)...(28)
<223> OTHER INFORMATION: n = t-butyl-benzyl-dA

<400> SEQUENCE: 58
aaccgggata aaaactacgg gtggagnn                                          28

<210> SEQ ID NO 59
<211> LENGTH: 26
<212> TYPE: DNA
<213> ORGANISM: Artificial Sequence
<220> FEATURE:
<223> OTHER INFORMATION: synthetic yellow fever virus upstream primer

<400> SEQUENCE: 59
ataaaaacta cgggtggaga accgga                                            26

<210> SEQ ID NO 60
<211> LENGTH: 26
<212> TYPE: DNA
<213> ORGANISM: Artificial Sequence
<220> FEATURE:
<223> OTHER INFORMATION: synthetic yellow fever virus upstream primer
<220> FEATURE:
<221> NAME/KEY: modified_base
<222> LOCATION: (26)...(26)
<223> OTHER INFORMATION: n = t-butyl-benzyl-dA

<400> SEQUENCE: 60
ataaaaacta cgggtggaga accggn                                            26

<210> SEQ ID NO 61
<211> LENGTH: 24
<212> TYPE: DNA
<213> ORGANISM: Artificial Sequence
<220> FEATURE:
```

```
<223> OTHER INFORMATION: synthetic yellow fever virus downstream primer

<400> SEQUENCE: 61
actccggtct ttccctggcg tcaa                                              24

<210> SEQ ID NO 62
<211> LENGTH: 24
<212> TYPE: DNA
<213> ORGANISM: Artificial Sequence
<220> FEATURE:
<223> OTHER INFORMATION: synthetic yellow fever virus downstream primer
<220> FEATURE:
<221> NAME/KEY: modified_base
<222> LOCATION: (24)...(24)
<223> OTHER INFORMATION: n = t-butyl-benzyl-dA

<400> SEQUENCE: 62
actccggtct ttccctggcg tcan                                              24

<210> SEQ ID NO 63
<211> LENGTH: 24
<212> TYPE: DNA
<213> ORGANISM: Artificial Sequence
<220> FEATURE:
<223> OTHER INFORMATION: synthetic yellow fever virus downstream primer
<220> FEATURE:
<221> NAME/KEY: modified_base
<222> LOCATION: (23)...(23)
<223> OTHER INFORMATION: n = methyl-dA
<220> FEATURE:
<221> NAME/KEY: modified_base
<222> LOCATION: (24)...(24)
<223> OTHER INFORMATION: n = t-butyl-benzyl-dA

<400> SEQUENCE: 63
actccggtct ttccctggcg tcnn                                              24

<210> SEQ ID NO 64
<211> LENGTH: 25
<212> TYPE: DNA
<213> ORGANISM: Artificial Sequence
<220> FEATURE:
<223> OTHER INFORMATION: synthetic St Louis encephalitis virus upstream
      primer

<400> SEQUENCE: 64
caaagcccct cattccgact cggga                                             25

<210> SEQ ID NO 65
<211> LENGTH: 25
<212> TYPE: DNA
<213> ORGANISM: Artificial Sequence
<220> FEATURE:
<223> OTHER INFORMATION: synthetic St Louis encephalitis virus upstream
      primer
<220> FEATURE:
<221> NAME/KEY: modified_base
<222> LOCATION: (25)...(25)
<223> OTHER INFORMATION: n = t-butyl-benzyl-dA

<400> SEQUENCE: 65
caaagcccct cattccgact cgggn                                             25

<210> SEQ ID NO 66
<211> LENGTH: 23
<212> TYPE: DNA
<213> ORGANISM: Artificial Sequence
<220> FEATURE:
<223> OTHER INFORMATION: synthetic St Louis encephalitis virus
```

-continued downstream primer

<400> SEQUENCE: 66
tctcctgtct ttccaggtgt caa                                            23

<210> SEQ ID NO 67
<211> LENGTH: 23
<212> TYPE: DNA
<213> ORGANISM: Artificial Sequence
<220> FEATURE:
<223> OTHER INFORMATION: synthetic St Louis encephalitis virus
      downstream primer
<220> FEATURE:
<221> NAME/KEY: modified_base
<222> LOCATION: (23)...(23)
<223> OTHER INFORMATION: n = t-butyl-benzyl-dA

<400> SEQUENCE: 67
tctcctgtct ttccaggtgt can                                            23

<210> SEQ ID NO 68
<211> LENGTH: 23
<212> TYPE: DNA
<213> ORGANISM: Artificial Sequence
<220> FEATURE:
<223> OTHER INFORMATION: synthetic St. Louis encephalitis virus (SLEV)
      first primer complement

<400> SEQUENCE: 68
ttgacacctg gaaagacagg aga                                            23

<210> SEQ ID NO 69
<211> LENGTH: 24
<212> TYPE: DNA
<213> ORGANISM: Artificial Sequence
<220> FEATURE:
<223> OTHER INFORMATION: synthetic St. Louis encephalitis virus (SLEV)
      second primer

<400> SEQUENCE: 69
caaagcccct cattccgact cggg                                           24

<210> SEQ ID NO 70
<211> LENGTH: 30
<212> TYPE: DNA
<213> ORGANISM: Artificial Sequence
<220> FEATURE:
<223> OTHER INFORMATION: synthetic flavivirus anti-sense probe

<400> SEQUENCE: 70
gggtctcctc taacctctag tccttccccc                                     30

<210> SEQ ID NO 71
<211> LENGTH: 98
<212> TYPE: DNA
<213> ORGANISM: West Nile virus
<220> FEATURE:
<223> OTHER INFORMATION: West Nile virus strain AF196835 region of
      conserved sequence in 3' untranslated region

<400> SEQUENCE: 71
caaccccagg aggactgggt gaacaaagcc gcgaagtgat ccatgtaagc cctcagaacc    60
gtctcggaag gaggacccca catgttgtaa cttcaaag                            98

<210> SEQ ID NO 72
<211> LENGTH: 105

<212> TYPE: DNA
<213> ORGANISM: West Nile virus
<220> FEATURE:
<223> OTHER INFORMATION: West Nile virus strain AF196835 region of
conserved sequence in 3' untranslated region

<400> SEQUENCE: 72
tgactgaagc tgtaggtcag gggaaggact agaggttagt ggagaccccg tgccacaaaa 60
caccacaaca aaacagcata ttgacacctg ggatagacta ggaga 105

<210> SEQ ID NO 73
<211> LENGTH: 121
<212> TYPE: DNA
<213> ORGANISM: West Nile virus
<220> FEATURE:
<223> OTHER INFORMATION: West Nile virus strain AF196835 region of
conserved sequence in 3' untranslated region

<400> SEQUENCE: 73
cagggcgaaa ggactagagg ttagaggaga ccccgcggtt taaagtgcac ggcccagcct 60
gactgaagct gtaggtcagg ggaaggacta gaggttagtg gagaccccgt gccacaaaac 120
a 121

<210> SEQ ID NO 74
<211> LENGTH: 25
<212> TYPE: DNA
<213> ORGANISM: Artificial Sequence
<220> FEATURE:
<223> OTHER INFORMATION: synthetic Example Primer 2, Japanese
encephalitis virus serogroup amplification primer

<400> SEQUENCE: 74
tctcctagtc tatcccaggt gtcaa 25

<210> SEQ ID NO 75
<211> LENGTH: 20
<212> TYPE: DNA
<213> ORGANISM: Artificial Sequence
<220> FEATURE:
<223> OTHER INFORMATION: synthetic detectably-labeled oligonucleotide
<220> FEATURE:
<221> NAME/KEY: modified_base
<222> LOCATION: (1)...(1)
<223> OTHER INFORMATION: n = g attached to 3' of deoxyribose phosphate
backbone modified by 6-carboxyfluorescein (FAM) (I) attached to 3'
of oligonucleotide 5'GGTCTAGA3', where 5' G is modified by
Cy5 quencher (F)

<400> SEQUENCE: 75
ngttagagga gaccctccag 20

<210> SEQ ID NO 76
<211> LENGTH: 20
<212> TYPE: DNA
<213> ORGANISM: Artificial Sequence
<220> FEATURE:
<223> OTHER INFORMATION: synthetic fluorescent moiety-quencher moiety
pair in probe variant of SEQ ID NO:28
<220> FEATURE:
<221> NAME/KEY: modified_base
<222> LOCATION: (1)...(1)
<223> OTHER INFORMATION: n = g attached to 3' of deoxyribose phosphate
backbone modified by 6-carboxyfluorescein (FAM) (I) attached to 3'
of oligonucleotide 5'GGACTAGA3', where 5' G is modified by
Cy5 quencher (F)
<220> FEATURE:
<221> NAME/KEY: modified_base
<222> LOCATION: (20)...(20)

<223> OTHER INFORMATION: n = phosphorylated g

<400> SEQUENCE: 76
ngttagagga gaccccgcgn                                           20

<210> SEQ ID NO 77
<211> LENGTH: 20
<212> TYPE: DNA
<213> ORGANISM: Artificial Sequence
<220> FEATURE:
<223> OTHER INFORMATION: synthetic fluorescent moiety-quencher moiety
      pair in probe variant of SEQ ID NO:28
<220> FEATURE:
<221> NAME/KEY: modified_base
<222> LOCATION: (1)...(1)
<223> OTHER INFORMATION: n = g attached to 3' of deoxyribose phosphate
      backbone modified by 6-carboxyfluorescein (FAM) (I) attached to 3'
      of oligonucleotide 5'GGA-5-methyl-dC-propynyl-dU-AGA3',
      where 5' G is modified by Cy5 quencher (F)
<220> FEATURE:
<221> NAME/KEY: modified_base
<222> LOCATION: (3)...(4)
<223> OTHER INFORMATION: n = propynyl-dU
<220> FEATURE:
<221> NAME/KEY: modified_base
<222> LOCATION: (13)...(18)
<223> OTHER INFORMATION: n = 5-methyl-dC
<220> FEATURE:
<221> NAME/KEY: modified_base
<222> LOCATION: (20)...(20)
<223> OTHER INFORMATION: n = phosphorylated g

<400> SEQUENCE: 77
ngnnagagga gannnngngn                                           20

<210> SEQ ID NO 78
<211> LENGTH: 22
<212> TYPE: DNA
<213> ORGANISM: Artificial Sequence
<220> FEATURE:
<223> OTHER INFORMATION: synthetic fluorescent moiety-quencher moiety
      pair in probe
      variant of SEQ ID NO:70
<220> FEATURE:
<221> NAME/KEY: modified_base
<222> LOCATION: (1)...(1)
<223> OTHER INFORMATION: n = t attached to 3' of deoxyribose phosphate
      backbone modified by 6-carboxyfluorescein (FAM) (I) attached to 3'
      of oligonucleotide 5'GGGTCTCC3', where 5' G is modified by
      Cy5 quencher (F)
<220> FEATURE:
<221> NAME/KEY: modified_base
<222> LOCATION: (22)...(22)
<223> OTHER INFORMATION: n = phosphorylated c

<400> SEQUENCE: 78
nctaacctct agtccttccc cn                                        22

<210> SEQ ID NO 79
<211> LENGTH: 22
<212> TYPE: DNA
<213> ORGANISM: Artificial Sequence
<220> FEATURE:
<223> OTHER INFORMATION: synthetic fluorescent moiety-quencher moiety
      pair in probe variant of SEQ ID NO:70
<220> FEATURE:
<221> NAME/KEY: modified_base
<222> LOCATION: (1)...(1)
<223> OTHER INFORMATION: n = propynyl-dU attached to 3' of deoxyribose
      phosphate backbone modified by 6-carboxyfluorescein (FAM) (I)
      attached to 3' of oligonucleotide 5'GGG-propynyl-dU-5-methyl-dC-
      propynyl-dU-5-methyl-dC-5-methyl-dC3', where 5' G is modified by
      Cy5 quencher (F)

<220> FEATURE:
<221> NAME/KEY: modified_base
<222> LOCATION: (2)...(2)
<223> OTHER INFORMATION: n = 5-methyl-dC
<220> FEATURE:
<221> NAME/KEY: modified_base
<222> LOCATION: (3)...(3)
<223> OTHER INFORMATION: n = propynyl-dU
<220> FEATURE:
<221> NAME/KEY: modified_base
<222> LOCATION: (22)...(22)
<223> OTHER INFORMATION: n = phosphorylated c

<400> SEQUENCE: 79
nnnaacctct agtccttccc cn 22

<210> SEQ ID NO 80
<211> LENGTH: 20
<212> TYPE: DNA
<213> ORGANISM: Artificial Sequence
<220> FEATURE:
<223> OTHER INFORMATION: synthetic fluorescent moiety-quencher moiety pair in probe variant of SEQ ID NO:25
<220> FEATURE:
<221> NAME/KEY: modified_base
<222> LOCATION: (1)...(1)
<223> OTHER INFORMATION: n = g attached to 3' of deoxyribose phosphate backbone modified by 6-carboxyfluorescein (FAM) (I) attached to 3' of oligonucleotide 5'GGTCTAGA3', where 5' G is modified by Cy5 quencher (F)
<220> FEATURE:
<221> NAME/KEY: modified_base
<222> LOCATION: (20)...(20)
<223> OTHER INFORMATION: n = phosphorylated g

<400> SEQUENCE: 80
ngttagagga gaccctccan 20

<210> SEQ ID NO 81
<211> LENGTH: 98
<212> TYPE: DNA
<213> ORGANISM: West Nile virus
<220> FEATURE:
<223> OTHER INFORMATION: West Nile virus strain AF260968 region of conserved sequence in 3' untranslated region

<400> SEQUENCE: 81
caaccccagg aggactgggt gaacaaagct gcgaagtgat ccatgtaagc cctcagaacc 60
gtctcggaag aggaccccca catgttgtaa cttcaaag 98

<210> SEQ ID NO 82
<211> LENGTH: 98
<212> TYPE: DNA
<213> ORGANISM: West Nile virus
<220> FEATURE:
<223> OTHER INFORMATION: West Nile virus strain AF260969 region of conserved sequence in 3' untranslated region

<400> SEQUENCE: 82
caaccccagg aggactgggt gaacaaagcc gcgaagtgat ccatgtaagc cctcagaacc 60
gtctcggaag aggaccccca catgttgtaa cttcaaag 98

<210> SEQ ID NO 83
<211> LENGTH: 98
<212> TYPE: DNA
<213> ORGANISM: West Nile virus
<220> FEATURE:
<223> OTHER INFORMATION: West Nile virus strain AF481864 region of conserved sequence in 3' untranslated region -continued

<400> SEQUENCE: 83 caacccccagg aggactgggt gaacaaagcc gcgaagtgat ccatgtaagc cctcagaacc    60
gtctcggaag gaggacccca catgttgtaa cttcaaag                            98

<210> SEQ ID NO 84
<211> LENGTH: 98
<212> TYPE: DNA
<213> ORGANISM: West Nile virus
<220> FEATURE:
<223> OTHER INFORMATION: West Nile virus strain M12294 region of
      conserved sequence in 3' untranslated region

<400> SEQUENCE: 84 caacccccagg aggactgggt gaccaaagct gcgaggtgat ccacgtaagc cctcagaacc    60
gtctcggaag gaggacccca cgtgctttag cctcaaag                            98

<210> SEQ ID NO 85
<211> LENGTH: 98
<212> TYPE: DNA
<213> ORGANISM: West Nile virus
<220> FEATURE:
<223> OTHER INFORMATION: West Nile virus strain AF206518 region of
      conserved sequence in 3' untranslated region

<400> SEQUENCE: 85 caacccccagg aggactgggt gaacaaagcc gcgaagtgat ccatgtaagc cctcagaacc    60
gtctcggaag gaggacccca catgttgtaa cttcaaag                            98

<210> SEQ ID NO 86
<211> LENGTH: 98
<212> TYPE: DNA
<213> ORGANISM: West Nile virus
<220> FEATURE:
<223> OTHER INFORMATION: West Nile virus strain AF317203 region of
      conserved sequence in 3' untranslated region

<400> SEQUENCE: 86 caacccccagg aggactgggt gaacaaagcc gcgaagtgat ccatgtaagc cctcagaacc    60
gtctcggaag gaggacccca catgttgtaa cttcaaag                            98

<210> SEQ ID NO 87
<211> LENGTH: 98
<212> TYPE: DNA
<213> ORGANISM: West Nile virus
<220> FEATURE:
<223> OTHER INFORMATION: West Nile virus strain AF202541 region of
      conserved sequence in 3' untranslated region

<400> SEQUENCE: 87 caacccccagg aggactgggt gaacaaagcc gcgaagtgat ccatgtaagc cctcagaacc    60
gtctcggaag gaggacccca catgttgtaa cttcaaag                            98

<210> SEQ ID NO 88
<211> LENGTH: 98
<212> TYPE: DNA
<213> ORGANISM: West Nile virus
<220> FEATURE:
<223> OTHER INFORMATION: West Nile virus strain AF404757 region of
      conserved sequence in 3' untranslated region

<400> SEQUENCE: 88 caacccccagg aggactgggt gaacaaagcc gtgaagtgat ccatgtaagc cctcagaacc    60

-continued gtctcggaag gaggacccca catgttgtaa cttcaaag                                    98

<210> SEQ ID NO 89
<211> LENGTH: 98
<212> TYPE: DNA
<213> ORGANISM: West Nile virus
<220> FEATURE:
<223> OTHER INFORMATION: West Nile virus strain AF404753 region of
      conserved sequence in 3' untranslated region

<400> SEQUENCE: 89 caacccagg aggactgggt gaacaaagcc gcgaagtgat ccatgtaagc cctcagaacc            60
gtctcggaag gaggacccca catgttgtaa cttcaaag                                    98

<210> SEQ ID NO 90
<211> LENGTH: 98
<212> TYPE: DNA
<213> ORGANISM: West Nile virus
<220> FEATURE:
<223> OTHER INFORMATION: West Nile virus strain AF404754 region of
      conserved sequence in 3' untranslated region

<400> SEQUENCE: 90 caacccagg aggactgggt gaacaaagcc gcgaagtgat ccatgtaagc cctcagaacc            60
gtctcggaag gaggacccca catgttgtaa cttcaaag                                    98

<210> SEQ ID NO 91
<211> LENGTH: 98
<212> TYPE: DNA
<213> ORGANISM: West Nile virus
<220> FEATURE:
<223> OTHER INFORMATION: West Nile virus strain AF404755 region of
      conserved sequence in 3' untranslated region

<400> SEQUENCE: 91 caacccagg aggactgggt gaacaaagcc gcgaagtgat ccatgtaagc cctcagaacc            60
gtctcggaag gaggacccca catgttgtaa cttcaaag                                    98

<210> SEQ ID NO 92
<211> LENGTH: 98
<212> TYPE: DNA
<213> ORGANISM: West Nile virus
<220> FEATURE:
<223> OTHER INFORMATION: West Nile virus strain AF404756 region of
      conserved sequence in 3' untranslated region

<400> SEQUENCE: 92 caacccagg aggactgggt gaacaaagcc gcgaagtgat ccatgtaagc cctcagaacc            60
gtctcggaag gaggacccca catgttgtaa cttcaaag                                    98

<210> SEQ ID NO 93
<211> LENGTH: 98
<212> TYPE: DNA
<213> ORGANISM: West Nile virus
<220> FEATURE:
<223> OTHER INFORMATION: West Nile virus strain AF017254 region of
      conserved sequence in 3' untranslated region

<400> SEQUENCE: 93 caacccagg aggactgggt gaacaaagct gcgaagtgat ccatgtaagc cctcagaacc            60
gtctcggaag gaggacccca catgttgtaa cttcaaag                                    98

```
<210> SEQ ID NO 94
<211> LENGTH: 98
<212> TYPE: DNA
<213> ORGANISM: West Nile virus
<220> FEATURE:
<223> OTHER INFORMATION: West Nile virus strain L48977 region of
      conserved sequence in 3' untranslated region

<400> SEQUENCE: 94 caacccccagg aggactgggt gaccaaagct gcgaggtgat ccacgtaagc cctcagaacc        60
gtctcggaag caggacccca cgtgctttag cctcaaag                                 98

<210> SEQ ID NO 95
<211> LENGTH: 98
<212> TYPE: DNA
<213> ORGANISM: West Nile virus
<220> FEATURE:
<223> OTHER INFORMATION: West Nile virus strain AF196536 region of
      conserved sequence in 3' untranslated region

<400> SEQUENCE: 95 caacccccagg aggactgggt gaacaaagcc gcgaagtgat ccatgtaagc cctcagaacc        60
gtctcggaag gaggacccca catgttgtaa cttcaaag                                 98

<210> SEQ ID NO 96
<211> LENGTH: 98
<212> TYPE: DNA
<213> ORGANISM: West Nile virus
<220> FEATURE:
<223> OTHER INFORMATION: West Nile virus strain AF196537 region of
      conserved sequence in 3' untranslated region

<400> SEQUENCE: 96 caacccccagg aggactgggt gaacaaagct gcggagcgat ccatgtaagc cctcagaacc        60
gtctcggaag taggacccca catgttgtag ctccaaag                                 98

<210> SEQ ID NO 97
<211> LENGTH: 98
<212> TYPE: DNA
<213> ORGANISM: West Nile virus
<220> FEATURE:
<223> OTHER INFORMATION: West Nile virus strain AF196538 region of
      conserved sequence in 3' untranslated region

<400> SEQUENCE: 97 caacccccagg aggactgggt gaacaaagct gcggagcgat ccatgtaagc cctcagaacc        60
gtctcggaag taggacccca catgttgtag ttccaaag                                 98

<210> SEQ ID NO 98
<211> LENGTH: 98
<212> TYPE: DNA
<213> ORGANISM: West Nile virus
<220> FEATURE:
<223> OTHER INFORMATION: West Nile virus strain AF196540 region of
      conserved sequence in 3' untranslated region

<400> SEQUENCE: 98 caacccccagg aggactgggt gaacaaagct gcggagcgat ccatgtaagc cctcagaacc        60
gtctcggaag taggacccca catgttgtag ttccaaag                                 98

<210> SEQ ID NO 99
<211> LENGTH: 98
<212> TYPE: DNA
<213> ORGANISM: West Nile virus
```

<220> FEATURE:
<223> OTHER INFORMATION: West Nile virus strain AF196541 region of
      conserved sequence in 3' untranslated region

<400> SEQUENCE: 99 caacccagg aggactgggt gaacaaagcc gcgaagtgat ccatgtaagc cctcagaacc    60
gtctcggaag gaggacccca catgttgtaa cttcaaag    98

<210> SEQ ID NO 100
<211> LENGTH: 98
<212> TYPE: DNA
<213> ORGANISM: West Nile virus
<220> FEATURE:
<223> OTHER INFORMATION: West Nile virus strain AF196542 region of
      conserved sequence in 3' untranslated region

<400> SEQUENCE: 100 caacccagg aggactgggt gaacaaagcc gcgaagtgat ccatgtaagc cctcagaacc    60
gtctcggaag gaggacccca catgttgtaa cttcaaag    98

<210> SEQ ID NO 101
<211> LENGTH: 98
<212> TYPE: DNA
<213> ORGANISM: West Nile virus
<220> FEATURE:
<223> OTHER INFORMATION: West Nile virus strain AF196543 region of
      conserved sequence in 3' untranslated region

<400> SEQUENCE: 101 caacccagg aggactgggt taccaaagcc gcgaggtgat ccacgtaagc cctcagaacc    60
gtctcggaaa gaggacccca cgtgttttag cctcaagg    98

<210> SEQ ID NO 102
<211> LENGTH: 98
<212> TYPE: DNA
<213> ORGANISM: West Nile virus
<220> FEATURE:
<223> OTHER INFORMATION: West Nile virus strain AF297840 region of
      conserved sequence in 3' untranslated region

<400> SEQUENCE: 102 caacccagg aggactgggt gaacaaagct gcgaagtgat ccatgtaagc cctcagaacc    60
gcctcggaaa gaggacccca catgttgtag cttcaagg    98

<210> SEQ ID NO 103
<211> LENGTH: 98
<212> TYPE: DNA
<213> ORGANISM: West Nile virus
<220> FEATURE:
<223> OTHER INFORMATION: West Nile virus strain AF458343 region of
      conserved sequence in 3' untranslated region

<400> SEQUENCE: 103 caacccagg aggactgggt gaacaaagcc gcgaagtgat ccatgtaagc ccccagaacc    60
gtctcggaag gaggacccca catgttgtaa cttcaagg    98

<210> SEQ ID NO 104
<211> LENGTH: 98
<212> TYPE: DNA
<213> ORGANISM: West Nile virus
<220> FEATURE:
<223> OTHER INFORMATION: West Nile virus strain AF458344 region of
      conserved sequence in 3' untranslated region

```
<400> SEQUENCE: 104 caacccagg aggactgggt gaacaaagct gcgaagtgat ccatgtaagc cctcagaacc      60
gtctcggaag gaggacccca catgttgtaa cttcaaag                            98

<210> SEQ ID NO 105
<211> LENGTH: 98
<212> TYPE: DNA
<213> ORGANISM: West Nile virus
<220> FEATURE:
<223> OTHER INFORMATION: West Nile virus strain AF458347 region of
      conserved sequence in 3' untranslated region

<400> SEQUENCE: 105 caacccagg aggactgggt gaacaaagct gcgaagtgat ccatgtaagc cctcagaacc      60
gtctcggaag gaggacccca catgttgtaa cttcaaag                            98

<210> SEQ ID NO 106
<211> LENGTH: 98
<212> TYPE: DNA
<213> ORGANISM: West Nile virus
<220> FEATURE:
<223> OTHER INFORMATION: West Nile virus strain AF458348 region of
      conserved sequence in 3' untranslated region

<400> SEQUENCE: 106 caacccagg aggactgggt gaacaaagcc gcgaagtgat ccatgtaagc cctcagaacc      60
gtctcggaag gaggacccca catgttgtaa cttcaaag                            98

<210> SEQ ID NO 107
<211> LENGTH: 98
<212> TYPE: DNA
<213> ORGANISM: West Nile virus
<220> FEATURE:
<223> OTHER INFORMATION: West Nile virus strain AF458350 region of
      conserved sequence in 3' untranslated region

<400> SEQUENCE: 107 caacccagg aggactgggt gaacaaagcc gcgaagtgat ccatgtaagc cctcagaacc      60
gtctcggaag gaggacccca catgttgtaa cttcaaag                            98

<210> SEQ ID NO 108
<211> LENGTH: 98
<212> TYPE: DNA
<213> ORGANISM: West Nile virus
<220> FEATURE:
<223> OTHER INFORMATION: West Nile virus strain AF458352 region of
      conserved sequence in 3' untranslated region

<400> SEQUENCE: 108 caacccagg aggactgggt gaacaaagct gcggagcgat ccatgtaagc cctcagaacc      60
gcctcggaag taggacccca catgttgtag ttycaaag                            98

<210> SEQ ID NO 109
<211> LENGTH: 98
<212> TYPE: DNA
<213> ORGANISM: West Nile virus
<220> FEATURE:
<223> OTHER INFORMATION: West Nile virus strain AF458353 region of
      conserved sequence in 3' untranslated region

<400> SEQUENCE: 109 caacccagg aggactgggt gaacaaagct gcggagcgat ccatgtaagc cctcagaacc      60
```

-continued

```
gtctcggaag taggacccca catgttgtag ttccaaag 98

<210> SEQ ID NO 110
<211> LENGTH: 98
<212> TYPE: DNA
<213> ORGANISM: West Nile virus
<220> FEATURE:
<223> OTHER INFORMATION: West Nile virus strain AF458355 region of conserved sequence in 3' untranslated region
<400> SEQUENCE: 110
caaccccagg aggactgggt gaacaaagct gcgaagtgat ccatgtaagc cctcagaacc 60
gtctcggaag gaggacccca catgttgtaa cttcaaag 98

<210> SEQ ID NO 111
<211> LENGTH: 98
<212> TYPE: DNA
<213> ORGANISM: West Nile virus
<220> FEATURE:
<223> OTHER INFORMATION: West Nile virus strain AF458358 region of conserved sequence in 3' untranslated region
<400> SEQUENCE: 111
caaccccagg aggactgggt taccaaagcc gcgaggtgat ccacgtaagc cctcagaacc 60
gtctcggaaa gaggacccca cgtgttttag cctcaagg 98

<210> SEQ ID NO 112
<211> LENGTH: 98
<212> TYPE: DNA
<213> ORGANISM: West Nile virus
<220> FEATURE:
<223> OTHER INFORMATION: West Nile virus strain AF458360 region of conserved sequence in 3' untranslated region
<400> SEQUENCE: 112
caaccccagg aggactgggt gaacaaagcc gcgaagtgat ccatgtaagc cctcagaacc 60
gtctcggaag gaggacccca catgttgtaa cttcaaag 98

<210> SEQ ID NO 113
<211> LENGTH: 98
<212> TYPE: DNA
<213> ORGANISM: West Nile virus
<220> FEATURE:
<223> OTHER INFORMATION: West Nile virus strain AF458361 region of conserved sequence in 3' untranslated region
<400> SEQUENCE: 113
caaccccagg aggactgggt gaacaaagcc gcgaagtgat ccatgtaagc cctcagaacc 60
gtctcggaag gaggacccca catgttgtaa cttcaaag 98

<210> SEQ ID NO 114
<211> LENGTH: 98
<212> TYPE: DNA
<213> ORGANISM: West Nile virus
<220> FEATURE:
<223> OTHER INFORMATION: West Nile virus strain AF208017 region of conserved sequence in 3' untranslated region
<400> SEQUENCE: 114
caaccccagg aggactgggt gaccaaagct gcgaggtgat ccacgtaagc cctcagaacc 60
gtctcggaag gaggacccca cgtgctttag cctcaaag 98

<210> SEQ ID NO 115

```
<211> LENGTH: 98
<212> TYPE: DNA
<213> ORGANISM: West Nile virus
<220> FEATURE:
<223> OTHER INFORMATION: West Nile virus strain AF196539 region of
      conserved sequence in 3' untranslated region

<400> SEQUENCE: 115 caacccagg aggactgggt gaccaaagct gcgaggtgat ccacgtaagc cctcagaacc      60
gtctcggaag gaggacccca cgtgctttag cctcaaag                            98

<210> SEQ ID NO 116
<211> LENGTH: 98
<212> TYPE: DNA
<213> ORGANISM: West Nile virus
<220> FEATURE:
<223> OTHER INFORMATION: West Nile virus strain AF196535 region of
      conserved sequence in 3' untranslated region

<400> SEQUENCE: 116 caacccagg aggactgggt gaccaaagcc gcgaggtgat ccacgtaagc cctcagaacc      60
gtctcggaag gaggacccca cgtgctttag cctcaagg                            98

<210> SEQ ID NO 117
<211> LENGTH: 98
<212> TYPE: DNA
<213> ORGANISM: West Nile virus
<220> FEATURE:
<223> OTHER INFORMATION: West Nile virus strain AF458359 region of
      conserved sequence in 3' untranslated region

<400> SEQUENCE: 117 caacccagg aggactgggt gaccaaagct gcgaggtgat ccacgtaagc cctcagaacc      60
gtctcggaag gaggacccca cgtgctttag cctcaaag                            98

<210> SEQ ID NO 118
<211> LENGTH: 98
<212> TYPE: DNA
<213> ORGANISM: West Nile virus
<220> FEATURE:
<223> OTHER INFORMATION: West Nile virus strain AF458357 region of
      conserved sequence in 3' untranslated region

<400> SEQUENCE: 118 caacccagg aggactgggt gaccaaagcc gcgaggtgat ccacgtaagc cctcagaacc      60
gtctcggaag gaggacccca cgtgctttag cctcaaag                            98

<210> SEQ ID NO 119
<211> LENGTH: 98
<212> TYPE: DNA
<213> ORGANISM: West Nile virus
<220> FEATURE:
<223> OTHER INFORMATION: West Nile virus strain AF458354 region of
      conserved sequence in 3' untranslated region

<400> SEQUENCE: 119 caacccagg aggactgggt gaccaaagct gcgaggtgat ccacgtaagc cctcagaacc      60
gtctcggaag gaggacccca cgtgctttag cctcaaag                            98

<210> SEQ ID NO 120
<211> LENGTH: 98
<212> TYPE: DNA
<213> ORGANISM: West Nile virus
<220> FEATURE:
```

```
<223> OTHER INFORMATION: West Nile virus strain AF458349 region of
      conserved sequence in 3' untranslated region

<400> SEQUENCE: 120 caacccagg aggactgggt gaccaaacct gcgaggtgat ccacgtaagc cctcagaacc    60
gtctcggaag gaggacccca cgtgctttag cctcaaag                          98

<210> SEQ ID NO 121
<211> LENGTH: 98
<212> TYPE: DNA
<213> ORGANISM: West Nile virus
<220> FEATURE:
<223> OTHER INFORMATION: West Nile virus strain AF458345 region of
      conserved sequence in 3' untranslated region

<400> SEQUENCE: 121 caacccagg aggactgggt gaccaaagct gcgaggtgat ccacgtaagc cctcagaacc    60
gtctcggaag gaggacccca cgtgctttag cctcaaag                          98

<210> SEQ ID NO 122
<211> LENGTH: 99
<212> TYPE: DNA
<213> ORGANISM: West Nile virus
<220> FEATURE:
<223> OTHER INFORMATION: West Nile virus strain AF458346 region of
      conserved sequence in 3' untranslated region

<400> SEQUENCE: 122 caacccagg aggactgggt gaccaaagct gcgaggtgat ccacgtaagc ctctcagaac    60
cgtttcggaa ggaggacccc acgtgcttta gccccaaag                         99

<210> SEQ ID NO 123
<211> LENGTH: 98
<212> TYPE: DNA
<213> ORGANISM: West Nile virus
<220> FEATURE:
<223> OTHER INFORMATION: West Nile virus strain AF533540 region of
      conserved sequence in 3' untranslated region

<400> SEQUENCE: 123 caacccagg aggactgggt gaacaaagcc gcgaagtgat ccatgtaagc cctcagaacc    60
gtctcggaag gaggacccca catgttgtaa cttcaaag                          98

<210> SEQ ID NO 124
<211> LENGTH: 98
<212> TYPE: DNA
<213> ORGANISM: West Nile virus
<220> FEATURE:
<223> OTHER INFORMATION: West Nile virus strain AY187012 region of
      conserved sequence in 3' untranslated region

<400> SEQUENCE: 124 caacccagg aggactgggt gaacaaagcc gcgaagtgat ccatgtaagc cctcagaacc    60
gtctcggaag gaggacccca catgttgtaa cttcaaag                          98

<210> SEQ ID NO 125
<211> LENGTH: 98
<212> TYPE: DNA
<213> ORGANISM: West Nile virus
<220> FEATURE:
<223> OTHER INFORMATION: West Nile virus strain AY187013 region of
      conserved sequence in 3' untranslated region

<400> SEQUENCE: 125
```

```
caaccccagg aggactgggt gaacaaagcc gcgaggtgat ccatgtaagc cctcagaacc    60
gtctcggaag gaggacccca catgttgtaa cttcaaag                            98
```

<210> SEQ ID NO 126
<211> LENGTH: 98
<212> TYPE: DNA
<213> ORGANISM: West Nile virus
<220> FEATURE:
<223> OTHER INFORMATION: West Nile virus strain AY187014 region of
      conserved sequence in 3' untranslated region

<400> SEQUENCE: 126

```
caaccccagg aggactgggt gaacaaagcc gcgaagtgat ccatgtaagc cctcagaacc    60
gtctcggaag gaggacccca catgttgtaa cttcaaag                            98
```

<210> SEQ ID NO 127
<211> LENGTH: 98
<212> TYPE: DNA
<213> ORGANISM: West Nile virus
<220> FEATURE:
<223> OTHER INFORMATION: West Nile virus strain AY187015 region of
      conserved sequence in 3' untranslated region

<400> SEQUENCE: 127

```
caaccccagg aggactgggt gaacaaagcc gcgaagtgat ccatgtaagc cctcagaacc    60
gtctcggaag gaggacccca catgttgtaa cttcaaag                            98
```

<210> SEQ ID NO 128
<211> LENGTH: 98
<212> TYPE: DNA
<213> ORGANISM: West Nile virus
<220> FEATURE:
<223> OTHER INFORMATION: West Nile virus strain AY262283 region of
      conserved sequence in 3' untranslated region

<400> SEQUENCE: 128

```
caaccccagg aggactgggt gaacaaagcc gcgaagtgat ccatgtaagc cctcagaacc    60
gtctcggaag gaggacccca catgttgtaa cttcaaag                            98
```

<210> SEQ ID NO 129
<211> LENGTH: 92
<212> TYPE: DNA
<213> ORGANISM: West Nile virus
<220> FEATURE:
<223> OTHER INFORMATION: West Nile virus strain AY277251 region of
      conserved sequence in 3' untranslated region

<400> SEQUENCE: 129

```
caaccccagg aggactggga tatcaaagcc atggagcgat ccacgtaagc cctcaatacc    60
gtttcggaac gaggacccca cgtgttgtag ct                                  92
```

<210> SEQ ID NO 130
<211> LENGTH: 98
<212> TYPE: DNA
<213> ORGANISM: West Nile virus
<220> FEATURE:
<223> OTHER INFORMATION: West Nile virus strain AY277252 region of
      conserved sequence in 3' untranslated region

<400> SEQUENCE: 130

```
caaccccagg aggactgggt gaacaaagcc gcgaagtgat ccatgtaagc cctcagaacc    60
gtctcggaag gaggacccca catgttgtaa cttcaaag                            98
```

<210> SEQ ID NO 131
<211> LENGTH: 98
<212> TYPE: DNA
<213> ORGANISM: West Nile virus
<220> FEATURE:
<223> OTHER INFORMATION: West Nile virus strain AY278441 region of
      conserved sequence in 3' untranslated region

<400> SEQUENCE: 131 caacccagg aggactgggt gaacaaagcc gcgaagtgat ccatgtaagc cctcagaacc    60
gtctcggaag gaggacccca catgttgtaa cttcaaag                          98

<210> SEQ ID NO 132
<211> LENGTH: 98
<212> TYPE: DNA
<213> ORGANISM: West Nile virus
<220> FEATURE:
<223> OTHER INFORMATION: West Nile virus strain AY278442 region of
      conserved sequence in 3' untranslated region

<400> SEQUENCE: 132 caacccagg aggactgggt gaacaaagcc gcgaagtgat ccatgtaagc cctcagaacc    60
gtctcggaag gaggacccca catgttgtaa cttcaaag                          98

<210> SEQ ID NO 133
<211> LENGTH: 98
<212> TYPE: DNA
<213> ORGANISM: West Nile virus
<220> FEATURE:
<223> OTHER INFORMATION: West Nile virus strain AY268132 region of
      conserved sequence in 3' untranslated region

<400> SEQUENCE: 133 caacccagg aggactgggt gaacaaagcc gcgaagtgat ccatgtaagc cctcaaaacc    60
gtctcggaag gaggacccca catgttgtaa cttcaaag                          98

<210> SEQ ID NO 134
<211> LENGTH: 98
<212> TYPE: DNA
<213> ORGANISM: West Nile virus
<220> FEATURE:
<223> OTHER INFORMATION: West Nile virus strain AY268133 region of
      conserved sequence in 3' untranslated region

<400> SEQUENCE: 134 caacccagg aggactgggt gaacaaagcc gcgaagtgat ccatgtaagc cctcagaacc    60
gtctcggaag gaggacccca catgttgtaa cttcaaag                          98

<210> SEQ ID NO 135
<211> LENGTH: 98
<212> TYPE: DNA
<213> ORGANISM: West Nile virus
<220> FEATURE:
<223> OTHER INFORMATION: West Nile virus strain AY490240 region of
      conserved sequence in 3' untranslated region

<400> SEQUENCE: 135 caacccagg aggactgggt gaacaaagct gcgaagtgat ccatgtaagc cctcagaacc    60
gtctcggaag gaggacccca catgttgtaa cttcaaag                          98

<210> SEQ ID NO 136
<211> LENGTH: 98

```
<212> TYPE: DNA
<213> ORGANISM: Kunjin virus
<220> FEATURE:
<223> OTHER INFORMATION: Kunjin virus strain D00246 region of conserved
      sequence in 3' untranslated region

<400> SEQUENCE: 136 caacccccagg aggactgggt gaacaaagct gcgaagtgat ccatgtaagc cctcagaacc     60
gtctcggaaa gaggacccca catgttgtag cttcaagg                              98

<210> SEQ ID NO 137
<211> LENGTH: 98
<212> TYPE: DNA
<213> ORGANISM: Kunjin virus
<220> FEATURE:
<223> OTHER INFORMATION: Kunjin virus strain AY274504 region of
      conserved sequence in 3' untranslated region

<400> SEQUENCE: 137 caacccccagg aggactgggt gaacaaagct gcgaagtgat ccatgtaagc cctcagaacc     60
gtctcggaaa gaggacccca catgttgtag cttcaagg                              98

<210> SEQ ID NO 138
<211> LENGTH: 98
<212> TYPE: DNA
<213> ORGANISM: Kunjin virus
<220> FEATURE:
<223> OTHER INFORMATION: Kunjin virus strain AY274505 region of
      conserved sequence in 3' untranslated region

<400> SEQUENCE: 138 caacccccagg aggactgggt gaacaaagct gcgaagtgat ccatgtaagc cctcagaacc     60
gtctcggaaa gaggacccca catgttgtag cttcaagg                              98

<210> SEQ ID NO 139
<211> LENGTH: 98
<212> TYPE: DNA
<213> ORGANISM: Kunjin virus
<220> FEATURE:
<223> OTHER INFORMATION: Kunjin virus strain L49311 region of conserved
      sequence in 3' untranslated region

<400> SEQUENCE: 139 caacccccagg aggactgggt gaacaaagct gcgaggtgat ccacgtaagc cctcagaacc     60
gtctcggaag aaggacccca cgtgttttag cctcaagg                              98

<210> SEQ ID NO 140
<211> LENGTH: 98
<212> TYPE: DNA
<213> ORGANISM: Kunjin virus
<220> FEATURE:
<223> OTHER INFORMATION: Kunjin virus strain L48978 region of conserved
      sequence in 3' untranslated region

<400> SEQUENCE: 140 caacccccagg aggactgggt gaacaaagct gcgaagtgat ccatgtaagc cctcagaacc     60
gtctcggaaa gaggacccca catgttgtag cttcaagg                              98

<210> SEQ ID NO 141
<211> LENGTH: 98
<212> TYPE: DNA
<213> ORGANISM: Kunjin virus
<220> FEATURE:
<223> OTHER INFORMATION: Kunjin virus strain L48979 region of conserved
``` sequence in 3' untranslated region

<400> SEQUENCE: 141 caacccagg aggactgggt gaacaaagct gcgaagtgat ccatgtaagc cctcagaacc    60
gtctcggaaa gaggacccca catgttgtag cttcaagg                           98

<210> SEQ ID NO 142
<211> LENGTH: 98
<212> TYPE: DNA
<213> ORGANISM: Kunjin virus
<220> FEATURE:
<223> OTHER INFORMATION: Kunjin virus strain AF297840 region of
      conserved sequence in 3' untranslated region

<400> SEQUENCE: 142 caacccagg aggactgggt gaacaaagct gcgaagtgat ccatgtaagc cctcagaacc    60
gcctcggaaa gaggacccca catgttgtag cttcaagg                           98

<210> SEQ ID NO 143
<211> LENGTH: 98
<212> TYPE: DNA
<213> ORGANISM: Kunjin virus
<220> FEATURE:
<223> OTHER INFORMATION: Kunjin virus strain AF297841 region of
      conserved sequence in 3' untranslated region

<400> SEQUENCE: 143 caacccagg aggactgggt gaacaaagct gcgaagtgat ccatgtaagc cctcagaacc    60
gtctcggaaa gaggacccca catgttgtag cttcaagg                           98

<210> SEQ ID NO 144
<211> LENGTH: 98
<212> TYPE: DNA
<213> ORGANISM: Kunjin virus
<220> FEATURE:
<223> OTHER INFORMATION: Kunjin virus strain AF297842 region of
      conserved sequence in 3' untranslated region

<400> SEQUENCE: 144 caacccagg aggactgggt gaacaaagct gcgaagtgat ccatgtaagc cctcagaacc    60
gtctcggaaa gaggacccca catgttgtag cttcaagg                           98

<210> SEQ ID NO 145
<211> LENGTH: 98
<212> TYPE: DNA
<213> ORGANISM: Kunjin virus
<220> FEATURE:
<223> OTHER INFORMATION: Kunjin virus strain AF297843 region of
      conserved sequence in 3' untranslated region

<400> SEQUENCE: 145 caacccagg aggactgggt gaacaaagct gcgaagtgat ccatgtaagc cctcagaacc    60
gtctcggaaa gaggacccca catgttgtag cttcaagg                           98

<210> SEQ ID NO 146
<211> LENGTH: 98
<212> TYPE: DNA
<213> ORGANISM: Kunjin virus
<220> FEATURE:
<223> OTHER INFORMATION: Kunjin virus strain AF297844 region of
      conserved sequence in 3' untranslated region

<400> SEQUENCE: 146

```
caaccccagg aggactgggt gaacaaagct gcgaagtgat ccatgtaagc cctcagaacc    60
gtctcggaaa gaggacccca catgttgtag cttcaagg                            98

<210> SEQ ID NO 147
<211> LENGTH: 98
<212> TYPE: DNA
<213> ORGANISM: Kunjin virus
<220> FEATURE:
<223> OTHER INFORMATION: Kunjin virus strain AF297845 region of
      conserved sequence in 3' untranslated region

<400> SEQUENCE: 147
caaccccagg aggactgggt gaacaaagct gcgaagtgat ccatgtaagc cctcagaacc    60
gtctcggaaa gaggacccca catgttgtag cttcaagg                            98

<210> SEQ ID NO 148
<211> LENGTH: 98
<212> TYPE: DNA
<213> ORGANISM: Kunjin virus
<220> FEATURE:
<223> OTHER INFORMATION: Kunjin virus strain AF297846 region of
      conserved sequence in 3' untranslated region

<400> SEQUENCE: 148
caaccccagg aggactgggt gaacaaagct gcgaagtgat ccatgtaagc cctcagaacc    60
gcctcggaaa gaggacccca cattttgtag cttcaagg                            98

<210> SEQ ID NO 149
<211> LENGTH: 98
<212> TYPE: DNA
<213> ORGANISM: Kunjin virus
<220> FEATURE:
<223> OTHER INFORMATION: Kunjin virus strain AF297847 region of
      conserved sequence in 3' untranslated region

<400> SEQUENCE: 149
caaccccagg atgactgggt gaacaaagct gcgaagtgat ccatgtaagc cctcagaacc    60
gcctcggaaa gaggacccca catgttgtag cttcaagg                            98

<210> SEQ ID NO 150
<211> LENGTH: 98
<212> TYPE: DNA
<213> ORGANISM: Kunjin virus
<220> FEATURE:
<223> OTHER INFORMATION: Kunjin virus strain AF297848 region of
      conserved sequence in 3' untranslated region

<400> SEQUENCE: 150
caaccccagg aggactgggt gaacaaagct gcgaagtgat ccatgtaagc cctcagaacc    60
gtctcggaaa gaggacccca catgttgtag cttcaagg                            98

<210> SEQ ID NO 151
<211> LENGTH: 98
<212> TYPE: DNA
<213> ORGANISM: Kunjin virus
<220> FEATURE:
<223> OTHER INFORMATION: Kunjin virus strain AF297849 region of
      conserved sequence in 3' untranslated region

<400> SEQUENCE: 151
caaccccagg aggactgggt gaacaaagct gcgaagtgat ccatgtaagc cctcagaacc    60
gtctcggaaa gaggacccca catgttgtag cttcaagg                            98
```

<210> SEQ ID NO 152
<211> LENGTH: 98
<212> TYPE: DNA
<213> ORGANISM: Kunjin virus
<220> FEATURE:
<223> OTHER INFORMATION: Kunjin virus strain AF297850 region of
      conserved sequence in 3' untranslated region

<400> SEQUENCE: 152
caaccccagg aggactgggt gaacaaagct gcgaagtgat ccatgtaagc cctcagaacc    60
gcctcggaaa gaggacccca catgttgtag cttcaagg                            98

<210> SEQ ID NO 153
<211> LENGTH: 98
<212> TYPE: DNA
<213> ORGANISM: Kunjin virus
<220> FEATURE:
<223> OTHER INFORMATION: Kunjin virus strain AF297851 region of
      conserved sequence in 3' untranslated region

<400> SEQUENCE: 153
caaccccagg aggactgggt gaacaaagct gcgaagtgat ccatgtaagc cctcagaacc    60
gcctcgggta gaggacgcga catgttgtag cagcaagc                            98

<210> SEQ ID NO 154
<211> LENGTH: 98
<212> TYPE: DNA
<213> ORGANISM: Kunjin virus
<220> FEATURE:
<223> OTHER INFORMATION: Kunjin virus strain AF297852 region of
      conserved sequence in 3' untranslated region

<400> SEQUENCE: 154
caaccccagg aggactgggt gaacaaagct gcgaagtgat ccatgtaagc cctcagaacc    60
gcctcggaaa gaggacccca catgttgtag cttcaagg                            98

<210> SEQ ID NO 155
<211> LENGTH: 98
<212> TYPE: DNA
<213> ORGANISM: Kunjin virus
<220> FEATURE:
<223> OTHER INFORMATION: Kunjin virus strain AF297853 region of
      conserved sequence in 3' untranslated region

<400> SEQUENCE: 155
caaccccagg aggactgggt gaacaaagct gcgaagtgat ccatgtaagc cctcagaacc    60
gcctcggaaa gaggacccca catgttgtag cttcaagg                            98

<210> SEQ ID NO 156
<211> LENGTH: 98
<212> TYPE: DNA
<213> ORGANISM: Kunjin virus
<220> FEATURE:
<223> OTHER INFORMATION: Kunjin virus strain AF297854 region of
      conserved sequence in 3' untranslated region

<400> SEQUENCE: 156
caaccccagg aggactgggt gaacaaagct gcgaagtgat ccatgtaagc cctcagaacc    60
gtctcggaaa gaggacccca catgttgtag cttcaaga                            98

<210> SEQ ID NO 157
<211> LENGTH: 98
<212> TYPE: DNA

```
<213> ORGANISM: Kunjin virus
<220> FEATURE:
<223> OTHER INFORMATION: Kunjin virus strain AF297855 region of
      conserved sequence in 3' untranslated region

<400> SEQUENCE: 157
caaccccagg aggactgggt gaacaaagct gcgaagtgat ccatgtaagc cctcagaacc    60
gtctcggaaa gaggacccca catgttgtag cttcaagg                           98

<210> SEQ ID NO 158
<211> LENGTH: 98
<212> TYPE: DNA
<213> ORGANISM: Kunjin virus
<220> FEATURE:
<223> OTHER INFORMATION: Kunjin virus strain AF297856 region of
      conserved sequence in 3' untranslated region

<400> SEQUENCE: 158
caaccccagg gggactgggt gatcaaagct gcgaagtgat ccatgtaagc cctcagaacc    60
gtctcggaaa gaggacccca catgttgtag cttcaagg                           98

<210> SEQ ID NO 159
<211> LENGTH: 98
<212> TYPE: DNA
<213> ORGANISM: Kunjin virus
<220> FEATURE:
<223> OTHER INFORMATION: Kunjin virus strain AF297857 region of
      conserved sequence in 3' untranslated region

<400> SEQUENCE: 159
caaccccagg aggactgggt gaacaaagcc gcgaagtgat ccatgtaagc cgtcagaacc    60
gtctcggaaa gaggacccca ccctttgtag attcaagg                           98

<210> SEQ ID NO 160
<211> LENGTH: 98
<212> TYPE: DNA
<213> ORGANISM: Kunjin virus
<220> FEATURE:
<223> OTHER INFORMATION: Kunjin virus strain AF297858 region of
      conserved sequence in 3' untranslated region

<400> SEQUENCE: 160
caaccccagg aggactgggt gaacaaagct gcgaagtgat ccatgtaagc cctcagaacc    60
gtctcggaaa gaggacccca catgttgtag cttcaagg                           98

<210> SEQ ID NO 161
<211> LENGTH: 98
<212> TYPE: DNA
<213> ORGANISM: Kunjin virus
<220> FEATURE:
<223> OTHER INFORMATION: Kunjin virus strain AF297859 region of
      conserved sequence in 3' untranslated region

<400> SEQUENCE: 161 caacccagg aggactgggt gaacaaagct gcgaagtgat ccatgtaagc cctcagaacc     60
gtctcggaaa gaggacccca catgttgtag cttcaagg                           98

<210> SEQ ID NO 162
<211> LENGTH: 98
<212> TYPE: DNA
<213> ORGANISM: Kunjin virus
<220> FEATURE:
<223> OTHER INFORMATION: Kunjin virus strain AF458351 region of
      conserved sequence in 3' untranslated region
```

```
<400> SEQUENCE: 162 caacccagg aggactgggt gaacaaagct gcgaagtgat ccatgtaagc cctcagaacc    60
gtctcgggaa gaggacccca catgttgtag cttcaagg                          98

<210> SEQ ID NO 163
<211> LENGTH: 98
<212> TYPE: DNA
<213> ORGANISM: Kunjin virus
<220> FEATURE:
<223> OTHER INFORMATION: Kunjin virus strain AF458356 region of
      conserved sequence in 3' untranslated region

<400> SEQUENCE: 163 caacccagg aggactgggt gaacaaagct gcgaagtgat ccatgtaagc cctcagaacc    60
gcctcggaaa gaggacccca catgttgtag cttcaagg                          98

<210> SEQ ID NO 164
<211> LENGTH: 98
<212> TYPE: DNA
<213> ORGANISM: Kunjin virus
<220> FEATURE:
<223> OTHER INFORMATION: Kunjin virus strain L24512 region of conserved
      sequence in 3' untranslated region

<400> SEQUENCE: 164 caacccagg aggactgggt gaacaaagct gcgaagtgat ccatgtaagc cctcagaacc    60
gtctcggaaa gaggacccca catgttgtag cttcaagg                          98

<210> SEQ ID NO 165
<211> LENGTH: 99
<212> TYPE: DNA
<213> ORGANISM: Japanese encephalitis virus
<220> FEATURE:
<223> OTHER INFORMATION: Japanese encephalitis virus strain AB051292
      region of conserved sequence in 3' untranslated region

<400> SEQUENCE: 165
cagttccagg aggactgggt taacaaatct gacaacggaa ggtgggaaag ccctcagaac    60
cgtctcggaa gcaggtccct gcgcaccgga agttgaaag                          99

<210> SEQ ID NO 166
<211> LENGTH: 99
<212> TYPE: DNA
<213> ORGANISM: Japanese encephalitis virus
<220> FEATURE:
<223> OTHER INFORMATION: Japanese encephalitis virus strain AF014160
      region of conserved sequence in 3' untranslated region

<400> SEQUENCE: 166
cagtcccagg aggactgggt taacaaatct gacaatagaa agtgagaaag ccctcagaac    60
cgtctcggaa gcaggtccct gctcactgga agttgaagg                          99

<210> SEQ ID NO 167
<211> LENGTH: 99
<212> TYPE: DNA
<213> ORGANISM: Japanese encephalitis virus
<220> FEATURE:
<223> OTHER INFORMATION: Japanese encephalitis virus strain AF014161
      region of conserved sequence in 3' untranslated region

<400> SEQUENCE: 167
cagtcccagg aggactgggt taacaaatct gacaatagaa agtgagaaag ccctcagaac    60
```

```
cgtctcggaa gcaggtccct gctcactgga agttgaagg                                  99

<210> SEQ ID NO 168
<211> LENGTH: 99
<212> TYPE: DNA
<213> ORGANISM: Japanese encephalitis virus
<220> FEATURE:
<223> OTHER INFORMATION: Japanese encephalitis virus strain AF045551
      region of conserved sequence in 3' untranslated region

<400> SEQUENCE: 168
cagttccagg aggactgggt taacaaatct gacaacggaa ggtgggaaag ccctcagaac      60
cgtctcggaa gcaggtccct gctcaccgga agttgaaag                             99

<210> SEQ ID NO 169
<211> LENGTH: 99
<212> TYPE: DNA
<213> ORGANISM: Japanese encephalitis virus
<220> FEATURE:
<223> OTHER INFORMATION: Japanese encephalitis virus strain AF069076
      region of conserved sequence in 3' untranslated region

<400> SEQUENCE: 169
cagtcccagg aggactgggt taacaaatct gacaacagaa agtgagaaag ccctcagaac      60
cgtctcggaa gcaggtccct gctcactgga agttgaagg                             99

<210> SEQ ID NO 170
<211> LENGTH: 99
<212> TYPE: DNA
<213> ORGANISM: Japanese encephalitis virus
<220> FEATURE:
<223> OTHER INFORMATION: Japanese encephalitis virus strain AF075723
      region of conserved sequence in 3' untranslated region

<400> SEQUENCE: 170
cagtcccagg cggactgggt taacaaatct gacaacagag agtgagaaag ccctcagaac      60
cgtctcggaa gcaggtccct gctcactgga agttgaaag                             99

<210> SEQ ID NO 171
<211> LENGTH: 99
<212> TYPE: DNA
<213> ORGANISM: Japanese encephalitis virus
<220> FEATURE:
<223> OTHER INFORMATION: Japanese encephalitis virus strain AF080251
      region of conserved sequence in 3' untranslated region

<400> SEQUENCE: 171
cagtcccagg aggactgggt taacaaatct gacaacagaa agtgagaaag ccctcggaac      60
cgtctcggaa gtaggtccct gctcaccgga agttgaaag                             99

<210> SEQ ID NO 172
<211> LENGTH: 99
<212> TYPE: DNA
<213> ORGANISM: Japanese encephalitis virus
<220> FEATURE:
<223> OTHER INFORMATION: Japanese encephalitis virus strain AF098735
      region of conserved sequence in 3' untranslated region

<400> SEQUENCE: 172
cagtcccagg aggactgggt taacaaatct gacaacagaa agtgagaaag ccctcagaac      60
cgtctcggaa gcaggtccct gctcactgga agttgaagg                             99
```

```
<210> SEQ ID NO 173
<211> LENGTH: 99
<212> TYPE: DNA
<213> ORGANISM: Japanese encephalitis virus
<220> FEATURE:
<223> OTHER INFORMATION: Japanese encephalitis virus strain AF098736
      region of conserved sequence in 3' untranslated region

<400> SEQUENCE: 173
cagtcccagg aggactgggt taacaaatct gacaacagaa agtgagaaag ccctcagaac    60
cgtctcggaa gcaggtccct gctcactgga agttgaaag                          99

<210> SEQ ID NO 174
<211> LENGTH: 99
<212> TYPE: DNA
<213> ORGANISM: Japanese encephalitis virus
<220> FEATURE:
<223> OTHER INFORMATION: Japanese encephalitis virus strain AF098737
      region of conserved sequence in 3' untranslated region

<400> SEQUENCE: 174
cagtcccagg aggactgggt taacaaatct gacaacagaa agtgagaaag ccctcagaac    60
cgtctcggaa gcaggtccct gctcactgga agttgaagg                          99

<210> SEQ ID NO 175
<211> LENGTH: 99
<212> TYPE: DNA
<213> ORGANISM: Japanese encephalitis virus
<220> FEATURE:
<223> OTHER INFORMATION: Japanese encephalitis virus strain AF217620
      region of conserved sequence in 3' untranslated region

<400> SEQUENCE: 175
cagttccagg aggactgggt taacaaatct gacaacagaa ggtgagaaag ccctcagaac    60
cgtctcggaa gtaggtccct gctcaccgga agttggaag                          99

<210> SEQ ID NO 176
<211> LENGTH: 99
<212> TYPE: DNA
<213> ORGANISM: Japanese encephalitis virus
<220> FEATURE:
<223> OTHER INFORMATION: Japanese encephalitis virus strain AF221499
      region of conserved sequence in 3' untranslated region

<400> SEQUENCE: 176
cagtcccagg aggactgggt taacaaatct gacaacagaa agtgagaaag ccctcagaac    60
cgtctcggaa gtaggtccct gctcactgga agttgaaag                          99

<210> SEQ ID NO 177
<211> LENGTH: 99
<212> TYPE: DNA
<213> ORGANISM: Japanese encephalitis virus
<220> FEATURE:
<223> OTHER INFORMATION: Japanese encephalitis virus strain AF221500
      region of conserved sequence in 3' untranslated region

<400> SEQUENCE: 177
cagtcccagg aggactgggt taacaaatct gacaacagaa agtgagaaag ccctcagaac    60
cgtctcggaa gtaggtccct gctcactgga agttgaaag                          99

<210> SEQ ID NO 178
<211> LENGTH: 99
<212> TYPE: DNA
<213> ORGANISM: Japanese encephalitis virus
```

```
<220> FEATURE:
<223> OTHER INFORMATION: Japanese encephalitis virus strain AF254452
      region of conserved sequence in 3' untranslated region

<400> SEQUENCE: 178
cagtcccagg aggactgggt taacaaatct gacaacagaa agtgagaaag ccctcagaac    60
cgtctcggaa gcaggtccct gctcactgga agttgaagg                          99

<210> SEQ ID NO 179
<211> LENGTH: 99
<212> TYPE: DNA
<213> ORGANISM: Japanese encephalitis virus
<220> FEATURE:
<223> OTHER INFORMATION: Japanese encephalitis virus strain AF254453
      region of conserved sequence in 3' untranslated region

<400> SEQUENCE: 179
cagtcccaga aggactgggt taacaaatct gacaacagaa agtgagaaag ccctcagaac    60
cgtctcggaa gcaggtccct gctcactgga agttgaagg                          99

<210> SEQ ID NO 180
<211> LENGTH: 99
<212> TYPE: DNA
<213> ORGANISM: Japanese encephalitis virus
<220> FEATURE:
<223> OTHER INFORMATION: Japanese encephalitis virus strain AF315119
      region of conserved sequence in 3' untranslated region

<400> SEQUENCE: 180
cagtcccagg aggactgggt taacaaatct gacaacagaa agtgagaaag ccctcagaac    60
tgtctcggaa gtaggtccct gctcactgga agttgaaag                          99

<210> SEQ ID NO 181
<211> LENGTH: 99
<212> TYPE: DNA
<213> ORGANISM: Japanese encephalitis virus
<220> FEATURE:
<223> OTHER INFORMATION: Japanese encephalitis virus strain AF416457
      region of conserved sequence in 3' untranslated region

<400> SEQUENCE: 181
cagtcccagg aggactgggt taacaaatct gacaacaaaa agtgagaaag ccctcagaac    60
cgtctcggaa gtaggtccct gctcactgga agttgaaag                          99

<210> SEQ ID NO 182
<211> LENGTH: 99
<212> TYPE: DNA
<213> ORGANISM: Japanese encephalitis virus
<220> FEATURE:
<223> OTHER INFORMATION: Japanese encephalitis virus strain AF486638
      region of conserved sequence in 3' untranslated region

<400> SEQUENCE: 182
cagtcccagg aggactgggt taacaaatct gacaacagaa agtgagaaag ccctcagaac    60
cgtctcggaa gcaggtccct gctcactgga agttgaagg                          99

<210> SEQ ID NO 183
<211> LENGTH: 99
<212> TYPE: DNA
<213> ORGANISM: Japanese encephalitis virus
<220> FEATURE:
<223> OTHER INFORMATION: Japanese encephalitis virus strain U14163
      region of conserved sequence in 3' untranslated region
```

```
<400> SEQUENCE: 183
cagtcccagg aggactgggt taacaaatct gacaacagaa agtgagaaag ccctcagaac    60
cgtctcggaa gtaggtccct gctcactgga agttgaaag                          99

<210> SEQ ID NO 184
<211> LENGTH: 99
<212> TYPE: DNA
<213> ORGANISM: Japanese encephalitis virus
<220> FEATURE:
<223> OTHER INFORMATION: Japanese encephalitis virus strain U15763
      region of conserved sequence in 3' untranslated region

<400> SEQUENCE: 184
cagtcccagg aggactgggt taacaaatct gacaacagaa agtgagaaag ccctcagaac    60
cgtctcggaa gtaggtccct gctcactgga agttgaaag                          99

<210> SEQ ID NO 185
<211> LENGTH: 99
<212> TYPE: DNA
<213> ORGANISM: Japanese encephalitis virus
<220> FEATURE:
<223> OTHER INFORMATION: Japanese encephalitis virus strain L48961
      region of conserved sequence in 3' untranslated region

<400> SEQUENCE: 185
cagtcccagg aggactgggt taacaaatct gacaacggaa agtgagaaag ccctcagaac    60
cgtctcggaa gtaggtccct gctcactgga agttgaaag                          99

<210> SEQ ID NO 186
<211> LENGTH: 99
<212> TYPE: DNA
<213> ORGANISM: Japanese encephalitis virus
<220> FEATURE:
<223> OTHER INFORMATION: Japanese encephalitis virus strain U47032
      region of conserved sequence in 3' untranslated region

<400> SEQUENCE: 186
cagtcccagg aggactgggt taacaaatct gacaacagaa agtgagaaag ccctcagaac    60
cgtctcggaa gtaggtccct gctcactgga agttgaaag                          99

<210> SEQ ID NO 187
<211> LENGTH: 99
<212> TYPE: DNA
<213> ORGANISM: Japanese encephalitis virus
<220> FEATURE:
<223> OTHER INFORMATION: Japanese encephalitis virus strain M18370
      region of conserved sequence in 3' untranslated region

<400> SEQUENCE: 187
cagtcccagg aggactgggt taacaaatct gacaacagaa agtgagaaag ccctcagaac    60
cgtctcggaa gtaggtccct gctcactgga agttgaaag                          99

<210> SEQ ID NO 188
<211> LENGTH: 99
<212> TYPE: DNA
<213> ORGANISM: Japanese encephalitis virus
<220> FEATURE:
<223> OTHER INFORMATION: Japanese encephalitis virus strain M55506
      region of conserved sequence in 3' untranslated region

<400> SEQUENCE: 188
cagtcccagg aggactgggt taacaaatct gacaacagaa agtgagaaag ccctcagaac    60
```

```
cgtctcggaa gtaggtccct gctcactgga agttgaaag                            99

<210> SEQ ID NO 189
<211> LENGTH: 99
<212> TYPE: DNA
<213> ORGANISM: Japanese encephalitis virus
<220> FEATURE:
<223> OTHER INFORMATION: Japanese encephalitis virus strain D90195
      region of conserved sequence in 3' untranslated region

<400> SEQUENCE: 189
cagtcccagg aggactgggt taacaaatct gacaacagaa agtgagaaag ccctcagaac   60
cgtctcggaa gtaggtccct gctcactgga agttgaaag                            99

<210> SEQ ID NO 190
<211> LENGTH: 99
<212> TYPE: DNA
<213> ORGANISM: Japanese encephalitis virus
<220> FEATURE:
<223> OTHER INFORMATION: Japanese encephalitis virus strain D90194
      region of conserved sequence in 3' untranslated region

<400> SEQUENCE: 190
cagtcccagg aggactgggt taacaaatct gacaacagaa agtgagaaag ccctcagaac   60
cgtctcggaa gtaggtccct gctcactgga agttgaaag                            99

<210> SEQ ID NO 191
<211> LENGTH: 99
<212> TYPE: DNA
<213> ORGANISM: Japanese encephalitis virus
<220> FEATURE:
<223> OTHER INFORMATION: Japanese encephalitis virus strain AF311748
      region of conserved sequence in 3' untranslated region

<400> SEQUENCE: 191
cagtcccagg aggactgggt taacaaatct gacaacagaa agtgagaaag ccctcagaac   60
cgtctcggaa gtaggtccct gctcactgga agttgaaag                            99

<210> SEQ ID NO 192
<211> LENGTH: 99
<212> TYPE: DNA
<213> ORGANISM: Japanese encephalitis virus
<220> FEATURE:
<223> OTHER INFORMATION: Japanese encephalitis virus strain AF092550
      region of conserved sequence in 3' untranslated region

<400> SEQUENCE: 192
cagttccagg aggactgggt taacaaatct gacaacagaa ggtgagaaag ccctcagaac   60
cgtctcggaa gtaggtccct gctcaccgga agttggaag                            99

<210> SEQ ID NO 193
<211> LENGTH: 99
<212> TYPE: DNA
<213> ORGANISM: Japanese encephalitis virus
<220> FEATURE:
<223> OTHER INFORMATION: Japanese encephalitis virus strain AF092552
      region of conserved sequence in 3' untranslated region

<400> SEQUENCE: 193
cagttccagg aggactgggt taacaaatct gacaacagaa ggtgagaaag ccctcagaac   60
cgtctcggaa gtaggtccct gctcaccgga agttggaag                            99

<210> SEQ ID NO 194
```

<210> SEQ ID NO 194
<211> LENGTH: 99
<212> TYPE: DNA
<213> ORGANISM: Japanese encephalitis virus
<220> FEATURE:
<223> OTHER INFORMATION: Japanese encephalitis virus strain AF092553
      region of conserved sequence in 3' untranslated region

<400> SEQUENCE: 194
cagttccagg aggactgggt taacaaatct gacaacagaa ggtgagaaag ccctcagaac     60
cgtctcggaa gtaggtccct gctcaccgga agttggaag                           99

<210> SEQ ID NO 195
<211> LENGTH: 99
<212> TYPE: DNA
<213> ORGANISM: Japanese encephalitis virus
<220> FEATURE:
<223> OTHER INFORMATION: Japanese encephalitis virus strain AF139531
      region of conserved sequence in 3' untranslated region

<400> SEQUENCE: 195
cagttccagg aggactgggt taacaaatct gacaacagaa ggtgagaaag ccctcagaac     60
cgtctcggaa gtaggtccct gctcaccgga agttggaag                           99

<210> SEQ ID NO 196
<211> LENGTH: 99
<212> TYPE: DNA
<213> ORGANISM: Japanese encephalitis virus
<220> FEATURE:
<223> OTHER INFORMATION: Japanese encephalitis virus strain AF148900
      region of conserved sequence in 3' untranslated region

<400> SEQUENCE: 196
cagttccagg aggactgggt taacaaatct gacaacagaa ggtgagaaag ccctcagaac     60
cgtctcggaa gtaggtccct gctcaccgga agttggaag                           99

<210> SEQ ID NO 197
<211> LENGTH: 52
<212> TYPE: DNA
<213> ORGANISM: Japanese encephalitis virus
<220> FEATURE:
<223> OTHER INFORMATION: Japanese encephalitis virus strain AF148901
      region of conserved sequence in 3' untranslated region

<400> SEQUENCE: 197
cagttccagg aggactgggt taacaaatct gacaacagaa ggtgagaaag cc             52

<210> SEQ ID NO 198
<211> LENGTH: 99
<212> TYPE: DNA
<213> ORGANISM: Japanese encephalitis virus
<220> FEATURE:
<223> OTHER INFORMATION: Japanese encephalitis virus strain AF148902
      region of conserved sequence in 3' untranslated region

<400> SEQUENCE: 198
cagttccagg aggactgggt taacaaatct gacaacagaa ggtgagaaag ccctcagaac     60
cgtctcggaa gtaggtccct gctcaccgga agttggaag                           99

<210> SEQ ID NO 199
<211> LENGTH: 99
<212> TYPE: DNA
<213> ORGANISM: Japanese encephalitis virus
<220> FEATURE:
<223> OTHER INFORMATION: Japanese encephalitis virus strain AF218068
      region of conserved sequence in 3' untranslated region

<400> SEQUENCE: 199
cagttccagg aggactgggt taacaaatct gacaacagaa ggtgagaaag ccctcagaac    60
cgtctcggaa gtaggtccct gctcaccgga agttggaag                          99

<210> SEQ ID NO 200
<211> LENGTH: 99
<212> TYPE: DNA
<213> ORGANISM: Japanese encephalitis virus
<220> FEATURE:
<223> OTHER INFORMATION: Japanese encephalitis virus strain AF289816
      region of conserved sequence in 3' untranslated region

<400> SEQUENCE: 200
cagtcccagg aggactgggt taacaaatct gacaacggaa ggtgggaaag ccctcagaac    60
cgtctcggaa gtaggtccct gctcaccgga agttgaaag                          99

<210> SEQ ID NO 201
<211> LENGTH: 99
<212> TYPE: DNA
<213> ORGANISM: Japanese encephalitis virus
<220> FEATURE:
<223> OTHER INFORMATION: Japanese encephalitis virus strain AF318291
      region of conserved sequence in 3' untranslated region

<400> SEQUENCE: 201
cagtcccagg aggactgggt taacaaatct gacaacggaa ggtgggaaag ccctcagaac    60
cgtctcggaa gtaggtccct gctcaccgga agttgaaag                          99

<210> SEQ ID NO 202
<211> LENGTH: 99
<212> TYPE: DNA
<213> ORGANISM: Japanese encephalitis virus
<220> FEATURE:
<223> OTHER INFORMATION: Japanese encephalitis virus strain L48967
      region of conserved sequence in 3' untranslated region

<400> SEQUENCE: 202
cagttccagg aggactgggt taacaaatct gacaacagaa ggtgagaaag ccctcagaac    60
cgtctcggaa gtaggtccct gctcaccgga agttggaag                          99

<210> SEQ ID NO 203
<211> LENGTH: 99
<212> TYPE: DNA
<213> ORGANISM: Japanese encephalitis virus
<220> FEATURE:
<223> OTHER INFORMATION: Japanese encephalitis virus strain L48968
      region of conserved sequence in 3' untranslated region

<400> SEQUENCE: 203
cagttccagg aggactgggt taacaaatct gacaacagaa ggtgagaaac ccctcagaac    60
cgtctcggaa gtaggtccct gctcaccgga agttggaag                          99

<210> SEQ ID NO 204
<211> LENGTH: 99
<212> TYPE: DNA
<213> ORGANISM: Japanese encephalitis virus
<220> FEATURE:
<223> OTHER INFORMATION: Japanese encephalitis virus strain AY184212
      region of conserved sequence in 3' untranslated region

<400> SEQUENCE: 204
cagtcccagg aggactgggt caacaaatct gacaacggag agtgagaaag ccctcagaac    60

```
cgtctcggaa gaaggtccct gctcactgga tgttggaag                              99
```

<210> SEQ ID NO 205
<211> LENGTH: 99
<212> TYPE: DNA
<213> ORGANISM: Japanese encephalitis virus
<220> FEATURE:
<223> OTHER INFORMATION: Japanese encephalitis virus strain AY251616
      region of conserved sequence in 3' untranslated region

<400> SEQUENCE: 205

```
cagtcccagg aggactgggt taacaaatct gacaacggaa ggtgggaaag ccctcagaac      60
cgtctcggaa gtaggtccct gctcaccgga agttgaaag                             99
```

<210> SEQ ID NO 206
<211> LENGTH: 99
<212> TYPE: DNA
<213> ORGANISM: Japanese encephalitis virus
<220> FEATURE:
<223> OTHER INFORMATION: Japanese encephalitis virus strain AY278556
      region of conserved sequence in 3' untranslated region

<400> SEQUENCE: 206

```
cagttccagg aggactgggt taacaaatct gacaacggaa ggtgggaaag ccctcagaac      60
cgtctcggaa gcaggtccct gctcaccgga agttgaaag                             99
```

<210> SEQ ID NO 207
<211> LENGTH: 99
<212> TYPE: DNA
<213> ORGANISM: Japanese encephalitis virus
<220> FEATURE:
<223> OTHER INFORMATION: Japanese encephalitis virus strain AY316157
      region of conserved sequence in 3' untranslated region

<400> SEQUENCE: 207

```
cagttccagg aggactgggt taacaaatct gacaacggaa ggtgggaaag ccctcaaaac      60
cgtctcggaa gcaggtccct gctcaccgga agttgaaag                             99
```

<210> SEQ ID NO 208
<211> LENGTH: 99
<212> TYPE: DNA
<213> ORGANISM: Japanese encephalitis virus
<220> FEATURE:
<223> OTHER INFORMATION: Japanese encephalitis virus strain L54067
      region of conserved sequence in 3' untranslated region

<400> SEQUENCE: 208

```
cagttccagg aggactgggt taacaaatct gacaacagaa ggtgagaaag ccctcagaac      60
cgtctcggaa gtaggtccct gctcaccgga agttggaag                             99
```

<210> SEQ ID NO 209
<211> LENGTH: 99
<212> TYPE: DNA
<213> ORGANISM: Japanese encephalitis virus
<220> FEATURE:
<223> OTHER INFORMATION: Japanese encephalitis virus strain L54068
      region of conserved sequence in 3' untranslated region

<400> SEQUENCE: 209

```
cagttccagg aggactgggt taacaaatct gacaacagaa ggtgagaaag ccctcagaac      60
cgtctcggaa gtaggtccct gctcaccgga agttggaag                             99
```

```
<210> SEQ ID NO 210
<211> LENGTH: 99
<212> TYPE: DNA
<213> ORGANISM: Japanese encephalitis virus
<220> FEATURE:
<223> OTHER INFORMATION: Japanese encephalitis virus strain L54069
      region of conserved sequence in 3' untranslated region

<400> SEQUENCE: 210
cagttccagg aggactgggt taacaaatct gacaacagaa ggtgagaaag ccctcagaac    60
cgtctcggaa gtaggtccct gctcaccgga agttggaag                          99

<210> SEQ ID NO 211
<211> LENGTH: 99
<212> TYPE: DNA
<213> ORGANISM: Japanese encephalitis virus
<220> FEATURE:
<223> OTHER INFORMATION: Japanese encephalitis virus strain L54070
      region of conserved sequence in 3' untranslated region

<400> SEQUENCE: 211
cagttccagg aggactgggt taacaaatct gacaacagaa ggtgagaaag ccctcagaac    60
cgtctcggaa gtaggtccct gctcaccgga agttggaag                          99

<210> SEQ ID NO 212
<211> LENGTH: 99
<212> TYPE: DNA
<213> ORGANISM: Japanese encephalitis virus
<220> FEATURE:
<223> OTHER INFORMATION: Japanese encephalitis virus strain L54071
      region of conserved sequence in 3' untranslated region

<400> SEQUENCE: 212
cagttccagg aggactgggt taacaaatct gacaacagaa ggtgagaaag ccctcagaac    60
cgtctcggaa gtaggtccct gctcaccgga agttggaag                          99

<210> SEQ ID NO 213
<211> LENGTH: 99
<212> TYPE: DNA
<213> ORGANISM: Japanese encephalitis virus
<220> FEATURE:
<223> OTHER INFORMATION: Japanese encephalitis virus strain L54072
      region of conserved sequence in 3' untranslated region

<400> SEQUENCE: 213
cagttccagg aggactgggt taacaaatct gacaacagaa ggtgagaaag ccctcagaac    60
cgtctcggaa gtaggtccct gctcaccgga agttggaag                          99

<210> SEQ ID NO 214
<211> LENGTH: 99
<212> TYPE: DNA
<213> ORGANISM: Japanese encephalitis virus
<220> FEATURE:
<223> OTHER INFORMATION: Japanese encephalitis virus strain L54122
      region of conserved sequence in 3' untranslated region

<400> SEQUENCE: 214
cagttccagg aggactgggt taacaaatct gacaacagaa ggtgagaaag ccctcagaac    60
cgtctcggaa gtaggtccct gctcaccgga agttggaag                          99

<210> SEQ ID NO 215
<211> LENGTH: 99
<212> TYPE: DNA
<213> ORGANISM: Japanese encephalitis virus
```

```
<220> FEATURE:
<223> OTHER INFORMATION: Japanese encephalitis virus strain L54123
      region of conserved sequence in 3' untranslated region

<400> SEQUENCE: 215
cagttccagg aggactgggt taacaaatct gacaacagaa ggtgagaaag ccctcagaac    60
cgtctcggaa gtaggtccct gctcaccgga agttggaag                          99

<210> SEQ ID NO 216
<211> LENGTH: 99
<212> TYPE: DNA
<213> ORGANISM: Japanese encephalitis virus
<220> FEATURE:
<223> OTHER INFORMATION: Japanese encephalitis virus strain AF306514
      region of conserved sequence in 3' untranslated region

<400> SEQUENCE: 216
cagttccagg aggactgggt taacaaattt gacaacggaa ggtgggaaag ccctcagaac    60
cgtctcggaa gctcctccct tctcaccgga agttgaaag                          99

<210> SEQ ID NO 217
<211> LENGTH: 99
<212> TYPE: DNA
<213> ORGANISM: Japanese encephalitis virus
<220> FEATURE:
<223> OTHER INFORMATION: Japanese encephalitis virus strain AF306515
      region of conserved sequence in 3' untranslated region

<400> SEQUENCE: 217
cagtcccagg aggagtgggt caacaaattt gacaacagaa agtgagaaag ccctcagaac    60
cgtttcggaa gtaggtccct tctcactgga agttgaaag                          99

<210> SEQ ID NO 218
<211> LENGTH: 99
<212> TYPE: DNA
<213> ORGANISM: Japanese encephalitis virus
<220> FEATURE:
<223> OTHER INFORMATION: Japanese encephalitis virus strain AF306516
      region of conserved sequence in 3' untranslated region

<400> SEQUENCE: 218
cattcccagg aggactgggt taacaaattt gacaacagaa agtgagaaag ccctcagaac    60
cgtttcggaa gtaggtccct tctcactgga agttgaaag                          99

<210> SEQ ID NO 219
<211> LENGTH: 99
<212> TYPE: DNA
<213> ORGANISM: Japanese encephalitis virus
<220> FEATURE:
<223> OTHER INFORMATION: Japanese encephalitis virus strain AF306517
      region of conserved sequence in 3' untranslated region

<400> SEQUENCE: 219
cagtcccagg aggactgggt taacaaatct gacaacagaa ggtgagaaag ccctcaaaac    60
cgtttcggaa gtaggtccct tctcactgga agttgaaag                          99

<210> SEQ ID NO 220
<211> LENGTH: 97
<212> TYPE: DNA
<213> ORGANISM: St. Louis encephalitis virus
<220> FEATURE:
<223> OTHER INFORMATION: St. Louis encephalitis virus strain BFS1750-C
      region of conserved sequence in 3' untranslated
      region
```

<400> SEQUENCE: 220
tggccccagg tgactgggtt atcaaagcca atctggccga gtgcaaagcc cctcattccg    60
actcgggagg gtccctagca cgtaggctgg agaggac                              97

<210> SEQ ID NO 221
<211> LENGTH: 97
<212> TYPE: DNA
<213> ORGANISM: St. Louis encephalitis virus
<220> FEATURE:
<223> OTHER INFORMATION: St. Louis encephalitis virus strain 1750-Std
      region of conserved sequence in 3' untranslated
      region

<400> SEQUENCE: 221
tggccccagg tgactgggtt atcaaagcca atctggccga gtgcaaagcc cctcattccg    60
actcgggagg gtccctagca cgtaggctgg agaggac                              97

<210> SEQ ID NO 222
<211> LENGTH: 97
<212> TYPE: DNA
<213> ORGANISM: St. Louis encephalitis virus
<220> FEATURE:
<223> OTHER INFORMATION: St. Louis encephalitis virus strain TD6-4G-C
      region of conserved sequence in 3' untranslated
      region

<400> SEQUENCE: 222
tggccccagg tgactgggtt atcaaagcca atctggccga gtgcaaagcc cctcattccg    60
actcgggagg gtccctggca cgtaggctgg agaggac                              97

<210> SEQ ID NO 223
<211> LENGTH: 97
<212> TYPE: DNA
<213> ORGANISM: St. Louis encephalitis virus
<220> FEATURE:
<223> OTHER INFORMATION: St. Louis encephalitis virus strain TD6-4G-20
      region of conserved sequence in 3' untranslated
      region

<400> SEQUENCE: 223
tggccccagg tgactgggtt atcaaagcca atctggccga gtgcaaagcc cctcattccg    60
actcgggagg gtccctggca cgtaggctgg agaggac                              97

<210> SEQ ID NO 224
<211> LENGTH: 97
<212> TYPE: DNA
<213> ORGANISM: St. Louis encephalitis virus
<220> FEATURE:
<223> OTHER INFORMATION: St. Louis encephalitis virus strain CoaV750
      region of conserved sequence in 3' untranslated
      region

<400> SEQUENCE: 224
tggccccagg tgactgggtt accaaagcca atctggctga gtgcaaagcc cctcgttccg    60
attcgggagg gtccctggca cgtaggctgg agaggac                              97

<210> SEQ ID NO 225
<211> LENGTH: 97
<212> TYPE: DNA
<213> ORGANISM: St. Louis encephalitis virus
<220> FEATURE:
<223> OTHER INFORMATION: St. Louis encephalitis virus strain L695121.05
      region of conserved sequence in 3' untranslated -continued region

<400> SEQUENCE: 225
tggccccagg tgactgggtt atcaaagcca atccggctgg gtgcaaagcc cctcattccg    60
actcgggagg gtccctggca tgtaggctgg agaggac                             97

<210> SEQ ID NO 226
<211> LENGTH: 97
<212> TYPE: DNA
<213> ORGANISM: St. Louis encephalitis virus
<220> FEATURE:
<223> OTHER INFORMATION: St. Louis encephalitis virus strain TNM771K-C
      region of conserved sequence in 3' untranslated
      region

<400> SEQUENCE: 226
tggccccagg tgactgggtc atcaaagcca atcggctgg gtgcaaagcc cctcattccg     60
actcgggagg gtccctggca cgtaggctgg agaggac                             97

<210> SEQ ID NO 227
<211> LENGTH: 97
<212> TYPE: DNA
<213> ORGANISM: St. Louis encephalitis virus
<220> FEATURE:
<223> OTHER INFORMATION: St. Louis encephalitis virus strain MSI-7-C
      region of conserved sequence in 3' untranslated
      region

<400> SEQUENCE: 227
tggccccagg cgactgggtt atcaaagcca atccggctgg gtgcaaagcc cctcattccg    60
actcgggagg gtccctggca cgtaggctgg agaggac                             97

<210> SEQ ID NO 228
<211> LENGTH: 97
<212> TYPE: DNA
<213> ORGANISM: St. Louis encephalitis virus
<220> FEATURE:
<223> OTHER INFORMATION: St. Louis encephalitis virus strain Kern217
      region of conserved sequence in 3' untranslated
      region

<400> SEQUENCE: 228
tggccccagg cgactgggtt atcaaagcca acccggctgg gtgcaaagcc cctcattccg    60
actcgggagg gtccctggca cgtaggctgg agaggac                             97

<210> SEQ ID NO 229
<211> LENGTH: 93
<212> TYPE: DNA
<213> ORGANISM: St. Louis encephalitis virus
<220> FEATURE:
<223> OTHER INFORMATION: St. Louis encephalitis virus strain CoaV608
      region of conserved sequence in 3' untranslated
      region

<400> SEQUENCE: 229
cccaggcgac tgggttatca aagccaatcc ggctgggtgc aaagcccctc attccgactc    60
gggagggtcc ctggcacgta ggctggagag gac                                 93

<210> SEQ ID NO 230
<211> LENGTH: 97
<212> TYPE: DNA
<213> ORGANISM: St. Louis encephalitis virus
<220> FEATURE:
<223> OTHER INFORMATION: St. Louis encephalitis virus strain TBH-28 region of conserved sequence in 3' untranslated
      region

<400> SEQUENCE: 230
tggccccagg tgactgggtt atcaaagcca acccggctgg gtgcaaagcc cctcattccg       60
actcgggagg gtccctggca cgtaggccgg agaggac                                97

<210> SEQ ID NO 231
<211> LENGTH: 97
<212> TYPE: DNA
<213> ORGANISM: St. Louis encephalitis virus
<220> FEATURE:
<223> OTHER INFORMATION: St. Louis encephalitis virus strain VR1265
      region of conserved sequence in 3' untranslated
      region

<400> SEQUENCE: 231
tggccccagg tgactgggtt atcaaagcca atctggctgg gtgcaaagcc cctcattccg       60
actcgggagg gtccctggca cgtaggctgg agcggac                                97

<210> SEQ ID NO 232
<211> LENGTH: 93
<212> TYPE: DNA
<213> ORGANISM: St. Louis encephalitis virus
<220> FEATURE:
<223> OTHER INFORMATION: St. Louis encephalitis virus strain CoaV353
      region of conserved sequence in 3' untranslated
      region

<400> SEQUENCE: 232
cccaggtgac tgggttatca aagccaatct agctgagtgc aaagcccctc attccgactc       60
gggagggtcc ctggcacgta ggctggagag gac                                   93

<210> SEQ ID NO 233
<211> LENGTH: 100
<212> TYPE: DNA
<213> ORGANISM: Murray Valley encephalitis virus
<220> FEATURE:
<223> OTHER INFORMATION: Murray Valley encephalitis virus strain VR77
      region of conserved sequence in 3' untranslated
      region

<400> SEQUENCE: 233
caaccccagg aggactgggt taccaaagct gattctccac ggttggaaag cctcccagaa       60
ccgtctcgga agaggagtcc ctgccaacaa tggagatgaa                            100

<210> SEQ ID NO 234
<211> LENGTH: 100
<212> TYPE: DNA
<213> ORGANISM: Murray Valley encephalitis virus
<220> FEATURE:
<223> OTHER INFORMATION: Murray Valley encephalitis virus strain
      AF161266 region of conserved sequence in 3' untranslated
      region

<400> SEQUENCE: 234
caaccccagg aggactgggt taccaaagct gattctccac ggttggaaag cctcccagaa       60
ccgtctcgga agaggagtcc ctgccaacaa tggagatgaa                            100

<210> SEQ ID NO 235
<211> LENGTH: 100
<212> TYPE: DNA
<213> ORGANISM: Murray Valley encephalitis virus
<220> FEATURE:

<223> OTHER INFORMATION: Murray Valley encephalitis virus strain M35172
region of conserved sequence in 3' untranslated
region

<400> SEQUENCE: 235 caacccagg aggactgggt taccaaagct gattctccac ggttggaaag cctcccagaa    60
ccgtctcgga agaggagtcc ctgccaacaa tggagatgaa                         100

<210> SEQ ID NO 236
<211> LENGTH: 100
<212> TYPE: DNA
<213> ORGANISM: Murray Valley encephalitis virus
<220> FEATURE:
<223> OTHER INFORMATION: Murray Valley encephalitis virus strain L48972
region of conserved sequence in 3' untranslated
region

<400> SEQUENCE: 236 caacccagg aggactgggt taccaaagct gattctccac ggttggaaag cctcccagaa    60
ccgtctcgga agaggagtcc ctcccaacaa tggagatgaa                         100

<210> SEQ ID NO 237
<211> LENGTH: 100
<212> TYPE: DNA
<213> ORGANISM: Murray Valley encephalitis virus
<220> FEATURE:
<223> OTHER INFORMATION: Murray Valley encephalitis virus strain L48973
region of conserved sequence in 3' untranslated
region

<400> SEQUENCE: 237 caacccagg aggactgggt taccaaagct gattttccac ggttggaaag cctcccagaa    60
ccgtctcgga agaggagtcc ctgccaacaa tggagatgaa                         100

<210> SEQ ID NO 238
<211> LENGTH: 100
<212> TYPE: DNA
<213> ORGANISM: Murray Valley encephalitis virus
<220> FEATURE:
<223> OTHER INFORMATION: Murray Valley encephalitis virus strain L48974
region of conserved sequence in 3' untranslated
region

<400> SEQUENCE: 238 caacccagg aggactgggt taccaaagct gactctctac ggttggaaag cctcccagac    60
ccgtctcgga agaggagccc ctgccaacaa tggagatgaa                         100

<210> SEQ ID NO 239
<211> LENGTH: 100
<212> TYPE: DNA
<213> ORGANISM: Murray Valley encephalitis virus
<220> FEATURE:
<223> OTHER INFORMATION: Murray Valley encephalitis virus strain L48975
region of conserved sequence in 3' untranslated
region

<400> SEQUENCE: 239 caacccagg aggactgggt taccaaaact gactctctac ggttggaaag cctcccagaa    60
ccgtctcgga agaggagtcc cttccaacaa tggagatgaa                         100

<210> SEQ ID NO 240
<211> LENGTH: 100
<212> TYPE: DNA
<213> ORGANISM: Murray Valley encephalitis virus

```
<220> FEATURE:
<223> OTHER INFORMATION: Murray Valley encephalitis virus strain L48976
      region of conserved sequence in 3' untranslated
      region

<400> SEQUENCE: 240 caacccagg aggactgggt taccaaagct gattctccac ggttggaaag cctcccagaa    60
ccgtttcgga agaggagtcc ctgctaacaa tggagatgaa                       100

<210> SEQ ID NO 241
<211> LENGTH: 98
<212> TYPE: DNA
<213> ORGANISM: Koutango virus
<220> FEATURE:
<223> OTHER INFORMATION: Koutango virus strain L48980 region of
      conserved sequence in 3' untranslated region

<400> SEQUENCE: 241 caacccagg aggactgggt caacaaatct gcgaggagat ccacgtaatc cctcagaacc    60
gtctcggaag gaggacccca cgtgttttat tctcaaag                           98

<210> SEQ ID NO 242
<211> LENGTH: 105
<212> TYPE: DNA
<213> ORGANISM: West Nile virus
<220> FEATURE:
<223> OTHER INFORMATION: West Nile virus strain AF260967 region of
      conserved sequence in 3' untranslated region

<400> SEQUENCE: 242
tggctgaagc tgtaggtcag gggaaggact agaggttagt ggagacccg tgccacaaaa    60 caccacaaca aaacagcata ttgacacctg ggatagacta ggaga                  105

<210> SEQ ID NO 243
<211> LENGTH: 105
<212> TYPE: DNA
<213> ORGANISM: West Nile virus
<220> FEATURE:
<223> OTHER INFORMATION: West Nile virus strain AF260968 region of
      conserved sequence in 3' untranslated region

<400> SEQUENCE: 243
tgactgaagc tgtaggtcag gggaaggact agaggttagt ggagacccg tgccacaaaa    60 caccacaaca aaacagcata ttgacacctg ggatagacta ggaga                  105

<210> SEQ ID NO 244
<211> LENGTH: 105
<212> TYPE: DNA
<213> ORGANISM: West Nile virus
<220> FEATURE:
<223> OTHER INFORMATION: West Nile virus strain AF260969 region of
      conserved sequence in 3' untranslated region

<400> SEQUENCE: 244
tggctgaagc tgtaggtcag gggaaggact agaggttagt ggagacccg tgccacaaaa    60 caccacaaca aaacagcata ttgacacctg ggatagacta ggaga                  105

<210> SEQ ID NO 245
<211> LENGTH: 105
<212> TYPE: DNA
<213> ORGANISM: West Nile virus
<220> FEATURE:
<223> OTHER INFORMATION: West Nile virus strain AF481864 region of
      conserved sequence in 3' untranslated region
```

<400> SEQUENCE: 245
tgactgaagc tgtaggtcag gggaaggact agaggttagt ggagaccccg tgccacaaaa    60
caccacaaca aaacagcata ttgacacctg ggatagacta ggaga                   105

<210> SEQ ID NO 246
<211> LENGTH: 103
<212> TYPE: DNA
<213> ORGANISM: West Nile virus
<220> FEATURE:
<223> OTHER INFORMATION: West Nile virus strain M12294 region of
      conserved sequence in 3' untranslated region

<400> SEQUENCE: 246
tggctgaagc tgtaagccaa gggaaggact agaggttaga ggagaccccg tgccaaaaac    60
accaaaagaa acagcatatt gacacctggg atagactagg gga                     103

<210> SEQ ID NO 247
<211> LENGTH: 105
<212> TYPE: DNA
<213> ORGANISM: West Nile virus
<220> FEATURE:
<223> OTHER INFORMATION: West Nile virus strain AF206518 region of
      conserved sequence in 3' untranslated region

<400> SEQUENCE: 247
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 248
<211> LENGTH: 105
<212> TYPE: DNA
<213> ORGANISM: West Nile virus
<220> FEATURE:
<223> OTHER INFORMATION: West Nile virus strain AF317203 region of
      conserved sequence in 3' untranslated region

<400> SEQUENCE: 248
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 249
<211> LENGTH: 105
<212> TYPE: DNA
<213> ORGANISM: West Nile virus
<220> FEATURE:
<223> OTHER INFORMATION: West Nile virus strain AF202541 region of
      conserved sequence in 3' untranslated region

<400> SEQUENCE: 249
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 250
<211> LENGTH: 105
<212> TYPE: DNA
<213> ORGANISM: West Nile virus
<220> FEATURE:
<223> OTHER INFORMATION: West Nile virus strain AF404757 region of
      conserved sequence in 3' untranslated region

<400> SEQUENCE: 250
tggctgaagc tgtaggtcag gggaaggact agaggttagt ggagaccccg tgccacaaaa    60

-continued caccacaaca aaacagcata ttgacacctg ggatagacta ggaga            105

<210> SEQ ID NO 251
<211> LENGTH: 105
<212> TYPE: DNA
<213> ORGANISM: West Nile virus
<220> FEATURE:
<223> OTHER INFORMATION: West Nile virus strain AF404753 region of
      conserved sequence in 3' untranslated region

<400> SEQUENCE: 251
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 252
<211> LENGTH: 105
<212> TYPE: DNA
<213> ORGANISM: West Nile virus
<220> FEATURE:
<223> OTHER INFORMATION: West Nile virus strain AF404754 region of
      conserved sequence in 3' untranslated region

<400> SEQUENCE: 252
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 253
<211> LENGTH: 105
<212> TYPE: DNA
<213> ORGANISM: West Nile virus
<220> FEATURE:
<223> OTHER INFORMATION: West Nile virus strain AF404755 region of
      conserved sequence in 3' untranslated region

<400> SEQUENCE: 253
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 254
<211> LENGTH: 105
<212> TYPE: DNA
<213> ORGANISM: West Nile virus
<220> FEATURE:
<223> OTHER INFORMATION: West Nile virus strain AF404756 region of
      conserved sequence in 3' untranslated region

<400> SEQUENCE: 254
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 255
<211> LENGTH: 105
<212> TYPE: DNA
<213> ORGANISM: West Nile virus
<220> FEATURE:
<223> OTHER INFORMATION: West Nile virus strain AF017254 region of
      conserved sequence in 3' untranslated region

<400> SEQUENCE: 255
tgactgaagc tgtaggtcag gggaaggact agaggttagt ggagaccccg tgccacaaaa    60
caccacaaca aaacagcata ttgatacctg ggatagacta ggaga                   105

```
<210> SEQ ID NO 256
<211> LENGTH: 105
<212> TYPE: DNA
<213> ORGANISM: West Nile virus
<220> FEATURE:
<223> OTHER INFORMATION: West Nile virus strain AF533540 region of
      conserved sequence in 3' untranslated region

<400> SEQUENCE: 256
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 257
<211> LENGTH: 105
<212> TYPE: DNA
<213> ORGANISM: West Nile virus
<220> FEATURE:
<223> OTHER INFORMATION: West Nile virus strain AY262283 region of
      conserved sequence in 3' untranslated region

<400> SEQUENCE: 257
tggctgaagc tgtaggtcag gggaaggact agaggttagt ggagaccccg tgccgcaaaa    60
caccacaaca aaacagcata ttgacacctg ggatagacta ggaga                   105

<210> SEQ ID NO 258
<211> LENGTH: 105
<212> TYPE: DNA
<213> ORGANISM: West Nile virus
<220> FEATURE:
<223> OTHER INFORMATION: West Nile virus strain AY278441 region of
      conserved sequence in 3' untranslated region

<400> SEQUENCE: 258
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 259
<211> LENGTH: 105
<212> TYPE: DNA
<213> ORGANISM: West Nile virus
<220> FEATURE:
<223> OTHER INFORMATION: West Nile virus strain AY268132 region of
      conserved sequence in 3' untranslated region

<400> SEQUENCE: 259
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 260
<211> LENGTH: 105
<212> TYPE: DNA
<213> ORGANISM: West Nile virus
<220> FEATURE:
<223> OTHER INFORMATION: West Nile virus strain AY268133 region of
      conserved sequence in 3' untranslated region

<400> SEQUENCE: 260
tggctgaagc tgtaggtcag gggaaggact agaggttagt ggagaccccg tgccacaaaa    60
caccacaaca aaacagcata ttgacacctg ggatagacta ggaga                   105

<210> SEQ ID NO 261
<211> LENGTH: 105
<212> TYPE: DNA
<213> ORGANISM: Kunjin virus
```

```
<220> FEATURE:
<223> OTHER INFORMATION: Kunjin virus strain AY274504 region of
      conserved sequence in 3' untranslated region

<400> SEQUENCE: 261
tggctgaagc tgtaggtcag gggaaggact agaggttagt ggagaccccg tgccgcaaaa    60
caccacaaca acacagcata ttgacacctg ggatagacta ggaga                  105

<210> SEQ ID NO 262
<211> LENGTH: 105
<212> TYPE: DNA
<213> ORGANISM: Kunjin virus
<220> FEATURE:
<223> OTHER INFORMATION: Kunjin virus strain AY274505 region of
      conserved sequence in 3' untranslated region

<400> SEQUENCE: 262
tggctgaagc tgtaggtcag gggaaggact agaggttagt ggagaccccg tgccgcaaaa    60
caccacaaca acacagcata ttgacacctg ggatagacta ggaga                  105

<210> SEQ ID NO 263
<211> LENGTH: 105
<212> TYPE: DNA
<213> ORGANISM: Kunjin virus
<220> FEATURE:
<223> OTHER INFORMATION: Kunjin virus strain L24512 region of conserved
      sequence in 3' untranslated region

<400> SEQUENCE: 263
tggctgaagc tgtaggtcag gggaaggact agaggttagt ggagaccccg tgccgcaaaa    60
caccacaaca acacagcata ttgacacctg ggatagacta ggaga                  105

<210> SEQ ID NO 264
<211> LENGTH: 99
<212> TYPE: DNA
<213> ORGANISM: Japanese encephalitis virus
<220> FEATURE:
<223> OTHER INFORMATION: Japanese encephalitis virus strain AB051292
      region of conserved sequence in 3' untranslated region

<400> SEQUENCE: 264
cccctcgaag ctgtggagga ggtggaagga ctagaggtta gaggagaccc cgcatttgca    60
tcaaaacagc atattgacac ctgggaatag actgggaga                          99

<210> SEQ ID NO 265
<211> LENGTH: 98
<212> TYPE: DNA
<213> ORGANISM: Japanese encephalitis virus
<220> FEATURE:
<223> OTHER INFORMATION: Japanese encephalitis virus strain AF014160
      region of conserved sequence in 3' untranslated region

<400> SEQUENCE: 265
cccctcgaag ctgtagagga ggtggaagga ctagaggtta gaggagaccc cgcatttgca    60
tcaaacagca tattgacacc tgggaataga ctgggaga                           98

<210> SEQ ID NO 266
<211> LENGTH: 98
<212> TYPE: DNA
<213> ORGANISM: Japanese encephalitis virus
<220> FEATURE:
<223> OTHER INFORMATION: Japanese encephalitis virus strain AF014161
      region of conserved sequence in 3' untranslated region
```

<400> SEQUENCE: 266
cccctcgaag ctgtagagga ggtggaagga ctagaggtta gaggagaccc cgcatttgca    60
tcaaacagca tattgacacc tgggaataga ctgggaga                            98

<210> SEQ ID NO 267
<211> LENGTH: 99
<212> TYPE: DNA
<213> ORGANISM: Japanese encephalitis virus
<220> FEATURE:
<223> OTHER INFORMATION: Japanese encephalitis virus strain AF045551
      region of conserved sequence in 3' untranslated region

<400> SEQUENCE: 267
cccctcgaag ctgtagagga ggtgtaagga atagaggtta gaggagaccc cgcaatttgc    60
atcaaacagc atattgacac ctgggaatag agtgggaga                           99

<210> SEQ ID NO 268
<211> LENGTH: 98
<212> TYPE: DNA
<213> ORGANISM: Japanese encephalitis virus
<220> FEATURE:
<223> OTHER INFORMATION: Japanese encephalitis virus strain AF069076
      region of conserved sequence in 3' untranslated region

<400> SEQUENCE: 268
cccctcgaag ctgtagagga ggtggaagga ctagaggtta gaggagaccc cgcatttgca    60
tcaaacagca tattgacacc tgggaataga ctgggaga                            98

<210> SEQ ID NO 269
<211> LENGTH: 98
<212> TYPE: DNA
<213> ORGANISM: Japanese encephalitis virus
<220> FEATURE:
<223> OTHER INFORMATION: Japanese encephalitis virus strain AF075723
      region of conserved sequence in 3' untranslated region

<400> SEQUENCE: 269
cccctcgaag ctgtagagga ggtggaagga ctagaggtta gaggagaccc cgcatttgca    60
tcaaacagca tattgacacc tgggaataga ctgggaga                            98

<210> SEQ ID NO 270
<211> LENGTH: 98
<212> TYPE: DNA
<213> ORGANISM: Japanese encephalitis virus
<220> FEATURE:
<223> OTHER INFORMATION: Japanese encephalitis virus strain AF080251
      region of conserved sequence in 3' untranslated region

<400> SEQUENCE: 270
cccctcgaag ctgtagagga ggtggaagga ctagaggtta gaggagaccc cgcatttgca    60
tcaaacagca tattgacacc tgggaataga ctgggaga                            98

<210> SEQ ID NO 271
<211> LENGTH: 98
<212> TYPE: DNA
<213> ORGANISM: Japanese encephalitis virus
<220> FEATURE:
<223> OTHER INFORMATION: Japanese encephalitis virus strain AF098735
      region of conserved sequence in 3' untranslated region

<400> SEQUENCE: 271
ctcctcgaag ctgtagagga ggtggaagga ctagaggtta gaggagaccc cgcatttgca    60

```
tcaaacagca tattgacacc tgggaataga ctgggaga                                    98

<210> SEQ ID NO 272
<211> LENGTH: 98
<212> TYPE: DNA
<213> ORGANISM: Japanese encephalitis virus
<220> FEATURE:
<223> OTHER INFORMATION: Japanese encephalitis virus strain AF098736
      region of conserved sequence in 3' untranslated region

<400> SEQUENCE: 272
cccctcgaag ctgtagagga ggtggaagga ctagaggtta gaggagaccc cgcatttgca           60
tcaaacagca tattgacacc tgggaataga ctgggaga                                    98

<210> SEQ ID NO 273
<211> LENGTH: 98
<212> TYPE: DNA
<213> ORGANISM: Japanese encephalitis virus
<220> FEATURE:
<223> OTHER INFORMATION: Japanese encephalitis virus strain AF098737
      region of conserved sequence in 3' untranslated region

<400> SEQUENCE: 273
cccctcgaag ctgtagagga ggtggaagga ctagaggtta gaggagaccc cgcatttgca           60
tcaaacagca tattgacacc tggagataga ctgggaga                                    98

<210> SEQ ID NO 274
<211> LENGTH: 98
<212> TYPE: DNA
<213> ORGANISM: Japanese encephalitis virus
<220> FEATURE:
<223> OTHER INFORMATION: Japanese encephalitis virus strain AF217620
      region of conserved sequence in 3' untranslated region

<400> SEQUENCE: 274
ttcctcgaag ctgtagagga agtggaagga ctagaggtta gaggagaccc cgcatttgca           60
tcaaacagca tattgacacc tgggaataga ctgggaga                                    98

<210> SEQ ID NO 275
<211> LENGTH: 98
<212> TYPE: DNA
<213> ORGANISM: Japanese encephalitis virus
<220> FEATURE:
<223> OTHER INFORMATION: Japanese encephalitis virus strain AF221499
      region of conserved sequence in 3' untranslated region

<400> SEQUENCE: 275
ctcctcgaag ctgtagagga ggtggaagga ctagaggtta gaggagaccc cgcatttgca           60
tcaaacagca tattgacacc tgggaataga ctgggaga                                    98

<210> SEQ ID NO 276
<211> LENGTH: 98
<212> TYPE: DNA
<213> ORGANISM: Japanese encephalitis virus
<220> FEATURE:
<223> OTHER INFORMATION: Japanese encephalitis virus strain AF221500
      region of conserved sequence in 3' untranslated region

<400> SEQUENCE: 276
ctcctcgaag ctgtagagga ggtggaagga ctagaggtta gaggagaccc cgcatttgca           60
tcaaacagca tattgacacc tgggaataga ctgggaga                                    98

<210> SEQ ID NO 277
```

<211> LENGTH: 98
<212> TYPE: DNA
<213> ORGANISM: Japanese encephalitis virus
<220> FEATURE:
<223> OTHER INFORMATION: Japanese encephalitis virus strain AF254452
      region of conserved sequence in 3' untranslated region

<400> SEQUENCE: 277
cccctcgaag ctgtagagga ggtggaagga ctagaggtta gaggagaccc cgcatttgca      60
tcaaacagca tattgacacc tgggaataga ctgggaga                              98

<210> SEQ ID NO 278
<211> LENGTH: 98
<212> TYPE: DNA
<213> ORGANISM: Japanese encephalitis virus
<220> FEATURE:
<223> OTHER INFORMATION: Japanese encephalitis virus strain AF254453
      region of conserved sequence in 3' untranslated region

<400> SEQUENCE: 278
cccctcgaag ctgtagagga ggtggaagga ctagaggtta gaggagaccc cgcatttgca      60
tcaaacagca tattgacacc tgggaataga ctgggaga                              98

<210> SEQ ID NO 279
<211> LENGTH: 98
<212> TYPE: DNA
<213> ORGANISM: Japanese encephalitis virus
<220> FEATURE:
<223> OTHER INFORMATION: Japanese encephalitis virus strain AF315119
      region of conserved sequence in 3' untranslated region

<400> SEQUENCE: 279
cccctcgaag ctgtagagga ggtggaagga ctagaggtta gaggagaccc cgcatttgca      60
tcaaacagca tattgacacc tgggaataga ctgggaga                              98

<210> SEQ ID NO 280
<211> LENGTH: 98
<212> TYPE: DNA
<213> ORGANISM: Japanese encephalitis virus
<220> FEATURE:
<223> OTHER INFORMATION: Japanese encephalitis virus strain AF416457
      region of conserved sequence in 3' untranslated region

<400> SEQUENCE: 280
cccctcgaag ctgtagagga ggtggaagga ctagaggtta gaggagaccc cgcatttgca      60
tcaaacagca tattgacacc tgggaataga ctgggaga                              98

<210> SEQ ID NO 281
<211> LENGTH: 98
<212> TYPE: DNA
<213> ORGANISM: Japanese encephalitis virus
<220> FEATURE:
<223> OTHER INFORMATION: Japanese encephalitis virus strain AF486638
      region of conserved sequence in 3' untranslated region

<400> SEQUENCE: 281
cccctcgaag ctgtagagga ggtggaagga ctagaggtta gaggagaccc cgcatttgca      60
tcaaacagca tattgacacc tgggaatata ctgggaga                              98

<210> SEQ ID NO 282
<211> LENGTH: 98
<212> TYPE: DNA
<213> ORGANISM: Japanese encephalitis virus
<220> FEATURE:

<223> OTHER INFORMATION: Japanese encephalitis virus strain U14163
      region of conserved sequence in 3' untranslated region

<400> SEQUENCE: 282
cccctcgaag ctgtagagga ggtggaagga ctagaggtta gaggagaccc cgcatttgca    60
tcaaacagca tattgacacc tgggaataga ctgggaga                            98

<210> SEQ ID NO 283
<211> LENGTH: 98
<212> TYPE: DNA
<213> ORGANISM: Japanese encephalitis virus
<220> FEATURE:
<223> OTHER INFORMATION: Japanese encephalitis virus strain U15763
      region of conserved sequence in 3' untranslated region

<400> SEQUENCE: 283
cccctcgaag ctgtagagga ggtggaagga ctagaggtta gaggagaccc cgcatttgca    60
tcaaacagca tattgacacc tgggaataga ctgggaga                            98

<210> SEQ ID NO 284
<211> LENGTH: 98
<212> TYPE: DNA
<213> ORGANISM: Japanese encephalitis virus
<220> FEATURE:
<223> OTHER INFORMATION: Japanese encephalitis virus strain L48961
      region of conserved sequence in 3' untranslated region

<400> SEQUENCE: 284
ctcctcgaag ctgtagagga ggtggaagga ctagaggtta gaggagaccc cgcatttgca    60
tcaaacagca tattgacacc tgggaataga ctgggaga                            98

<210> SEQ ID NO 285
<211> LENGTH: 98
<212> TYPE: DNA
<213> ORGANISM: Japanese encephalitis virus
<220> FEATURE:
<223> OTHER INFORMATION: Japanese encephalitis virus strain U47032
      region of conserved sequence in 3' untranslated region

<400> SEQUENCE: 285
cccctcgaag ctgtagagga ggtggaggga ctagaggtta gaggagaccc cgcatttgca    60
tcaaacagca tattgacacc tgggaataga ctaggaga                            98

<210> SEQ ID NO 286
<211> LENGTH: 98
<212> TYPE: DNA
<213> ORGANISM: Japanese encephalitis virus
<220> FEATURE:
<223> OTHER INFORMATION: Japanese encephalitis virus strain M18370
      region of conserved sequence in 3' untranslated region

<400> SEQUENCE: 286
cccctcgaag ctgtagagga ggtggaagga ctagaggtta gaggagaccc cgcatttgca    60
tcaaacagca tattgacacc tgggaataga ctgggaga                            98

<210> SEQ ID NO 287
<211> LENGTH: 98
<212> TYPE: DNA
<213> ORGANISM: Japanese encephalitis virus
<220> FEATURE:
<223> OTHER INFORMATION: Japanese encephalitis virus strain M55506
      region of conserved sequence in 3' untranslated region

<400> SEQUENCE: 287

```
ccccctcgaag ctgtagagga ggtggaagga ctagaggtta gaggagaccc cgcatttgca    60
tcaaacagca tattgacacc tgggaataga ctgggaga                             98

<210> SEQ ID NO 288
<211> LENGTH: 98
<212> TYPE: DNA
<213> ORGANISM: Japanese encephalitis virus
<220> FEATURE:
<223> OTHER INFORMATION: Japanese encephalitis virus strain L78128
      region of conserved sequence in 3' untranslated region

<400> SEQUENCE: 288 ccccctcgaag ctgtagagga ggtggaagga ctagaggtta gaggagaccc cgcatttgca    60
tcaaacagca tattgacacc tgggaataga ctgggaga                             98

<210> SEQ ID NO 289
<211> LENGTH: 98
<212> TYPE: DNA
<213> ORGANISM: Japanese encephalitis virus
<220> FEATURE:
<223> OTHER INFORMATION: Japanese encephalitis virus strain D90195
      region of conserved sequence in 3' untranslated region

<400> SEQUENCE: 289 ccccctcgaag ctgtagagga ggtggaagga ctagaggtta gaggagaccc cgcatttgca    60
tcaaacagca tattgacacc tgggaataga ctgggaga                             98

<210> SEQ ID NO 290
<211> LENGTH: 98
<212> TYPE: DNA
<213> ORGANISM: Japanese encephalitis virus
<220> FEATURE:
<223> OTHER INFORMATION: Japanese encephalitis virus strain D90194
      region of conserved sequence in 3' untranslated region

<400> SEQUENCE: 290 ccccctcgaag ctgtagagga ggtggaagga ctagaggtta gaggagaccc cgcatttgca    60
tcaaacagca tattgacacc tgggaataga ctgggaga                             98

<210> SEQ ID NO 291
<211> LENGTH: 98
<212> TYPE: DNA
<213> ORGANISM: Japanese encephalitis virus
<220> FEATURE:
<223> OTHER INFORMATION: Japanese encephalitis virus strain AF311748
      region of conserved sequence in 3' untranslated region

<400> SEQUENCE: 291 ccccctcgaag ctgtagagga ggtggaagga ctagaggtta gaggagaccc cgcatttgca    60
tcaaacagca tattgacacc tgggaataga ctgggaga                             98

<210> SEQ ID NO 292
<211> LENGTH: 98
<212> TYPE: DNA
<213> ORGANISM: Japanese encephalitis virus
<220> FEATURE:
<223> OTHER INFORMATION: Japanese encephalitis virus strain AY184212
      region of conserved sequence in 3' untranslated region

<400> SEQUENCE: 292
cccttcgaag ctgtagaaga ggtggaagga ctagaggtta gaggagaccc cgcatctgca     60
tcaaacagca tattgacacc tgggaataga ctaggaga                             98
```

<210> SEQ ID NO 293
<211> LENGTH: 99
<212> TYPE: DNA
<213> ORGANISM: Japanese encephalitis virus
<220> FEATURE:
<223> OTHER INFORMATION: Japanese encephalitis virus strain AY316157
      region of conserved sequence in 3' untranslated region

<400> SEQUENCE: 293
cccctcgaag ctgtagagga ggtggaagga ctagaggtta gaggagaccc cgcaatttgc    60
atcaaacagc atattgacac ctgggaatag actgggaga                          99

<210> SEQ ID NO 294
<211> LENGTH: 99
<212> TYPE: DNA
<213> ORGANISM: Japanese encephalitis virus
<220> FEATURE:
<223> OTHER INFORMATION: Japanese encephalitis virus strain AF306514
      region of conserved sequence in 3' untranslated region

<400> SEQUENCE: 294
cccctcgaag ctgtagagga ggtgtaagga atagaggtta gaggagaccc cgcaatttgc    60
atcaaacagc atattgacac ctgggaatag agtgggaga                          99

<210> SEQ ID NO 295
<211> LENGTH: 98
<212> TYPE: DNA
<213> ORGANISM: Japanese encephalitis virus
<220> FEATURE:
<223> OTHER INFORMATION: Japanese encephalitis virus strain AF306515
      region of conserved sequence in 3' untranslated region

<400> SEQUENCE: 295
cccctcgaag ctgtagagga ggtggaagga ctagaggtta gaggagaccc cgcatttgca    60
tcaaacagca tattgacacc tgggaataga ctgggaga                           98

<210> SEQ ID NO 296
<211> LENGTH: 98
<212> TYPE: DNA
<213> ORGANISM: Japanese encephalitis virus
<220> FEATURE:
<223> OTHER INFORMATION: Japanese encephalitis virus strain AF306516
      region of conserved sequence in 3' untranslated region

<400> SEQUENCE: 296
cccctcgaag ctgtagaggg ggtggaagga ctagaggtta gaggagaccc cgcatttgca    60
tcaaacagca tattgacacc tgggaataga ctgggaga                           98

<210> SEQ ID NO 297
<211> LENGTH: 98
<212> TYPE: DNA
<213> ORGANISM: Japanese encephalitis virus
<220> FEATURE:
<223> OTHER INFORMATION: Japanese encephalitis virus strain AF306517
      region of conserved sequence in 3' untranslated region

<400> SEQUENCE: 297
cccctcgaag ctgtagagga ggtggaagga ctagaggtta gaggagaccc cgcatttgca    60
tcaaacagca tattgacacc tgggaataga gtgggaga                           98

<210> SEQ ID NO 298
<211> LENGTH: 98

-continued

```
<212> TYPE: DNA
<213> ORGANISM: Japanese encephalitis virus
<220> FEATURE:
<223> OTHER INFORMATION: Japanese encephalitis virus strain D00037
      region of conserved sequence in 3' untranslated region

<400> SEQUENCE: 298
cctcttgtag cttttgaggt ggttgaaggt cttgaggttt gaggagtccc cgtctttgca      60
tcaaacagca tattgacacc tgggaataga ctgggaga                              98

<210> SEQ ID NO 299
<211> LENGTH: 98
<212> TYPE: DNA
<213> ORGANISM: Japanese encephalitis virus
<220> FEATURE:
<223> OTHER INFORMATION: Japanese encephalitis virus strain M14933
      region of conserved sequence in 3' untranslated region

<400> SEQUENCE: 299
cctcttgtag cttttgaggt ggttgaaggt cttgaggttt gaggagtccc cgtctttgca      60
tcaaacagca tattgacacc tgggaataga ctgggaga                              98

<210> SEQ ID NO 300
<211> LENGTH: 100
<212> TYPE: DNA
<213> ORGANISM: St. Louis encephalitis virus
<220> FEATURE:
<223> OTHER INFORMATION: St. Louis encephalitis virus strain BFS1750-C
      region of conserved sequence in 3' untranslated
      region

<400> SEQUENCE: 300
ccgctcgaag ctgtagagac gggggaagga ctagaggtta gaggagaccc cttgccgtta      60
acgcaaacaa cagcatattg acacctggaa agacaggaga                          100

<210> SEQ ID NO 301
<211> LENGTH: 27
<212> TYPE: DNA
<213> ORGANISM: St. Louis encephalitis virus
<220> FEATURE:
<223> OTHER INFORMATION: St. Louis encephalitis virus strain 1750-Std
      region of conserved sequence in 3' untranslated
      region

<400> SEQUENCE: 301
ccgctcgaag ctgtagagac gggggaa                                         27

<210> SEQ ID NO 302
<211> LENGTH: 100
<212> TYPE: DNA
<213> ORGANISM: St. Louis encephalitis virus
<220> FEATURE:
<223> OTHER INFORMATION: St. Louis encephalitis virus strain TD6-4G-C
      region of conserved sequence in 3' untranslated
      region

<400> SEQUENCE: 302
ccgctcgaag ctgtagagat gggggaagga ctagaggtta gaggagaccc cttgccgtta      60
acgcaaacaa cagcatattg acacctggaa agacaggaga                          100

<210> SEQ ID NO 303
<211> LENGTH: 100
<212> TYPE: DNA
<213> ORGANISM: St. Louis encephalitis virus
<220> FEATURE:
```

<223> OTHER INFORMATION: St. Louis encephalitis virus strain TD6-4G-20
      region of conserved sequence in 3' untranslated
      region

<400> SEQUENCE: 303
ccgctcgaag ctgtagagat gggggaagga ctagaggtta gaggagaccc cttgccgtta    60
acgcaaacaa cagcatattg acacctggaa agacaggaga                         100

<210> SEQ ID NO 304
<211> LENGTH: 27
<212> TYPE: DNA
<213> ORGANISM: St. Louis encephalitis virus
<220> FEATURE:
<223> OTHER INFORMATION: St. Louis encephalitis virus strain CoaV750
      region of conserved sequence in 3' untranslated
      region

<400> SEQUENCE: 304
ccgctcgaag ctgtagagat gggggaa                                        27

<210> SEQ ID NO 305
<211> LENGTH: 100
<212> TYPE: DNA
<213> ORGANISM: St. Louis encephalitis virus
<220> FEATURE:
<223> OTHER INFORMATION: St. Louis encephalitis virus strain L695121.05
      region of conserved sequence in 3' untranslated
      region

<400> SEQUENCE: 305
ccgctcgaag ctgtagagac gggggaagga ctagaggtta gaggagaccc cttgccgtta    60
acgcaaacaa cagcatattg acacctggaa agacaggaga                         100

<210> SEQ ID NO 306
<211> LENGTH: 100
<212> TYPE: DNA
<213> ORGANISM: St. Louis encephalitis virus
<220> FEATURE:
<223> OTHER INFORMATION: St. Louis encephalitis virus strain TNM771K-C
      region of conserved sequence in 3' untranslated
      region
<220> FEATURE:
<221> NAME/KEY: modified_base
<222> LOCATION: (68)...(68)
<223> OTHER INFORMATION: n = g, a, c or t

<400> SEQUENCE: 306
ccgctcgaag ctgtagagac gggggaagga ctagaggtta gaggagaccc cttgccgtta    60
acgcaaanaa cagcatattg acacctggaa agacaggaga                         100

<210> SEQ ID NO 307
<211> LENGTH: 100
<212> TYPE: DNA
<213> ORGANISM: St. Louis encephalitis virus
<220> FEATURE:
<223> OTHER INFORMATION: St. Louis encephalitis virus strain MSI-7-C
      region of conserved sequence in 3' untranslated
      region

<400> SEQUENCE: 307
ccgctcaaag ctgtagagac gggggaagga ctagaggtta gaggagaccc cttgccgtta    60
acgcaaacaa cagcatattg acacctggaa agacaggaga                         100

<210> SEQ ID NO 308
<211> LENGTH: 95

<212> TYPE: DNA
<213> ORGANISM: St. Louis encephalitis virus
<220> FEATURE:
<223> OTHER INFORMATION: St. Louis encephalitis virus strain Kern217
      region of conserved sequence in 3' untranslated
      region

<400> SEQUENCE: 308
ccgctcaaag ctgtagagac gggggaagga ctagaggtta gaggagaccc cttgccgtta    60
acgcaaacaa cagcatattg acacctggaa agaca                              95

<210> SEQ ID NO 309
<211> LENGTH: 100
<212> TYPE: DNA
<213> ORGANISM: St. Louis encephalitis virus
<220> FEATURE:
<223> OTHER INFORMATION: St. Louis encephalitis virus strain CoaV608
      region of conserved sequence in 3' untranslated
      region

<400> SEQUENCE: 309
ccgctcaaag ctgtagagac gggggaagga ctagaggtta gaggagaccc cttgccgtta    60
acgcaaacaa cagcatattg acacctggaa agacaggaga                        100

<210> SEQ ID NO 310
<211> LENGTH: 95
<212> TYPE: DNA
<213> ORGANISM: St. Louis encephalitis virus
<220> FEATURE:
<223> OTHER INFORMATION: St. Louis encephalitis virus strain TBH-28
      region of conserved sequence in 3' untranslated
      region

<400> SEQUENCE: 310
ccgctcgaag ctgtagagac gggggaagga ctagaggtta gaggagaccc cttgccgtta    60
acgcaaacaa cagcatattg acacctggaa agaca                              95

<210> SEQ ID NO 311
<211> LENGTH: 92
<212> TYPE: DNA
<213> ORGANISM: St. Louis encephalitis virus
<220> FEATURE:
<223> OTHER INFORMATION: St. Louis encephalitis virus strain VR1265
      region of conserved sequence in 3' untranslated
      region

<400> SEQUENCE: 311
ccgctcgaag ctgtagagac gggggaagga ctagaggtta gaggagaccc cttgccgtca    60
acgcaaacaa cagcatattg acacctggaa ag                                 92

<210> SEQ ID NO 312
<211> LENGTH: 100
<212> TYPE: DNA
<213> ORGANISM: St. Louis encephalitis virus
<220> FEATURE:
<223> OTHER INFORMATION: St. Louis encephalitis virus strain CoaV353
      region of conserved sequence in 3' untranslated
      region

<400> SEQUENCE: 312
ccgctcgaag ctgtagagac gggggaagga ctagaggtta gaggagaccc cttgccgtta    60
acgcaaacaa cagcatattg acacctggaa agacaggaga                        100

<210> SEQ ID NO 313

-continued

```
<211> LENGTH: 104
<212> TYPE: DNA
<213> ORGANISM: Murray Valley encephalitis virus
<220> FEATURE:
<223> OTHER INFORMATION: Murray Valley encephalitis virus strain VR77
      region of conserved sequence in 3' untranslated
      region

<400> SEQUENCE: 313
tcgccgaagc tgtaaggcgg gtggacggac tagaggttag aggagacccc actctcaaaa    60
gcatcaaaca acagcatatt gacacctggg aaaagactag gaga                    104

<210> SEQ ID NO 314
<211> LENGTH: 104
<212> TYPE: DNA
<213> ORGANISM: Murray Valley encephalitis virus
<220> FEATURE:
<223> OTHER INFORMATION: Murray Valley encephalitis virus strain
      AF161266 region of conserved sequence in 3' untranslated
      region

<400> SEQUENCE: 314
tcgccgaagc tgtaaggcgg gtggacggac tagaggttag aggagacccc actctcaaaa    60
gcatcaaaca acagcatatt gacacctggg aaaagactag gaga                    104

<210> SEQ ID NO 315
<211> LENGTH: 100
<212> TYPE: DNA
<213> ORGANISM: Murray Valley encephalitis virus
<220> FEATURE:
<223> OTHER INFORMATION: Murray Valley encephalitis virus strain M35172
      region of conserved sequence in 3' untranslated
      region

<400> SEQUENCE: 315
tcgccgaagc tgtaaggcgg gtggacggac tagaggttag aggagacccc actctcaaaa    60
gcatcaaaca acagcatatt gacacctggg aaaagactag                         100

<210> SEQ ID NO 316
<211> LENGTH: 121
<212> TYPE: DNA
<213> ORGANISM: West Nile virus
<220> FEATURE:
<223> OTHER INFORMATION: West Nile virus strain AF260967 region of
      conserved sequence in 3' untranslated region

<400> SEQUENCE: 316
cagggcgaaa ggactagagg ttagaggaga ccccgcggtt taaagtgcac ggcccagcct    60
ggctgaagct gtaggtcagg ggaaggacta gaggttagtg gagacccccgt gccacaaaac  120 a                                                                   121

<210> SEQ ID NO 317
<211> LENGTH: 121
<212> TYPE: DNA
<213> ORGANISM: West Nile virus
<220> FEATURE:
<223> OTHER INFORMATION: West Nile virus strain AF260968 region of
      conserved sequence in 3' untranslated region

<400> SEQUENCE: 317
cagggcgaaa ggactagagg ttagaggaga ccccgcggtt taaagtgcac ggcccagcct    60
gactgaagct gtaggtcagg ggaaggacta gaggttagtg gagacccccgt gccacaaaac  120 a                                                                   121
```

<210> SEQ ID NO 318
<211> LENGTH: 121
<212> TYPE: DNA
<213> ORGANISM: West Nile virus
<220> FEATURE:
<223> OTHER INFORMATION: West Nile virus strain AF260969 region of
      conserved sequence in 3' untranslated region

<400> SEQUENCE: 318
cagggcgaaa ggactagagg ttagaggaga ccccgcggtt tgaagtgcac ggcccagcct    60
ggctgaagct gtaggtcagg ggaaggacta gaggttagtg agacccccgt gccacaaaac   120
a                                                                   121

<210> SEQ ID NO 319
<211> LENGTH: 121
<212> TYPE: DNA
<213> ORGANISM: West Nile virus
<220> FEATURE:
<223> OTHER INFORMATION: West Nile virus strain AF481864 region of
      conserved sequence in 3' untranslated region

<400> SEQUENCE: 319
cagggcgaaa ggactagagg ttagaggaga ccccgcggtt taaagtgcac ggcccagcct    60
gactgaagct gtaggtcagg ggaaggacta gaggttagtg agacccccgt gccacaaaac   120
a                                                                   121

<210> SEQ ID NO 320
<211> LENGTH: 120
<212> TYPE: DNA
<213> ORGANISM: West Nile virus
<220> FEATURE:
<223> OTHER INFORMATION: West Nile virus strain M12294 region of
      conserved sequence in 3' untranslated region

<400> SEQUENCE: 320
cagggagaag ggactagagg ttagaggaga ccccgcgtaa aaaagtgcac ggcccaactt    60
ggctgaagct gtaagccaag ggaaggacta gaggttagag gagacccccgt gccaaaaaca  120

<210> SEQ ID NO 321
<211> LENGTH: 121
<212> TYPE: DNA
<213> ORGANISM: West Nile virus
<220> FEATURE:
<223> OTHER INFORMATION: West Nile virus strain AF206518 region of
      conserved sequence in 3' untranslated region

<400> SEQUENCE: 321
cagggcgaaa ggactagagg ttagaggaga ccccgcggtt taaagtgcac ggcccagcct    60
ggctgaagct gtaggtcagg ggaaggacta gaggttagtg agacccccgt gccacaaaac   120
a                                                                   121

<210> SEQ ID NO 322
<211> LENGTH: 121
<212> TYPE: DNA
<213> ORGANISM: West Nile virus
<220> FEATURE:
<223> OTHER INFORMATION: West Nile virus strain AF317203 region of
      conserved sequence in 3' untranslated region

<400> SEQUENCE: 322
cagggcgaaa ggactagagg ttagaggaga ccccgcggtt tgaagtgcac ggcccagcct    60

```
ggctgaagct gtaggtcagg ggaaggacta gaggttagtg gagacccgt gccacaaaac    120 a                                                                    121

<210> SEQ ID NO 323
<211> LENGTH: 121
<212> TYPE: DNA
<213> ORGANISM: West Nile virus
<220> FEATURE:
<223> OTHER INFORMATION: West Nile virus strain AF202541 region of
      conserved sequence in 3' untranslated region

<400> SEQUENCE: 323
cagggcgaaa ggactagagg ttagaggaga ccccgcggtt taaagtgcac ggcccagcct    60
ggctgaagct gtaggtcagg ggaaggacta gaggttagtg gagacccgt gccacaaaac    120 a                                                                    121

<210> SEQ ID NO 324
<211> LENGTH: 121
<212> TYPE: DNA
<213> ORGANISM: West Nile virus
<220> FEATURE:
<223> OTHER INFORMATION: West Nile virus strain AF404757 region of
      conserved sequence in 3' untranslated region

<400> SEQUENCE: 324
cagggcgaaa ggactagagg ttagaggaga ccccgcggtt tgaagagcac ggcccagcct    60
ggctgaagct gtaggtcagg ggaaggacta gaggttagtg gagacccgt gccacaaaac    120 a                                                                    121

<210> SEQ ID NO 325
<211> LENGTH: 121
<212> TYPE: DNA
<213> ORGANISM: West Nile virus
<220> FEATURE:
<223> OTHER INFORMATION: West Nile virus strain AF404753 region of
      conserved sequence in 3' untranslated region

<400> SEQUENCE: 325
cagggcgaaa ggactagagg ttagaggaga ccccgcggtt taaagtgcac ggcccagcct    60
ggctgaagct gtaggtcagg ggaaggacta gaggttagtg gagacccgt gccacaaaac    120 a                                                                    121

<210> SEQ ID NO 326
<211> LENGTH: 121
<212> TYPE: DNA
<213> ORGANISM: West Nile virus
<220> FEATURE:
<223> OTHER INFORMATION: West Nile virus strain AF404754 region of
      conserved sequence in 3' untranslated region

<400> SEQUENCE: 326
cagggcgaaa ggactagagg ttagaggaga ccccgcggtt taaagtgcac ggcccagcct    60
ggctgaagct gtaggtcagg ggaaggacta gaggttagtg gagacccgt gccacaaaac    120 a                                                                    121

<210> SEQ ID NO 327
<211> LENGTH: 121
<212> TYPE: DNA
<213> ORGANISM: West Nile virus
<220> FEATURE:
```

```
<223> OTHER INFORMATION: West Nile virus strain AF404755 region of
      conserved sequence in 3' untranslated region

<400> SEQUENCE: 327
cagggcgaaa ggactagagg ttagaggaga ccccgcggtt taaagtgcac ggcccagcct      60
ggctgaagct gtaggtcagg ggaaggacta gaggttagtg agacccccgt gccacaaaac    120
a                                                                    121

<210> SEQ ID NO 328
<211> LENGTH: 121
<212> TYPE: DNA
<213> ORGANISM: West Nile virus
<220> FEATURE:
<223> OTHER INFORMATION: West Nile virus strain AF404756 region of
      conserved sequence in 3' untranslated region

<400> SEQUENCE: 328
cagggcgaaa ggactagagg ttagaggaga ccccgcggtt taaagtgcac ggcccagcct      60
ggctgaagct gtaggtcagg ggaaggacta gaggttagtg agacccccgt gccacaaaac    120
a                                                                    121

<210> SEQ ID NO 329
<211> LENGTH: 121
<212> TYPE: DNA
<213> ORGANISM: West Nile virus
<220> FEATURE:
<223> OTHER INFORMATION: West Nile virus strain AF017254 region of
      conserved sequence in 3' untranslated region

<400> SEQUENCE: 329
cagggcgaaa ggactagagg ttagaggaga ccccgcggtt taaagtgcac ggcccagcct      60
gactgaagct gtaggtcagg ggaaggacta gaggttagtg agacccccgt gccacaaaac    120
a                                                                    121

<210> SEQ ID NO 330
<211> LENGTH: 87
<212> TYPE: DNA
<213> ORGANISM: West Nile virus
<220> FEATURE:
<223> OTHER INFORMATION: West Nile virus strain AF208017 region of
      conserved sequence in 3' untranslated region

<400> SEQUENCE: 330
cagggagaag ggactagtgg ttagaggaga ccccacgtta aaaagtgcac ggcccaacttt      60 ggctgaagct gtaagccaag ggaagga                                         87

<210> SEQ ID NO 331
<211> LENGTH: 121
<212> TYPE: DNA
<213> ORGANISM: West Nile virus
<220> FEATURE:
<223> OTHER INFORMATION: West Nile virus strain AF533540 region of
      conserved sequence in 3' untranslated region

<400> SEQUENCE: 331
cagggcgaaa ggactagagg ttagaggaga ccccgcggtt taaagtgcac ggcccagcct      60
ggctgaagct gtaggtcagg ggaaggacta gaggttagtg agacccccgt gccacaaaac    120
a                                                                    121

<210> SEQ ID NO 332
```

```
<211> LENGTH: 121
<212> TYPE: DNA
<213> ORGANISM: West Nile virus
<220> FEATURE:
<223> OTHER INFORMATION: West Nile virus strain AY262283 region of
      conserved sequence in 3' untranslated region

<400> SEQUENCE: 332
cagggcgaaa ggactagagg ttagaggaga ccccgcggtt tgaagtgcac ggcccagcct      60
ggctgaagct gtaggtcagg ggaaggacta gaggttagtg agacccccgt gccgcaaaac    120
a                                                                    121

<210> SEQ ID NO 333
<211> LENGTH: 95
<212> TYPE: DNA
<213> ORGANISM: West Nile virus
<220> FEATURE:
<223> OTHER INFORMATION: West Nile virus strain AY277251 region of
      conserved sequence in 3' untranslated region

<400> SEQUENCE: 333
caaggagaag ggactagagg ttagcggaga ccctgcgcat atagaaagag aggcacggcc      60
cagcctgaca gaagctgtaa gtcaggggaa ggact                                95

<210> SEQ ID NO 334
<211> LENGTH: 118
<212> TYPE: DNA
<213> ORGANISM: West Nile virus
<220> FEATURE:
<223> OTHER INFORMATION: West Nile virus strain AY277252 region of
      conserved sequence in 3' untranslated region

<400> SEQUENCE: 334
cagggcgaaa ggactagagg ttagaggaga ccccgcggtt tgaagtgcac ggcccatggc      60
tgaagctgta ggtcagggga aggactagag gttagtggag accccgtgcc acaaaaca     118

<210> SEQ ID NO 335
<211> LENGTH: 59
<212> TYPE: DNA
<213> ORGANISM: West Nile virus
<220> FEATURE:
<223> OTHER INFORMATION: West Nile virus strain AY278441 region of
      conserved sequence in 3' untranslated region

<400> SEQUENCE: 335
cagggcgaaa ggactagagg ttagaggaga ccccgcggtt tgaagtgcac ggcccagcc       59

<210> SEQ ID NO 336
<211> LENGTH: 115
<212> TYPE: DNA
<213> ORGANISM: West Nile virus
<220> FEATURE:
<223> OTHER INFORMATION: West Nile virus strain AY278442 region of
      conserved sequence in 3' untranslated region

<400> SEQUENCE: 336
cagggcgaaa ggactagagg ttagaggaga ccccgcggtt tgaagtgcac ggctggctga      60
agctgtaggt caggggaagg actagaggtt agtggagacc ccgtgccaca aaaca         115

<210> SEQ ID NO 337
<211> LENGTH: 121
<212> TYPE: DNA
<213> ORGANISM: West Nile virus
<220> FEATURE:
```

<223> OTHER INFORMATION: West Nile virus strain AY268132 region of
conserved sequence in 3' untranslated region

<400> SEQUENCE: 337
cagggcgaaa ggactagagg ttagaggaga ccccgcggtt tgaagtgcac ggcccagcct    60
ggctgaagct gtaggtcagg ggaaggacta gaggttagtg agaccccgt gccacaaaac    120 a    121

<210> SEQ ID NO 338
<211> LENGTH: 121
<212> TYPE: DNA
<213> ORGANISM: West Nile virus
<220> FEATURE:
<223> OTHER INFORMATION: West Nile virus strain AY268133 region of
conserved sequence in 3' untranslated region

<400> SEQUENCE: 338
cagggcgaaa ggactagagg ttagaggaga ccccgcggtt taaagtgcac ggcccagcct    60
gactgaagct gtaggtcagg ggaaggacta gaggttagtg agaccccgt gccacagaac    120 a    121

<210> SEQ ID NO 339
<211> LENGTH: 59
<212> TYPE: DNA
<213> ORGANISM: West Nile virus
<220> FEATURE:
<223> OTHER INFORMATION: West Nile virus strain AY490240 region of
conserved sequence in 3' untranslated region

<400> SEQUENCE: 339
cagggcgaaa ggactagagg ttagaggaga ccccgcggtt taaagtgcac ggcccagcc    59

<210> SEQ ID NO 340
<211> LENGTH: 121
<212> TYPE: DNA
<213> ORGANISM: Kunjin virus
<220> FEATURE:
<223> OTHER INFORMATION: Kunjin virus strain AY274504 region of
conserved sequence in 3' untranslated region

<400> SEQUENCE: 340
cagagtgaaa ggactagagg ttagaggaga ccccgcgttc tgaagtgcac ggcccagcct    60
ggctgaagct gtaggtcagg ggaaggacta gaggttagtg agaccccgt gccgcaaaac    120 a    121

<210> SEQ ID NO 341
<211> LENGTH: 121
<212> TYPE: DNA
<213> ORGANISM: Kunjin virus
<220> FEATURE:
<223> OTHER INFORMATION: Kunjin virus strain AY274505 region of
conserved sequence in 3' untranslated region

<400> SEQUENCE: 341
cagagtgaaa ggactagagg ttagaggaga ccccgcgttc tgaagtgcac ggcccagcct    60
ggctgaagct gtaggtcagg ggaaggacta gaggttagtg agaccccgt gccgcaaaac    120 a    121

<210> SEQ ID NO 342
<211> LENGTH: 121
<212> TYPE: DNA

```
<213> ORGANISM: Kunjin virus
<220> FEATURE:
<223> OTHER INFORMATION: Kunjin virus strain L24512 region of conserved
      sequence in 3' untranslated region

<400> SEQUENCE: 342
cagagtgaaa ggactagagg ttagaggaga ccccgcgttc tgaagtgcac ggcccagcct    60
ggctgaagct gtaggtcagg ggaaggacta gaggttagtg gagacccgt gccgcaaaac    120 a                                                                    121

<210> SEQ ID NO 343
<211> LENGTH: 125
<212> TYPE: DNA
<213> ORGANISM: Japanese encephalitis virus
<220> FEATURE:
<223> OTHER INFORMATION: Japanese encephalitis virus strain AB051292
      region of conserved sequence in 3' untranslated region

<400> SEQUENCE: 343
ctaggtgtaa ggactagagg ttagaggaga ccccgtggaa acaacattat gcggcccaag    60 cccccctcgaa gctgtggagg aggtggaagg actagaggtt agaggagacc ccgcatttgc   120
atcaa                                                                125

<210> SEQ ID NO 344
<211> LENGTH: 125
<212> TYPE: DNA
<213> ORGANISM: Japanese encephalitis virus
<220> FEATURE:
<223> OTHER INFORMATION: Japanese encephalitis virus strain AF014160
      region of conserved sequence in 3' untranslated region

<400> SEQUENCE: 344
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                                125

<210> SEQ ID NO 345
<211> LENGTH: 125
<212> TYPE: DNA
<213> ORGANISM: Japanese encephalitis virus
<220> FEATURE:
<223> OTHER INFORMATION: Japanese encephalitis virus strain AF014161
      region of conserved sequence in 3' untranslated region

<400> SEQUENCE: 345
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                                125

<210> SEQ ID NO 346
<211> LENGTH: 125
<212> TYPE: DNA
<213> ORGANISM: Japanese encephalitis virus
<220> FEATURE:
<223> OTHER INFORMATION: Japanese encephalitis virus strain AF045551
      region of conserved sequence in 3' untranslated region

<400> SEQUENCE: 346
ttaggtgtaa ggactagagg ttagaggaga ccccgtggaa acaaaattat gcggcccaag    60 cccccctcgaa gctgtagagg aggtgtaagg aatagaggtt agaggagacc ccgcaatttg   120
```

-continued catca                                                             125

<210> SEQ ID NO 347
<211> LENGTH: 125
<212> TYPE: DNA
<213> ORGANISM: Japanese encephalitis virus
<220> FEATURE:
<223> OTHER INFORMATION: Japanese encephalitis virus strain AF069076
      region of conserved sequence in 3' untranslated region

<400> SEQUENCE: 347
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                             125

<210> SEQ ID NO 348
<211> LENGTH: 125
<212> TYPE: DNA
<213> ORGANISM: Japanese encephalitis virus
<220> FEATURE:
<223> OTHER INFORMATION: Japanese encephalitis virus strain AF075723
      region of conserved sequence in 3' untranslated region

<400> SEQUENCE: 348
cgaggtgtaa ggactagagg ttagaggaga ccccgtggaa ataacaacat gcggcccaag    60 cccccctcgaa gctgtagagg aggtggaagg actagaggtt agaggagacc ccgcatttgc   120
atcaa                                                             125

<210> SEQ ID NO 349
<211> LENGTH: 125
<212> TYPE: DNA
<213> ORGANISM: Japanese encephalitis virus
<220> FEATURE:
<223> OTHER INFORMATION: Japanese encephalitis virus strain AF080251
      region of conserved sequence in 3' untranslated region

<400> SEQUENCE: 349
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                             125

<210> SEQ ID NO 350
<211> LENGTH: 125
<212> TYPE: DNA
<213> ORGANISM: Japanese encephalitis virus
<220> FEATURE:
<223> OTHER INFORMATION: Japanese encephalitis virus strain AF098735
      region of conserved sequence in 3' untranslated region

<400> SEQUENCE: 350
cgaggtgtaa ggactagagg ttagaggaga ccccgtggaa acaacaacat gcggcccaag    60
cctcctcgaa gctgtagagg aggtggaagg actagaggtt agaggagacc ccgcatttgc   120
atcaa                                                             125

<210> SEQ ID NO 351
<211> LENGTH: 125
<212> TYPE: DNA
<213> ORGANISM: Japanese encephalitis virus
<220> FEATURE:
<223> OTHER INFORMATION: Japanese encephalitis virus strain AF098736
      region of conserved sequence in 3' untranslated region

```
<400> SEQUENCE: 351
cgaggtgtaa ggactagagg ttagaggaga ccccgtggaa acaacaacat gcggcccaag        60 cccccctcgaa gctgtagagg aggtggaagg actagaggtt agaggagacc ccgcatttgc      120
atcaa                                                                  125

<210> SEQ ID NO 352
<211> LENGTH: 125
<212> TYPE: DNA
<213> ORGANISM: Japanese encephalitis virus
<220> FEATURE:
<223> OTHER INFORMATION: Japanese encephalitis virus strain AF098737
      region of conserved sequence in 3' untranslated region

<400> SEQUENCE: 352
cgaggtgtaa ggactagagg ttagaggaga ccccgtggaa acaacaacat gcggcccaag        60 cccccctcgaa gctgtagagg aggtggaagg actagaggtt agaggagacc ccgcatttgc      120
atcaa                                                                  125

<210> SEQ ID NO 353
<211> LENGTH: 125
<212> TYPE: DNA
<213> ORGANISM: Japanese encephalitis virus
<220> FEATURE:
<223> OTHER INFORMATION: Japanese encephalitis virus strain AF217620
      region of conserved sequence in 3' untranslated region

<400> SEQUENCE: 353
cgaggtgtaa ggactagagg ttagaggaga ccccgtggaa acaacaatat gcggcccaag        60
cttcctcgaa gctgtagagg aagtggaagg actagaggtt agaggagacc ccgcatttgc      120
atcaa                                                                  125

<210> SEQ ID NO 354
<211> LENGTH: 125
<212> TYPE: DNA
<213> ORGANISM: Japanese encephalitis virus
<220> FEATURE:
<223> OTHER INFORMATION: Japanese encephalitis virus strain AF221499
      region of conserved sequence in 3' untranslated region

<400> SEQUENCE: 354
cgaggtgtaa ggactagagg ttagaggaga ccccgtggaa acaataacat gcggcccaag        60
cctcctcgaa gctgtagagg aggtggaagg actagaggtt agaggagacc ccgcatttgc      120
atcaa                                                                  125

<210> SEQ ID NO 355
<211> LENGTH: 125
<212> TYPE: DNA
<213> ORGANISM: Japanese encephalitis virus
<220> FEATURE:
<223> OTHER INFORMATION: Japanese encephalitis virus strain AF221500
      region of conserved sequence in 3' untranslated region

<400> SEQUENCE: 355
cgaggtgtaa ggactagagg ttagaggaga ccccgtggaa acaataacat gcggcccaag        60
cctcctcgaa gctgtagagg aggtggaagg actagaggtt agaggagacc ccgcatttgc      120
atcaa                                                                  125

<210> SEQ ID NO 356
<211> LENGTH: 125
```

<212> TYPE: DNA
<213> ORGANISM: Japanese encephalitis virus
<220> FEATURE:
<223> OTHER INFORMATION: Japanese encephalitis virus strain AF254452
    region of conserved sequence in 3' untranslated region

<400> SEQUENCE: 356
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                               125

<210> SEQ ID NO 357
<211> LENGTH: 125
<212> TYPE: DNA
<213> ORGANISM: Japanese encephalitis virus
<220> FEATURE:
<223> OTHER INFORMATION: Japanese encephalitis virus strain AF254453
    region of conserved sequence in 3' untranslated region

<400> SEQUENCE: 357
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                               125

<210> SEQ ID NO 358
<211> LENGTH: 125
<212> TYPE: DNA
<213> ORGANISM: Japanese encephalitis virus
<220> FEATURE:
<223> OTHER INFORMATION: Japanese encephalitis virus strain AF315119
    region of conserved sequence in 3' untranslated region

<400> SEQUENCE: 358
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                               125

<210> SEQ ID NO 359
<211> LENGTH: 125
<212> TYPE: DNA
<213> ORGANISM: Japanese encephalitis virus
<220> FEATURE:
<223> OTHER INFORMATION: Japanese encephalitis virus strain AF416457
    region of conserved sequence in 3' untranslated region

<400> SEQUENCE: 359
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120
atcaa                                                               125

<210> SEQ ID NO 360
<211> LENGTH: 125
<212> TYPE: DNA
<213> ORGANISM: Japanese encephalitis virus
<220> FEATURE:
<223> OTHER INFORMATION: Japanese encephalitis virus strain AF486638
    region of conserved sequence in 3' untranslated region

<400> SEQUENCE: 360
cgaggtgtaa ggactagagg ttagaggaga ccccgtggaa acaacaacat gcggcccaag    60 cccccctcgaa gctgtagagg aggtggaagg actagaggtt agaggagacc ccgcatttgc   120

```
atcaa                                                             125

<210> SEQ ID NO 361
<211> LENGTH: 125
<212> TYPE: DNA
<213> ORGANISM: Japanese encephalitis virus
<220> FEATURE:
<223> OTHER INFORMATION: Japanese encephalitis virus strain U14163
      region of conserved sequence in 3' untranslated region

<400> SEQUENCE: 361
cgaggtgtaa ggactagagg ttagaggaga ccccgtggaa acaacaacat gcggcccaag    60 cccctcgaa gctgtagagg aggtggaagg actagaggtt agaggagacc ccgcatttgc    120
atcaa                                                             125

<210> SEQ ID NO 362
<211> LENGTH: 125
<212> TYPE: DNA
<213> ORGANISM: Japanese encephalitis virus
<220> FEATURE:
<223> OTHER INFORMATION: Japanese encephalitis virus strain U15763
      region of conserved sequence in 3' untranslated region

<400> SEQUENCE: 362
cgaggtgtaa ggactagagg ttagaggaga ccccgtggaa acaacaacat gcggcccaag    60 cccctcgaa gctgtagagg aggtggaagg actagaggtt agaggagacc ccgcatttgc    120
atcaa                                                             125

<210> SEQ ID NO 363
<211> LENGTH: 125
<212> TYPE: DNA
<213> ORGANISM: Japanese encephalitis virus
<220> FEATURE:
<223> OTHER INFORMATION: Japanese encephalitis virus strain L48961
      region of conserved sequence in 3' untranslated region

<400> SEQUENCE: 363
cgaggtgtaa ggactagagg ttagaggaga ccccgtggaa acaacaacat gcggcccaag    60
cctcctcgaa gctgtagagg aggtggaagg actagaggtt agaggagacc ccgcatttgc    120
atcaa                                                             125

<210> SEQ ID NO 364
<211> LENGTH: 125
<212> TYPE: DNA
<213> ORGANISM: Japanese encephalitis virus
<220> FEATURE:
<223> OTHER INFORMATION: Japanese encephalitis virus strain U47032
      region of conserved sequence in 3' untranslated region

<400> SEQUENCE: 364
cgaggtgtaa ggactagagg ttagaggaga ccccgtggaa acaacaacat gcggcccaag    60 cccctcgaa gctgtagagg aggtggaggg actagaggtt agaggagacc ccgcatttgc    120
atcaa                                                             125

<210> SEQ ID NO 365
<211> LENGTH: 125
<212> TYPE: DNA
<213> ORGANISM: Japanese encephalitis virus
<220> FEATURE:
<223> OTHER INFORMATION: Japanese encephalitis virus strain M18370
      region of conserved sequence in 3' untranslated region
```

```
<400> SEQUENCE: 365
cgaggtgtaa ggactagagg ttagaggaga ccccgtggaa acaacaatat gcggcccaag      60 cccctcgaa gctgtagagg aggtggaagg actagaggtt agaggagacc ccgcatttgc     120
atcaa                                                                125

<210> SEQ ID NO 366
<211> LENGTH: 125
<212> TYPE: DNA
<213> ORGANISM: Japanese encephalitis virus
<220> FEATURE:
<223> OTHER INFORMATION: Japanese encephalitis virus strain M55506
      region of conserved sequence in 3' untranslated region

<400> SEQUENCE: 366
cgaggtgtaa ggactagagg ttagaggaga ccccgtggaa acaacaacat gcggcccaag      60 cccctcgaa gctgtagagg aggtggaagg actagaggtt agaggagacc ccgcatttgc     120
atcaa                                                                125

<210> SEQ ID NO 367
<211> LENGTH: 125
<212> TYPE: DNA
<213> ORGANISM: Japanese encephalitis virus
<220> FEATURE:
<223> OTHER INFORMATION: Japanese encephalitis virus strain L78128
      region of conserved sequence in 3' untranslated region

<400> SEQUENCE: 367
cgaggtgtaa ggactagagg ttagaggaga ccccgtggaa acaacaacat gcggcccaag      60 cccctcgaa gctgtagagg aggtggaagg actagaggtt agaggagacc ccgcatttgc     120
atcaa                                                                125

<210> SEQ ID NO 368
<211> LENGTH: 125
<212> TYPE: DNA
<213> ORGANISM: Japanese encephalitis virus
<220> FEATURE:
<223> OTHER INFORMATION: Japanese encephalitis virus strain D90195
      region of conserved sequence in 3' untranslated region

<400> SEQUENCE: 368
cgaggtgtaa ggactagagg ttagaggaga ccccgtggaa acaacaatat gcggcccaag      60 cccctcgaa gctgtagagg aggtggaagg actagaggtt agaggagacc ccgcatttgc     120
atcaa                                                                125

<210> SEQ ID NO 369
<211> LENGTH: 125
<212> TYPE: DNA
<213> ORGANISM: Japanese encephalitis virus
<220> FEATURE:
<223> OTHER INFORMATION: Japanese encephalitis virus strain D90194
      region of conserved sequence in 3' untranslated region

<400> SEQUENCE: 369
cgaggtgtaa ggactagagg ttagaggaga ccccgtggaa acaacaacat gcggcccaag      60 cccctcgaa gctgtagagg aggtggaagg actagaggtt agaggagacc ccgcatttgc     120
atcaa                                                                125

<210> SEQ ID NO 370
```

```
<211> LENGTH: 125
<212> TYPE: DNA
<213> ORGANISM: Japanese encephalitis virus
<220> FEATURE:
<223> OTHER INFORMATION: Japanese encephalitis virus strain AF311748
      region of conserved sequence in 3' untranslated region

<400> SEQUENCE: 370
cgaggtgtaa ggactagagg ttagaggaga ccccgtggaa acaacaacat gcggcccaag    60
ccccctcgaa gctgtagagg aggtggaagg actagaggtt agaggagacc ccgcatttgc   120
atcaa                                                               125

<210> SEQ ID NO 371
<211> LENGTH: 125
<212> TYPE: DNA
<213> ORGANISM: Japanese encephalitis virus
<220> FEATURE:
<223> OTHER INFORMATION: Japanese encephalitis virus strain AY184212
      region of conserved sequence in 3' untranslated region

<400> SEQUENCE: 371
cgagatgtaa ggactagagg ttagaggaga ccccgtggaa acaacaacat gcggcccaag    60
ccccttcgaa gctgtagaag aggtggaagg actagaggtt agaggagacc ccgcatctgc   120
atcaa                                                               125

<210> SEQ ID NO 372
<211> LENGTH: 125
<212> TYPE: DNA
<213> ORGANISM: Japanese encephalitis virus
<220> FEATURE:
<223> OTHER INFORMATION: Japanese encephalitis virus strain AY316157
      region of conserved sequence in 3' untranslated region

<400> SEQUENCE: 372
ctaggtgtaa ggactagagg ttagaggaga ccccgtggaa acaacatcat gcggcccaag    60
ccccctcgaa gctgtagagg aggtggaagg actagaggtt agaggagacc ccgcaatttg   120
catca                                                               125

<210> SEQ ID NO 373
<211> LENGTH: 125
<212> TYPE: DNA
<213> ORGANISM: Japanese encephalitis virus
<220> FEATURE:
<223> OTHER INFORMATION: Japanese encephalitis virus strain AF306514
      region of conserved sequence in 3' untranslated region

<400> SEQUENCE: 373
ttaggtgtaa ggactagagg ttagaggaga ccccgtggaa acaaaattat gcggcccaag    60
ccccctcgaa gctgtagagg aggtgtaagg aatagaggtt agaggagacc ccgcaatttg   120
catca                                                               125

<210> SEQ ID NO 374
<211> LENGTH: 125
<212> TYPE: DNA
<213> ORGANISM: Japanese encephalitis virus
<220> FEATURE:
<223> OTHER INFORMATION: Japanese encephalitis virus strain AF306515
      region of conserved sequence in 3' untranslated region

<400> SEQUENCE: 374
cgaggtgtaa ggactagagg ttagaggaga ccccgtggaa acaaaaaaat gcggcccaag    60
```

```
cccctcgaa gctgtagagg aggtggaagg actagaggtt agaggagacc ccgcatttgc    120
atcaa                                                              125

<210> SEQ ID NO 375
<211> LENGTH: 125
<212> TYPE: DNA
<213> ORGANISM: Japanese encephalitis virus
<220> FEATURE:
<223> OTHER INFORMATION: Japanese encephalitis virus strain AF306516
      region of conserved sequence in 3' untranslated region

<400> SEQUENCE: 375
cgaggtgtaa ggactagagg ttagaggaga ccccgtggaa acaaaaaaat gcggcccaag    60 cccctcgaa gctgtagagg gggtggaagg actagaggtt agaggagacc ccgcatttgc    120
atcaa                                                              125

<210> SEQ ID NO 376
<211> LENGTH: 125
<212> TYPE: DNA
<213> ORGANISM: Japanese encephalitis virus
<220> FEATURE:
<223> OTHER INFORMATION: Japanese encephalitis virus strain AF306517
      region of conserved sequence in 3' untranslated region

<400> SEQUENCE: 376
cgaggtgtaa ggactagagg ttagaggaga ccccgtggaa acaaaaaaat gcggcccaag    60 cccctcgaa gctgtagagg aggtggaagg actagaggtt agaggagacc ccgcatttgc    120
atcaa                                                              125

<210> SEQ ID NO 377
<211> LENGTH: 122
<212> TYPE: DNA
<213> ORGANISM: St. Louis encephalitis virus
<220> FEATURE:
<223> OTHER INFORMATION: St. Louis encephalitis virus strain BFS1750
      region of conserved sequence in 3' untranslated region

<400> SEQUENCE: 377
catggcgtaa ggactagagg ttagaggaga ccccgctgca acttggcaag gcccaaaccc    60
gctcgaagct gtagagacgg gggaaggact agaggttaga ggagacccct tgccgttaac    120
gc                                                                  122

<210> SEQ ID NO 378
<211> LENGTH: 85
<212> TYPE: DNA
<213> ORGANISM: St. Louis encephalitis virus
<220> FEATURE:
<223> OTHER INFORMATION: St. Louis encephalitis virus strain 1750-Std
      region of conserved sequence in 3' untranslated region

<400> SEQUENCE: 378
catggcgtaa ggactagagg ttagaggaga ccccgckgca acttggcaag gcccaaaccc    60
gctcgaagct gtagagacgg gggaa                                         85

<210> SEQ ID NO 379
<211> LENGTH: 122
<212> TYPE: DNA
<213> ORGANISM: St. Louis encephalitis virus
<220> FEATURE:
<223> OTHER INFORMATION: St. Louis encephalitis virus strain TD6-4G
      region of conserved sequence in 3' untranslated region
```

```
<400> SEQUENCE: 379
catggcgtaa ggactagagg ttagaggaga ccccgctgca actcggcaag gcccaaaccc    60
gctcgaagct gtagagatgg gggaaggact agaggttaga ggagacccct tgccgttaac   120
gc                                                                  122

<210> SEQ ID NO 380
<211> LENGTH: 85
<212> TYPE: DNA
<213> ORGANISM: St. Louis encephalitis virus
<220> FEATURE:
<223> OTHER INFORMATION: St. Louis encephalitis virus strain CoaV750
      region of conserved sequence in 3' untranslated region

<400> SEQUENCE: 380
catggcgtaa ggactagagg ttagaggaga ccccgckgca acttggcaag gccaaaaccc    60
gctcgaagct gtagagatgg gggaa                                          85

<210> SEQ ID NO 381
<211> LENGTH: 122
<212> TYPE: DNA
<213> ORGANISM: St. Louis encephalitis virus
<220> FEATURE:
<223> OTHER INFORMATION: St. Louis encephalitis virus strain L695121.05
      region of conserved sequence in 3' untranslated region

<400> SEQUENCE: 381
catggcgtaa ggactagagg ttagaggaga ccccgctgta acttggcaag gcccaaaccc    60
gctcgaagct gtagagacgg gggaaggact agaggttaga ggagacccct tgccgttaac   120
gc                                                                  122

<210> SEQ ID NO 382
<211> LENGTH: 122
<212> TYPE: DNA
<213> ORGANISM: St. Louis encephalitis virus
<220> FEATURE:
<223> OTHER INFORMATION: St. Louis encephalitis virus strain TNM771K
      region of conserved sequence in 3' untranslated region

<400> SEQUENCE: 382
catggcgtaa ggactagagg ttagaggaga ccccgctgta acttggcaag gcccaaaccc    60
gctcgaagct gtagagacgg gggaaggact agaggttaga ggagacccct tgccgttaac   120
gc                                                                  122

<210> SEQ ID NO 383
<211> LENGTH: 122
<212> TYPE: DNA
<213> ORGANISM: St. Louis encephalitis virus
<220> FEATURE:
<223> OTHER INFORMATION: St. Louis encephalitis virus strain MSI-7
      region of conserved sequence in 3' untranslated region

<400> SEQUENCE: 383
catggcgtaa ggactagagg ttagaggaga ccccgctgta acttggcaag gcccaaaccc    60
gctcaaagct gtagagacgg gggaaggact agaggttaga ggagacccct tgccgttaac   120
gc                                                                  122

<210> SEQ ID NO 384
<211> LENGTH: 122
<212> TYPE: DNA
<213> ORGANISM: St. Louis encephalitis virus
```

```
<220> FEATURE:
<223> OTHER INFORMATION: St. Louis encephalitis virus strain Kern217
      region of conserved sequence in 3' untranslated region

<400> SEQUENCE: 384
catggcgtaa ggactagagg ttagaggaga ccccgctgta acttggcaag gcccaaaccc      60
gctcaaagct gtagagacgg gggaaggact agaggttaga ggagacccct tgccgttaac     120
gc                                                                    122

<210> SEQ ID NO 385
<211> LENGTH: 122
<212> TYPE: DNA
<213> ORGANISM: St. Louis encephalitis virus
<220> FEATURE:
<223> OTHER INFORMATION: St. Louis encephalitis virus strain CoAV608
      region of conserved sequence in 3' untranslated region

<400> SEQUENCE: 385
catggcgtaa ggactagagg ttagaggaga ccccgctgta acttggcaag gcccaaaccc      60
gctcaaagct gtagagacgg gggaaggact agaggttaga ggagacccct tgccgttaac     120
gc                                                                    122

<210> SEQ ID NO 386
<211> LENGTH: 122
<212> TYPE: DNA
<213> ORGANISM: St. Louis encephalitis virus
<220> FEATURE:
<223> OTHER INFORMATION: St. Louis encephalitis virus strain TBH-28
      region of conserved sequence in 3' untranslated region

<400> SEQUENCE: 386
catggcgtaa ggactagagg ttagaggaga ccccgctgta atttggcaag gcccaaaccc      60
gctcgaagct gtagagacgg gggaaggact agaggttaga ggagacccct tgccgttaac     120
gc                                                                    122

<210> SEQ ID NO 387
<211> LENGTH: 122
<212> TYPE: DNA
<213> ORGANISM: St. Louis encephalitis virus
<220> FEATURE:
<223> OTHER INFORMATION: St. Louis encephalitis virus strain VR1265
      region of conserved sequence in 3' untranslated region

<400> SEQUENCE: 387
catggcgtaa ggactagagg ttagaggaga ccccgctgta acttggcaag gcccaaaccc      60
gctcgaagct gtagagacgg gggaaggact agaggttaga ggagacccct tgccgtcaac     120
gc                                                                    122

<210> SEQ ID NO 388
<211> LENGTH: 122
<212> TYPE: DNA
<213> ORGANISM: St. Louis encephalitis virus
<220> FEATURE:
<223> OTHER INFORMATION: St. Louis encephalitis virus strain CoAV353
      region of conserved sequence in 3' untranslated region

<400> SEQUENCE: 388
catggcgtaa ggactagagg ttagaggaga ccccgctgca acttggcaag gcccaaaccc      60
gctcgaagct gtagagacgg gggaaggact agaggttaga ggagacccct tgccgttaac     120
gc                                                                    122
```

<210> SEQ ID NO 389
<211> LENGTH: 119
<212> TYPE: DNA
<213> ORGANISM: Murray Valley encephalitis virus
<220> FEATURE:
<223> OTHER INFORMATION: Murray Valley encephalitis virus strain VR77 region of conserved sequence in 3' untranslated region

<400> SEQUENCE: 389

```
cccggcgaag gactagaggt tagaggagac cctgcggaag aaatgagtgg cccaagctcg      60
ccgaagctgt aaggcgggtg gacggactag aggttagagg agaccccact ctcaaaagc     119
```

<210> SEQ ID NO 390
<211> LENGTH: 119
<212> TYPE: DNA
<213> ORGANISM: Murray Valley encephalitis virus
<220> FEATURE:
<223> OTHER INFORMATION: Murray Valley encephalitis virus strain AF161266 region of conserved sequence in 3' untranslated region

<400> SEQUENCE: 390

```
cccggcgaag gactagaggt tagaggagac cctgcggaag aaatgagtgg cccaagctcg      60
ccgaagctgt aaggcgggtg gacggactag aggttagagg agaccccact ctcaaaagc     119
```

<210> SEQ ID NO 391
<211> LENGTH: 119
<212> TYPE: DNA
<213> ORGANISM: Murray Valley encephalitis virus
<220> FEATURE:
<223> OTHER INFORMATION: Murray Valley encephalitis virus strain M35172 region of conserved sequence in 3' untranslated region

<400> SEQUENCE: 391

```
cccggcgaag gactagaggt tagaggagac cctgcggaag aaatgagtgg cccaagctcg      60
ccgaagctgt aaggcgggtg gacggactag aggttagagg agaccccact ctcaaaagc     119
```

<210> SEQ ID NO 392
<211> LENGTH: 131
<212> TYPE: DNA
<213> ORGANISM: Dengue virus type 1
<220> FEATURE:
<223> OTHER INFORMATION: Dengue virus type 1 strain U88537 region of conserved sequence in 3' untranslated region

<400> SEQUENCE: 392

```
atggggtagc agactagtgg ttagaggaga cccctcccaa gacacaacgc agcagcgggg      60
cccaacacca ggggaagctg taccctggtg gtaaggacta gaggttagag gagaccccc     120 gcacaacaac a                                                         131
```

<210> SEQ ID NO 393
<211> LENGTH: 131
<212> TYPE: DNA
<213> ORGANISM: Dengue virus type 1
<220> FEATURE:
<223> OTHER INFORMATION: Dengue virus type 1 strain U88536 region of conserved sequence in 3' untranslated region

<400> SEQUENCE: 393

```
atggggtagc agactagtgg ttagaggaga cccctcccaa gacacaacgc agcagcgggg      60
```

<210> SEQ ID NO 394
<211> LENGTH: 131
<212> TYPE: DNA
<213> ORGANISM: Dengue virus type 1
<220> FEATURE:
<223> OTHER INFORMATION: Dengue virus type 1 strain U88535 region of
conserved sequence in 3' untranslated region

<400> SEQUENCE: 394
atggggtagc agactagtgg ttagaggaga cccctcccaa dacacaacgc agcagcgggg    60
cccaacacca ggggaagctg taccctggtg gtaaggacta gaggttagag gagaccccccc   120 gcacaacaac a                                                        131

<210> SEQ ID NO 395
<211> LENGTH: 131
<212> TYPE: DNA
<213> ORGANISM: Dengue virus type 1
<220> FEATURE:
<223> OTHER INFORMATION: Dengue virus type 1 strain M87512 region of
conserved sequence in 3' untranslated region

<400> SEQUENCE: 395
atggggtagc agactagtgg ttagaggaga cccctcccaa aacataacgc agcagcgggg    60
cccaacacca ggggaagctg tatcctggtg gtaaggacta gaggttagag gagaccccccg   120 gcataacaat a                                                        131

<210> SEQ ID NO 396
<211> LENGTH: 131
<212> TYPE: DNA
<213> ORGANISM: Dengue virus type 1
<220> FEATURE:
<223> OTHER INFORMATION: Dengue virus type 1 strain AY206457 region of
conserved sequence in 3' untranslated region

<400> SEQUENCE: 396
atggggtagc agactagtgg ttagaggaga cccctcccaa dacacaacgc agcagcgggg    60
cccaacacca ggggaagctg taccttggtg gtaaggacta gaggttagag gagaccccccc   120 gcacaacaac a                                                        131

<210> SEQ ID NO 397
<211> LENGTH: 101
<212> TYPE: DNA
<213> ORGANISM: Dengue virus type 1
<220> FEATURE:
<223> OTHER INFORMATION: Dengue virus type 1 strain AY145123 region of
conserved sequence in 3' untranslated region

<400> SEQUENCE: 397
atggggtagc agactagtgg ttagaggaga cccctcccaa dacacaacgc agcagcgggg    60
cccaagacta gaggttagag gagaccccccc gcacaacaac a                      101

<210> SEQ ID NO 398
<211> LENGTH: 131
<212> TYPE: DNA
<213> ORGANISM: Dengue virus type 1
<220> FEATURE:
<223> OTHER INFORMATION: Dengue virus type 1 strain AY145122 region of
conserved sequence in 3' untranslated region

<400> SEQUENCE: 398
atggggtagc agactagtgg ttagaggaga cccctcccaa gacacaacgc agcagcgggg 60
cccaagccag gaggaagctg tactcctggt ggaaggacta gaggttagag gagaccccc 120 gcacaacaac a 131

<210> SEQ ID NO 399
<211> LENGTH: 131
<212> TYPE: DNA
<213> ORGANISM: Dengue virus type 1
<220> FEATURE:
<223> OTHER INFORMATION: Dengue virus type 1 strain AY145121 region of
      conserved sequence in 3' untranslated region

<400> SEQUENCE: 399
atggggtagc agactagtgg ttagaggaga cccctcccaa gacacaacgc agcagcgggg 60
cccaagccag gaggaagctg tactcctggt ggaaggacta gaggttagag gagaccccc 120 gcacaacaac a 131

<210> SEQ ID NO 400
<211> LENGTH: 131
<212> TYPE: DNA
<213> ORGANISM: Dengue virus type 1
<220> FEATURE:
<223> OTHER INFORMATION: Dengue virus type 1 strain AF514889 region of
      conserved sequence in 3' untranslated region

<400> SEQUENCE: 400
atggggtagc agactagtgg ttagaggaga cccctcccaa gacacaacgc agcagcgggg 60
cccaacacca ggggaagctg taccttggtg gtaaggacta gaggttagag gagaccccc 120 gcacaacaac a 131

<210> SEQ ID NO 401
<211> LENGTH: 131
<212> TYPE: DNA
<213> ORGANISM: Dengue virus type 1
<220> FEATURE:
<223> OTHER INFORMATION: Dengue virus type 1 strain AF514885 region of
      conserved sequence in 3' untranslated region

<400> SEQUENCE: 401
atggggtagc agactagtgg ttagaggaga cccctcccta gacataacgc agcagcgggg 60
cccaacacca tgggaagctg taccttggtg gtaaggacta gaggttagag gagaccccc 120 gcataacaac a 131

<210> SEQ ID NO 402
<211> LENGTH: 131
<212> TYPE: DNA
<213> ORGANISM: Dengue virus type 1
<220> FEATURE:
<223> OTHER INFORMATION: Dengue virus type 1 strain AF514883 region of
      conserved sequence in 3' untranslated region

<400> SEQUENCE: 402
atggggtagc agactagtgg ttagaggaga cccctcccta gacataacgc agcagcgggg 60
cccaacacca tgggaagctg taccttggtg gtaaggacta gaggttagag gagaccccc 120 gcataacaac a 131

<210> SEQ ID NO 403
<211> LENGTH: 131

```
<212> TYPE: DNA
<213> ORGANISM: Dengue virus type 1
<220> FEATURE:
<223> OTHER INFORMATION: Dengue virus type 1 strain AF514878 region of
      conserved sequence in 3' untranslated region

<400> SEQUENCE: 403
atggggtagc agactagtgg ttagaggaga cccctcccaa gacacaacgc agcagcgggg    60
cccaacacca ggggaagctg taccttggtg gtaaggacta gaggttagag gagaccccc   120 gcacaacaac a                                                       131

<210

```
gctcaacaac a                                                          131

<210> SEQ ID NO 408
<211> LENGTH: 131
<212> TYPE: DNA
<213> ORGANISM: Dengue virus type 1
<220> FEATURE:
<223> OTHER INFORMATION: Dengue virus type 1 strain AF311957 region of
      conserved sequence in 3' untranslated region

<400> SEQUENCE: 408
atggggtagc agactagtgg ttagaggaga cccctcccta gacataacgc agcagcgggg      60
cccaacacca tgggaagctg taccttggtg gtaaggacta gaggttagag gagacccccc    120
gcacaacaac a                                                          131

<210> SEQ ID NO 409
<211> LENGTH: 131
<212> TYPE: DNA
<213> ORGANISM: Dengue virus type 1
<220> FEATURE:
<223> OTHER INFORMATION: Dengue virus type 1 strain AF311956 region of
      conserved sequence in 3' untranslated region

<400> SEQUENCE: 409
atggggtagc agactagtgg ttagaggaga cccctcccta gacataacgc agcagcgggg      60
cccaacacca tgggaagctg taccttggtg gtaaggacta gaggttagag gagacccccc    120
gcacaacaac a                                                          131

<210> SEQ ID NO 410
<211> LENGTH: 97
<212> TYPE: DNA
<213> ORGANISM: Dengue virus type 1
<220> FEATURE:
<223> OTHER INFORMATION: Dengue virus type 1 strain AF310148 region of
      conserved sequence in 3' untranslated region

<400> SEQUENCE: 410
atggggtagc agactagtgg ttagaggaga cccctcccaa gacataacgc agcagcgggg      60
cccaacacca ggggaagctg taccctggtg gtaagga                               97

<210> SEQ ID NO 411
<211> LENGTH: 131
<212> TYPE: DNA
<213> ORGANISM: Dengue virus type 1
<220> FEATURE:
<223> OTHER INFORMATION: Dengue virus type 1 strain AF310147 region of
      conserved sequence in 3' untranslated region

<400> SEQUENCE: 411
atggggtagc agactagtgg ttagaggaga cccctcccaa aacacaacgc agcagcgggg      60
cccaacacca ggggaagctg taccctggtg gtaaggacta gaggttagag gagacccccc    120
gcataacaat a                                                          131

<210> SEQ ID NO 412
<211> LENGTH: 131
<212> TYPE: DNA
<213> ORGANISM: Dengue virus type 1
<220> FEATURE:
<223> OTHER INFORMATION: Dengue virus type 1 strain AF310146 region of
      conserved sequence in 3' untranslated region

<400> SEQUENCE: 412
```

```
atggggtagc agactagtgg ttagaggaga cccctcccta gacataacgc agcagcgggg    60
cccaacacca tgggaagctg taccttggtg gtaaggacta gaggttagag gagacccccc   120
gcacaacaac a                                                         131
```

<210> SEQ ID NO 413
<211> LENGTH: 131
<212> TYPE: DNA
<213> ORGANISM: Dengue virus type 1
<220> FEATURE:
<223> OTHER INFORMATION: Dengue virus type 1 strain AF309641 region of conserved sequence in 3' untranslated region

<400> SEQUENCE: 413

```
atggggtagc agactagtgg ttagaggaga cccctcccga acataacgc agcagcgggg     60 cccaacacca gggaagctg taccctggtg gtaaggacta gaggttagag gagacccccc   120
gcataacaat a                                                        131
```

<210> SEQ ID NO 414
<211> LENGTH: 131
<212> TYPE: DNA
<213> ORGANISM: Dengue virus type 1
<220> FEATURE:
<223> OTHER INFORMATION: Dengue virus type 1 strain AF298808 region of conserved sequence in 3' untranslated region

<400> SEQUENCE: 414

```
atggggtagc agactagtgg ttagaggaga cccctcccaa aacacaacgc agcagcgggg    60
cccaacacta ggggatgctg taccctggtg gtaaggacta gaggttagag gagacccccc   120
gcataacaat a                                                        131
```

<210> SEQ ID NO 415
<211> LENGTH: 131
<212> TYPE: DNA
<213> ORGANISM: Dengue virus type 1
<220> FEATURE:
<223> OTHER INFORMATION: Dengue virus type 1 strain AF298807 region of conserved sequence in 3' untranslated region

<400> SEQUENCE: 415

```
atggggtagc agactagtgg ttagaggaga cccctcccaa aacataacgc agcagcgggg    60
cccaacacca ggggaagctg taccctggtg gtaaggacta gaggttagag gagacccccc   120
gcacaacaac a                                                        131
```

<210> SEQ ID NO 416
<211> LENGTH: 131
<212> TYPE: DNA
<213> ORGANISM: Dengue virus type 1
<220> FEATURE:
<223> OTHER INFORMATION: Dengue virus type 1 strain AF226687 region of conserved sequence in 3' untranslated region

<400> SEQUENCE: 416

```
atggggtagc agactagtgg ttagaggaga cccctcccaa gacataacgc agcagcgggg    60
cccaacacca ggggaagctg taccttggtg gtaaggacta gaggttagag gagacccccc   120
gcacaacaac a                                                        131
```

<210> SEQ ID NO 417
<211> LENGTH: 131
<212> TYPE: DNA

<213> ORGANISM: Dengue virus type 1
<220> FEATURE:
<223> OTHER INFORMATION: Dengue virus type 1 strain AF226686 region of
      conserved sequence in 3' untranslated region

<400> SEQUENCE: 417
atggggtagc agactagtgg ttagaggaga cccctcccaa gacataacgc agcagcgggg    60
cccaacacca ggggaagctg taccttggtg gtaaggacta gaggttagag gagaccccccc  120 gcacaacaac a                                                        131

<210> SEQ ID NO 418
<211> LENGTH: 131
<212> TYPE: DNA
<213> ORGANISM: Dengue virus type 1
<220> FEATURE:
<223> OTHER INFORMATION: Dengue virus type 1 strain AF226685 region of
      conserved sequence in 3' untranslated region

<400> SEQUENCE: 418
atggggtagc agactagtgg ttagaggaga cccctcccta gacataacgc agcagcgggg    60
cccaacacca tgggaagctg taccttggtg gtaaggacta gaggttagag gagaccccccc  120 gcacaacaac a                                                        131

<210> SEQ ID NO 419
<211> LENGTH: 131
<212> TYPE: DNA
<213> ORGANISM: Dengue virus type 1
<220> FEATURE:
<223> OTHER INFORMATION: Dengue virus type 1 strain AF180818 region of
      conserved sequence in 3' untranslated region

<400> SEQUENCE: 419
atggggtagc agactagtgg ttagaggaga cccctcccaa gacacaacgc agcagcgggg    60
cccaacacca ggggaagctg taccctggtg gtaaggacta gaggttagag gagaccccccc  120 gcgtaacaat a                                                        131

<210> SEQ ID NO 420
<211> LENGTH: 131
<212> TYPE: DNA
<213> ORGANISM: Dengue virus type 1
<220> FEATURE:
<223> OTHER INFORMATION: Dengue virus type 1 strain AF180817 region of
      conserved sequence in 3' untranslated region

<400> SEQUENCE: 420
atggggtagc agactagtgg ttagaggaga cccctcccaa gacacaacgc agcagcgggg    60
cccaacacca ggggaagctg taccctggtg gtaaggacta gaggttagag gagaccccccc  120 gcgtaacaat a                                                        131

<210> SEQ ID NO 421
<211> LENGTH: 131
<212> TYPE: DNA
<213> ORGANISM: Dengue virus type 1
<220> FEATURE:
<223> OTHER INFORMATION: Dengue virus type 1 strain AB074761 region of
      conserved sequence in 3' untranslated region

<400> SEQUENCE: 421
atggggttgc agactagtgg ttagaggaga cccctcccaa gacacaacgc agcagcgggg    60
cccaacacca ggaaagctg taccctggtg gtaaggacta gaggttagag gagaccccccc   120

-continued

```
gcataataat a                                                            131

<210> SEQ ID NO 422
<211> LENGTH: 131
<212> TYPE: DNA
<213> ORGANISM: Dengue virus type 1
<220> FEATURE:
<223> OTHER INFORMATION: Dengue virus type 1 strain AB074760 region of
      conserved sequence in 3' untranslated region

<400> SEQUENCE: 422
atggggtagc agactagtgg ttagaggaga cccctcccaa aacacaacgc agcagcgggg       60
cccaacacca ggggaagctg taccctggtg gtaaggacta gaggttagag gagaccccccc    120 gcataacaat a                                                            131

<210> SEQ ID NO 423
<211> LENGTH: 131
<212> TYPE: DNA
<213> ORGANISM: Dengue virus type 1
<220> FEATURE:
<223> OTHER INFORMATION: Dengue virus type 1 strain VR344-3 region of
      conserved sequence in 3' untranslated region

<400> SEQUENCE: 423
atggggtagc agactaatgg ttagaggaga cccctcccaa gacacaacgc agcagcgggg       60
cccaacacca ggggaagctg taccctggtg gtaaggacta gaggttagag gagaccccccc    120 gcataacaat a                                                            131

<210> SEQ ID NO 424
<211> LENGTH: 133
<212> TYPE: DNA
<213> ORGANISM: Dengue virus type 2
<220> FEATURE:
<223> OTHER INFORMATION: Dengue virus type 2 strain AF022434 region of
      conserved sequence in 3' untranslated region

<400> SEQUENCE: 424
atggcgtagt ggactagcgg ttagaggaga cccctccctt acaaatcgca gcaacaatgg       60
gggcccaagg cgagatgaag ctgtagtctc gctggaagga ctagaggtta gaggagaccc     120
ccccgaaaca gaa                                                          133

<210> SEQ ID NO 425
<211> LENGTH: 133
<212> TYPE: DNA
<213> ORGANISM: Dengue virus type 2
<220> FEATURE:
<223> OTHER INFORMATION: Dengue virus type 2 strain AF022435 region of
      conserved sequence in 3' untranslated region

<400> SEQUENCE: 425
atggcgtagt ggactagcgg ttagaggaga cccctccctc acaaatcgca gcaacaatgg       60
gggcccaagg cgagatgaag ctgtagtctc gctggaagga ctagaggtta gaggagaccc     120
ccccgaaaca aaa                                                          133

<210> SEQ ID NO 426
<211> LENGTH: 133
<212> TYPE: DNA
<213> ORGANISM: Dengue virus type 2
<220> FEATURE:
<223> OTHER INFORMATION: Dengue virus type 2 strain AF022436 region of
      conserved sequence in 3' untranslated region
```

<400> SEQUENCE: 426
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 427
<211> LENGTH: 133
<212> TYPE: DNA
<213> ORGANISM: Dengue virus type 2
<220> FEATURE:
<223> OTHER INFORMATION: Dengue virus type 2 strain AF022437 region of conserved sequence in 3' untranslated region

<400> SEQUENCE: 427
atggcgtagt ggactagcgg ttagaggaga cccctccctt acaaatcgca gcaacaatgg 60
gggcccaagg cgagatgaag ctgtagtctc gctggaagga ctagaggtta gaggagaccc 120
ccccgaaaca aaa 133

<210> SEQ ID NO 428
<211> LENGTH: 133
<212> TYPE: DNA
<213> ORGANISM: Dengue virus type 2
<220> FEATURE:
<223> OTHER INFORMATION: Dengue virus type 2 strain AF022438 region of conserved sequence in 3' untranslated region

<400> SEQUENCE: 428
atggcgtagt ggactagcgg ttagaggaga cccctccctt acaaatcgca gcaacaatgg 60
gggcccaagg cgagatgaag ctgtagtctc gctggaagga ctagaggtta gaggagaccc 120
ccccgaaaca aaa 133

<210> SEQ ID NO 429
<211> LENGTH: 133
<212> TYPE: DNA
<213> ORGANISM: Dengue virus type 2
<220> FEATURE:
<223> OTHER INFORMATION: Dengue virus type 2 strain AF022439 region of conserved sequence in 3' untranslated region

<400> SEQUENCE: 429
atggcgtagt ggactagcgg ttagaggaga cccctccctt acaaatcgca gcaacaatgg 60
gggcccaagg cgagatgaag ctgtagtctc gctggaagga atagaggtta gaggagaccc 120
ccccgaaaca aaa 133

<210> SEQ ID NO 430
<211> LENGTH: 133
<212> TYPE: DNA
<213> ORGANISM: Dengue virus type 2
<220> FEATURE:
<223> OTHER INFORMATION: Dengue virus type 2 strain AF022440 region of conserved sequence in 3' untranslated region

<400> SEQUENCE: 430
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 431
<211> LENGTH: 133

<212> TYPE: DNA
<213> ORGANISM: Dengue virus type 2
<220> FEATURE:
<223> OTHER INFORMATION: Dengue virus type 2 strain AF022441 region of
      conserved sequence in 3' untranslated region

<400> SEQUENCE: 431
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 432
<211> LENGTH: 133
<212> TYPE: DNA
<213> ORGANISM: Dengue virus type 2
<220> FEATURE:
<223> OTHER INFORMATION: Dengue virus type 2 strain AF038402 region of
      conserved sequence in 3' untranslated region

<400> SEQUENCE: 432
atggcgtagt ggactagcgg ttagaggaga cccctccctt acaaatcgca gcaacaatgg      60
gggcccaagg tgagatgaag ctgtagtctc actggaagga ctagaggtta gaggagaccc     120
ccccaaaaca aaa                                                        133

<210> SEQ ID NO 433
<211> LENGTH: 133
<212> TYPE: DNA
<213> ORGANISM: Dengue virus type 2
<220> FEATURE:
<223> OTHER INFORMATION: Dengue virus type 2 strain AF038403 region of
      conserved sequence in 3' untranslated region

<400> SEQUENCE: 433
atggcgtagt ggactagcgg ttagaggaga cccctccctt acaaatcgca gcaacaatgg      60
gggcccaagg tgagatgaag ctgtagtctc actggaagga ctagaggtta gaggagaccc     120
ccccaaaaca aaa                                                        133

<210> SEQ ID NO 434
<211> LENGTH: 133
<212> TYPE: DNA
<213> ORGANISM: Dengue virus type 2
<220> FEATURE:
<223> OTHER INFORMATION: Dengue virus type 2 strain AF100145 region of
      conserved sequence in 3' untranslated region

<400> SEQUENCE: 434
atggcgtagt ggactagcgg ttagaggaga cccctccctt acaaatcgca gcaacaacgg      60
gggcccaagg tgagatgaag ctgtagtctc actggaagga ctagaggtta gaggagaccc     120
ccccaaaata aaa                                                        133

<210> SEQ ID NO 435
<211> LENGTH: 133
<212> TYPE: DNA
<213> ORGANISM: Dengue virus type 2
<220> FEATURE:
<223> OTHER INFORMATION: Dengue virus type 2 strain AF100146 region of
      conserved sequence in 3' untranslated region

<400> SEQUENCE: 435
atggcgtagt ggactagcgg ttagaggaga cccctccctt acaaatcgca gcaacaatgg      60
gggcccaagg cgagatgaag ctgtagtctc gctggaagga ctagaggtta gaggagaccc     120
ccccgaagca aaa                                                          133

<210> SEQ ID NO 436
<211> LENGTH: 133
<212> TYPE: DNA
<213> ORGANISM: Dengue virus type 2
<220> FEATURE:
<223> OTHER INFORMATION: Dengue virus type 2 strain AF100147 region of conserved sequence in 3' untranslated region

<400> SEQUENCE: 436
atggcgtagt ggactagcgg ttagaggaga cccctccctt acaaatcgca gcaacaatgg 60
gggcccaagg cgagatgaag ctgtagtctc gctggaagga ctagaggtta gaggagaccc 120
ccccgaaaca aaa 133

<210> SEQ ID NO 437
<211> LENGTH: 133
<212> TYPE: DNA
<213> ORGANISM: Dengue virus type 2
<220> FEATURE:
<223> OTHER INFORMATION: Dengue virus type 2 strain AF100148 region of conserved sequence in 3' untranslated region

<400> SEQUENCE: 437
atggtgtagt ggactagcgg ttagaggaga cccctccctt tcagatcgca gcaacaatgg 60
gggcccaagg tgagatgaag ctgtagtctc actggaagga ctagaggtta gaggagaccc 120
ccccaaaaca aaa 133

<210> SEQ ID NO 438
<211> LENGTH: 133
<212> TYPE: DNA
<213> ORGANISM: Dengue virus type 2
<220> FEATURE:
<223> OTHER INFORMATION: Dengue virus type 2 strain AF100149 region of conserved sequence in 3' untranslated region

<400> SEQUENCE: 438
atggcgtagt ggactagcgg ttagaggaga cccctccctt acagatcgca gcaacaatgg 60
gggcccaagg tgagatgaag ctgtagcctc actggaagga ctagaggtta gaggagaccc 120
ccccaaaaca aaa 133

<210> SEQ ID NO 439
<211> LENGTH: 133
<212> TYPE: DNA
<213> ORGANISM: Dengue virus type 2
<220> FEATURE:
<223> OTHER INFORMATION: Dengue virus type 2 strain AF100150 region of conserved sequence in 3' untranslated region

<400> SEQUENCE: 439
atggcgtagt ggactagcgg ttagaggaga cccctccctt acaaatcgca gcaacaacgg 60
gggcccaagg tgagatgaag ctgtagtctc actggaagga ctagaggtta gaggagaccc 120
ccccaaaaca aaa 133

<210> SEQ ID NO 440
<211> LENGTH: 133
<212> TYPE: DNA
<213> ORGANISM: Dengue virus type 2
<220> FEATURE:
<223> OTHER INFORMATION: Dengue virus type 2 strain AF100151 region of conserved sequence in 3' untranslated region

<400> SEQUENCE: 440
atggcgtagt ggactagcgg ttagaggaga cccctccctt acagatcgca gcaacaatgg    60
gggcccaagg tgagatgaag ctgtagtctc actggaagga ctagaggtta gaggagaccc   120
ccccaagaca aaa                                                      133

<210> SEQ ID NO 441
<211> LENGTH: 134
<212> TYPE: DNA
<213> ORGANISM: Dengue virus type 2
<220> FEATURE:
<223> OTHER INFORMATION: Dengue virus type 2 strain AF100458 region of
      conserved sequence in 3' untranslated region

<400> SEQUENCE: 441
atggcgtagt ggactagcgg ttagaggaga cccctccctt acagatcgca gcaacaatgg    60
gggcccaagg tgagatgaag ctgtagtctc actggaagga ctagaggtta gaggagaccc   120
ccccaaaaac aaaa                                                     134

<210> SEQ ID NO 442
<211> LENGTH: 133
<212> TYPE: DNA
<213> ORGANISM: Dengue virus type 2
<220> FEATURE:
<223> OTHER INFORMATION: Dengue virus type 2 strain AF100459 region of
      conserved sequence in 3' untranslated region

<400> SEQUENCE: 442
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 443
<211> LENGTH: 133
<212> TYPE: DNA
<213> ORGANISM: Dengue virus type 2
<220> FEATURE:
<223> OTHER INFORMATION: Dengue virus type 2 strain AF100460 region of
      conserved sequence in 3' untranslated region

<400> SEQUENCE: 443
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 444
<211> LENGTH: 133
<212> TYPE: DNA
<213> ORGANISM: Dengue virus type 2
<220> FEATURE:
<223> OTHER INFORMATION: Dengue virus type 2 strain AF100461 region of
      conserved sequence in 3' untranslated region

<400> SEQUENCE: 444
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 445

```
<211> LENGTH: 133
<212> TYPE: DNA
<213> ORGANISM: Dengue virus type 2
<220> FEATURE:
<223> OTHER INFORMATION: Dengue virus type 2 strain AF100462 region of
      conserved sequence in 3' untranslated region

<400> SEQUENCE: 445
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 446
<211> LENGTH: 133
<212> TYPE: DNA
<213> ORGANISM: Dengue virus type 2
<220> FEATURE:
<223> OTHER INFORMATION: Dengue virus type 2 strain AF100463 region of
      conserved sequence in 3' untranslated region

<400> SEQUENCE: 446
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 447
<211> LENGTH: 133
<212> TYPE: DNA
<213> ORGANISM: Dengue virus type 2
<220> FEATURE:
<223> OTHER INFORMATION: Dengue virus type 2 strain AF100464 region of
      conserved sequence in 3' untranslated region

<400> SEQUENCE: 447
atggcgtagt ggactagcgg ttagaggaga cccctccctt acaaatcgca gcaacaatgg    60
gggcccaagg caagatgaag ctgtagtctc gctggaagga ctagaggtta gaggagaccc   120
ccccgaaaca aaa                                                      133

<210> SEQ ID NO 448
<211> LENGTH: 133
<212> TYPE: DNA
<213> ORGANISM: Dengue virus type 2
<220> FEATURE:
<223> OTHER INFORMATION: Dengue virus type 2 strain AF100465 region of
      conserved sequence in 3' untranslated region

<400> SEQUENCE: 448
atggcgtagt ggactagcgg ttagaggaga cccctccctt acagatcgca gcaacaatgg    60
gggcccaagg tgagatgaag ctgtagtctc actggaagga ctagaggtta gaggagaccc   120
ccccaagaca aaa                                                      133

<210> SEQ ID NO 449
<211> LENGTH: 133
<212> TYPE: DNA
<213> ORGANISM: Dengue virus type 2
<220> FEATURE:
<223> OTHER INFORMATION: Dengue virus type 2 strain AF100466 region of
      conserved sequence in 3' untranslated region

<400> SEQUENCE: 449
atggcgtagt ggactagcgg ttagaggaga cccctccctt acaaatcgca gcaacaacgg    60
```
gggcccaagg tgagatgaag ctgtagtctc actggaagga ctagaggtta gaggagaccc    120
ccccaaaata aaa    133

<210> SEQ ID NO 450
<211> LENGTH: 134
<212> TYPE: DNA
<213> ORGANISM: Dengue virus type 2
<220> FEATURE:
<223> OTHER INFORMATION: Dengue virus type 2 strain AF100467 region of
      conserved sequence in 3' untranslated region

<400> SEQUENCE: 450
atggcgtagt ggactagcgg ttagaggaga cccctcccett acagatcgca gcaacaatgg    60
gggcccaagg tgagatgaag ctgtagtctc actggaagga ctagaggtta gaggagaccc    120
ccccaaaaaa caaa    134

<210> SEQ ID NO 451
<211> LENGTH: 134
<212> TYPE: DNA
<213> ORGANISM: Dengue virus type 2
<220> FEATURE:
<223> OTHER INFORMATION: Dengue virus type 2 strain AF100468 region of
      conserved sequence in 3' untranslated region

<400> SEQUENCE: 451
atggcgtagt ggactagcgg ttagaggaga cccctccctt acagatcgca gcaacaatgg    60
gggcccaagg tgagatgaag ctgtagtctc actggaagga ctagaggtta gaggagaccc    120
ccccaaaaaa caaa    134

<210> SEQ ID NO 452
<211> LENGTH: 133
<212> TYPE: DNA
<213> ORGANISM: Dengue virus type 2
<220> FEATURE:
<223> OTHER INFORMATION: Dengue virus type 2 strain AF100469 region of
      conserved sequence in 3' untranslated region

<400> SEQUENCE: 452
atggcgtagt ggactagcgg ttagaggaga cccctccctt tcagatcgca gcaacaatgg    60
gggcccatgg tgagatgaag ctgtagtctc actggaagga ctagaggtta gaggagaccc    120
ccccaaaaca aaa    133

<210> SEQ ID NO 453
<211> LENGTH: 133
<212> TYPE: DNA
<213> ORGANISM: Dengue virus type 2
<220> FEATURE:
<223> OTHER INFORMATION: Dengue virus type 2 strain AF119661 region of
      conserved sequence in 3' untranslated region

<400> SEQUENCE: 453
atggcgtagg ggactagcgg ttagaggaga cccctccctt acaaatcgca gcaacaacgg    60
gggcccaagg tgagatgaag ctgtagtctc actggaagga ctagaggtta gattagaccc    120
ccccaaaaca aaa    133

<210> SEQ ID NO 454
<211> LENGTH: 133
<212> TYPE: DNA
<213> ORGANISM: Dengue virus type 2
<220> FEATURE:
<223> OTHER INFORMATION: Dengue virus type 2 strain AF169687 region of conserved sequence in 3' untranslated region

<400> SEQUENCE: 454
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 455
<211> LENGTH: 133
<212> TYPE: DNA
<213> ORGANISM: Dengue virus type 2
<220> FEATURE:
<223> OTHER INFORMATION: Dengue virus type 2 strain AF169678 region of
conserved sequence in 3' untranslated region

<400> SEQUENCE: 455
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 456
<211> LENGTH: 133
<212> TYPE: DNA
<213> ORGANISM: Dengue virus type 2
<220> FEATURE:
<223> OTHER INFORMATION: Dengue virus type 2 strain AF169688 region of
conserved sequence in 3' untranslated region

<400> SEQUENCE: 456
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 457
<211> LENGTH: 133
<212> TYPE: DNA
<213> ORGANISM: Dengue virus type 2
<220> FEATURE:
<223> OTHER INFORMATION: Dengue virus type 2 strain AF169679 region of
conserved sequence in 3' untranslated region

<400> SEQUENCE: 457
atggcgtagt ggactagcgg ttagaggaga cccctccctt acaaatcgca gcaacaatgg 60
gggcccaaag tgagatgaag ctgtagtctc actggaagga ctagaggtta gaggagaccc 120
ccccgaaaca aaa 133

<210> SEQ ID NO 458
<211> LENGTH: 133
<212> TYPE: DNA
<213> ORGANISM: Dengue virus type 2
<220> FEATURE:
<223> OTHER INFORMATION: Dengue virus type 2 strain AF169680 region of
conserved sequence in 3' untranslated region

<400> SEQUENCE: 458
atggcgtagt ggactagcgg ttagaggaga cccctccctc acaaatcgca gcaacaatgg 60
gggcccaagg cgagatgaag ctgtagtctc gcttgaagga ctagaggtta gaggagaccc 120
ccccgaaaca aaa 133

```
<210> SEQ ID NO 459
<211> LENGTH: 133
<212> TYPE: DNA
<213> ORGANISM: Dengue virus type 2
<220> FEATURE:
<223> OTHER INFORMATION: Dengue virus type 2 strain AF169681 region of
      conserved sequence in 3' untranslated region

<400> SEQUENCE: 459
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                         133

<210> SEQ ID NO 460
<211> LENGTH: 133
<212> TYPE: DNA
<213> ORGANISM: Dengue virus type 2
<220> FEATURE:
<223> OTHER INFORMATION: Dengue virus type 2 strain AF169682 region of
      conserved sequence in 3' untranslated region

<400> SEQUENCE: 460
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                         133

<210> SEQ ID NO 461
<211> LENGTH: 133
<212> TYPE: DNA
<213> ORGANISM: Dengue virus type 2
<220> FEATURE:
<223> OTHER INFORMATION: Dengue virus type 2 strain AF169683 region of
      conserved sequence in 3' untranslated region

<400> SEQUENCE: 461
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                         133

<210> SEQ ID NO 462
<211> LENGTH: 133
<212> TYPE: DNA
<213> ORGANISM: Dengue virus type 2
<220> FEATURE:
<223> OTHER INFORMATION: Dengue virus type 2 strain AF169684 region of
      conserved sequence in 3' untranslated region

<400> SEQUENCE: 462
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                         133

<210> SEQ ID NO 463
<211> LENGTH: 133
<212> TYPE: DNA
<213> ORGANISM: Dengue virus type 2
<220> FEATURE:
<223> OTHER INFORMATION: Dengue virus type 2 strain AF169685 region of
      conserved sequence in 3' untranslated region

<400> SEQUENCE: 463
atggcgtagt ggactagcgg ttagaggaga cccctccctc acaaatcgca gcaacaatgg      60
```
gggcccaagg cgagatgaag ctgtagtctc gctggaagga ctagaggtta gaggagaccc 120
ccccgaaaca aaa 133

<210> SEQ ID NO 464
<211> LENGTH: 133
<212> TYPE: DNA
<213> ORGANISM: Dengue virus type 2
<220> FEATURE:
<223> OTHER INFORMATION: Dengue virus type 2 strain AF169686 region of conserved sequence in 3' untranslated region

<400> SEQUENCE: 464
atggcgtagt ggactagcgg ttagaggaga cccctccctc acaaatcgca gcaacaatgg 60
gggcccaagg cgagatgaag ctgtagtctc gctggaagga ctagaggtta gaggagaccc 120
ccccgaaaca aaa 133

<210> SEQ ID NO 465
<211> LENGTH: 133
<212> TYPE: DNA
<213> ORGANISM: Dengue virus type 2
<220> FEATURE:
<223> OTHER INFORMATION: Dengue virus type 2 strain AF204177 region of conserved sequence in 3' untranslated region

<400> SEQUENCE: 465
atggcgtagt ggactagcgg ttagaggaga cccctccctt acaaatcgca gcaacaatgg 60
gggcccaagg tgagatgaag ctgtagtctc actggaagga ctagaggtta gaggagaccc 120
ccccaaaaca aaa 133

<210> SEQ ID NO 466
<211> LENGTH: 133
<212> TYPE: DNA
<213> ORGANISM: Dengue virus type 2
<220> FEATURE:
<223> OTHER INFORMATION: Dengue virus type 2 strain AF204178 region of conserved sequence in 3' untranslated region

<400> SEQUENCE: 466
atggcgtagt ggactagcgg ttagaggaga cccctccctt acaaatcgca gcaacaatgg 60
gggcccaagg tgagatgaag ctgtagtctc actggaagga ctagaggtta gaggagaccc 120
ccccaaaaca aaa 133

<210> SEQ ID NO 467
<211> LENGTH: 133
<212> TYPE: DNA
<213> ORGANISM: Dengue virus type 2
<220> FEATURE:
<223> OTHER INFORMATION: Dengue virus type 2 strain AF208496 region of conserved sequence in 3' untranslated region

<400> SEQUENCE: 467
atggcgtagt ggactagcgg ttagaggaga cccctccctt acaaatcgca gcaacaacgg 60
gggcccaagg tgagatgaag ctgtagtctc actggaagga ctagaggtta gaggagaccc 120
ccccaaaaca aaa 133

<210> SEQ ID NO 468
<211> LENGTH: 133
<212> TYPE: DNA
<213> ORGANISM: Dengue virus type 2
<220> FEATURE:

<223> OTHER INFORMATION: Dengue virus type 2 strain AF276619 region of
      conserved sequence in 3' untranslated region

<400> SEQUENCE: 468
atggcgtagt ggactagcgg ttagaggaga cccctccctt gcaaatcgca gcaacaatgg    60
gggcccaagg tgagatgaag ctgtagtctc actggaagga ctagaggtta gaggagaccc   120
ccccgaaata aaa                                                      133

<210> SEQ ID NO 469
<211> LENGTH: 133
<212> TYPE: DNA
<213> ORGANISM: Dengue virus type 2
<220> FEATURE:
<223> OTHER INFORMATION: Dengue virus type 2 strain AF309950 region of
      conserved sequence in 3' untranslated region

<400> SEQUENCE: 469
atggcgtagt ggactagcgg ttagaggaga cccctccctt acaaatcgca gcaacaatgg    60
gggcccaagg tgagatgaag ctgtagtctc actggaagga ctagaggtta gaggagaccc   120
ccccgaaata aaa                                                      133

<210> SEQ ID NO 470
<211> LENGTH: 133
<212> TYPE: DNA
<213> ORGANISM: Dengue virus type 2
<220> FEATURE:
<223> OTHER INFORMATION: Dengue virus type 2 strain AF309951 region of
      conserved sequence in 3' untranslated region

<400> SEQUENCE: 470
atggcgtagt ggactagcgg ttagaggaga cccctccctt acagatcgca gcaacaacgg    60
gggcccaagg tgagataaag ctgtagtctc accggaagga ctagaggtta gaggagaccc   120
ccccaaaaca aaa                                                      133

<210> SEQ ID NO 471
<211> LENGTH: 133
<212> TYPE: DNA
<213> ORGANISM: Dengue virus type 2
<220> FEATURE:
<223> OTHER INFORMATION: Dengue virus type 2 strain AF305592 region of
      conserved sequence in 3' untranslated region

<400> SEQUENCE: 471
atggtgtagt ggactagcgg ttagaggaga cccctccctt aagaatcgca gcaaaatggg    60
ggcccaaggt gtgttgaagc tgtagccaca ctggaaggac cagaggttag aggagacccc   120
cccagacaaa aaa                                                      133

<210> SEQ ID NO 472
<211> LENGTH: 134
<212> TYPE: DNA
<213> ORGANISM: Dengue virus type 2
<220> FEATURE:
<223> OTHER INFORMATION: Dengue virus type 2 strain AF309953 region of
      conserved sequence in 3' untranslated region

<400> SEQUENCE: 472
gtggtgtagt ggactagcgg ttagaggaga cccctccctt aagaatcgca gcaaaaatgg    60
gggcccaagg tgtgttgaag ctgtagccac actggaagga ctagaggtta gaggagaccc   120
ccccagacaa aaaa                                                     134

<210> SEQ ID NO 473
<211> LENGTH: 134
<212> TYPE: DNA
<213> ORGANISM: Dengue virus type 2
<220> FEATURE:
<223> OTHER INFORMATION: Dengue virus type 2 strain AF309954 region of
      conserved sequence in 3' untranslated region

<400> SEQUENCE: 473
atggtgtagt ggactagcgg ttagaggaga cccctcccctt aagaatcgca gcaaaatgg      60 gggcccaagg tgtgttgaag ctgtagccac actggaagga ctagaggtta gaggagaccc    120
ccccagacaa aaaa                                                       134

<210> SEQ ID NO 474
<211> LENGTH: 133
<212> TYPE: DNA
<213> ORGANISM: Dengue virus type 2
<220> FEATURE:
<223> OTHER INFORMATION: Dengue virus type 2 strain AF309955 region of
      conserved sequence in 3' untranslated region

<400> SEQUENCE: 474
atggtgtagt ggactagcgg ttagaggaga cccctcccctt aagaatcgca gcaaaattgg     60
ggcccaaggt gtgttgaagc tgtagccaca ctggaaggac cagaggttag aggagacccc    120
cccagacaaa aaa                                                        133

<210> SEQ ID NO 475
<211> LENGTH: 133
<212> TYPE: DNA
<213> ORGANISM: Dengue virus type 2
<220> FEATURE:
<223> OTHER INFORMATION: Dengue virus type 2 strain AF309956 region of
      conserved sequence in 3' untranslated region

<400> SEQUENCE: 475
atggtgtagt ggactagcgg ttagaggaga cccctcccctt aagaatcgca gcaaaatggg    60
ggcccaaggt gtgttgaagc tgtagccaca ctggaaggac cagaggttag aggagacccc    120
cccagacaaa aaa                                                        133

<210> SEQ ID NO 476
<211> LENGTH: 133
<212> TYPE: DNA
<213> ORGANISM: Dengue virus type 2
<220> FEATURE:
<223> OTHER INFORMATION: Dengue virus type 2 strain AF309957 region of
      conserved sequence in 3' untranslated region

<400> SEQUENCE: 476
atggtgtagt ggactagcgg ttagaggaga cccctcccctt aagaatcgca gcaaaatggg    60
ggcccaaggt gtgttgaagc tgtagccaca ctggaaggac cagaggttag aggagacccc    120
cccagacaaa aaa                                                        133

<210> SEQ ID NO 477
<211> LENGTH: 133
<212> TYPE: DNA
<213> ORGANISM: Dengue virus type 2
<220> FEATURE:
<223> OTHER INFORMATION: Dengue virus type 2 strain AF309958 region of
      conserved sequence in 3' untranslated region

<400> SEQUENCE: 477

```
atggcgtagt ggactagcgg ttagaggaga cccctccctt acaaatcgca gcaacaatgg    60
gggcccaagg tgagatgaag ctgtagtctc actggaagga ctagaggtta gaggagaccc   120
ccccgaaata aaa                                                      133

<210> SEQ ID NO 478
<211> LENGTH: 133
<212> TYPE: DNA
<213> ORGANISM: Dengue virus type 2
<220> FEATURE:
<223> OTHER INFORMATION: Dengue virus type 2 strain AF309959 region of
      conserved sequence in 3' untranslated region

<400> SEQUENCE: 478
atggtgtagt ggactagcgg ttagaggaga ccctccctt aaaaatcgca gcaaaaatgg     60
gggcccaagg tgtggtgaag ctgtagccac attggaagga ctagaggtta gaggagaccc   120
ccccagacaa aaa                                                      133

<210> SEQ ID NO 479
<211> LENGTH: 133
<212> TYPE: DNA
<213> ORGANISM: Dengue virus type 2
<220> FEATURE:
<223> OTHER INFORMATION: Dengue virus type 2 strain AF309960 region of
      conserved sequence in 3' untranslated region

<400> SEQUENCE: 479
atggcgtagt ggactagcgg ttagaggaga cccctccctt acaaatcgca gcaacaatgg    60
gggcccaagg tgagatgaag ctgtagtctc actggaagga ctagaggtta gaggagaccc   120
ccccgaaata aaa                                                      133

<210> SEQ ID NO 480
<211> LENGTH: 132
<212> TYPE: DNA
<213> ORGANISM: Dengue virus type 2
<220> FEATURE:
<223> OTHER INFORMATION: Dengue virus type 2 strain AF309961 region of
      conserved sequence in 3' untranslated region

<400> SEQUENCE: 480
atggtgtagt ggactagcgg ttagaggaga cccctccctt aaggatcgca gcaaaatggg    60
ggcccaaggt gtggtgaagc tgtagccaca ctggaaggac tagaggttag aggagacccc   120
cccacaaata at                                                       132

<210> SEQ ID NO 481
<211> LENGTH: 133
<212> TYPE: DNA
<213> ORGANISM: Dengue virus type 2
<220> FEATURE:
<223> OTHER INFORMATION: Dengue virus type 2 strain AF309962 region of
      conserved sequence in 3' untranslated region

<400> SEQUENCE: 481
atggcgtagt ggactagcgg ttagaggaga cccctccctt gcaaatcgca gcaacaatgg    60
gggcccaagg tgagatgaag ctgtagtctc actggaagga ctagaggtta gaggagaccc   120
ccccgaaata aaa                                                      133

<210> SEQ ID NO 482
<211> LENGTH: 133
<212> TYPE: DNA
<213> ORGANISM: Dengue virus type 2
```

-continued

```
<220> FEATURE:
<223> OTHER INFORMATION: Dengue virus type 2 strain AF309963 region of
      conserved sequence in 3' untranslated region

<400> SEQUENCE: 482
atggcgtagt ggactagcgg ttagaggaga cccctccc

<210> SEQ ID NO 487
<211> LENGTH: 133
<212> TYPE: DNA
<213> ORGANISM: Dengue virus type 2
<220> FEATURE:
<223> OTHER INFORMATION: Dengue virus type 2 strain AJ487271 region of
      conserved sequence in 3' untranslated region

<400> SEQUENCE: 487
atggcgtagt ggactagcgg ttagaggaga cccctccctt acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 488
<211> LENGTH: 133
<212> TYPE: DNA
<213> ORGANISM: Dengue virus type 2
<220> FEATURE:
<223> OTHER INFORMATION: Dengue virus type 2 strain AY037116 region of
      conserved sequence in 3' untranslated region

<400> SEQUENCE: 488
atggcgtagt ggactagcgg ttagaggaga cccctccctt acaaatcgca gcaacaatgg      60
gggcccaagg tgagatgaag ctgtagtctc actgaaagga ctagaggtta gaggagaccc     120
ccccgaaata aaa                                                        133

<210> SEQ ID NO 489
<211> LENGTH: 133
<212> TYPE: DNA
<213> ORGANISM: Dengue virus type 2
<220> FEATURE:
<223> OTHER INFORMATION: Dengue virus type 2 strain M19197 region of
      conserved sequence in 3' untranslated region

<400> SEQUENCE: 489
atggcgtagt ggactagcgg ttagaggaga cccctccctt acagatcgca gcaacaatgg      60
gggcccaagg tgagatgaag ctgtagtctc actggaagga ctagaggtta gaggagaccc     120
ccccaaaaca aaa                                                        133

<210> SEQ ID NO 490
<211> LENGTH: 133
<212> TYPE: DNA
<213> ORGANISM: Dengue virus type 2
<220> FEATURE:
<223> OTHER INFORMATION: Dengue virus type 2 strain M20558 region of
      conserved sequence in 3' untranslated region

<400> SEQUENCE: 490
atggcgtagt ggactagcgg ttagaggaga cccctccctt acaaatcgca gcaacaacgg      60
gggcccaagg tgagatgaag ctgtagtctc actggaagga ctagaggtta gaggagaccc     120
ccccaaaaca aaa                                                        133

<210> SEQ ID NO 491
<211> LENGTH: 133
<212> TYPE: DNA
<213> ORGANISM: Dengue virus type 2
<220> FEATURE:
<223> OTHER INFORMATION: Dengue virus type 2 strain M29095 region of
      conserved sequence in 3' untranslated region

<400> SEQUENCE: 491

```
atggcgtagt ggactagcgg ttagaggaga cccctccctt acaaatcgca gcaacaatgg    60
gggcccaagg tgagatgaag ctgtagtctc actggaagga ctagaggtta gaggagaccc   120
ccccaaaaca aaa                                                      133

<210> SEQ ID NO 492
<211> LENGTH: 133
<212> TYPE: DNA
<213> ORGANISM: Dengue virus type 2
<220> FEATURE:
<223> OTHER INFORMATION: Dengue virus type 2 strain M84727 region of
      conserved sequence in 3' untranslated region

<400> SEQUENCE: 492
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 493
<211> LENGTH: 133
<212> TYPE: DNA
<213> ORGANISM: Dengue virus type 2
<220> FEATURE:
<223> OTHER INFORMATION: Dengue virus type 2 strain M84728 region of
      conserved sequence in 3' untranslated region

<400> SEQUENCE: 493
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 494
<211> LENGTH: 133
<212> TYPE: DNA
<213> ORGANISM: Dengue virus type 2
<220> FEATURE:
<223> OTHER INFORMATION: Dengue virus type 2 strain U61245 region of
      conserved sequence in 3' untranslated region

<400> SEQUENCE: 494
atggcgtagt ggactagcgg ttagaggaga cccctccctt acaaatcgca gcaacaatgg    60
gggcccaagg cgagatgaag ctgtagtctc gctggaagga ctagaggtta gaggagaccc   120
ccccgaaaca gaa                                                      133

<210> SEQ ID NO 495
<211> LENGTH: 133
<212> TYPE: DNA
<213> ORGANISM: Dengue virus type 2
<220> FEATURE:
<223> OTHER INFORMATION: Dengue virus type 2 strain U61246 region of
      conserved sequence in 3' untranslated region

<400> SEQUENCE: 495
atggcgtagt ggactagcgg ttagaggaga cccctccctc acaaatcgca gcaacaatgg    60
gggcccaagg cgagatgaag ctgtagtctc gctggaagga ctagaggtta gaggagaccc   120
ccccgaaaca aaa                                                      133

<210> SEQ ID NO 496
<211> LENGTH: 133
<212> TYPE: DNA
```

```
<213> ORGANISM: Dengue virus type 2
<220> FEATURE:
<223> OTHER INFORMATION: Dengue virus type 2 strain U61247 region of
      conserved sequence in 3' untranslated region

<400> SEQUENCE: 496
atggcgtagt ggactagcgg ttagaggaga cccctccctc acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 497
<211> LENGTH: 133
<212> TYPE: DNA
<213> ORGANISM: Dengue virus type 2
<220> FEATURE:
<223> OTHER INFORMATION: Dengue virus type 2 strain U61248 region of
      conserved sequence in 3' untranslated region

<400> SEQUENCE: 497
atggcgtagt ggactagcgg ttagaggaga cccctccctt acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 498
<211> LENGTH: 133
<212> TYPE: DNA
<213> ORGANISM: Dengue virus type 2
<220> FEATURE:
<223> OTHER INFORMATION: Dengue virus type 2 strain U87411 region of
      conserved sequence in 3' untranslated region

<400> SEQUENCE: 498
atggcgtagt ggactagcgg ttagaggaga cccctccctt acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 499
<211> LENGTH: 133
<212> TYPE: DNA
<213> ORGANISM: Dengue virus type 2
<220> FEATURE:
<223> OTHER INFORMATION: Dengue virus type 2 strain U87412 region of
      conserved sequence in 3' untranslated region

<400> SEQUENCE: 499
atggcgtagt ggactagcgg ttagaggaga cccctccctt acaaatcgca gcaacaatgg      60
gggcccaagg cgagatgaag ctgtagtctc gctggaagga ctagaggtta gaggagaccc     120
ccccgaaaca aaa                                                        133

<210> SEQ ID NO 500
<211> LENGTH: 133
<212> TYPE: DNA
<213> ORGANISM: Dengue virus type 2
<220> FEATURE:
<223> OTHER INFORMATION: Dengue virus type 2 strain VR345-2 region of
      conserved sequence in 3' untranslated region

<400> SEQUENCE: 500
atggcgtagt ggactagcgg ttagaggaga cccctccctt acaaatcgca gcaacaatgg      60
gggcccaagg cgagatgaag ctgtagtccc gctggaagga ctagaggtta gaggagaccc     120
```
ccccgaaaca aaa 133

<210> SEQ ID NO 501
<211> LENGTH: 130
<212> TYPE: DNA
<213> ORGANISM: Dengue virus type 3
<220> FEATURE:
<223> OTHER INFORMATION: Dengue virus type 3 strain AF310149 region of
conserved sequence in 3' untranslated region

<400> SEQUENCE: 501
acggtgtagc agactagcgg ttagaggaga cccctcccat gacacaacgc agcagcgggg 60
cccgagcact gagggaagct gtacctcctt gcaaaggact agaggttaga ggagaccccc 120
cgcaaataaa 130

<210> SEQ ID NO 502
<211> LENGTH: 130
<212> TYPE: DNA
<213> ORGANISM: Dengue virus type 3
<220> FEATURE:
<223> OTHER INFORMATION: Dengue virus type 3 strain M93130 region of
conserved sequence in 3' untranslated region

<400> SEQUENCE: 502
acggtgtagc agactagtgg ttagaggaga cccctcccat gacacaacgc agcagcgggg 60
cccgagcact gagggaagct gtacctcctt gcaaaggact agaggttata ggagaccccc 120
cgcaaacaaa 130

<210> SEQ ID NO 503
<211> LENGTH: 130
<212> TYPE: DNA
<213> ORGANISM: Dengue virus type 3
<220> FEATURE:
<223> OTHER INFORMATION: Dengue virus type 3 strain AF317645 region of
conserved sequence in 3' untranslated region

<400> SEQUENCE: 503
acggtgtagc agactagtgg ttagaggaga cccctcccat gacacaacgc agcagcgggg 60
cccgagcact gagggaagct gtacctcctt gcaaaggact agaggttata ggagaccccc 120
cgcaaacaaa 130

<210> SEQ ID NO 504
<211> LENGTH: 130
<212> TYPE: DNA
<213> ORGANISM: Dengue virus type 3
<220> FEATURE:
<223> OTHER INFORMATION: Dengue virus type 3 strain AY099336 region of
conserved sequence in 3' untranslated region

<400> SEQUENCE: 504
acggtgtagc agactagcgg ttagaggaga cccctcccat gacacaacgc agcagcgggg 60
cccgagcact gagggaagct gtacctcctt gcaaaggact agaggttaga ggagaccccc 120
cgcaaataaa 130

<210> SEQ ID NO 505
<211> LENGTH: 130
<212> TYPE: DNA
<213> ORGANISM: Dengue virus type 3
<220> FEATURE:
<223> OTHER INFORMATION: Dengue virus type 3 strain AY099337 region of
conserved sequence in 3' untranslated region

<400> SEQUENCE: 505
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 506
<211> LENGTH: 130
<212> TYPE: DNA
<213> ORGANISM: Dengue virus type 3
<220> FEATURE:
<223> OTHER INFORMATION: Dengue virus type 3 strain AY099343 region of
      conserved sequence in 3' untranslated region

<400> SEQUENCE: 506
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 507
<211> LENGTH: 130
<212> TYPE: DNA
<213> ORGANISM: Dengue virus type 3
<220> FEATURE:
<223> OTHER INFORMATION: Dengue virus type 3 strain AY099344 region of
      conserved sequence in 3' untranslated region

<400> SEQUENCE: 507
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 508
<211> LENGTH: 130
<212> TYPE: DNA
<213> ORGANISM: Dengue virus type 3
<220> FEATURE:
<223> OTHER INFORMATION: Dengue virus type 3 strain AY099345 region of
      conserved sequence in 3' untranslated region

<400> SEQUENCE: 508
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 509
<211> LENGTH: 130
<212> TYPE: DNA
<213> ORGANISM: Dengue virus type 3
<220> FEATURE:
<223> OTHER INFORMATION: Dengue virus type 3 strain AY099346 region of
      conserved sequence in 3' untranslated region

<400> SEQUENCE: 509
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 510
<211> LENGTH: 130

<212> TYPE: DNA
<213> ORGANISM: Dengue virus type 3
<220> FEATURE:
<223> OTHER INFORMATION: Dengue virus type 3 strain AY099347 region of
conserved sequence in 3' untranslated region

<400> SEQUENCE: 510
acggtgtagc agactagcgg ttagaggaga cccctcccat gacacaacgc agcagcgggg    60
cccgagcact gagggaagct gtacctcctt gcaaaggact agaggttaga ggagaccccc   120
cgcaaataaa                                                          130

<210> SEQ ID NO 511
<211> LENGTH: 130
<212> TYPE: DNA
<213> ORGANISM: Dengue virus type 3
<220> FEATURE:
<223> OTHER INFORMATION: Dengue virus type 3 strain VR1256-3 region of
conserved sequence in 3' untranslated region

<400> SEQUENCE: 511
acggtgtagc agactagtgg ttagaggaga cccctcccat gacacaacgc agcagcgggg    60
cccgagcact gagggaagct gtacctcctt gcaaaggact agaggttata ggagaccccc   120
cgcaaacaaa                                                          130

<210> SEQ ID NO 512
<211> LENGTH: 130
<212> TYPE: DNA
<213> ORGANISM: Dengue virus type 3
<220> FEATURE:
<223> OTHER INFORMATION: Dengue virus type 3 strain VR1256-5 region of
conserved sequence in 3' untranslated region

<400> SEQUENCE: 512
acggtgtagc agactagtgg ttagaggaga cccctcccat gacacaacgc agcagcgggg    60
cccgagcact gagggaagct gtacctcctt gcaaaggact agaggttata ggagaccccc   120
cgcaaacaaa                                                          130

<210> SEQ ID NO 513
<211> LENGTH: 135
<212> TYPE: DNA
<213> ORGANISM: Dengue virus type 4
<220> FEATURE:
<223> OTHER INFORMATION: Dengue virus type 4 strain M14931 region of
conserved sequence in 3' untranslated region

<400> SEQUENCE: 513
gtggcatatt ggactagcgg ttagaggaga cccctcccat cactgacaaa acgcagcaaa    60
agggggcccg aagccaggag gaagctgtac tcctggtgga aggactagag gttagaggag   120
acccccccaa cacaa                                                    135

<210> SEQ ID NO 514
<211> LENGTH: 138
<212> TYPE: DNA
<213> ORGANISM: Dengue virus type 4
<220> FEATURE:
<223> OTHER INFORMATION: Dengue virus type 4 strain AF289029 region of
conserved sequence in 3' untranslated region

<400> SEQUENCE: 514
gtggcatatt ggactagcgg ttagaggaga cccctcccat caccaacaaa acgcagcaaa    60
aaggggggcc cgaagccagg aggaagctgt actcctggtg gaaggactag aggttagagg   120

```
agaccccccc aacacaaa                                                       138

<210> SEQ ID NO 515
<211> LENGTH: 104
<212> TYPE: DNA
<213> ORGANISM: Dengue virus type 4
<220> FEATURE:
<223> OTHER INFORMATION: Dengue virus type 4 strain AF310150 region of
      conserved sequence in 3' untranslated region

<400> SEQUENCE: 515
gtggcatatt ggactagtgg ttagaggaga cccctcccat tatcaacaaa cgcagcacaa        60 aggggggcccg aagtcaggat gaagctgtac tcctgatgga agga                       104

<210> SEQ ID NO 516
<211> LENGTH: 104
<212> TYPE: DNA
<213> ORGANISM: Dengue virus type 4
<220> FEATURE:
<223> OTHER INFORMATION: Dengue virus type 4 strain AF310152 region of
      conserved sequence in 3' untranslated region

<400> SEQUENCE: 516
gtggcatatt ggactagtgg ttagaggaga cccctcccat tatcaacaaa cgcagcacaa        60 aggggggcccg aagtcaggat gaagctgtac tcctgatgga agga                       104

<210> SEQ ID NO 517
<211> LENGTH: 136
<212> TYPE: DNA
<213> ORGANISM: Dengue virus type 4
<220> FEATURE:
<223> OTHER INFORMATION: Dengue virus type 4 strain AF310153 region of
      conserved sequence in 3' untranslated region

<400> SEQUENCE: 517
gtggcatatt ggactagcgg ttagaggaga cccctcccat cactgacaaa acgcagcaaa        60 aggggggcccg aagccaggag gaagctgtac tcctggtgga aggactagag gttagaggag      120
acccccccaa cacaaa                                                       136

<210> SEQ ID NO 518
<211> LENGTH: 136
<212> TYPE: DNA
<213> ORGANISM: Dengue virus type 4
<220> FEATURE:
<223> OTHER INFORMATION: Dengue virus type 4 strain AF326573 region of
      conserved sequence in 3' untranslated region

<400> SEQUENCE: 518
gtggcatatt ggactagcgg ttagaggaga cccctcccat cactgacaaa acgcagcaaa        60 aggggggcccg aagccaggag gaagctgtac tcctggtgga aggactagag gttagaggag      120
acccccccaa cacaaa                                                       136

<210> SEQ ID NO 519
<211> LENGTH: 136
<212> TYPE: DNA
<213> ORGANISM: Dengue virus type 4
<220> FEATURE:
<223> OTHER INFORMATION: Dengue virus type 4 strain AF326825 region of
      conserved sequence in 3' untranslated region

<400> SEQUENCE: 519
gtggcatatt ggactagcgg ttagaggaga cccctcccat cactgataaa acgcagcaaa        60
```

```
aggggggcccg aagccaggag gaagctgtac tcctggtgga aggactagag gttagaggag    120
acccccccaa cacaaa                                                    136
```

<210> SEQ ID NO 520
<211> LENGTH: 105
<212> TYPE: DNA
<213> ORGANISM: Dengue virus type 4
<220> FEATURE:
<223> OTHER INFORMATION: Dengue virus type 4 strain AF326826 region of
      conserved sequence in 3' untranslated region

<400> SEQUENCE: 520

```
gtggcatatt ggactagcgg ttagaggaga cccctcccat cactgacaaa acgcagcaaa     60 aggggggccca agactagagg ttagaggaga ccccccaac acaaa                    105
```

<210> SEQ ID NO 521
<211> LENGTH: 105
<212> TYPE: DNA
<213> ORGANISM: Dengue virus type 4
<220> FEATURE:
<223> OTHER INFORMATION: Dengue virus type 4 strain AF326827 region of
      conserved sequence in 3' untranslated region

<400> SEQUENCE: 521

```
gtggcatatt ggactagcgg ttagaggaga cccctcccat cactgacaaa acgcagcaaa     60 aggggggccca agactagagg ttagaggaga ccccccaac acaaa                    105
```

<210> SEQ ID NO 522
<211> LENGTH: 136
<212> TYPE: DNA
<213> ORGANISM: Dengue virus type 4
<220> FEATURE:
<223> OTHER INFORMATION: Dengue virus type 4 strain AF375822 region of
      conserved sequence in 3' untranslated region

<400> SEQUENCE: 522

```
gtggcatatt ggactagcgg ttagaggaga cccctcccat cactgacaaa acgcagcaaa     60 aggggggcccg aagccaggag gaagctgtac tcctggtgga aggactagag gttagaggag   120
acccccccaa cacaaa                                                   136
```

<210> SEQ ID NO 523
<211> LENGTH: 136
<212> TYPE: DNA
<213> ORGANISM: Dengue virus type 4
<220> FEATURE:
<223> OTHER INFORMATION: Dengue virus type 4 strain AY152039 region of
      conserved sequence in 3' untranslated region

<400> SEQUENCE: 523

```
gtggcatatt ggactagcgg ttagaggaga cccctcccat cactgacaaa acgcagcaaa     60 aggggggcccg aagccaggag gaagctgtac tcctggtgga aggactagag gttagaggag   120
acccccccaa cacaaa                                                   136
```

<210> SEQ ID NO 524
<211> LENGTH: 136
<212> TYPE: DNA
<213> ORGANISM: Dengue virus type 4
<220> FEATURE:
<223> OTHER INFORMATION: Dengue virus type 4 strain AY152043 region of
      conserved sequence in 3' untranslated region

<400> SEQUENCE: 524

```
gtggcatatt ggactagcgg ttagaggaga cccctcccat cactgacaaa acgcagcaaa

<213> ORGANISM: Dengue virus type 4
<220> FEATURE:
<223> OTHER INFORMATION: Dengue virus type 4 strain AY152063 region of
      conserved sequence in 3' untranslated region

<400> SEQUENCE: 529

```
gtggcatatt ggactagcgg ttagaggaga cccctcccat cactgacaaa acgcagcaaa    60
agggggcccg aagccaggag gaagctgtac tcctggtgga aggactagag gttagaggag   120 accccccaa cacaaa                                                    136
```

<210> SEQ ID NO 530
<211> LENGTH: 136
<212> TYPE: DNA
<213> ORGANISM: Dengue virus type 4
<220> FEATURE:
<223> OTHER INFORMATION: Dengue virus type 4 strain AY152067 region of
      conserved sequence in 3' untranslated region

<400> SEQUENCE: 530

```
gtggcatatt ggactagcgg ttagaggaga cccctcccat cactgacaaa acgcagcaaa    60
agggggcccg aagccaggag gaagctgtac tcctggtgga aggactagag gttagaggag   120 accccccaa cacaaa                                                    136
```

<210> SEQ ID NO 531
<211> LENGTH: 136
<212> TYPE: DNA
<213> ORGANISM: Dengue virus type 4
<220> FEATURE:
<223> OTHER INFORMATION: Dengue virus type 4 strain AY152071 region of
      conserved sequence in 3' untranslated region

<400> SEQUENCE: 531

```
gtggcatatt ggactagcgg ttagaggaga cccctcccat cactgacaaa acgcagcaaa    60
agggggcccg aagccaggag gaagctgtac tcctggtgga aggactagag gttagaggag   120 accccccaa cacaaa                                                    136
```

<210> SEQ ID NO 532
<211> LENGTH: 136
<212> TYPE: DNA
<213> ORGANISM: Dengue virus type 4
<220> FEATURE:
<223> OTHER INFORMATION: Dengue virus type 4 strain AY152075 region of
      conserved sequence in 3' untranslated region

<400> SEQUENCE: 532

```
gtggcatatt ggactagcgg ttagaggaga cccctcccat cactgacaaa acgcagcaaa    60
agggggcccg aagccaggag gaagctgtac tcctggtgga aggactagag gttagaggag   120 accccccaa cacaaa                                                    136
```

<210> SEQ ID NO 533
<211> LENGTH: 136
<212> TYPE: DNA
<213> ORGANISM: Dengue virus type 4
<220> FEATURE:
<223> OTHER INFORMATION: Dengue virus type 4 strain AY152079 region of
      conserved sequence in 3' untranslated region

<400> SEQUENCE: 533

```
gtggcatatt ggactagcgg ttagaggaga cccctcccat cactgacaaa acgcagcaaa    60
agggggcccg aagccaggag gaagctgtac tcctggtgga aggactagag gttagaggag   120
```

```
acccccccaa cacaaa                                                      136

<210> SEQ ID NO 534
<211> LENGTH: 136
<212> TYPE: DNA
<213> ORGANISM: Dengue virus type 4
<220> FEATURE:
<223> OTHER INFORMATION: Dengue virus type 4 strain AY152083 region of
      conserved sequence in 3' untranslated region

<400> SEQUENCE: 534
gtggcatatt ggactagcgg ttagaggaga cccctcccac cactgacaaa acgcagcaaa      60
aggggggccg aagccaggag gaagctgtac tcctggtgga aggactagag gttagaggag     120
acccccccaa cacaaa                                                      136

<210> SEQ ID NO 535
<211> LENGTH: 136
<212> TYPE: DNA
<213> ORGANISM: Dengue virus type 4
<220> FEATURE:
<223> OTHER INFORMATION: Dengue virus type 4 strain AY152087 region of
      conserved sequence in 3' untranslated region

<400> SEQUENCE: 535
gtggcatatt ggactagcgg ttagaggaga cccctcccat cactgacaaa acgcagcaaa      60
aggggggccg aagccaggag gaagctgtac tcctggtgga aggactagag gttagaggag     120
acccccccaa cacaaa                                                      136

<210> SEQ ID NO 536
<211> LENGTH: 136
<212> TYPE: DNA
<213> ORGANISM: Dengue virus type 4
<220> FEATURE:
<223> OTHER INFORMATION: Dengue virus type 4 strain AY152091 region of
      conserved sequence in 3' untranslated region

<400> SEQUENCE: 536
gtggcatatt ggactagcgg ttagaggaga cccctcccat cactgacaaa acgcagcaaa      60
aggggggccg aagccaggag gaagctgtac tcctggtgga aggactagag gttagaggag     120
acccccccaa cacaaa                                                      136

<210> SEQ ID NO 537
<211> LENGTH: 136
<212> TYPE: DNA
<213> ORGANISM: Dengue virus type 4
<220> FEATURE:
<223> OTHER INFORMATION: Dengue virus type 4 strain AY152095 region of
      conserved sequence in 3' untranslated region

<400> SEQUENCE: 537
gtggcatatt ggactagcgg ttagaggaga cccctcccat cactgacaaa acgcagcaaa      60
aggggggccg aagccaggag gaagctgtac tcctggtgga aggactagag gttagaggag     120
acccccccaa cacaaa                                                      136

<210> SEQ ID NO 538
<211> LENGTH: 136
<212> TYPE: DNA
<213> ORGANISM: Dengue virus type 4
<220> FEATURE:
<223> OTHER INFORMATION: Dengue virus type 4 strain AY152099 region of
      conserved sequence in 3' untranslated region
```

-continued

```
<400> SEQUENCE: 538
gtggcatatt ggactagcgg ttagaggaga cccctcccat cactaacaaa acgcagcaaa    60
agggggcccg aagccaggag gaagctgtac tcctggtgga aggactagag gttagaggag   120
acccccccaa cacaaa                                                    136

<210> SEQ ID NO 539
<211> LENGTH: 137
<212> TYPE: DNA
<213> ORGANISM: Dengue virus type 4
<220> FEATURE:
<223> OTHER INFORMATION: Dengue virus type 4 strain AY152103 region of
      conserved sequence in 3' untranslated region

<400> SEQUENCE: 539
gtggcatatt ggactagcgg ttagaggaga cccctcccat cactgacaaa acgcagcaaa    60
aagggggccc gaagccagga ggaagctgta ctcctggtgg aaggactaga ggttagagga   120
gaccccccca acacaaa                                                   137

<210> SEQ ID NO 540
<211> LENGTH: 136
<212> TYPE: DNA
<213> ORGANISM: Dengue virus type 4
<220> FEATURE:
<223> OTHER INFORMATION: Dengue virus type 4 strain AY152107 region of
      conserved sequence in 3' untranslated region

<400> SEQUENCE: 540
gtggtatatt ggactagcgg ttagaggaga cccctcccat cactgacaaa acgcagcaaa    60
agggggcccg aagccaggag gaagctgtac tcctggtgga aggactagag gttagaggag   120
acccccccaa cacaaa                                                    136

<210> SEQ ID NO 541
<211> LENGTH: 136
<212> TYPE: DNA
<213> ORGANISM: Dengue virus type 4
<220> FEATURE:
<223> OTHER INFORMATION: Dengue virus type 4 strain AY152111 region of
      conserved sequence in 3' untranslated region

<400> SEQUENCE: 541
gtggcatatt ggactagcgg ttagaggaga cccctcccat cactgacaaa acgcagcaaa    60
agggggcccg aagccaggag gaagctgtac tcctggtgga aggactagag gttagaggag   120
acccccccaa cacaaa                                                    136

<210> SEQ ID NO 542
<211> LENGTH: 136
<212> TYPE: DNA
<213> ORGANISM: Dengue virus type 4
<220> FEATURE:
<223> OTHER INFORMATION: Dengue virus type 4 strain AY152115 region of
      conserved sequence in 3' untranslated region

<400> SEQUENCE: 542
gtggcatatt ggactagcgg ttagaggaga cccctcccat cactgacaaa acgcagcaaa    60
agggggcccg aagccaggag gaagctgtac tcctggtgga aggactagag gttagaggag   120
acccccccaa cacaaa                                                    136

<210> SEQ ID NO 543
<211> LENGTH: 136
```

<210> SEQ ID NO 544
<211> LENGTH: 136
<212> TYPE: DNA
<213> ORGANISM: Dengue virus type 4
<220> FEATURE:
<223> OTHER INFORMATION: Dengue virus type 4 strain AY152119 region of
conserved sequence in 3' untranslated region

<400> SEQUENCE: 543

```
gtggcatatt ggactagcgg ttagaggaga cccctcccat cactgacaaa acgcagcaaa    60
aggggggcccg aagccaggag gaagctgtac tcctggtgga aggactagag gttagaggag   120
accccccccaa cacaaa                                                   136
```

<210> SEQ ID NO 544
<211> LENGTH: 136
<212> TYPE: DNA
<213> ORGANISM: Dengue virus type 4
<220> FEATURE:
<223> OTHER INFORMATION: Dengue virus type 4 strain AY152123 region of
conserved sequence in 3' untranslated region

<400> SEQUENCE: 544

```
gtggcatatt ggactagcgg ttagaggaga cccctcccat cactgacaaa acgcagcaaa    60
aggggggcccg aagccaggag gaagctgtac tcctggtgga aggactagag gttagaggag   120
accccccccaa cacaaa                                                   136
```

<210> SEQ ID NO 545
<211> LENGTH: 136
<212> TYPE: DNA
<213> ORGANISM: Dengue virus type 4
<220> FEATURE:
<223> OTHER INFORMATION: Dengue virus type 4 strain AY152127 region of
conserved sequence in 3' untranslated region

<400> SEQUENCE: 545

```
gtggcatatt ggactagcgg ttagaggaga cccctcccat cactgacaaa acgcagcaaa    60
aggggggcccg aagccaggag gaagctgtac tcctggtgga aggactagag gttagaggag   120
accccccccaa cacaaa                                                   136
```

<210> SEQ ID NO 546
<211> LENGTH: 136
<212> TYPE: DNA
<213> ORGANISM: Dengue virus type 4
<220> FEATURE:
<223> OTHER INFORMATION: Dengue virus type 4 strain AY152131 region of
conserved sequence in 3' untranslated region

<400> SEQUENCE: 546

```
gtggcatatt ggactagcgg ttagaggaga cccctcccat cactgacaaa acgcagcaaa    60
aggggggcccg aagccaggag gaagctgtac tcctggtgga aggactagag gttagaggag   120
accccccccaa cacaaa                                                   136
```

<210> SEQ ID NO 547
<211> LENGTH: 136
<212> TYPE: DNA
<213> ORGANISM: Dengue virus type 4
<220> FEATURE:
<223> OTHER INFORMATION: Dengue virus type 4 strain AY152135 region of
conserved sequence in 3' untranslated region

<400> SEQUENCE: 547

```
gtggcatatt ggactagcgg ttagaggaga cccctcccat cactgacaaa acgcagcaaa    60
aggggggcccg aagccaggag gaagctgtac tcctggtgga aggactagag gttagaggag   120
```
acccccccaa cacaaa                                                          136

<210> SEQ ID NO 548
<211> LENGTH: 136
<212> TYPE: DNA
<213> ORGANISM: Dengue virus type 4
<220> FEATURE:
<223> OTHER INFORMATION: Dengue virus type 4 strain AY152139 region of
      conserved sequence in 3' untranslated region

<400> SEQUENCE: 548
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 549
<211> LENGTH: 135
<212> TYPE: DNA
<213> ORGANISM: Dengue virus type 4
<220> FEATURE:
<223> OTHER INFORMATION: Dengue virus type 4 strain AY152143 region of conserved sequence in 3' untranslated region

<400> SEQUENCE: 549
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaa 135

<210> SEQ ID NO 550
<211> LENGTH: 136
<212> TYPE: DNA
<213> ORGANISM: Dengue virus type 4
<220> FEATURE:
<223> OTHER INFORMATION: Dengue virus type 4 strain AY152147 region of conserved sequence in 3' untranslated region

<400> SEQUENCE: 550
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 551
<211> LENGTH: 136
<212> TYPE: DNA
<213> ORGANISM: Dengue virus type 4
<220> FEATURE:
<223> OTHER INFORMATION: Dengue virus type 4 strain AY152151 region of conserved sequence in 3' untranslated region

<400> SEQUENCE: 551
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 552
<211> LENGTH: 137
<212> TYPE: DNA
<213> ORGANISM: Dengue virus type 4
<220> FEATURE:
<223> OTHER INFORMATION: Dengue virus type 4 strain AY152155 region of conserved sequence in 3' untranslated region

<400> SEQUENCE: 552
gtggcatatt ggactagcgg ttagaggaga cccctcccat cactgacaaa acgcagcaaa      60 aaggggccc gaagccagga ggaagctgta ctcctggtgg aaggactaga ggttagagga     120
gaccccccca acacaaa                                                    137

<210> SEQ ID NO 553
<211> LENGTH: 136
<212> TYPE: DNA
<213> ORGANISM: Dengue virus type 4
<220> FEATURE:
<223> OTHER INFORMATION: Dengue virus type 4 strain AY152159 region of
      conserved sequence in 3' untranslated region

<400> SEQUENCE: 553
gtggcatatt ggactagcgg ttagaggaga cccctcccat cactgacaaa acgcagcaaa      60 aggggggcccg aagccaggag gaagctgtac tcctggtgga aggactagag gttagaggag   120
acccccccaa cacaaa                                                     136

<210> SEQ ID NO 554
<211> LENGTH: 136
<212> TYPE: DNA
<213> ORGANISM: Dengue virus type 4
<220> FEATURE:
<223> OTHER INFORMATION: Dengue virus type 4 strain AY152163 region of
      conserved sequence in 3' untranslated region

<400> SEQUENCE: 554
gtggcatatt ggactagcgg ttagaggaga cccctcccat cactgacaaa acgcagcaaa      60
aggggccccg aagccaggag gaagctgtac tcctggtgga aggactagag gttagaggag    120
acccccccaa cacaaa                                                     136

<210> SEQ ID NO 555
<211> LENGTH: 136
<212> TYPE: DNA
<213> ORGANISM: Dengue virus type 4
<220> FEATURE:
<223> OTHER INFORMATION: Dengue virus type 4 strain AY152167 region of
      conserved sequence in 3' untranslated region

<400> SEQUENCE: 555
gtggcatatt ggactagcgg ttagaggaga cccctcccat cactgacaaa acgcagcaaa      60
aggggccccg aagccaggag gaagctgtac tcctggtgga aggactagag gttagaggag    120
acccccccaa cacaaa                                                     136

<210> SEQ ID NO 556
<211> LENGTH: 136
<212> TYPE: DNA
<213> ORGANISM: Dengue virus type 4
<220> FEATURE:
<223> OTHER INFORMATION: Dengue virus type 4 strain AY152175 region of
      conserved sequence in 3' untranslated region

<400> SEQUENCE: 556
gtggcatatt ggactagcgg ttagaggaga cccctcccat cactgacaaa acgcagcaaa      60
aggggccccg aagccaggag gaagctgtac tcctggtgga aggactagag gttagaggag    120
acccccccaa cacaaa                                                     136

<210> SEQ ID NO 557

```
<211> LENGTH: 136
<212> TYPE: DNA
<213> ORGANISM: Dengue virus type 4
<220> FEATURE:
<223> OTHER INFORMATION: Dengue virus type 4 strain AY152179 region of
      conserved sequence in 3' untranslated region

<400> SEQUENCE: 557
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136

<210> SEQ ID NO 558
<211> LENGTH: 136
<212> TYPE: DNA
<213> ORGANISM: Dengue virus type 4
<220> FEATURE:
<223> OTHER INFORMATION: Dengue virus type 4 strain AY152183 region of
      conserved sequence in 3' untranslated region

<400> SEQUENCE: 558
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136

<210> SEQ ID NO 559
<211> LENGTH: 136
<212> TYPE: DNA
<213> ORGANISM: Dengue virus type 4
<220> FEATURE:
<223> OTHER INFORMATION: Dengue virus type 4 strain AY152187 region of
      conserved sequence in 3' untranslated region

<400> SEQUENCE: 559
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136

<210> SEQ ID NO 560
<211> LENGTH: 136
<212> TYPE: DNA
<213> ORGANISM: Dengue virus type 4
<220> FEATURE:
<223> OTHER INFORMATION: Dengue virus type 4 strain AY152191 region of
      conserved sequence in 3' untranslated region

<400> SEQUENCE: 560
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136

<210> SEQ ID NO 561
<211> LENGTH: 136
<212> TYPE: DNA
<213> ORGANISM: Dengue virus type 4
<220> FEATURE:
<223> OTHER INFORMATION: Dengue virus type 4 strain AY152195 region of
      conserved sequence in 3' untranslated region

<400> SEQUENCE: 561
gtggcatatt ggactagcgg ttagaggaga cccctcccat cactgacaaa acgcagcaaa    60
```

```
aggggccccg aagccaggag gaagctgtac tcctggtgga aggactagag gttagaggag    120 accccccaa cacaaa                                                    136

<210> SEQ ID NO 562
<211> LENGTH: 136
<212> TYPE: DNA
<213> ORGANISM: Dengue virus type 4
<220> FEATURE:
<223> OTHER INFORMATION: Dengue virus type 4 strain AY152199 region of
      conserved sequence in 3' untranslated region

<400> SEQUENCE: 562
gtggcatatt ggactagcgg ttagaggaga ccctcccat cactgacaaa acgcagcaaa    60
aggggccccg aagccaggag gaagctgtac tcctggtgga aggactagag gttataggag    120 accccccaa cacaaa                                                    136

<210> SEQ ID NO 563
<211> LENGTH: 136
<212> TYPE: DNA
<213> ORGANISM: Dengue virus type 4
<220> FEATURE:
<223> OTHER INFORMATION: Dengue virus type 4 strain AY152203 region of
      conserved sequence in 3' untranslated region

<400> SEQUENCE: 563
gtggcatatt ggactagcgg ttagaggaga ccctcccat cactgacaaa acgcagcaaa    60
aggggccccg aagccaggag gaagctgtac tcctggtgga aggactagag gttagaggag    120 accccccaa cacaaa                                                    136

<210> SEQ ID NO 564
<211> LENGTH: 136
<212> TYPE: DNA
<213> ORGANISM: Dengue virus type 4
<220> FEATURE:
<223> OTHER INFORMATION: Dengue virus type 4 strain AY152207 region of
      conserved sequence in 3' untranslated region

<400> SEQUENCE: 564
gtggcatatt ggactagcgg ttagaggaga ccctcccat cactgacaaa acgcagcaaa    60
aggggccccg aagccaggag gaagctgtac tcctggtgga aggactagag gttagaggag    120 accccccaa cacaaa                                                    136

<210> SEQ ID NO 565
<211> LENGTH: 136
<212> TYPE: DNA
<213> ORGANISM: Dengue virus type 4
<220> FEATURE:
<223> OTHER INFORMATION: Dengue virus type 4 strain AY152211 region of
      conserved sequence in 3' untranslated region

<400> SEQUENCE: 565
gtggcatatt ggactagcgg ttagaggaga ccctcccat cactgacaaa acgcagcaaa    60
aggggccccg aagccaggag gaagctgtac tcctggtgga aggactagag gttagaggag    120 accccccaa cacaaa                                                    136

<210> SEQ ID NO 566
<211> LENGTH: 136
<212> TYPE: DNA
<213> ORGANISM: Dengue virus type 4
<220> FEATURE:
<223> OTHER INFORMATION: Dengue virus type 4 strain AY152215 region of
``` conserved sequence in 3' untranslated region

<400> SEQUENCE: 566

```
gtggcatatt ggactagcgg ttagaggaga cccctcccat cactgacaaa acgcagcaaa    60
aggggggccg aagccaggag gaagctgtac tcctggtgga aggactagag gttagaggag   120
accccccccaa cacaaa                                                   136
```

<210> SEQ ID NO 567
<211> LENGTH: 136
<212> TYPE: DNA
<213> ORGANISM: Dengue virus type 4
<220> FEATURE:
<223> OTHER INFORMATION: Dengue virus type 4 strain AY152219 region of
      conserved sequence in 3' untranslated region

<400> SEQUENCE: 567

```
gtggcatatt ggactagcgg ttagaggaga cccctcccat cactgacaaa acgcagcaaa    60
aggggggccg aagccaggag gaagctgtac tcctggtgga aggactagag gttagaggag   120
accccccccaa cacaaa                                                   136
```

<210> SEQ ID NO 568
<211> LENGTH: 136
<212> TYPE: DNA
<213> ORGANISM: Dengue virus type 4
<220> FEATURE:
<223> OTHER INFORMATION: Dengue virus type 4 strain AY152223 region of
      conserved sequence in 3' untranslated region

<400> SEQUENCE: 568

```
gtggcatatt ggactagcgg ttagaggaga cccctcccat cactgacaaa acgcagcaaa    60
aggggggccg aagccaggag gaagctgtac tcctggtgga aggactagag gttagaggag   120
accccccccaa cacaaa                                                   136
```

<210> SEQ ID NO 569
<211> LENGTH: 136
<212> TYPE: DNA
<213> ORGANISM: Dengue virus type 4
<220> FEATURE:
<223> OTHER INFORMATION: Dengue virus type 4 strain AY152227 region of
      conserved sequence in 3' untranslated region

<400> SEQUENCE: 569

```
gtggcatatt ggactagcgg ttagaggaga cccctcccat cactgacaaa acgcagcaaa    60
aggggggccg aagccaggag gaagctgtac tcctggtgga aggactagag gttagaggag   120
accccccccaa cacaaa                                                   136
```

<210> SEQ ID NO 570
<211> LENGTH: 136
<212> TYPE: DNA
<213> ORGANISM: Dengue virus type 4
<220> FEATURE:
<223> OTHER INFORMATION: Dengue virus type 4 strain AY152231 region of
      conserved sequence in 3' untranslated region

<400> SEQUENCE: 570

```
gtggcatatt ggactagcgg ttagaggaga cccctcccat cactgacaaa acgcagcaaa    60
aggggggccg aagccaggag gaagctgtac tcctggtgga aggactagag gttagaggag   120
accccccccaa cacaaa                                                   136
```

<210> SEQ ID NO 571
<211> LENGTH: 136
<212> TYPE: DNA
<213> ORGANISM: Dengue virus type 4
<220> FEATURE:
<223> OTHER INFORMATION: Dengue virus type 4 strain AY152235 region of conserved sequence in 3' untranslated region

<400> SEQUENCE: 571

```
gtggcatatt ggactagcgg ttagaggaga cccctcccat cactgacaaa acgcagcaaa      60 aggggggcccg aagccaggag gaagctgtac tcctggtgga aggactagag gttagaggag     120
acccccccaa cacaaa                                                     136
```

<210> SEQ ID NO 572
<211> LENGTH: 136
<212> TYPE: DNA
<213> ORGANISM: Dengue virus type 4
<220> FEATURE:
<223> OTHER INFORMATION: Dengue virus type 4 strain AY152239 region of conserved sequence in 3' untranslated region

<400> SEQUENCE: 572

```
gtggcatatt ggactagcgg ttagaggaga cccctcccat cactgacaaa acgcagcaaa      60 aggggggcccg aagccaggag gaagctgtac tcctggtgga aggactagag gttagaggag     120
acccccccaa cacaaa                                                     136
```

<210> SEQ ID NO 573
<211> LENGTH: 136
<212> TYPE: DNA
<213> ORGANISM: Dengue virus type 4
<220> FEATURE:
<223> OTHER INFORMATION: Dengue virus type 4 strain AY152243 region of conserved sequence in 3' untranslated region

<400> SEQUENCE: 573

```
gtggcatatt ggactagcgg ttagaggaga cccctcccat cactgacaaa acgcagcaaa      60 aggggggcccg aagccaggag gaagctgtac tcctggtgga aggactagag gttagaggag     120
acccccccaa cacaaa                                                     136
```

<210> SEQ ID NO 574
<211> LENGTH: 136
<212> TYPE: DNA
<213> ORGANISM: Dengue virus type 4
<220> FEATURE:
<223> OTHER INFORMATION: Dengue virus type 4 strain AY152247 region of conserved sequence in 3' untranslated region

<400> SEQUENCE: 574

```
gtggcatatt ggactagtgg ttagaggaga cccctcccat cactgacaaa acgcagcaaa      60 aggggggcccg aagccaggag gaagctgtac tcctggtgga aggactagag gttagaggag     120
acccccccaa cacaaa                                                     136
```

<210> SEQ ID NO 575
<211> LENGTH: 136
<212> TYPE: DNA
<213> ORGANISM: Dengue virus type 4
<220> FEATURE:
<223> OTHER INFORMATION: Dengue virus type 4 strain AY152251 region of conserved sequence in 3' untranslated region

<400> SEQUENCE: 575

```
gtggcatatt ggactagcgg ttagaggaga cccctcccat cactgacaaa acgcagcaaa      60
```

```
aggggggcccg aagccaggag gaagctgtac tcctggtgga aggactagag gttagaggag    120
acccccccaa cacaaa                                                     136

<210> SEQ ID NO 576
<211> LENGTH: 136
<212> TYPE: DNA
<213> ORGANISM: Dengue virus type 4
<220> FEATURE:
<223> OTHER INFORMATION: Dengue virus type 4 strain AY152255 region of
      conserved sequence in 3' untranslated region

<400> SEQUENCE: 576
gtggcatatt ggactagcgg ttagaggaga ccccctcccat cactgacaaa acgcagcaaa    60 aggggggcccg aagccaggag gaagctgtac tcctggtgga aggactagag gttagaggag   120
acccccccaa cacaaa                                                    136

<210> SEQ ID NO 577
<211> LENGTH: 136
<212> TYPE: DNA
<213> ORGANISM: Dengue virus type 4
<220> FEATURE:
<223> OTHER INFORMATION: Dengue virus type 4 strain AY152259 region of
      conserved sequence in 3' untranslated region

<400> SEQUENCE: 577
gtggcatatt ggactagcgg ttagaggaga ccccctcccat cactgacaaa acgcagcaaa    60 aggggggcccg aagccaggag gaagctgtac tcctggtgga aggactagag gttagaggag   120
acccccccaa cacaaa                                                    136

<210> SEQ ID NO 578
<211> LENGTH: 136
<212> TYPE: DNA
<213> ORGANISM: Dengue virus type 4
<220> FEATURE:
<223> OTHER INFORMATION: Dengue virus type 4 strain AY152263 region of
      conserved sequence in 3' untranslated region

<400> SEQUENCE: 578
gtggcatatt ggactagcgg ttagaggaga ccccctcccat cactgacaaa acgcagcaaa    60 aggggggcccg aagccaggag gaagctgtac tcctggtgga aggactagag gttagaggag   120
acccccccaa cacaaa                                                    136

<210> SEQ ID NO 579
<211> LENGTH: 136
<212> TYPE: DNA
<213> ORGANISM: Dengue virus type 4
<220> FEATURE:
<223> OTHER INFORMATION: Dengue virus type 4 strain AY152267 region of
      conserved sequence in 3' untranslated region

<400> SEQUENCE: 579
gtggcatatt ggactagcgg ttagaggaga ccccctcccat cactgacaaa acgcagcaaa    60 aggggggcccg aagccaggag gaagctgtac tcctggtgga aggactagag gttagaggag   120
acccccccaa cacaaa                                                    136

<210> SEQ ID NO 580
<211> LENGTH: 136
<212> TYPE: DNA
<213> ORGANISM: Dengue virus type 4
<220> FEATURE:
```

<223> OTHER INFORMATION: Dengue virus type 4 strain AY152271 region of
      conserved sequence in 3' untranslated region

<400> SEQUENCE: 580
gtggcatatt ggactagcgg ttagaggaga cccctcccat cactgacaaa acgcagcaaa      60
agggggcccg aagccaggag gaagctgtac tcctggtgga aggactagag gttagaggag     120 accccccaa cacaaa                                                      136

<210> SEQ ID NO 581
<211> LENGTH: 136
<212> TYPE: DNA
<213> ORGANISM: Dengue virus type 4
<220> FEATURE:
<223> OTHER INFORMATION: Dengue virus type 4 strain AY152275 region of
      conserved sequence in 3' untranslated region

<400> SEQUENCE: 581
gtggcatatt ggactagcgg ttagaggaga cccctcccat cactgacaaa acgcagcaaa      60
agggggcccg aagccaggag gaagctgtac tcctggtgga aggactagag gttagaggag     120 accccccaa cacaaa                                                      136

<210> SEQ ID NO 582
<211> LENGTH: 137
<212> TYPE: DNA
<213> ORGANISM: Dengue virus type 4
<220> FEATURE:
<223> OTHER INFORMATION: Dengue virus type 4 strain AY152279 region of
      conserved sequence in 3' untranslated region

<400> SEQUENCE: 582
gtggcatatt ggactagcgg ttagaggaga cccctcccat cactgacaaa acgcagcaaa      60 aaggggccc gaagccagga ggaagctgta ctcctggtgg aaggactaga ggttagagga     120
gaccccccca acacaaa                                                    137

<210> SEQ ID NO 583
<211> LENGTH: 136
<212> TYPE: DNA
<213> ORGANISM: Dengue virus type 4
<220> FEATURE:
<223> OTHER INFORMATION: Dengue virus type 4 strain AY152283 region of
      conserved sequence in 3' untranslated region

<400> SEQUENCE: 583
gtggcatatt ggactagcgg ttagaggaga cccctcccat cactgacaaa acgcagcaaa      60
agggggcccg aagccaggag gaagctgtac tcctggtgga aggactagag gttagaggag     120 accccccaa cacaaa                                                      136

<210> SEQ ID NO 584
<211> LENGTH: 136
<212> TYPE: DNA
<213> ORGANISM: Dengue virus type 4
<220> FEATURE:
<223> OTHER INFORMATION: Dengue virus type 4 strain AY152287 region of
      conserved sequence in 3' untranslated region

<400> SEQUENCE: 584
gtggcatatt ggactagcgg ttagaggaga cccctcccat gactgacaaa acgcagcaaa      60
agggggcccg aagccaggag gaagctgtac tcctggtgga aggactagag gttagaggag     120 accccccaa cacaaa                                                      136

```
<210> SEQ ID NO 585
<211> LENGTH: 136
<212> TYPE: DNA
<213> ORGANISM: Dengue virus type 4
<220> FEATURE:
<223> OTHER INFORMATION: Dengue virus type 4 strain AY152291 region of
      conserved sequence in 3' untranslated region

<400> SEQUENCE: 585
gtggcatatt ggactagcgg ttagaggaga cccctcccat cactgacaaa acgcagcaaa    60 aggggggcccg aagccaggag gaagctgtac tcctggtgga aggactagag gttagaggag  120 accccccccaa cacaaa                                                  136

<210> SEQ ID NO 586
<211> LENGTH: 136
<212> TYPE: DNA
<213> ORGANISM: Dengue virus type

```
gtggcatatt ggactagcgg ttagaggaga cccctcccat cactgacaaa acgcagcaaa      60 aggggggcccg aagccaggag gaagctgtac tcctggtgga aggactagag gttagaggag    120 accccccccaa cacaaa                                                     136

<210> SEQ ID NO 590
<211> LENGTH: 136
<212> TYPE: DNA
<213> ORGANISM: Dengue virus type 4
<220> FEATURE:
<223> OTHER INFORMATION: Dengue virus type 4 strain AY152311 region of
      conserved sequence in 3' untranslated region

<400> SEQUENCE: 590
gtggcatatt ggactagcgg ttagaggaga cccctcccat cactgacaaa acgcagcaaa      60 aggggggcccg aagccaggag gaagctgtac tcctggtgga aggactagag gttagaggag    120 accccccccaa cacaaa                                                     136

<210> SEQ ID NO 591
<211> LENGTH: 136
<212> TYPE: DNA
<213> ORGANISM: Dengue virus type 4
<220> FEATURE:
<223> OTHER INFORMATION: Dengue virus type 4 strain AY152315 region of
      conserved sequence in 3' untranslated region

<400> SEQUENCE: 591
gtggcatatt ggactagcgg ttagaggaga cccctcccat cactgacaaa acgcagcaaa      60 aggggggcccg aagccaggag gaagctgtac tcctggtgga aggactagag gttagaggag    120 accccccccaa cacaaa                                                     136

<210> SEQ ID NO 592
<211> LENGTH: 136
<212> TYPE: DNA
<213> ORGANISM: Dengue virus type 4
<220> FEATURE:
<223> OTHER INFORMATION: Dengue virus type 4 strain AY152319 region of
      conserved sequence in 3' untranslated region

<400> SEQUENCE: 592
gtggcatatt ggactagcgg ttagaggaga cccctcccat cactgacaaa acgcagcaaa      60 aggggggcccg aagccaggag gaagctgtac tcctggtgga aggactagag gttagaggag    120 accccccccaa cacaaa                                                     136

<210> SEQ ID NO 593
<211> LENGTH: 135
<212> TYPE: DNA
<213> ORGANISM: Dengue virus type 4
<220> FEATURE:
<223> OTHER INFORMATION: Dengue virus type 4 strain AY152323 region of
      conserved sequence in 3' untranslated region

<400> SEQUENCE: 593
gtggcatatt ggactagcgg ttagaggaga cccctcccat cactgacaaa acgcagcaaa      60 aggggggcccg aagccaggag gaagctgtac tcctggtgga aggactagag gttagaggag    120 accccccccaa cacaa                                                      135

<210> SEQ ID NO 594
<211> LENGTH: 135
<212> TYPE: DNA
<213> ORGANISM: Dengue virus type 4
```

```
<220> FEATURE:
<223> OTHER INFORMATION: Dengue virus type 4 strain AY152327 region of
      conserved sequence in 3' untranslated region

<400> SEQUENCE: 594
gtggcatatt ggactagcgg ttagaggaga cccctcccat cactgacaaa acgcagcaaa      60
aggggccccg aagccaggag gaagctgtac tcctggtgga aggactagag gttagaggag    120 accccccaa cacaa                                                      135

<210> SEQ ID NO 595
<211> LENGTH: 136
<212> TYPE: DNA
<213> ORGANISM: Dengue virus type 4
<220> FEATURE:
<223> OTHER INFORMATION: Dengue virus type 4 strain AY152331 region of
      conserved sequence in 3' untranslated region

<400> SEQUENCE: 595
gtggcatatt ggactagcgg ttagaggaga cccctcccat cactgacaaa acgcagcaaa      60
aggggccccg aagccaggag gaagctgtac tcctggtgga aggactagag gttagaggag    120 accccccaa cacaaa                                                     136

<210> SEQ ID NO 596
<211> LENGTH: 136
<212> TYPE: DNA
<213> ORGANISM: Dengue virus type 4
<220> FEATURE:
<223> OTHER INFORMATION: Dengue virus type 4 strain AY152335 region of
      conserved sequence in 3' untranslated region

<400> SEQUENCE: 596
gtggcatatt ggactagcgg ttagaggaga cccctcccat cactgacaaa acgcagcaaa      60
aggggccccg aagccaggag gaagctgtac tcctggtgga aggactagag gttagaggag    120 accccccaa cacaaa                                                     136

<210> SEQ ID NO 597
<211> LENGTH: 136
<212> TYPE: DNA
<213> ORGANISM: Dengue virus type 4
<220> FEATURE:
<223> OTHER INFORMATION: Dengue virus type 4 strain AY152339 region of
      conserved sequence in 3' untranslated region

<400> SEQUENCE: 597
gtggcatatt ggactagcgg ttagaggaga cccctcccat cactgacaaa acgcagcaaa      60
aggggccccg aagccaggag gaagctgtac tcctggtgga aggactagag gttagaggag    120 accccccaa cacaaa                                                     136

<210> SEQ ID NO 598
<211> LENGTH: 136
<212> TYPE: DNA
<213> ORGANISM: Dengue virus type 4
<220> FEATURE:
<223> OTHER INFORMATION: Dengue virus type 4 strain AY152343 region of
      conserved sequence in 3' untranslated region

<400> SEQUENCE: 598
gtggcatatt ggactagcgg ttagaggaga cccctcccat cactgacaaa acgcagcaaa      60
aggggccccg aagccaggag gaagctgtac tcctggtgga aggactagag gttagaggag    120 accccccaa cacaaa                                                     136
```

<210> SEQ ID NO 599
<211> LENGTH: 136
<212> TYPE: DNA
<213> ORGANISM: Dengue virus type 4
<220> FEATURE:
<223> OTHER INFORMATION: Dengue virus type 4 strain AY152347 region of
conserved sequence in 3' untranslated region

<400> SEQUENCE: 599
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 600
<211> LENGTH: 136
<212> TYPE: DNA
<213> ORGANISM: Dengue virus type 4
<220> FEATURE:
<223> OTHER INFORMATION: Dengue virus type 4 strain AY152351 region of
conserved sequence in 3' untranslated region

<400> SEQUENCE: 600
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 601
<211> LENGTH: 136
<212> TYPE: DNA
<213> ORGANISM: Dengue virus type 4
<220> FEATURE:
<223> OTHER INFORMATION: Dengue virus type 4 strain AY152355 region of
conserved sequence in 3' untranslated region

<400> SEQUENCE: 601
gtggtatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 602
<211> LENGTH: 136
<212> TYPE: DNA
<213> ORGANISM: Dengue virus type 4
<220> FEATURE:
<223> OTHER INFORMATION: Dengue virus type 4 strain AY152359 region of
conserved sequence in 3' untranslated region

<400> SEQUENCE: 602
gtggcatatt ggactagcgg ttagaggaga cccctcccat cactgacaaa acgcagcaaa 60
agggggcccg aagccaggag gaagctgtac tcctggtgga aggactagag gttagaggag 120
acccccccaa cacaaa 136

<210> SEQ ID NO 603
<211> LENGTH: 136
<212> TYPE: DNA
<213> ORGANISM: Dengue virus type 4
<220> FEATURE:
<223> OTHER INFORMATION: Dengue virus type 4 strain AY152363 region of
conserved sequence in 3' untranslated region

<400> SEQUENCE: 603

```
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136
```

<210> SEQ ID NO 604
<211> LENGTH: 136
<212> TYPE: DNA
<213> ORGANISM: Dengue virus type 4
<220> FEATURE:
<223> OTHER INFORMATION: Dengue virus type 4 strain AY152171 region of
      conserved sequence in 3' untranslated region

<400> SEQUENCE: 604

```
gtggcatatt ggactagcgg ttagaggaga cccctcccat cactgacaaa acgcagcaaa    60 aggggggcccg aagccaggag gaagctgtac tcctggtgga aggactagag gttagaggag   120 accccccccaa cacaaa                                                   136
```

<210> SEQ ID NO 605
<211> LENGTH: 137
<212> TYPE: DNA
<213> ORGANISM: Dengue virus type 4
<220> FEATURE:
<223> OTHER INFORMATION: Dengue virus type 4 strain VR217-1 region of
      conserved sequence in 3' untranslated region

<400> SEQUENCE: 605

```
gtggcatatt ggactagcgg ttagaggaga cccctcccat cactaacaaa acgcagcaaa    60 agggggggccc gaagccagga ggaagctgta ctcctggtgg aaggactaga ggttagagga   120
gaccccccca acacaaa                                                   137
```

<210> SEQ ID NO 606
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF317203

<400> SEQUENCE: 606

```
gtaagccctc agaaccgtct cggaa                                           25
```

<210> SEQ ID NO 607
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196835

<400> SEQUENCE: 607

```
gtaagccctc agaaccgtct cggaa                                           25
```

<210> SEQ ID NO 608
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260967

<400> SEQUENCE: 608

```
gtaagccctc agaaccgtct cggaa                                           25
```

<210> SEQ ID NO 609
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260968

<400> SEQUENCE: 609
gtaagccctc agaaccgtct cggaa                                            25

<210> SEQ ID NO 610
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260969

<400> SEQUENCE: 610
gtaagccctc agaaccgtct cggaa                                            25

<210> SEQ ID NO 611
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF481864

<400> SEQUENCE: 611
gtaagccctc agaaccgtct cggaa                                            25

<210> SEQ ID NO 612
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus M12294

<400> SEQUENCE: 612
gtaagccctc agaaccgtct cggaa                                            25

<210> SEQ ID NO 613
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF206518

<400> SEQUENCE: 613
gtaagccctc agaaccgtct cggaa                                            25

<210> SEQ ID NO 614
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF317203

<400> SEQUENCE: 614
gtaagccctc agaaccgtct cggaa                                            25

```
<210> SEQ ID NO 615
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF202541

<400> SEQUENCE: 615
gtaagccctc agaaccgtct cggaa                                               25

<210> SEQ ID NO 616
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404757

<400> SEQUENCE: 616
gtaagccctc agaaccgtct cggaa                                               25

<210> SEQ ID NO 617
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404753

<400> SEQUENCE: 617
gtaagccctc agaaccgtct cggaa                                               25

<210> SEQ ID NO 618
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404754

<400> SEQUENCE: 618
gtaagccctc agaaccgtct cggaa                                               25

<210> SEQ ID NO 619
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404755

<400> SEQUENCE: 619
gtaagccctc agaaccgtct cggaa                                               25

<210> SEQ ID NO 620
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404756

<400> SEQUENCE: 620
gtaagccctc agaaccgtct cggaa                                               25
```

-continued

```
<210> SEQ ID NO 621
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF017254

<400> SEQUENCE: 621
gtaagccctc agaaccgtct cggaa                                              25

<210> SEQ ID NO 622
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus L48977

<400> SEQUENCE: 622
gtaagccctc agaaccgtct cggaa                                              25

<210> SEQ ID NO 623
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196536

<400> SEQUENCE: 623
gtaagccctc agaaccgtct cggaa                                              25

<210> SEQ ID NO 624
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196537

<400> SEQUENCE: 624
gtaagccctc agaaccgtct cggaa                                              25

<210> SEQ ID NO 625
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196538

<400> SEQUENCE: 625
gtaagccctc agaaccgtct cggaa                                              25

<210> SEQ ID NO 626
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196540

<400> SEQUENCE: 626
gtaagccctc agaaccgtct cggaa                                              25

<210> SEQ ID NO 627
```

-continued

```
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196541

<400> SEQUENCE: 627
gtaagccctc agaaccgtct cggaa                                              25

<210> SEQ ID NO 628
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196542

<400> SEQUENCE: 628
gtaagccctc agaaccgtct cggaa                                              25

<210> SEQ ID NO 629
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196543

<400> SEQUENCE: 629
gtaagccctc agaaccgtct cggaa                                              25

<210> SEQ ID NO 630
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458343

<400> SEQUENCE: 630
gtaagccccc agaaccgtct cggaa                                              25

<210> SEQ ID NO 631
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458344

<400> SEQUENCE: 631
gtaagccctc agaaccgtct cggaa                                              25

<210> SEQ ID NO 632
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458347

<400> SEQUENCE: 632
gtaagccctc agaaccgtct cggaa                                              25

<210> SEQ ID NO 633
<211> LENGTH: 25
```

```
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458348

<400> SEQUENCE: 633
gtaagccctc agaaccgtct cggaa                                          25

<210> SEQ ID NO 634
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458350

<400> SEQUENCE: 634
gtaagccctc agaaccgtct cggaa                                          25

<210> SEQ ID NO 635
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458352

<400> SEQUENCE: 635
gtaagccctc agaaccgcct cggaa                                          25

<210> SEQ ID NO 636
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458353

<400> SEQUENCE: 636
gtaagccctc agaaccgtct cggaa                                          25

<210> SEQ ID NO 637
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458355

<400> SEQUENCE: 637
gtaagccctc agaaccgtct cggaa                                          25

<210> SEQ ID NO 638
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458358

<400> SEQUENCE: 638
gtaagccctc agaaccgtct cggaa                                          25

<210> SEQ ID NO 639
<211> LENGTH: 25
<212> TYPE: DNA
```

```
<213> ORGANISM: Artificial Sequence
<220> FEATURE:
<223> OTHER INFORMATION: synthetic  region of conserved sequence in 3'
      untranslated region of the genome of West Nile virus AF458360

<400> SEQUENCE: 639
gtaagccctc agaaccgtct cggaa                                              25

<210> SEQ ID NO 640
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458361

<400> SEQUENCE: 640
gtaagccctc agaaccgtct cggaa                                              25

<210> SEQ ID NO 641
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF208017

<400> SEQUENCE: 641
gtaagccctc agaaccgtct cggaa                                              25

<210> SEQ ID NO 642
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196539

<400> SEQUENCE: 642
gtaagccctc agaaccgtct cggaa                                              25

<210> SEQ ID NO 643
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196535

<400> SEQUENCE: 643
gtaagccctc agaaccgtct cggaa                                              25

<210> SEQ ID NO 644
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF458359

<400> SEQUENCE: 644
gtaagccctc agaaccgtct cggaa                                              25

<210> SEQ ID NO 645
<211> LENGTH: 25
<212> TYPE: DNA
<213> ORGANISM: Artificial Sequence
```

<220> FEATURE:
<223> OTHER INFORMATION: synthetic region of conserved sequence in 3'
      untranslated region of the genome of West Nile virus AF458357

<400> SEQUENCE: 645
gtaagccctc agaaccgtct cggaa                                          25

<210> SEQ ID NO 646
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF458354

<400> SEQUENCE: 646
gtaagccctc agaaccgtct cggaa                                          25

<210> SEQ ID NO 647
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF458349

<400> SEQUENCE: 647
gtaagccctc agaaccgtct cggaa                                          25

<210> SEQ ID NO 648
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF458345

<400> SEQUENCE: 648
gtaagccctc agaaccgtct cggaa                                          25

<210> SEQ ID NO 649
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF458346

<400> SEQUENCE: 649
gtaagcctct cagaaccgtt tcggaa                                         26

<210> SEQ ID NO 650
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF533540

<400> SEQUENCE: 650
gtaagccctc agaaccgtct cggaa                                          25

<210> SEQ ID NO 651
<211> LENGTH: 25
<212> TYPE: DNA
<213> ORGANISM: Artificial Sequence
<220> FEATURE:

```
<223> OTHER INFORMATION: synthetic  region of conserved sequence in 3'
      untranslated region of the genome of Japanese encephalitis
      virus AB051292

<400> SEQUENCE: 651
gaaagccctc agaaccgtct cggaa                                              25

<210> SEQ ID NO 652
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF014160

<400> SEQUENCE: 652
gaaagccctc agaaccgtct cggaa                                              25

<210> SEQ ID NO 653
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF014161

<400> SEQUENCE: 653
gaaagccctc agaaccgtct cggaa                                              25

<210> SEQ ID NO 654
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF045551

<400> SEQUENCE: 654
gaaagccctc agaaccgtct cggaa                                              25

<210> SEQ ID NO 655
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF069076

<400> SEQUENCE: 655
gaaagccctc agaaccgtct cggaa                                              25

<210> SEQ ID NO 656
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF075723

<400> SEQUENCE: 656
gaaagccctc agaaccgtct cggaa                                              25
```

```
<210> SEQ ID NO 657
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF080251

<400> SEQUENCE: 657
gaaagccctc ggaaccgtct cggaa                                          25

<210> SEQ ID NO 658
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098735

<400> SEQUENCE: 658
gaaagccctc agaaccgtct cggaa                                          25

<210> SEQ ID NO 659
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098736

<400> SEQUENCE: 659
gaaagccctc agaaccgtct cggaa                                          25

<210> SEQ ID NO 660
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098737

<400> SEQUENCE: 660
gaaagccctc agaaccgtct cggaa                                          25

<210> SEQ ID NO 661
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF217620

<400> SEQUENCE: 661
gaaagccctc agaaccgtct cggaa                                          25

<210> SEQ ID NO 662
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221499
```

<400> SEQUENCE: 662
gaaagccctc agaaccgtct cggaa                    25

<210> SEQ ID NO 663
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221500

<400> SEQUENCE: 663
gaaagccctc agaaccgtct cggaa                    25

<210> SEQ ID NO 664
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF254452

<400> SEQUENCE: 664
gaaagccctc agaaccgtct cggaa                    25

<210> SEQ ID NO 665
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF254453

<400> SEQUENCE: 665
gaaagccctc agaaccgtct cggaa                    25

<210> SEQ ID NO 666
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF315119

<400> SEQUENCE: 666
gaaagccctc agaactgtct cggaa                    25

<210> SEQ ID NO 667
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF416457

<400> SEQUENCE: 667
gaaagccctc agaaccgtct cggaa                    25

<210> SEQ ID NO 668
<211> LENGTH: 25
<212> TYPE: DNA
<213> ORGANISM: Artificial Sequence

```
<220> FEATURE:
<223> OTHER INFORMATION: synthetic region of conserved sequence in 3'
      untranslated region of the genome of Japanese encephalitis
      virus AF486638

<400> SEQUENCE: 668
gaaagccctc agaaccgtct cggaa                                           25

<210> SEQ ID NO 669
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus U14163

<400> SEQUENCE: 669
gaaagccctc agaaccgtct cggaa                                           25

<210> SEQ ID NO 670
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus U15763

<400> SEQUENCE: 670
gaaagccctc agaaccgtct cggaa                                           25

<210> SEQ ID NO 671
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus L48961

<400> SEQUENCE: 671
gaaagccctc agaaccgtct cggaa                                           25

<210> SEQ ID NO 672
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus U47032

<400> SEQUENCE: 672
gaaagccctc agaaccgtct cggaa                                           25

<210> SEQ ID NO 673
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus M18370

<400> SEQUENCE: 673
gaaagccctc agaaccgtct cggaa                                           25
```

<210> SEQ ID NO 674
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus M55506

<400> SEQUENCE: 674
gaaagccctc agaaccgtct cggaa                                           25

<210> SEQ ID NO 675
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus L78128

<400> SEQUENCE: 675
gaaagccctc agaaccgtct cggaa                                           25

<210> SEQ ID NO 676
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus D90195

<400> SEQUENCE: 676
gaaagccctc agaaccgtct cggaa                                           25

<210> SEQ ID NO 677
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus D90194

<400> SEQUENCE: 677
gaaagccctc agaaccgtct cggaa                                           25

<210> SEQ ID NO 678
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF311748

<400> SEQUENCE: 678
gaaagccctc agaaccgtct cggaa                                           25

<210> SEQ ID NO 679
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF092550

<400> SEQUENCE: 679
gaaagccctc agaaccgtct cggaa                                         25

<210> SEQ ID NO 680
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF092552

<400> SEQUENCE: 680
gaaagccctc agaaccgtct cggaa                                         25

<210> SEQ ID NO 681
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF092553

<400> SEQUENCE: 681
gaaagccctc agaaccgtct cggaa                                         25

<210> SEQ ID NO 682
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF139531

<400> SEQUENCE: 682
gaaagccctc agaaccgtct cggaa                                         25

<210> SEQ ID NO 683
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF148900

<400> SEQUENCE: 683
gaaagccctc agaaccgtct cggaa                                         25

<210> SEQ ID NO 684
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF148902

<400> SEQUENCE: 684
gaaagccctc agaaccgtct cggaa                                         25

<210> SEQ ID NO 685
<211> LENGTH: 25
<212> TYPE: DNA

<210> SEQ ID NO 685
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF218068

<400> SEQUENCE: 685
gaaagccctc agaaccgtct cggaa                                          25

<210> SEQ ID NO 686
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF289816

<400> SEQUENCE: 686
gaaagccctc agaaccgtct cggaa                                          25

<210> SEQ ID NO 687
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF318291

<400> SEQUENCE: 687
gaaagccctc agaaccgtct cggaa                                          25

<210> SEQ ID NO 688
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus L48967

<400> SEQUENCE: 688
gaaagccctc agaaccgtct cggaa                                          25

<210> SEQ ID NO 689
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus L48968

<400> SEQUENCE: 689 gaaaccctc agaaccgtct cggaa                                           25

<210> SEQ ID NO 690
<211> LENGTH: 25
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus L54067

<400> SEQUENCE: 690
gaaagccctc agaaccgtct cggaa                                          25

<210> SEQ ID NO 691
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54068

<400> SEQUENCE: 691
gaaagccctc agaaccgtct cggaa                                              25

<210> SEQ ID NO 692
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54069

<400> SEQUENCE: 692
gaaagccctc agaaccgtct cggaa                                              25

<210> SEQ ID NO 693
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54070

<400> SEQUENCE: 693
gaaagccctc agaaccgtct cggaa                                              25

<210> SEQ ID NO 694
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54071

<400> SEQUENCE: 694
gaaagccctc agaaccgtct cggaa                                              25

<210> SEQ ID NO 695
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54070

<400> SEQUENCE: 695
gaaagccctc agaaccgtct cggaa                                              25

<210> SEQ ID NO 696
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis virus L54122

<400> SEQUENCE: 696
gaaagccctc agaaccgtct cggaa                                              25

<210> SEQ ID NO 697
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L54123

<400> SEQUENCE: 697
gaaagccctc agaaccgtct cggaa                                              25

<210> SEQ ID NO 698
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306514

<400> SEQUENCE: 698
gaaagccctc agaaccgtct cggaa                                              25

<210> SEQ ID NO 699
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306515

<400> SEQUENCE: 699
gaaagccctc agaaccgttt cggaa                                              25

<210> SEQ ID NO 700
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306516

<400> SEQUENCE: 700
gaaagccctc agaaccgttt cggaa                                              25

<210> SEQ ID NO 701
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306517

<400> SEQUENCE: 701
gaaagccctc aaaaccgttt cggaa                                              25

<210> SEQ ID NO 702
<211> LENGTH: 26

<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus AF161266

<400> SEQUENCE: 702
gaaagcctcc cagaaccgtc tcggaa                                          26

<210> SEQ ID NO 703
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus M35172

<400> SEQUENCE: 703
gaaagcctcc cagaaccgtc tcggaa                                          26

<210> SEQ ID NO 704
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus L48972

<400> SEQUENCE: 704
gaaagcctcc cagaaccgtc tcggaa                                          26

<210> SEQ ID NO 705
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus L48973

<400> SEQUENCE: 705
gaaagcctcc cagaaccgtc tcggaa                                          26

<210> SEQ ID NO 706
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus L48974

<400> SEQUENCE: 706
gaaagcctcc cagacccgtc tcggaa                                          26

<210> SEQ ID NO 707
<211> LENGTH: 26
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus L48975

<400> SEQUENCE: 707

```
gaaagcctcc cagaaccgtc tcggaa                                           26
```

```
<210> SEQ ID NO 708
<211> LENGTH: 26
<212> TYPE: DNA
<213> ORGANISM: Artificial Sequence
<220> FEATURE:
<223> OTHER INFORMATION: synthetic  region of conserved sequence in 3'
      untranslated region of the genome of Murray Valley encephalitis
      virus L48976

<400> SEQUENCE: 708
gaaagcctcc cagaaccgtt tcggaa                                           26
```

```
<210> SEQ ID NO 709
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF458351

<400> SEQUENCE: 709
gtaagccctc agaaccgtct cggga                                            25
```

```
<210> SEQ ID NO 710
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF458356

<400> SEQUENCE: 710
gtaagccctc agaaccgcct cggaa                                            25
```

```
<210> SEQ ID NO 711
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297840

<400> SEQUENCE: 711
gtaagccctc agaaccgcct cggaa                                            25
```

```
<210> SEQ ID NO 712
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297841

<400> SEQUENCE: 712
gtaagccctc agaaccgtct cggaa                                            25
```

```
<210> SEQ ID NO 713
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297842

<400> SEQUENCE: 713
```
gtaagccctc agaaccgtct cggaa                                          25

<210> SEQ ID NO 714
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297843

<400> SEQUENCE: 714
gtaagccctc agaaccgtct cggaa                                          25

<210> SEQ ID NO 715
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297844

<400> SEQUENCE: 715
gtaagccctc agaaccgtct cggaa                                          25

<210> SEQ ID NO 716
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297845

<400> SEQUENCE: 716
gtaagccctc agaaccgtct cggaa                                          25

<210> SEQ ID NO 717
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297846

<400> SEQUENCE: 717
gtaagccctc agaaccgcct cggaa                                          25

<210> SEQ ID NO 718
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297847

<400> SEQUENCE: 718
gtaagccctc agaaccgcct cggaa                                          25

<210> SEQ ID NO 719
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297848

<400> SEQUENCE: 719
gtaagccctc agaaccgtct cggaa                                          25

<210> SEQ ID NO 720
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297849

<400> SEQUENCE: 720
gtaagccctc agaaccgtct cggaa                                             25

<210> SEQ ID NO 721
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297850

<400> SEQUENCE: 721
gtaagccctc agaaccgcct cggaa                                             25

<210> SEQ ID NO 722
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297851

<400> SEQUENCE: 722
gtaagccctc agaaccgcct cgggt                                             25

<210> SEQ ID NO 723
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297852

<400> SEQUENCE: 723
gtaagccctc agaaccgcct cggaa                                             25

<210> SEQ ID NO 724
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297853

<400> SEQUENCE: 724
gtaagccctc agaaccgcct cggaa                                             25

<210> SEQ ID NO 725
<211> LENGTH: 25
<212> TYPE: DNA
<213> ORGANISM: Artificial Sequence
<220> FEATURE:
<223> OTHER INFORMATION: synthetic region of conserved sequence in 3'
      untranslated region of the genome of Kunjin virus AF297854

<400> SEQUENCE: 725
gtaagccctc agaaccgtct cggaa                                             25

```
<210> SEQ ID NO 726
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297855

<400> SEQUENCE: 726
gtaagccctc agaaccgtct cggaa                                          25

<210> SEQ ID NO 727
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297856

<400> SEQUENCE: 727
gtaagccctc agaaccgtct cggaa                                          25

<210> SEQ ID NO 728
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297857

<400> SEQUENCE: 728
gtaagccgtc agaaccgtct cggaa                                          25

<210> SEQ ID NO 729
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297858

<400> SEQUENCE: 729
gtaagccctc agaaccgtct cggaa                                          25

<210> SEQ ID NO 730
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus AF297859

<400> SEQUENCE: 730
gtaagccctc agaaccgtct cggaa                                          25

<210> SEQ ID NO 731
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L48978

<400> SEQUENCE: 731
gtaagccctc agaaccgtct cggaa                                          25
```

```
<210> SEQ ID NO 732
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L49311

<400> SEQUENCE: 732
gtaagccctc agaaccgtct cggaa                                          25

<210> SEQ ID NO 733
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus D00246

<400> SEQUENCE: 733
gtaagccctc agaaccgtct cggaa                                          25

<210> SEQ ID NO 734
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L48979

<400> SEQUENCE: 734
gtaagccctc agaaccgtct cggaa                                          25

<210> SEQ ID NO 735
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L24512

<400> SEQUENCE: 735
gtaagccctc agaaccgtct cggaa                                          25

<210> SEQ ID NO 736
<211> LENGTH: 25
<212> TYPE: DNA
<213> ORGANISM: Artificial Sequence
<220> FEATURE:
<223> OTHER INFORMATION: synthetic  region of conserved sequence in 3'
      untranslated region of the genome of Koutango virus L48980

<400> SEQUENCE: 736
gtaatccctc agaaccgtct cggaa                                          25

<210> SEQ ID NO 737
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF196835

<400> SEQUENCE: 737
tcctagtcta tcccaggtgt caa                                            23

<210> SEQ ID NO 738
```

```
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260967

<400> SEQUENCE: 738
tcctagtcta tcccaggtgt caa                                             23

<210> SEQ ID NO 739
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260968

<400> SEQUENCE: 739
tcctagtcta tcccaggtgt caa                                             23

<210> SEQ ID NO 740
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF260969

<400> SEQUENCE: 740
tcctagtcta tcccaggtgt caa                                             23

<210> SEQ ID NO 741
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF481864

<400> SEQUENCE: 741
tcctagtcta tcccaggtgt caa                                             23

<210> SEQ ID NO 742
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus M12294

<400> SEQUENCE: 742
ccctagtcta tcccaggtgt caa                                             23

<210> SEQ ID NO 743
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF206518

<400> SEQUENCE: 743
tcctagtcta tcccaggtgt caa                                             23

<210> SEQ ID NO 744
<211> LENGTH: 23
```

```
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF317203

<400> SEQUENCE: 744
tcctagtcta tcccaggtgt caa                                              23

<210> SEQ ID NO 745
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF202541

<400> SEQUENCE: 745
tcctagtcta tcccaggtgt caa                                              23

<210> SEQ ID NO 746
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404757

<400> SEQUENCE: 746
tcctagtcta tcccaggtgt caa                                              23

<210> SEQ ID NO 747
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404753

<400> SEQUENCE: 747
tcctagtcta tcccaggtgt caa                                              23

<210> SEQ ID NO 748
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404754

<400> SEQUENCE: 748
tcctagtcta tcccaggtgt caa                                              23

<210> SEQ ID NO 749
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404755

<400> SEQUENCE: 749
tcctagtcta tcccaggtgt caa                                              23

<210> SEQ ID NO 750
<211> LENGTH: 23
<212> TYPE: DNA
```

```
<213> ORGANISM: Artificial Sequence
<220> FEATURE:
<223> OTHER INFORMATION: synthetic  region of conserved sequence in 3'
      untranslated region of the genome of West Nile virus AF404756

<400> SEQUENCE: 750
tcctagtcta tcccaggtgt caa                                           23

<210> SEQ ID NO 751
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF017254

<400> SEQUENCE: 751
tcctagtcta tcccaggtat caa                                           23

<210> SEQ ID NO 752
<211> LENGTH: 23
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L24512

<400> SEQUENCE: 752
tcctagtcta tcccaggtgt caa                                           23

<210> SEQ ID NO 753
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AB051292

<400> SEQUENCE: 753
tcccagtcta ttcccaggtg tcaa                                          24

<210> SEQ ID NO 754
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF014160

<400> SEQUENCE: 754
tcccagtcta ttcccaggtg tcaa                                          24

<210> SEQ ID NO 755
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF014161

<400> SEQUENCE: 755
tcccagtcta ttcccaggtg tcaa                                          24

<210> SEQ ID NO 756
```

<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF045551

<400> SEQUENCE: 756
tcccactcta ttcccaggtg tcaa                                          24

<210> SEQ ID NO 757
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF069076

<400> SEQUENCE: 757
tcccagtcta ttcccaggtg tcaa                                          24

<210> SEQ ID NO 758
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF075723

<400> SEQUENCE: 758
tcccagtcta ttcccaggtg tcaa                                          24

<210> SEQ ID NO 759
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF080251

<400> SEQUENCE: 759
tcccagtcta ttcccaggtg tcaa                                          24

<210> SEQ ID NO 760
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098735

<400> SEQUENCE: 760
tcccagtcta ttcccaggtg tcaa                                          24

<210> SEQ ID NO 761
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098736

<400> SEQUENCE: 761
tcccagtcta ttcccaggtg tcaa                                              24

<210> SEQ ID NO 762
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098737

<400> SEQUENCE: 762
tcccagtcta tctccaggtg tcaa                                              24

<210> SEQ ID NO 763
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF217620

<400> SEQUENCE: 763
tcccagtcta ttcccaggtg tcaa                                              24

<210> SEQ ID NO 764
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221499

<400> SEQUENCE: 764
tcccagtcta ttcccaggtg tcaa                                              24

<210> SEQ ID NO 765
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221500

<400> SEQUENCE: 765
tcccagtcta ttcccaggtg tcaa                                              24

<210> SEQ ID NO 766
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF254452

<400> SEQUENCE: 766
tcccagtcta ttcccaggtg tcaa                                              24

<210> SEQ ID NO 767
<211> LENGTH: 24
<212> TYPE: DNA
<213> ORGANISM: Artificial Sequence
<220> FEATURE:

```
<223> OTHER INFORMATION: synthetic  region of conserved sequence in 3'
      untranslated region of the genome of Japanese encephalitis
      virus AF254453

<400> SEQUENCE: 767
tcccagtcta ttcccaggtg tcaa                                              24

<210> SEQ ID NO 768
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF315119

<400> SEQUENCE: 768
tcccagtcta ttcccaggtg tcaa                                              24

<210> SEQ ID NO 769
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF416457

<400> SEQUENCE: 769
tcccagtcta ttcccaggtg tcaa                                              24

<210> SEQ ID NO 770
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF486638

<400> SEQUENCE: 770
tcccagtata ttcccaggtg tcaa                                              24

<210> SEQ ID NO 771
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U14163

<400> SEQUENCE: 771
tcccagtcta ttcccaggtg tcaa                                              24

<210> SEQ ID NO 772
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U15763

<400> SEQUENCE: 772
tcccagtcta ttcccaggtg tcaa                                              24
```

```
<210> SEQ ID NO 773
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L48961

<400> SEQUENCE: 773
tcccagtcta ttcccaggtg tcaa                                            24

<210> SEQ ID NO 774
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U47032

<400> SEQUENCE: 774
tcctagtcta ttcccaggtg tcaa                                            24

<210> SEQ ID NO 775
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus M18370

<400> SEQUENCE: 775
tcccagtcta ttcccaggtg tcaa                                            24

<210> SEQ ID NO 776
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus M55506

<400> SEQUENCE: 776
tcccagtcta ttcccaggtg tcaa                                            24

<210> SEQ ID NO 777
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L78128

<400> SEQUENCE: 777
tcccagtcta ttcccaggtg tcaa                                            24

<210> SEQ ID NO 778
<211> LENGTH: 24
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus D90195
```

<400> SEQUENCE: 778
tcccagtcta ttcccaggtg tcaa    24

<210> SEQ ID NO 779
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus D90194

<400> SEQUENCE: 779
tcccagtcta ttcccaggtg tcaa    24

<210> SEQ ID NO 780
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF311748

<400> SEQUENCE: 780
tcccagtcta ttcccaggtg tcaa    24

<210> SEQ ID NO 781
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF306514

<400> SEQUENCE: 781
tcccactcta ttcccaggtg tcaa    24

<210> SEQ ID NO 782
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF306515

<400> SEQUENCE: 782
tcccagtcta ttcccaggtg tcaa    24

<210> SEQ ID NO 783
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus AF306516

<400> SEQUENCE: 783
tcccagtcta ttcccaggtg tcaa    24

<210> SEQ ID NO 784
<211> LENGTH: 24
<212> TYPE: DNA
<213> ORGANISM: Artificial Sequence

```
<220> FEATURE:
<223> OTHER INFORMATION: synthetic region of conserved sequence in 3'
      untranslated region of the genome of Japanese encephalitis
      virus AF306517

<400> SEQUENCE: 784
tcccactcta ttcccaggtg tcaa                                             24

<210> SEQ ID NO 785
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus D00037

<400> SEQUENCE: 785
tcccagtcta ttcccaggtg tcaa                                             24

<210> SEQ ID NO 786
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Japanese encephalitis
      virus M14933

<400> SEQUENCE: 786
tcccagtcta ttcccaggtg tcaa                                             24

<210> SEQ ID NO 787
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus AF161266

<400> SEQUENCE: 787
tcctagtctt ttcccaggtg tcaa                                             24

<210> SEQ ID NO 788
<211> LENGTH: 24
<212> TYPE: DNA
<213> ORGANISM: Artificial Sequence
<220> FEATURE:
<223> OTHER INFORMATION: synthetic region of conserved sequence in 3'
      untranslated region of the genome of Murray Valley encephalitis
      virus M35172

<400> SEQUENCE: 788
tcctagtctt ttcccaggtg tcaa                                             24

<210> SEQ ID NO 789
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of West Nile virus AF196835

<400> SEQUENCE: 789
ggactagagg ttagaggaga ccccgcgg                                         28
```

<210> SEQ ID NO 790
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus AF260967

<400> SEQUENCE: 790
ggactagagg ttagaggaga ccccgcgg 28

<210> SEQ ID NO 791
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus AF260968

<400> SEQUENCE: 791
ggactagagg ttagaggaga ccccgcgg 28

<210> SEQ ID NO 792
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus AF260969

<400> SEQUENCE: 792
ggactagagg ttagaggaga ccccgcgg 28

<210> SEQ ID NO 793
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus AF481864

<400> SEQUENCE: 793
ggactagagg ttagaggaga ccccgcgg 28

<210> SEQ ID NO 794
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus M12294

<400> SEQUENCE: 794
ggactagagg ttagaggaga ccccgcgt 28

<210> SEQ ID NO 795
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of West Nile virus AF206518

<400> SEQUENCE: 795
ggactagagg ttagaggaga ccccgcgg 28

<210> SEQ ID NO 796

```
<210> SEQ ID NO 796
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF317203

<400> SEQUENCE: 796
ggactagagg ttagaggaga ccccgcgg                                            28

<210> SEQ ID NO 797
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF202541

<400> SEQUENCE: 797
ggactagagg ttagaggaga ccccgcgg                                            28

<210> SEQ ID NO 798
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404757

<400> SEQUENCE: 798
ggactagagg ttagaggaga ccccgcgg                                            28

<210> SEQ ID NO 799
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404753

<400> SEQUENCE: 799
ggactagagg ttagaggaga ccccgcgg                                            28

<210> SEQ ID NO 800
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404754

<400> SEQUENCE: 800
ggactagagg ttagaggaga ccccgcgg                                            28

<210> SEQ ID NO 801
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404755

<400> SEQUENCE: 801
ggactagagg ttagaggaga ccccgcgg                                            28

<210> SEQ ID NO 802
<211> LENGTH: 28
```

```
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF404756

<400> SEQUENCE: 802
ggactagagg ttagaggaga ccccgcgg                                               28

<210> SEQ ID NO 803
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF017254

<400> SEQUENCE: 803
ggactagagg ttagaggaga ccccgcgg                                               28

<210> SEQ ID NO 804
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of West Nile virus AF208017

<400> SEQUENCE: 804
ggactagtgg ttagaggaga ccccacgt                                               28

<210> SEQ ID NO 805
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Kunjin virus L24512

<400> SEQUENCE: 805
ggactagagg ttagaggaga ccccgcgt                                               28

<210> SEQ ID NO 806
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AB051292

<400> SEQUENCE: 806
ggactagagg ttagaggaga ccccgtgg                                               28

<210> SEQ ID NO 807
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF014160

<400> SEQUENCE: 807
ggactagagg ttagaggaga ccccgtgg                                               28

<210> SEQ ID NO 808
```

<210> SEQ ID NO 808
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF014161

<400> SEQUENCE: 808
ggactagagg ttagaggaga ccccgtgg                                28

<210> SEQ ID NO 809
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF045551

<400> SEQUENCE: 809
ggactagagg ttagaggaga ccccgtgg                                28

<210> SEQ ID NO 810
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF069076

<400> SEQUENCE: 810
ggactagagg ttagaggaga ccccgtgg                                28

<210> SEQ ID NO 811
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF075723

<400> SEQUENCE: 811
ggactagagg ttagaggaga ccccgtgg                                28

<210> SEQ ID NO 812
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF080251

<400> SEQUENCE: 812
ggactagagg ttagaggaga ccccgtgg                                28

<210> SEQ ID NO 813
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Japanese encephalitis virus AF098735

<400> SEQUENCE: 813
ggactagagg ttagaggaga ccccgtgg                                              28

<210> SEQ ID NO 814
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098736

<400> SEQUENCE: 814
ggactagagg ttagaggaga ccccgtgg                                              28

<210> SEQ ID NO 815
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF098737

<400> SEQUENCE: 815
ggactagagg ttagaggaga ccccgtgg                                              28

<210> SEQ ID NO 816
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF217620

<400> SEQUENCE: 816
ggactagagg ttagaggaga ccccgtgg                                              28

<210> SEQ ID NO 817
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221499

<400> SEQUENCE: 817
ggactagagg ttagaggaga ccccgtgg                                              28

<210> SEQ ID NO 818
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF221500

<400> SEQUENCE: 818
ggactagagg ttagaggaga ccccgtgg                                              28

<210> SEQ ID NO 819
<211> LENGTH: 28
<212> TYPE: DNA
<213> ORGANISM: Artificial Sequence
<220> FEATURE:

```
<223> OTHER INFORMATION: synthetic  region of conserved sequence in 3'
      untranslated region of the genome of Japanese encephalitis
      virus AF254452

<400> SEQUENCE: 819
ggactagagg ttagaggaga ccccgtgg                                         28

<210> SEQ ID NO 820
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF254453

<400> SEQUENCE: 820
ggactagagg ttagaggaga ccccgtgg                                         28

<210> SEQ ID NO 821
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF315119

<400> SEQUENCE: 821
ggactagagg ttagaggaga ccccgtgg                                         28

<210> SEQ ID NO 822
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF416457

<400> SEQUENCE: 822
ggactagagg ttagaggaga ccccgtgg                                         28

<210> SEQ ID NO 823
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF486638

<400> SEQUENCE: 823
ggactagagg ttagaggaga ccccgtgg                                         28

<210> SEQ ID NO 824
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U14163

<400> SEQUENCE: 824
ggactagagg ttagaggaga ccccgtgg                                         28
```

```
<210> SEQ ID NO 825
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U15763

<400> SEQUENCE: 825
ggactagagg ttagaggaga ccccgtgg                                            28

<210> SEQ ID NO 826
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L48961

<400> SEQUENCE: 826
ggactagagg ttagaggaga ccccgtgg                                            28

<210> SEQ ID NO 827
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus U47032

<400> SEQUENCE: 827
ggactagagg ttagaggaga ccccgtgg                                            28

<210> SEQ ID NO 828
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus M18370

<400> SEQUENCE: 828
ggactagagg ttagaggaga ccccgtgg                                            28

<210> SEQ ID NO 829
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus M55506

<400> SEQUENCE: 829
ggactagagg ttagaggaga ccccgtgg                                            28

<210> SEQ ID NO 830
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus L78128
```

```
<400> SEQUENCE: 830
ggactagagg ttagaggaga ccccgtgg                                          28

<210> SEQ ID NO 831
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus D90195

<400> SEQUENCE: 831
ggactagagg ttagaggaga ccccgtgg                                          28

<210> SEQ ID NO 832
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus D90194

<400> SEQUENCE: 832
ggactagagg ttagaggaga ccccgtgg                                          28

<210> SEQ ID NO 833
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF311748

<400> SEQUENCE: 833
ggactagagg ttagaggaga ccccgtgg                                          28

<210> SEQ ID NO 834
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306514

<400> SEQUENCE: 834
ggactagagg ttagaggaga ccccgtgg                                          28

<210> SEQ ID NO 835
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306515

<400> SEQUENCE: 835
ggactagagg ttagaggaga ccccgtgg                                          28

<210> SEQ ID NO 836
<211> LENGTH: 28
<212> TYPE: DNA
<213> ORGANISM: Artificial Sequence
```

```
<220> FEATURE:
<223> OTHER INFORMATION: synthetic  region of conserved sequence in 3'
      untranslated region of the genome of Japanese encephalitis
      virus AF306516

<400> SEQUENCE: 836
ggactagagg ttagaggaga ccccgtgg                                          28

<210> SEQ ID NO 837
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Japanese encephalitis
      virus AF306517

<400> SEQUENCE: 837
ggactagagg ttagaggaga ccccgtgg                                          28

<210> SEQ ID NO 838
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Murray Valley encephalitis
      virus AF161266

<400> SEQUENCE: 838
ggactagagg ttagaggaga ccccactc                                          28

<210> SEQ ID NO 839
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Murray Valley encephalitis
      virus M35172

<400> SEQUENCE: 839
ggactagagg ttagaggaga ccccactc                                          28

<210> SEQ ID NO 840
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF226685

<400> SEQUENCE: 840
ggactagagg ttagaggaga cccccgc                                           28

<210> SEQ ID NO 841
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF311956

<400> SEQUENCE: 841
ggactagagg ttagaggaga cccccgc                                           28
```

<210> SEQ ID NO 842
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF311957

<400> SEQUENCE: 842
ggactagagg ttagaggaga cccccgc                                        28

<210> SEQ ID NO 843
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF311958

<400> SEQUENCE: 843
ggactagagg ttagaggaga cccccgc                                        28

<210> SEQ ID NO 844
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AY145121

<400> SEQUENCE: 844
ggactagagg ttagaggaga cccccgc                                        28

<210> SEQ ID NO 845
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AY145122

<400> SEQUENCE: 845
ggactagagg ttagaggaga cccccgc                                        28

<210> SEQ ID NO 846
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF514878

<400> SEQUENCE: 846
ggactagagg ttagaggaga cccccgc                                        28

<210> SEQ ID NO 847
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF514885

<400> SEQUENCE: 847
ggactagagg ttagaggaga cccccccgc                28

<210> SEQ ID NO 848
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF514889

<400> SEQUENCE: 848
ggactagagg ttagaggaga cccccccgc                28

<210> SEQ ID NO 849
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 2
      AF489932

<400> SEQUENCE: 849
ggactagagg ttagaggaga cccccca                28

<210> SEQ ID NO 850
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AF226687

<400> SEQUENCE: 850
ggactagagg ttagaggaga cccccccgc                28

<210> SEQ ID NO 851
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AX224213

<400> SEQUENCE: 851
ggactagagg ttagaggaga ccccccg                28

<210> SEQ ID NO 852
<211> LENGTH: 28
<212> TYPE: DNA
<213> ORGANISM: Artificial Sequence
<220> FEATURE:
<223> OTHER INFORMATION: synthetic region of conserved sequence in 3'
      untranslated region of the genome of Dengue virus type 1
      AX224215

<400> SEQUENCE: 852
ggactagagg ttagaggaga ccccccg                28

<210> SEQ ID NO 853
<211> LENGTH: 28
<212> TYPE: DNA

<213> ORGANISM: Artificial Sequence
<220> FEATURE:
<223> OTHER INFORMATION: synthetic region of conserved sequence in 3' untranslated region of the genome of Dengue virus type 1 AX224217

<400> SEQUENCE: 853
ggactagagg ttagaggaga ccccccg 28

<210> SEQ ID NO 854
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Dengue virus type 1 AX224219

<400> SEQUENCE: 854
ggactagagg ttagaggaga ccccccg 28

<210> SEQ ID NO 855
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Dengue virus type 1 AX224225

<400> SEQUENCE: 855
ggactagagg ttagaggaga ccccccg 28

<210> SEQ ID NO 856
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Dengue virus type 1 AX224227

<400> SEQUENCE: 856
ggactagagg ttagaggaga cccccgc 28

<210> SEQ ID NO 857
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Dengue virus type 1 AX224233

<400> SEQUENCE: 857
ggactagagg ttagaggaga cccccgc 28

<210> SEQ ID NO 858
<211> LENGTH: 28
<212> TYPE: DNA
<213> ORGANISM: Artificial Sequence
<220> FEATURE:
<223> OTHER INFORMATION: synthetic region of conserved sequence in 3' untranslated region of the genome of Dengue virus type 1 AB074760

<400> SEQUENCE: 858
ggactagagg ttagaggaga cccccgc 28

<210> SEQ ID NO 859
<211> LENGTH: 28
<212> TYPE: DNA
<213> ORGANISM: Artificial Sequence
<220> FEATURE:
<223

```
              U61246

<400> SEQUENCE: 864
ggactagagg ttagaggaga cccccccg                                         28

<210> SEQ ID NO 865
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      U61247

<400> SEQUENCE: 865
ggactagagg ttagaggaga cccccccg                                         28

<210> SEQ ID NO 866
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100465

<400> SEQUENCE: 866
ggactagagg ttagaggaga ccccccca                                         28

<210> SEQ ID NO 867
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100466

<400> SEQUENCE: 867
ggactagagg ttagaggaga ccccccca                                         28

<210> SEQ ID NO 868
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AX224209

<400> SEQUENCE: 868
ggactagagg ttagaggaga cccccgc                                          28

<210> SEQ ID NO 869
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF180818

<400> SEQUENCE: 869
ggactagagg ttagaggaga cccccgc                                          28

<210> SEQ ID NO 870
<211> LENGTH: 28
```

```
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      AF326573

<400> SEQUENCE: 870
ggactagagg ttagaggaga ccccccca                                       28

<210> SEQ ID NO 871
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF350498

<400> SEQUENCE: 871
ggactagagg ttagaggaga cccccgc                                        28

<210> SEQ ID NO 872
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF359579

<400> SEQUENCE: 872
ggactagagg ttagaggaga ccccccg                                        28

<210> SEQ ID NO 873
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AY037116

<400> SEQUENCE: 873
ggactagagg ttagaggaga ccccccg                                        28

<210> SEQ ID NO 874
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309950

<400> SEQUENCE: 874
ggactagagg ttagaggaga ccccccg                                        28

<210> SEQ ID NO 875
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309953

<400> SEQUENCE: 875
```
ggactagagg ttagaggaga ccccccca                                              28

<210> SEQ ID NO 876
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309954

<400> SEQUENCE: 876
ggactagagg ttagaggaga ccccccca                                              28

<210> SEQ ID NO 877
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309959

<400> SEQUENCE: 877
ggactagagg ttagaggaga ccccccca                                              28

<210> SEQ ID NO 878
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309962

<400> SEQUENCE: 878
ggactagagg ttagaggaga cccccccg                                              28

<210> SEQ ID NO 879
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309963

<400> SEQUENCE: 879
ggactagagg ttagaggaga cccccccg                                              28

<210> SEQ ID NO 880
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF309964

<400> SEQUENCE: 880
ggactagagg ttagaggaga cccccccg                                              28

<210> SEQ ID NO 881
<211> LENGTH: 28
<212> TYPE: DNA
<213> ORGANISM: Artificial Sequence
<220> FEATURE:
<223> OTHER INFORMATION: synthetic  region of conserved sequence in 3' untranslated region of the genome of Dengue virus type 2
AF309965

<400> SEQUENCE: 881
ggactagagg ttagaggaga ccccccca                                    28

<210> SEQ ID NO 882
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      AF289029

<400> SEQUENCE: 882
ggactagagg ttagaggaga ccccccca                                    28

<210> SEQ ID NO 883
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF208496

<400> SEQUENCE: 883
ggactagagg ttagaggaga ccccccca                                    28

<210> SEQ ID NO 884
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF310146

<400> SEQUENCE: 884
ggactagagg ttagaggaga cccccgc                                     28

<210> SEQ ID NO 885
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 3
      AF310149

<400> SEQUENCE: 885
ggactagagg ttagaggaga cccccgc                                     28

<210> SEQ ID NO 886
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      AF310153

<400> SEQUENCE: 886
ggactagagg ttagaggaga ccccccca                                    28

<210> SEQ ID NO 887

```
<210> SEQ ID NO 887
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      AF226686

<400> SEQUENCE: 887
ggactagagg ttagaggaga ccccccgc                                              28

<210> SEQ ID NO 888
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF276619

<400> SEQUENCE: 888
ggactagagg ttagaggaga cccccccg                                              28

<210> SEQ ID NO 889
<211> LENGTH: 28
<212> TYPE: DNA
<213> ORGANISM: Artificial Sequence
<220> FEATURE:
<223> OTHER INFORMATION: synthetic  region of conserved sequence in 3'
    untranslated region of the genome of Dengue virus type 2
      AF169678

<400> SEQUENCE: 889
ggactagagg ttagaggaga cccccccg                                              28

<210> SEQ ID NO 890
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169679

<400> SEQUENCE: 890
ggactagagg ttagaggaga cccccccg                                              28

<210> SEQ ID NO 891
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169680

<400> SEQUENCE: 891
ggactagagg ttagaggaga cccccccg                                              28

<210> SEQ ID NO 892
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169681

<400> SEQUENCE: 892
```
ggactagagg ttagaggaga cccccccg                                              28

<210> SEQ ID NO 893
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169682

<400> SEQUENCE: 893
ggactagagg ttagaggaga cccccccg                                              28

<210> SEQ ID NO 894
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169683

<400> SEQUENCE: 894
ggactagagg ttagaggaga cccccccg                                              28

<210> SEQ ID NO 895
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169684

<400> SEQUENCE: 895
ggactagagg ttagaggaga cccccccg                                              28

<210> SEQ ID NO 896
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169685

<400> SEQUENCE: 896
ggactagagg ttagaggaga cccccccg                                              28

<210> SEQ ID NO 897
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169686

<400> SEQUENCE: 897
ggactagagg ttagaggaga cccccccg                                              28

<210> SEQ ID NO 898
<211> LENGTH: 28
<212> TYPE: DNA
<213> ORGANISM: Artificial Sequence
<220> FEATURE:

```
<223> OTHER INFORMATION: synthetic  region of conserved sequence in 3'
      untranslated region of the genome of Dengue virus type 2
      AF169687

<400> SEQUENCE: 898
ggactagagg ttagaggaga ccccccg                                          28

<210> SEQ ID NO 899
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF169688

<400> SEQUENCE: 899
ggactagagg ttagaggaga ccccccg                                          28

<210> SEQ ID NO 900
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100145

<400> SEQUENCE: 900
ggactagagg ttagaggaga ccccccca                                         28

<210> SEQ ID NO 901
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100467

<400> SEQUENCE: 901
ggactagagg ttagaggaga ccccccca                                         28

<210> SEQ ID NO 902
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100468

<400> SEQUENCE: 902
ggactagagg ttagaggaga ccccccca                                         28

<210> SEQ ID NO 903
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF100149

<400> SEQUENCE: 903
ggactagagg ttagaggaga ccccccca                                         28
```

```
<210> SEQ ID NO 904
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      M20558

<400> SEQUENCE: 904
ggactagagg ttagaggaga cccccca                                       28

<210> SEQ ID NO 905
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      M29095

<400> SEQUENCE: 905
ggactagagg ttagaggaga cccccca                                       28

<210> SEQ ID NO 906
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      M19197

<400> SEQUENCE: 906
ggactagagg ttagaggaga cccccca                                       28

<210> SEQ ID NO 907
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      M14931

<400> SEQUENCE: 907
ggactagagg ttagaggaga cccccca                                       28

<210> SEQ ID NO 908
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      U87411

<400> SEQUENCE: 908
ggactagagg ttagaggaga ccccccg                                       28

<210> SEQ ID NO 909
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      U88536
```

-continued

<400> SEQUENCE: 909
ggactagagg ttagaggaga cccccgc                                    28

<210> SEQ ID NO 910
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 1
      U88537

<400> SEQUENCE: 910
ggactagagg ttagaggaga cccccgc                                    28

<210> SEQ ID NO 911
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 2
      AF038403

<400> SEQUENCE: 911
ggactagagg ttagaggaga ccccccca                                   28

<210> SEQ ID NO 912
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      AF326826

<400> SEQUENCE: 912
ggactagagg ttagaggaga ccccccca                                   28

<210> SEQ ID NO 913
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Dengue virus type 4
      AF326827

<400> SEQUENCE: 913
ggactagagg ttagaggaga ccccccca                                   28

<210> SEQ ID NO 914
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of Montana myotis
      leukoencephalitis virus NC_004119

<400> SEQUENCE: 914
ggactagagg ttagaggaga cccctccc                                   28

<210> SEQ ID NO 915
<211> LENGTH: 28
<212> TYPE: DNA
<213> ORGANISM: Artificial Sequence -continued

```
<220> FEATURE:
<223> OTHER INFORMATION: synthetic  region of conserved sequence in 3'
      untranslated region of the genome of Modoc virus NC_003635

<400> SEQUENCE: 915
ggactagagg ttagaggaga cccccggc                                              28

<210> SEQ ID NO 916
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of yellow fever virus X03700

<400> SEQUENCE: 916
ggtctagagg ttagaggaga ccctccag                                              28

<210> SEQ ID NO 917
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of yellow fever virus U52393

<400> SEQUENCE: 917
ggtctagagg ttagaggaga ccctccag                                              28

<210> SEQ ID NO 918
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of yellow fever virus U52407

<400> SEQUENCE: 918
ggtctagagg ttagaggaga ccctccag                                              28

<210> SEQ ID NO 919
<211> LENGTH: 28
<212> TYPE: DNA
<213> ORGANISM: Artificial Sequence
<220> FEATURE:
<223> OTHER INFORMATION: synthetic  region of conserved sequence in 3'
      untranslated region of the genome of yellow fever virus AF052448

<400> SEQUENCE: 919
ggtctagagg ttagaggaga ccctccag                                              28
```

What is claimed is:

1. A method for detecting the presence or absence of a St. Louis encephalitis virus (SLEV) nucleic acid in a sample, the method comprising:
   contacting the sample with a nucleic acid polymerase and a plurality of primers, wherein the plurality of primers comprises a first primer comprising SEQ ID NO:64 and a second primer comprising SEQ ID NO:66;
   amplifying the SLEV nucleic acid by template-dependent extension of the primers, thereby generating an amplicon if the SLEV nucleic acid is present in the sample; and
   detecting the presence or absence of the amplicon and correlating the presence or absence of the amplicon to the presence or absence, respectively, of the SLEV nucleic acid, thereby detecting the presence or absence of a St. Louis encephalitis virus (SLEV) nucleic acid in the sample.

2. The method of claim 1, further comprising contacting the sample with a probe that hybridizes to SEQ ID NO: 16 or a complement thereof.

3. The method of claim 2, wherein the probe is detectably labeled.

4. The method of claim 3, further comprising detecting hybridization of the probe to the amplified SLEV nucleic acid.

5. The method of claim 1, wherein the SLEV nucleic acid comprises SEQ ID NO: 29.

* * * * *